United States Patent
Harding et al.

(10) Patent No.: US 9,677,100 B2
(45) Date of Patent: *Jun. 13, 2017

(54) SPHINGOMONAS STRAINS PRODUCING GREATLY INCREASED YIELD OF PHB-DEFICIENT SPHINGAN (DIUTAN)

(71) Applicant: CP Kelco U.S., Inc., Atlanta, GA (US)

(72) Inventors: Nancy E. Harding, San Diego, CA (US); Todd A. Talashek, San Diego, CA (US); Yamini N. Patel, San Diego, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/973,911

(22) Filed: Dec. 18, 2015

(65) Prior Publication Data
US 2016/0130619 A1    May 12, 2016

Related U.S. Application Data

(60) Continuation of application No. 13/733,933, filed on Jan. 4, 2013, now Pat. No. 9,260,734, and a division of application No. 12/533,649, filed on Jul. 31, 2009, now abandoned.

(51) Int. Cl.

| | |
|---|---|
| *C12P 19/04* | (2006.01) |
| *C12N 1/12* | (2006.01) |
| *C12N 1/20* | (2006.01) |
| *C12N 1/00* | (2006.01) |
| *C08B 37/00* | (2006.01) |
| *C08L 5/00* | (2006.01) |
| *C12N 15/74* | (2006.01) |
| *C12R 1/01* | (2006.01) |

(52) U.S. Cl.
CPC .......... *C12P 19/04* (2013.01); *C08B 37/0003* (2013.01); *C08B 37/006* (2013.01); *C08L 5/00* (2013.01); *C12N 1/00* (2013.01); *C12N 1/20* (2013.01); *C12N 15/74* (2013.01); *C12R 1/01* (2013.01)

(58) Field of Classification Search
None
See application file for complete search history.

(56) References Cited

U.S. PATENT DOCUMENTS

| | | | |
|---|---|---|---|
| 5,416,206 A | 5/1995 | Nagura et al. | |
| 5,854,034 A | 12/1998 | Pollock et al. | |
| 5,985,623 A | 11/1999 | Pollock et al. | |
| 6,284,516 B1 | 9/2001 | Pollock et al. | |
| 7,868,167 B2 | 1/2011 | Harding et al. | |
| 7,887,866 B2 | 2/2011 | Bower et al. | |
| 7,888,333 B2 | 2/2011 | Harding et al. | |
| 8,282,962 B2 | 10/2012 | Farhat et al. | |
| 8,709,782 B2 | 4/2014 | Harding et al. | |
| 8,716,003 B2 | 5/2014 | Harding et al. | |
| 8,759,071 B2 | 6/2014 | Harding et al. | |
| 9,260,734 B2* | 2/2016 | Harding | C08B 37/0003 |
| 2008/0319186 A1 | 12/2008 | Harding et al. | |
| 2014/0342436 A1 | 11/2014 | Harding et al. | |

FOREIGN PATENT DOCUMENTS

| | | |
|---|---|---|
| CA | 2 169 434 C | 1/1997 |
| WO | 01/64897 A2 | 9/2001 |
| WO | 2007/053612 A2 | 5/2007 |
| WO | 2008/076719 A2 | 6/2008 |

OTHER PUBLICATIONS

ATCC Search for PTA-10102. Conducted on Sep. 23, 2016, 1 page.*
ATCC Search for PTA-10103. Conducted on Sep. 23, 2016, 1 page.*
Thorne et al., 2000, "Increasing the yield and viscosity of exopolysaccharides secreted by Sphingomonas by augmentation of chromosomal genes with multiple copies of cloned biosynthetic genes," J. Ind. Microbiol. Biotechnol. 25:49-57.
Coleman et al., 2008, "Identification and Organization of Genes for Diutan Polysaccharide Synthesis from *Sphingomonas* sp. ATCC 53159," J. Ind. Microbiol Biotechnol, 35;263-274.
International Search Report for PCT/IB2010/053485 dated Jan. 19, 2011 (4 pages).
ATCC Search for PTA-10102. Conducted on Oct. 17, 2014, 1 page.
ATCC Search for PTA-10103. Conducted on Oct. 17, 2014, 1 page.
ATCC Search for ATCC 31853. Conducted on Oct. 17, 2014, 1 page.
ATCC Search for ATCC 53159 Conducted on Oct. 17, 2014, 1 page.
ATCC Search for ATCC 21423. Conducted on Oct. 17, 2014, 1 page.
ATCC Search for ATCC 53272. Conducted on Oct. 17, 2014, 1 page.
Japanese Office Action for JP Application No. 2013-526176 mailed Jan. 5, 2016 (10 pages).
Borges et al., "Xanthan Synthesized by Strains of Xanthomonas Campestris pv Pruni: Production, Viscoscity and Chemical Composition," Biosci. J., 2007, 23(4):67-73.

* cited by examiner

*Primary Examiner* — Channing S Mahatan
(74) *Attorney, Agent, or Firm* — Eversheds Sutherland (US) LLP

(57) ABSTRACT

PHB-deficient *Sphingomonas* strains having improved sphingan yield are provided. Certain of the *Sphingomonas* strains are diutan-producing strains that exhibit a dramatic improvement in productivity and yield due to a combination of certain genetic modifications that affect PHB and sphingan synthesis. Moreover, the sphingans produced from such strains have superior characteristics including improved filterability, clarity, and improved rheology-modifying characteristics. The sphingans provided are, thus, highly desirable in a variety of commercial and industrial uses, including personal care items, cement applications, and oilfield applications.

26 Claims, 31 Drawing Sheets

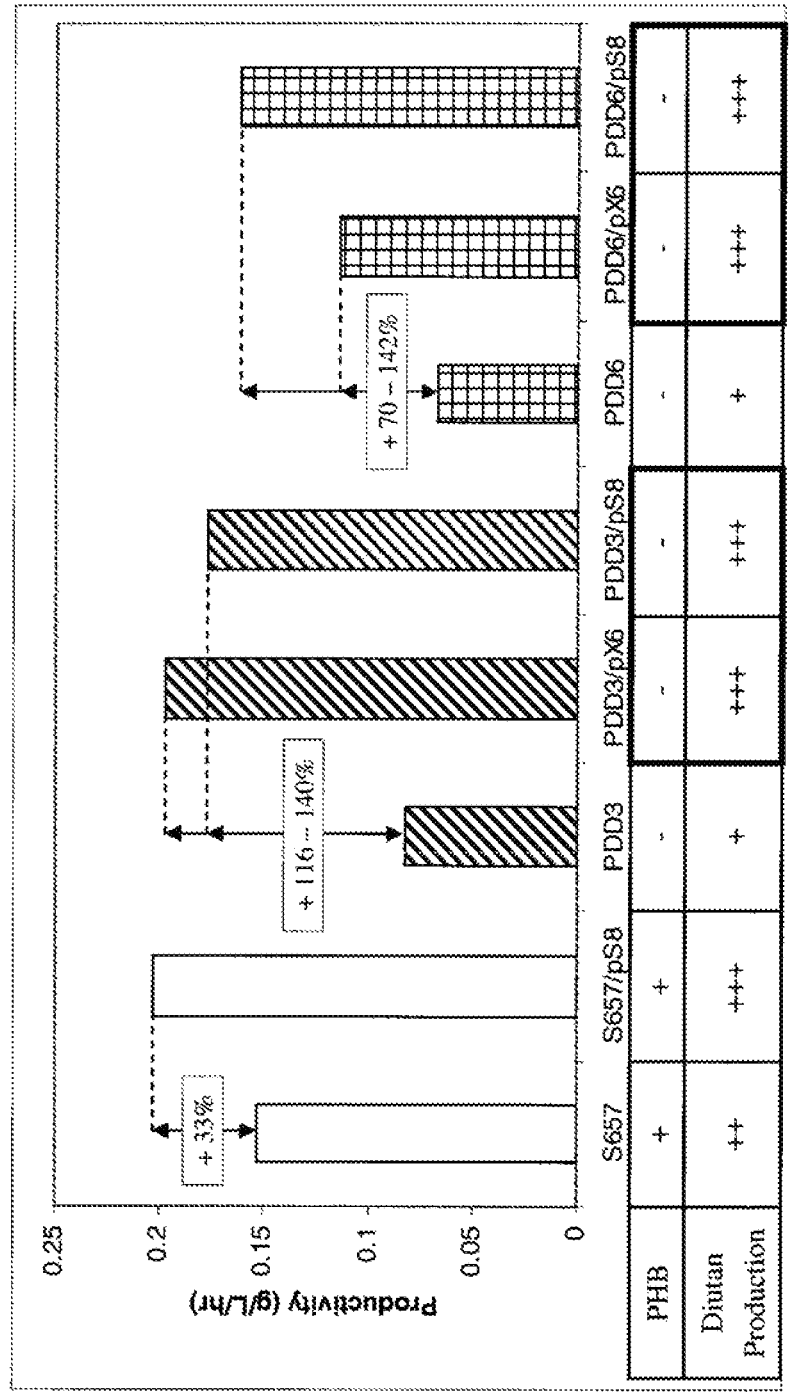
FIG. 1. Plasmids pX6 and pS8 greatly increased diutan productivity (g/L/hr) in PHB-deficient strains (PPD3 and PPD6).

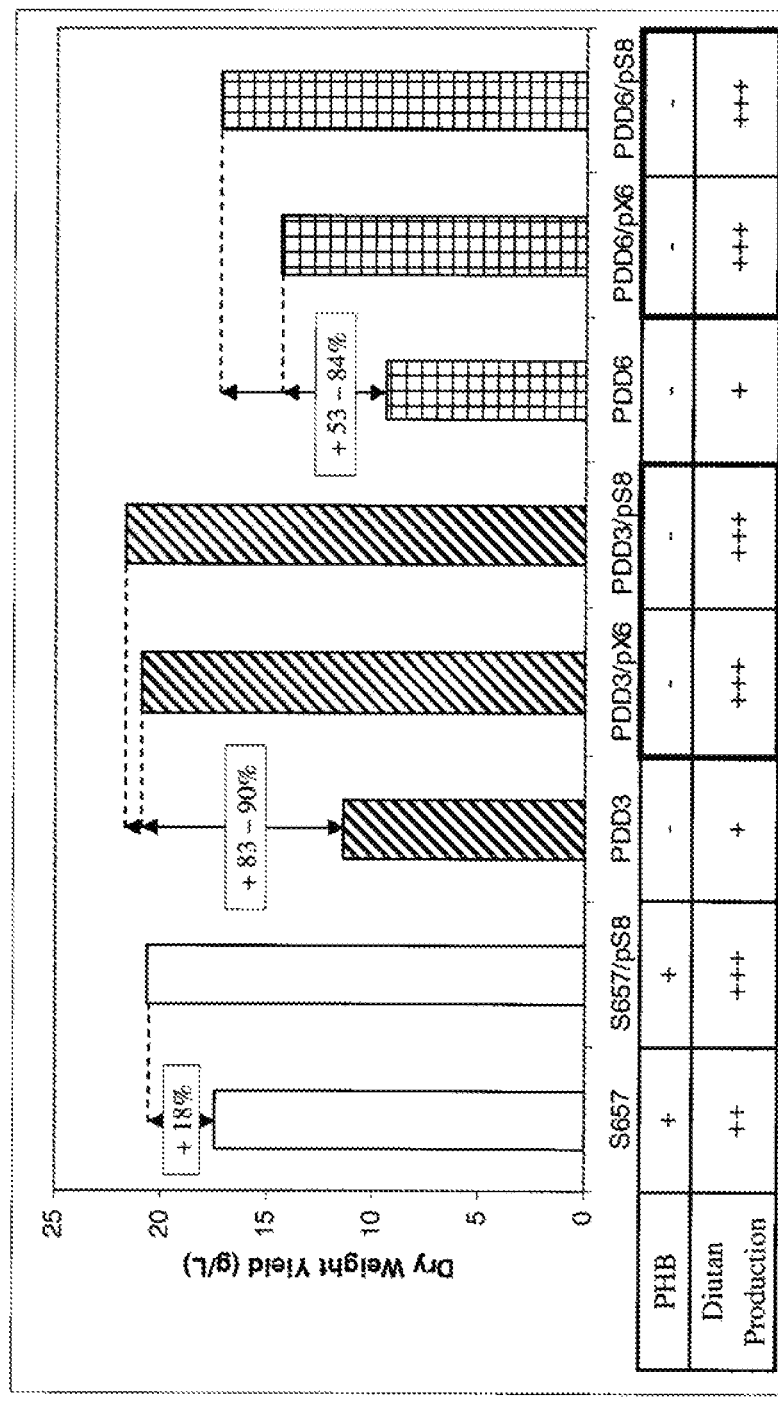
FIG. 2. Plasmids pX6 and pS8 greatly increase diutan yield (g/L) from PHB-deficient strains (PPD3 and PPD6).

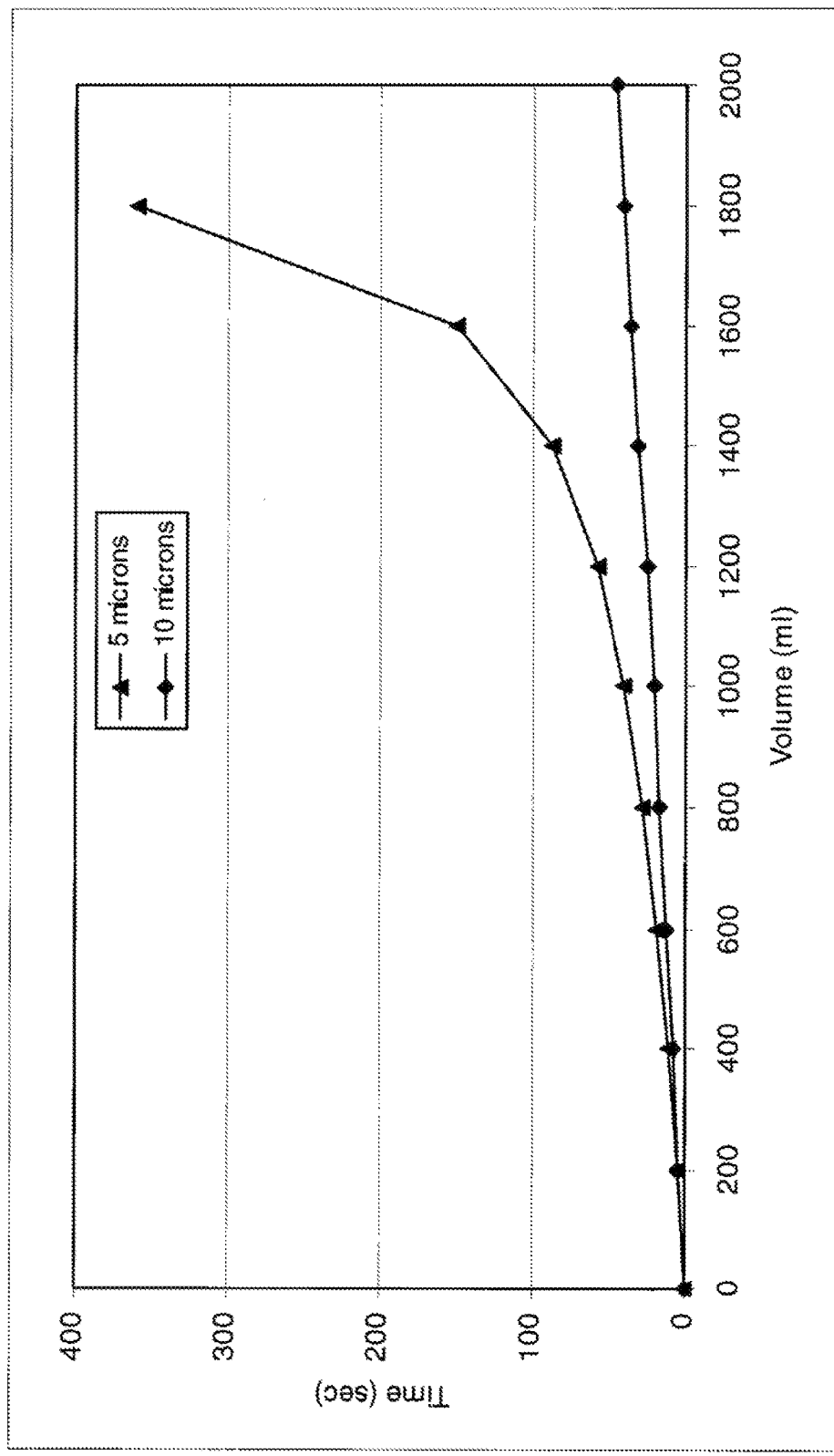
FIG. 3A. Poor filterability of a PHB-containing diutan preparation (0.04% S657/pS8 diutan in seawater).

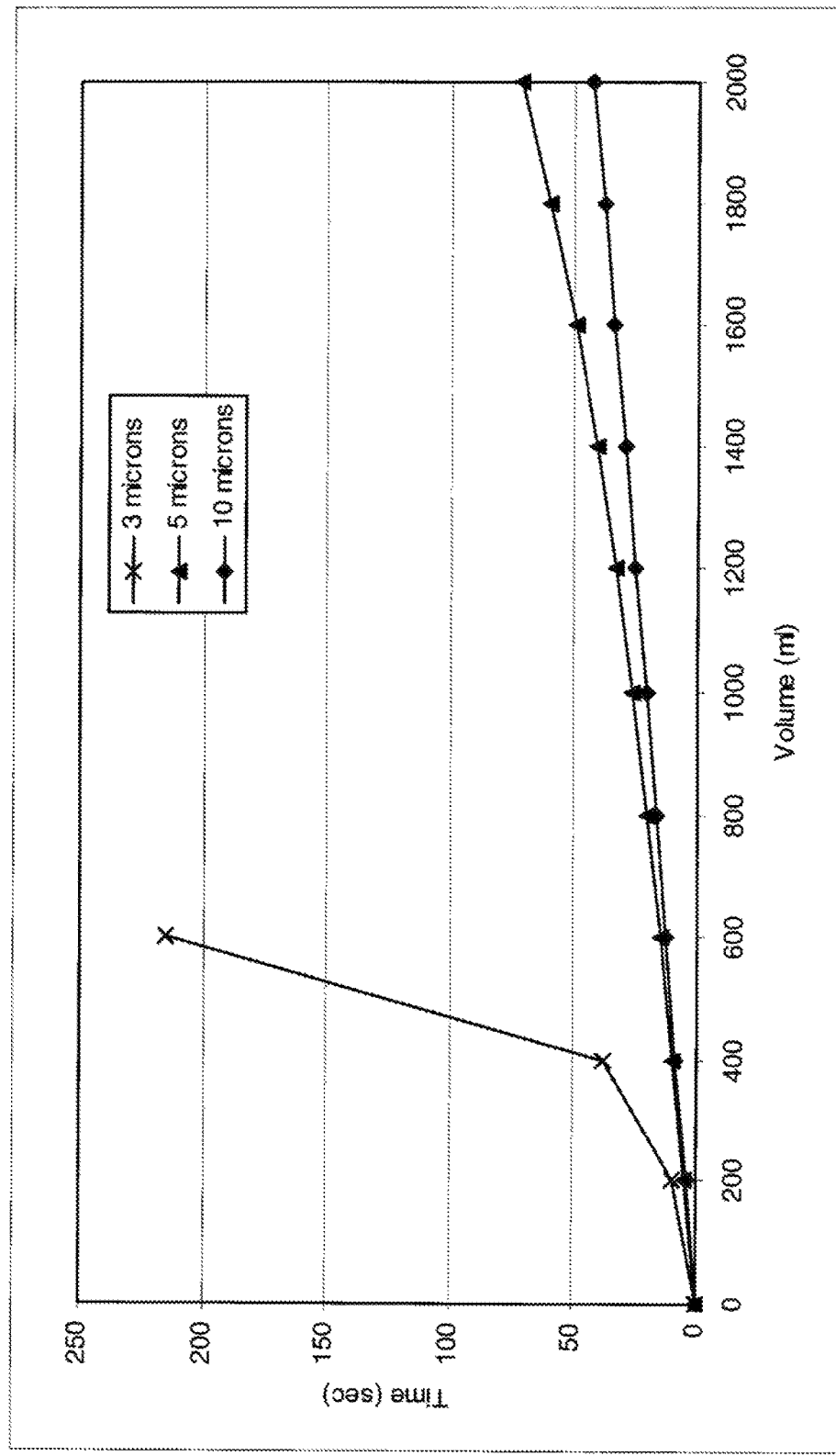
FIG. 3B. Poor filterability of a PHB-containing diutan preparation (0.04% S657/pS8 diutan in seawater).

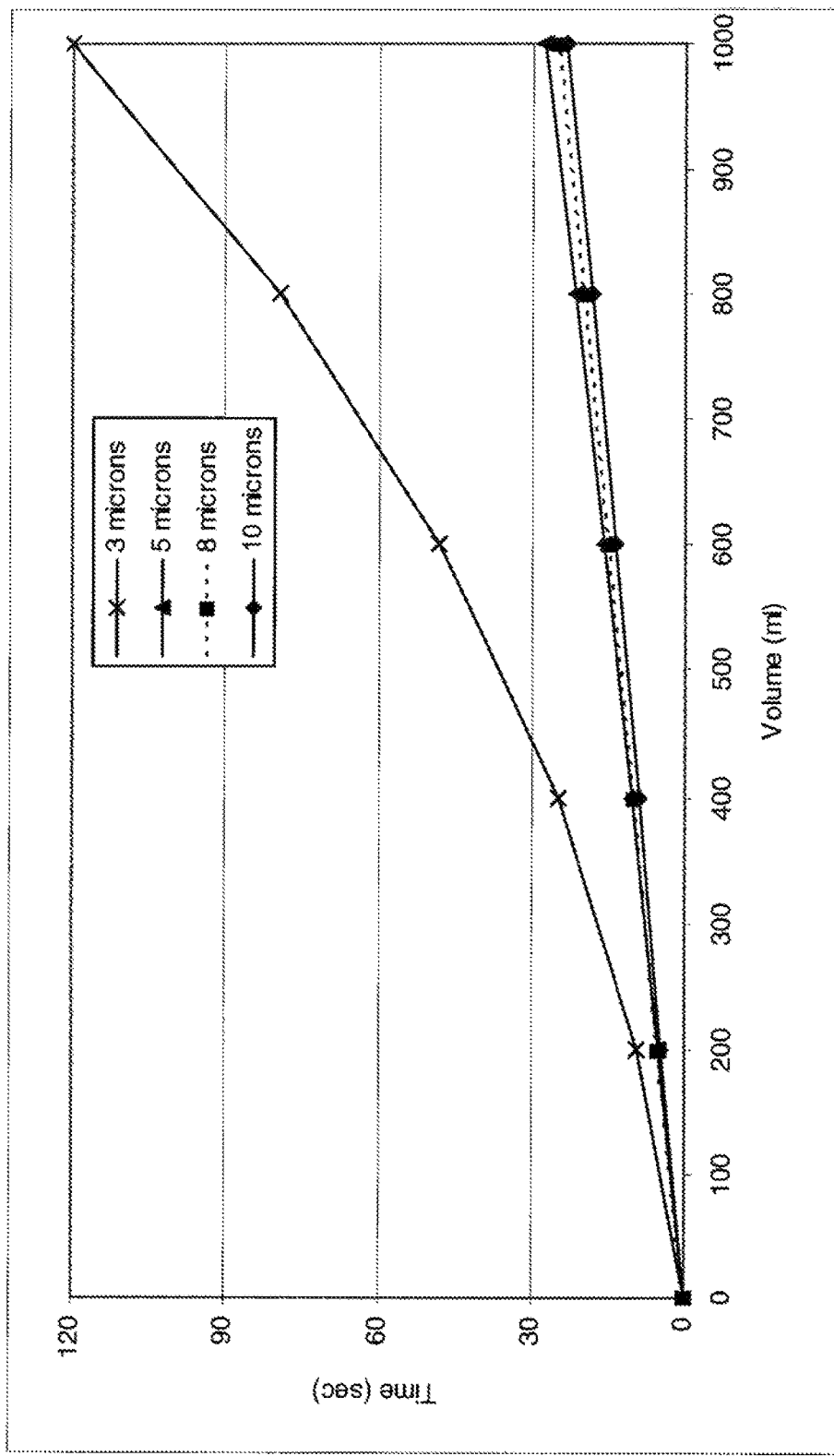
FIG. 4A. Improved filterability of a PHB-deficient diutan preparation (0.04% PDD3/pS8 diutan in seawater).

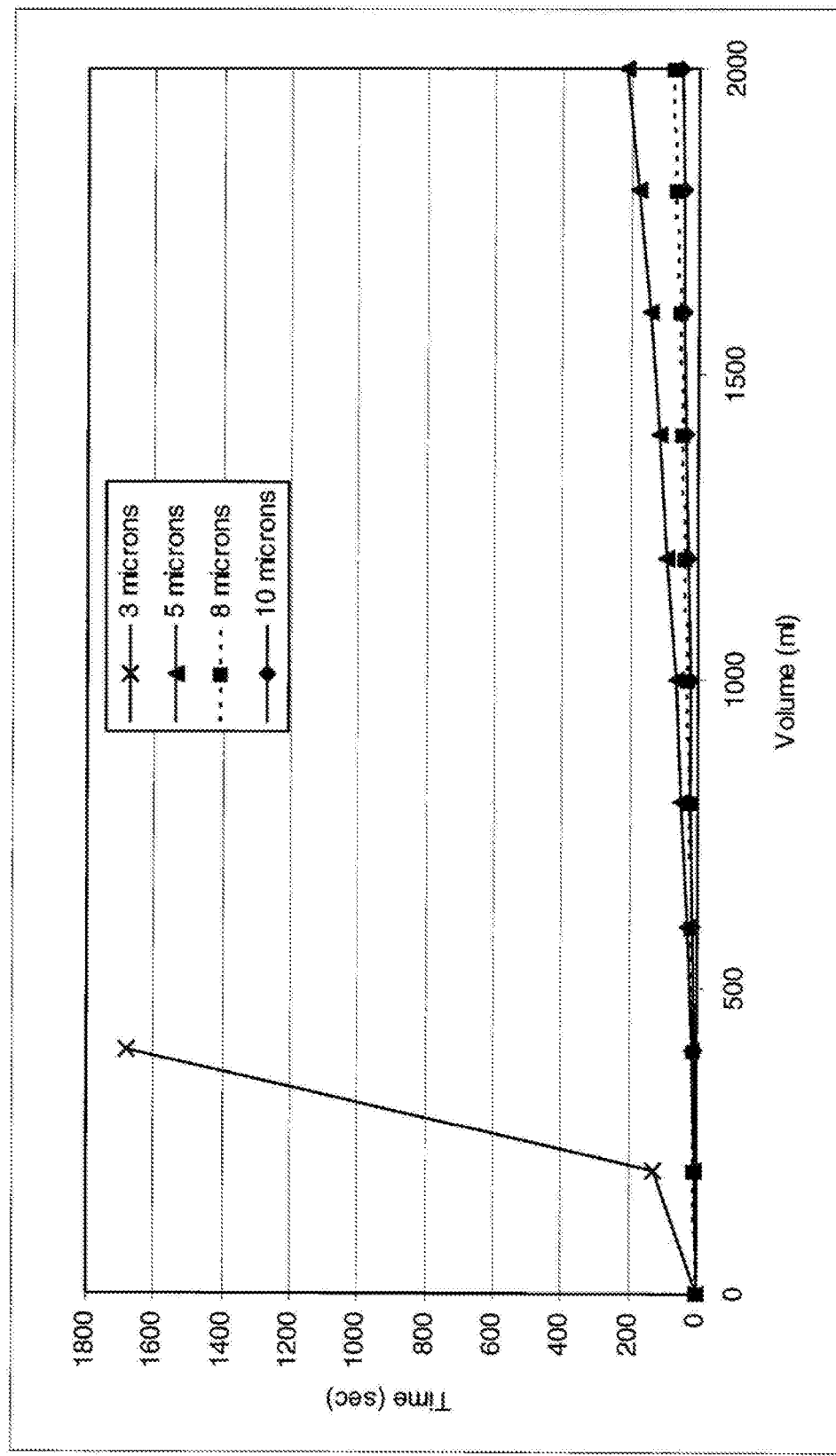
FIG. 4B. Improved filterability of a PHB-deficient diutan preparation (0.04% PDD3/pS8 diutan in seawater).

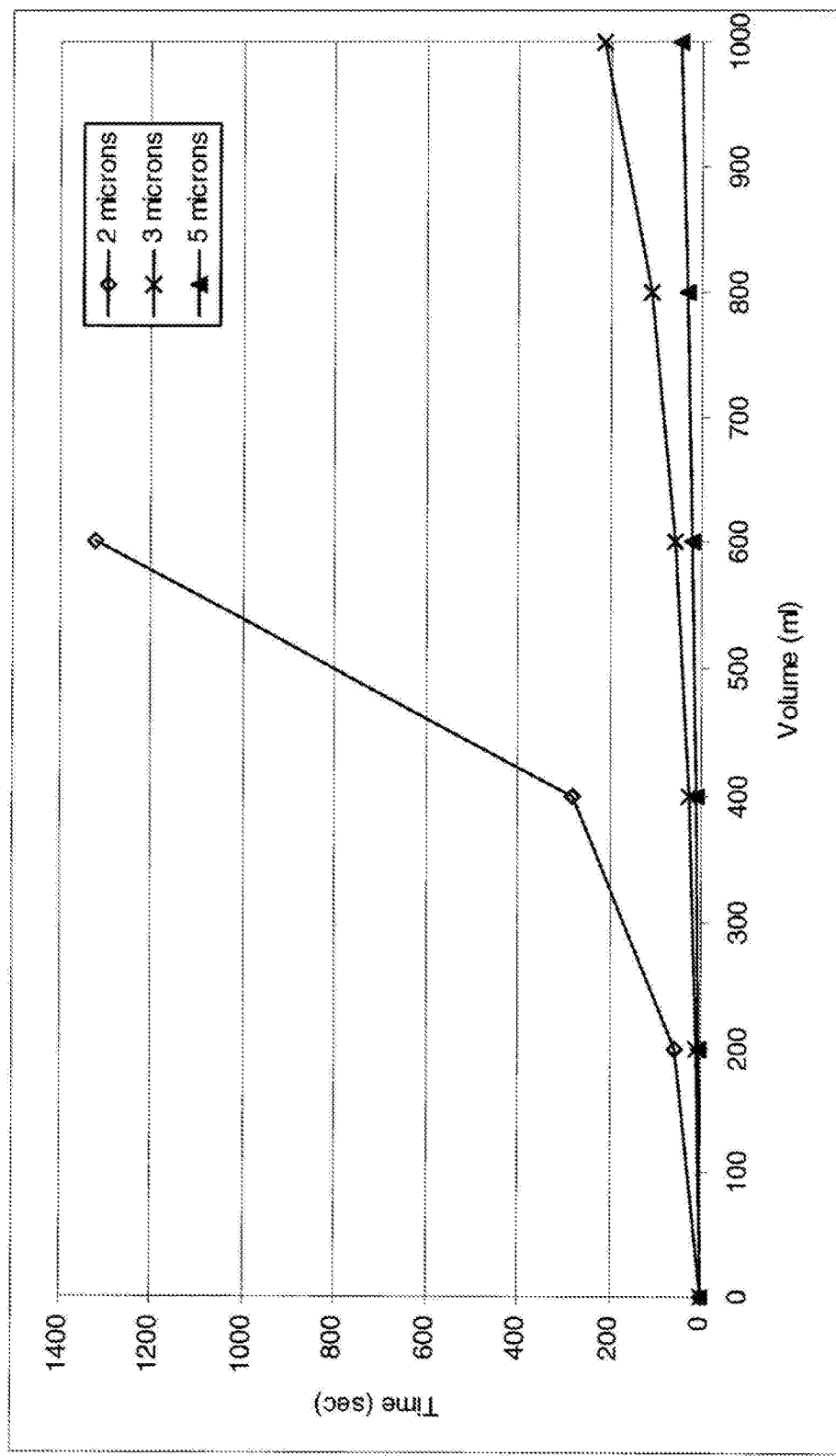
FIG. 4C. Improved filterability of a PHB-deficient diutan preparation (0.04% PDD3/pS8 diutan in seawater).

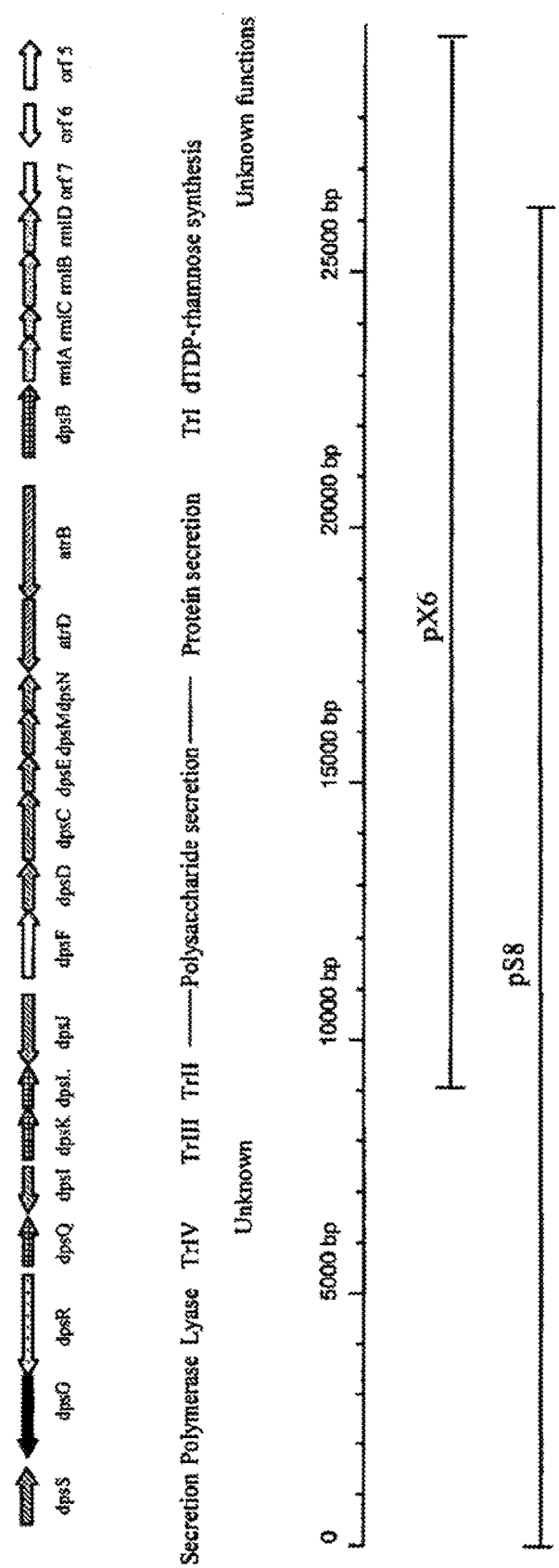
FIG. 5. Map of plasmid inserts containing genes involved in diutan production.

FIG. 6    Sequence of insert contained in plasmid pS8 (SEQ ID NO: 1).

```
gatcaacggc gccttgctcg gacggcacaa attcgtcctg gtcaatgtgt ccacggtcgc    60
ctcttcgata ctgttccagc tgtcccgct tgtcgtcgcc tggatgatcg gcccggacct   120
gcgaacgctg ctgatcgccg cgctcgttgg ccgggcggtt ccgatgatcg gcatgctgcc   180
cgcgtgtat cgaaacctt tgcgcggcaa cacgccgcgt tttcacgcca gcgaggcgcg    240
cttcctgata ggctatggcg gtgggcctc gctcacgacc gtggtagcga cgtgtcat    300
gatgggac cgcttctga ttggcgcact tcttgggccc gtcgccgtga ccatctacac   360
ggcccctg caactgcac agcgcgtatc gctgtcgccc tccgcactgt cgcccgcgt    420
gttcccgcgc ctgccagcg cgacgccggc ggagcgcatg gcgcttcaga tccgctcgct   480
gtcgctgatc atgggcggcc ttaccgggat gatcggcggc ggactattgc tggccgcgcc   540
gttctcgat ctctggatcg gcaagtcgct cggccatgcg ggaacgccgg tcgctcttt    600
cctgttcttc ggcgcatggt ggaatgcgct ggcgatcatt tcgttcagcg gctgcaggc   660
gagcggacgg ccgaaagcga gcgcgatcgt ccaggggca gagctgctac cgtgttgat    720
cgcgctgtat gcaggatcc gatggggcgg cgtgaccggc gccgcagcgg tctttctggg   780
acgctccgcc ctggatttcg tcctgttgac ctgcaggca ggcctgctcc gccagacggt   840
gaagcaagta tccgtatgcg gcgcgttct caccgtcgcg atgctcgtgg gcgacctta    900
tcgctattcg gtgccgtct ggtgctact cagcgcctgc tgcctggtcg cgctggcagc   960
ctgtcctgg tggacattgg cgcgccagga caactgactg ctgattggac gattgagccg  1020
aattctacca aagcaggcc aactcgacct atagcctttc cgcaatgcac cgatggacca  1080
caccaaccgg tttaattga cacacacaaa tgctacaccg acaaagacac aggccgagag  1140
cgatatagaa gcgctatgcc tagcccagc gtcataaaga tgaacgggtc attgtcactt  1200
tgcgacagga ctgaccgcgt atttaaaaga acagccagga ccaccagga aagtgctac  1260
agcgggtagc catctccgct catcttaaga ccacgaaacg cgagcaaaat cattaacgta  1320
atcatcgtgc cgtatcgcga aacaaaaccc agcaagccgt aatcagccgc tacgacagg  1380
aaaccactgt cgatcgatag gaagccttgc tgattacgcc acccgacagc gccagcaccc  1440
tctccgggc catagccgaa gaaagggcgg cgagcgatgg caggcacgcc caagcacgac  1500
tgctcctgcc tgcttgatt gctaagttga gaagcgcctc caccgagaaa cggtttgtgg  1560
acgcaggca cgaacatgac cgccagac agcgccacca tcaaggcggg atacgtcaac  1620
gtcagcgaaa tgccgacaag ccccgatcgc gtggtccgcc accgccgaat tgcccaaata  1680
agcaaataca cgtatgcgc caccaatcgc cccaccattg ccagtcgaga accgctaaga  1740
aatccggacg caactacaag aaaatcgaag aaaatccaaa atgccaatct cctacgcca   1800
cgggaattcg ctatacggtg cagcacgaaa ggaatcgtca aagccgtcaa ctctcccag   1860
acaagcggac tgctgaaagt cgtcaaaacg cggtaagtac cccggaaaac gggcgtaagc  1920
actacggtaa gaaactgctc atcaaacgcg aggaagctcg gaatcgagtg ggccagagg   1980
acgtgcttca cccggaactc cagcacgcca atcgccatca gcacgcccac gcaccaaaac  2040
aagcgcgtaa cccacactc cggggtgcgc cgatcagcca cgatcagcca tagcgagatg  2100
```

FIG. 6  Sequence of insert contained in plasmid pS8 (SEQ ID NO: 1), continued.

```
aatgccatcg gcgtcaccgt cagaacgatg ccaatcaacc gcggaattgt ttgccgaggcc 2160
gctgggtcg caatggaggc gacgatctgg accataatga aggcaagcaa tagtcgcgat 2220
gggatcgggcg ccgcccgcat aatccgcgcc atctccggatc gaaacttttt cgagaccgaa 2280
agcgagatca tgagcgtgag caatgcgatc gaaccgatca tccgcctgat cgagatccaa 2340
ggcaaaccac caacgctgag cgcaagatag ttcggccaca cgagcgccgc caccatatag 2400
gcgagtata gttttgccag caggcgagta ggcgcctgcc ggcgctcggg tagcgcccag 2460
atcactacga gcgccatcag aacgaggggc acggccggga tcgccagcat ctggagcggc 2520
agaactgcgg cgagcaggcc gtagactgcg gcaagaaaca tcaccgtgac cagcagaacg 2580
gtaccgcgcg ccgcgatcgt cacgcctgat cgctcggctt tgtagacggg cagtaccggg 2640
atcgtggct ttgtcagaaa ccgaaccagt cgcaactgc gaagccgctg catcgctccg 2700
tggaaggccg ggcgacgaaa tgccgtcgc atgatcgagg gttcgcgaa aagcaaggtc 2760
caagaggcgc tgccgctcgc atgtgccgcc ggatcgcagg agggcacggg cggcgccggc 2820
actccctgcg ccccgcctca gccgcggtac aggtgtact aggtgtact agcgctcagt 2880
tcaccgcccg tgcggattgc gcccatcgcc cccggtca gtaccatag accgatcttg 2940
gtccgcgc tgaccgagcg cgatctgcga ggacgcggca gtacctatag acagcgtact gcccaccgtg 3000
ctgacgagcg cgatctgcga ggacgcggca gcggcggcgg caccccgcca cagcgagcg 3060
gccaccgtcg caagcggcgt tgccgtgcta gcggcgcgg caccggccag cagcgagcg 3120
gcctgcgcg ccgcgggt gacgaggctg tcctttgaccg tgccgccgc gctggcgctc 3180
gacgggtca ccagcgcctg cactcgggcg gcgctgatcg cgccatcgcg gatctcgatg 3240
tcgccgaccg ttccgctgaa tcggtcgag acgggctgc aacgggtcgc ccccaggat 3300
tcggcgggc gggtcgtgcc ggtcatcgtc gctgtgcgc gttgcatgcc gttcgtacgtac 3360
agaatcgcgg tttccgcgt caccattgtc tggctgacgc tcttgtgt ggcagcatca 3420
agcagctttgg cgccgtcgt ccaccattggc gtcagggcga tggctgacgc gcgcatggtg 3480
aagctcagtt ccccattggc ctgcagcgaa accgaccagc tctggaagat gccaagaatt 3540
tgcccggccg tggccgtagc cgagtcccgc ttgaggtcga agctgagcgt gaacgccgac 3600
aatgcgtaaa tctgccgcga atagctccgg tttagttcca ccccgtgcc cgtcgagacg 3660
tggaaggccgc tgccaacacg cgccgacacg tccaccgcct ttgtcgtctg gcggtattc 3720
cagtgcgaaa ggtccacgac gccgtgttg ctgaacgaca gatcgagcag cagcgacgga 3780
tttgccgcct tcgcagtcga cagttccggta gtcacctgag cggcagcagc gctcgacacg 3840
ggcggctggt accgacgcc gggaacgatc cagttgtgcc gccgcgcgt agccccatcg 3900
ttgaggccat agatcttgcg gatcgttgcg gagtcactcg tcagctacg attgcctgtc 3960
tgcacgatat tgctcgagga gcttgtgacg gtgatcaggt ccgcaacatt gttcttgatc 4020
gtcgccgccat tggttttgtc gaggcgaatc caaaatgatg tgccatccac ttgcgatatc 4080
acgctattgg attcgatatt gacattaaacg ccgttaacaa cgttgatacc gtggtaataa 4140
ccattcagat agataagatt gttttttgatg tttacattga caaggaag attaccggcc 4200
```

FIG. 6   Sequence of insert contained in plasmid pS8 (SEQ ID NO: 1), continued.

```
tcgtcattca tgaaatccc ttgcgcgca gagcccgcgc cctgcatgat gacgttattg      4260
gagatggtga tgttggtatt gcccttgacc ttgcccgccg tgaagaactg aatggcgtcg      4320
ggatgttcgg tgcccacggg aaacaggttc gtgaacgaat ttccgtcgat gacaagattg      4380
ttcatctcag tgaagttcgt atgatcgcgc cggttgtcgt ggaagctgct gtctggacc      4440
accatgccat cgacgttgta ggcctcaagg cccagaccga agtggtcgat agacgaattc      4500
tgcatcgtca ccgacgtgct gttgcgcacg aacaagcccg cccccttcga gagcgaaggg      4560
tcaccagtgc cgccgtgaa ccgcacgccg tccaaaacga tgttggccga accctggatc      4620
gtattcagtc gattccagtc atcgcggggc ttgtaatcgg tgcagcgac catgttttg      4680
acggtaacgt tgctactgtt cccgatcacc agcttttgga tattgaccgg gttcgacgag      4740
tcgagcgact caattgtcac catgctggta aacgtctgg tcattacagt gagatctgtg      4800
tagaccccgg cggcaagctt gatgtttcg ccaccttcg cgcgcgat tgcagcattc      4860
aactccgtct gattcttgac aatgatatcc ggcatgttga ctaccccgt acgacgaaac      4920
ccgggccgat attgacccct ccattgtcat aaataccaga acagccatga aatttgctcg      4980
aagggataca gttaagaaac ccctctacg gggcgcatg ccggcccat gcacgcccga      5040
cttcgccgg caccgtctcg acggcgcaac acagtcagc ggtcgcttc tactagggtg cgatgcagat      5100
gctcccaacg ccgatgtca gcatactcgt ggtcgcttc aactcgaccg agtatatcga      5160
agactgcctg cgcggcatcg ccgaaggagc gggcaagacc ccccagaagc ttctgctgat      5220
cgacaatggc gacgggcaat attggtttcgg ggtccggcag acgttccacc acgtccgcat      5280
cgttcccagt gagggcgaa ttggtttcgg gcggcaaat aatcgcctgg cagcgcaggc      5340
tgccgggccg ctcctgctgc tcgtcaacc cgatgccatt cccagcccg gcgcaatcga      5400
tcagttggtc acctttgcca aacagcatcc cgaggcggcg gcatgggcg gccgttccta      5460
ctcgccagc ggcgatctag aaccgcatcc cgaggtcgcc ctgccgacgc cgcgacttt      5520
tctgacggcg attttcaacg cgcgtcgct tttcatgtcc gggctgcaag aagcgcgac      5580
caccccgga gcggtcgagg tgttgaatgg cggcttcatg atggtacgca ccgatgtctg      5640
gcaggcgatc ggcggttttg acgagagctt tttctttat tggaagaga tcgatctctt      5700
ccagcgaatc cgcacgttgg gcacaaggt gctcgtcgac ccctcggtca aagtggtaca      5760
caatacgggg agtggtcagt cgatgtccca gaaccgcctg atgtatctca cgaccgggcg      5820
catgcactat gcgcgaaagc atttttggcgc actggcacc cttgccaccg ggtgcgcgct      5880
ttggctgatc gccgccaaat acacgttggt cgggcggca ctctggcgcc gtgtcgccgg      5940
gacgggcacg cgatacaaag agctgagcaa cggtggcgt gccgtatta gcaatcctgg      6000
ccgatggtgg agcggctatc gcgtcgcta aaagtccagc tccccccccc ctaaagcgc      6060
cgtgggagg cggcgttg gttgcaacaa cgcgccccgc ggcggtgcgc tttcagacct ctgtatttc      6120
gccggcttgc gcgccgctgcc gaaagctgc actggcacc gggtgcgcgt cagtcccc      6180
acggtttccc gcgccttctt caggcggtcg ttgagctgtg cgtcagccgc cttgccgaag      6240
cgtccggtac gcagccgct gagcgcgatc tcgcgcgcct ggtcggccgg caccggcagc      6300
```

FIG. 6  Sequence of insert contained in plasmid pS8 (SEQ ID NO: 1), continued.

```
acgtggtcg  acgtgatgat  attcgcggtc  agtccctgct  gggtcggcag  gatgaacatc  6360
tcctgtgccg  gcagcgacgc  gatcttggca  gcgattccg   gggcagcgc   agcggtgtcg  6420
atctgcgacg  gcgcgcgacg  gaactggaca  ttgtccgccg  agagcttggc  ggttagctgg  6480
tccagcgtct  tcagcggcgc  gaattgcttg  agctttgcgg  ccgagctcgg  cggagcgaag  6540
acgacctgat  cgatcggcgta gatcttgcgc tgcggaacc   gtccggatg   cggagcctga  6600
tatttctcga  tctggcatc   ggtcggctgg  gcgatgccgc  cggcgatctt  gtcgcgcagc  6660
atggcggtga  ggatcagctc  gtcggcccgg  gacctggcg   cgctcctgga  tcaggaaggc  aggcgtcttg  6720
tccagcttct  gctcgcgggc  gaccttggcg  aggatcttgc  gtcgatgat   gcgctgcagc  6780
gccagctgct  cggccagctt  cgatcggtc   cccggggta   cctgggaggc  ctgcagttcg  6840
gcattcagct  cgaagacggt  gattcttcg   ccatcgacgc  tggcgaccac  ctgcccttg   6900
tccagcttgc  cgccctttgcc gccacatccg gagacggcca  gcgcggccgc  agccaccgcc  6960
gtaaccaggt  acaatttctt  catgaagacc  tccccgccgg  cacggaattg  cgcacggcac  7020
aaacttctac  ttgaacctat  tcggacgggc  gggcatccgc  aatagcgttg  gcagtgcagc  7080
atggttctaa  gcggagccag  gcgcaacaa   ggggacgag   atggcagaag  cgaacgggt   7140
agatggaaag  gcctccaagc  cgctgaaaaat gtgccttgca  gcgtcggcg   gcgccatct   7200
cccgcaaatc  ctgatctgg   aatcggtgtg  gccttgcga   aaaacatccc  gattatttct  tcgttactga  7260
agataccgcg  ctcggccgga  gccttgccga  gtcgaactgg  gtcgaactgg  tggagcacta  7320
tgcgctcggc  caggccaagc  tgggccatc   cttgcgccg   ctgggcggcg  catggcgcaa  7380
cctgcgccag  agcctttcga  tctgcgccg   gcacaagccg  gatgtggtga  tttccaccgg  7440
cgcgggcgca  gtctatttca  ccgcgctgct  cgccaaactg  tcgggcgcca  agttcgtcca  7500
tatcgaaagc  ttcgcgcgct  tgaccaccc   gtctgcctt   ggcaagatgg  tgaagggcat  7560
cgcgacggtg  acgatcgtcc  agtcggcggc  gctgaaagaa  acctggcctg  atgccgagct  7620
gttcgatccg  ttccggctgc  tcgatacac   gcgcccgcc   gcagtgctcg  taatcttcgc  7680
gacggtcggc  gccaccctgc  ccttcccgcg  gctgttgcag  gcagtgctcg  acctgaagcg  7740
cgcggcgggg  ctgccgggca  agctgatcct  gcaatatggc  gaccaggacc  tgcccgatcc  7800
cggcatccg   gacgtcgaga  tccgccgtac  catcccgttc  gacgatctgc  agctgctgct  7860
cggcgatgcg  gatatggtga  tatgccacgg  cggcaccgga  tcctgtgtca  cggcgctgcg  7920
cgcggctgc   cgggtcgcg   cgtttccgcg  ccgccacgat  ctgggcgagc  attatgacga  7980
tcaccaggaa  gagatcgccc  agaccttcgc  cgaccgggc   ctgtccagg   cggtgcgca   8040
cgagccagg   ctcggcgcg   ctgtggaagc  ggccaaggca  cgagccgc    agcggcgac   8100
caccgaccac  acggccctcg  cggcgggct   gcgcagctg   acggcagt    ggagtgccaa  8160
gcgatgagca  cgccccgat   cagcgtcgc   atcccgcact  ataacgatcc  gcaatccttg  8220
cggctctgcc  tggatgcgct  ggagcggcag  acgatcggtc  gcgacgcgtt  cgagatcatc  8280
gtcggcgaca  acaattcgcc  ctgtgggctc  ctgtggcgtgg aggcggcggt cgccgacgt   8340
gcgcggatcg  tgaccattct  ggaaaagggg  gcgggcccg   cgcgcaacgg  ggcggcagcc  8400
```

FIG. 6 Sequence of insert contained in plasmid pS8 (SEQ ID NO: 1), continued.

```
gcagcgcgtg gcgagatcct cgcctttacc gacagtgact gcgtggtgga gccggctgg    8460
ctggcgggcg gcacgaccag gtcgcgcct ggcgtttca tcggcgggca catgtatgtg    8520
cgcaagcccg aagggccgcc gaacggcgcc gaggcgctgg agatggcgct ggcgttcgac    8580
aatgaaggct atgtgcggcg caccagttc acggtcaccg caaacctgtt cgtgatgcgc    8640
gccgatttcg aacgggtcgg cgcttccgc gttggcgtgt ccgaggatct ggaatggtgc    8700
caccgggcga tcgccagcgg cctcaccatc aactatgcac cggatgcatc ggtgggccac    8760
ccgccccggc ccgactgtc ggccctgctg gtgaagacgc ggcgcatcca gcgcgaactc    8820
tatctgttca acatcgagcg gccgaagggc aggctgcgct ggctggtccg ttccgtggcg    8880
caaccgggca tgatccaca ggacgtggcc aagatcctgc gcacaccggg taccaagggc    8940
gcgcgcctcg ctgcgtcac cacgctggtc cggctgcggc tgtgccgcg cggcgccggc    9000
ttgttgcagt tgctcggccg cgacatctga tcgaccggcg atcggcgac gagcgcgtcg    9060
ccggccgatc gcattgcatc agacggtggc cagcgcgtct tccagcgtgc cgctgtcgag    9120
ccgcaggcgg ccgatcatca gccacagata gaccggcagc gtatcgtcgg tgaagcggaa    9180
gccgcaatcg cgtcctgcg tttcggattc gaggcgagt tgacggtga gctcgccag    9240
ctcctgctcg acctgcgccg cggtgatgtg ccgtccgccc agcagatcca ccacggcttg    9300
gccgctgaac cagccatccg ccgagccgcga ggcctcgcc agcgccgcca cgagtggatc    9360
gtagcggccg ccgacgaact tgcgcatctc gatcaccgcg cgcggggca cgtggccctc    9420
gatctcaagg atcgcctggt cgagcgcacg acgcagatgc ccggccgtga ccgtgaggcg    9480
gccctgccc agggctcca gcgcggaatg gtggcacagc agccgcgcga ataggggcga    9540
cccagcgcg agcaggtgga tcatgtgagt caggtccgga tcccgattcc tccagccggg    9600
ggttcgccg agcgcgatca tctcctgcac ctccgcac agctcctgcc gcatcggcag    9660
gccgatgacg ttgcgcgga tcgacgggcc ataaccgatc agctcctgca ggttcgaggc    9720
gacgcccgcg atcaccagct ggacgcgcgc cgaacggtcc gacaggtcct tgatcagctc    9780
ggcgacctgc tgacggaagg cggaatcgct gacgcgatca tattcgtcga ggatgatcag    9840
cacgcgtgtg cccgtgatgt cggcgcacag gtcggccagt tcgccggccc cgaagctgcc    9900
cgtcgccagg cggtcggcca agttgccgcc agttcgccg cgctccgcc tcgccggcgt    9960
gccgatgg aacagcagcg gcacgtcttc cagcacgcg cggaagacat cgctgaaatt    10020
cgcgttcgca cgcagtgcg catagctg gatatagctg gatatagctg gatatagctg gatatagctg    10080
cagcacgtgg agcagcgagg tcttgccgat gccgcgctcg ccatagagca cgacatggct    10140
gcgctggctc tgatcgagg agattaggcg cgcagcgcc ccgaggcgcc cgagcgaagt    10200
cgaccgatcg gccaccggct gggtgggtgt gaagaaggtc gccagcgcga accgggcgcg    10260
cgtgatctcg cggcgtcgt cgcggcggcg atccagcggg cgttccagcg cggaggcacg    10320
gaaggtttggg aaatccgggc gaccacggcc gctatgggca togcgatgcg gcaccactgt    10380
cgcagtcagc gggaaataagc ctctctttct aggttcttct cgacggccga acggccacaa    10440
gaatccagc gcggaaccta cagcccactcg aacacctctt aaattcgtgc gccatcggca    10500
```

FIG. 6    Sequence of insert contained in plasmid pS8 (SEQ ID NO: 1), continued.

```
ccgacggcgc acccctggttc gcgcccctg gcgcccctc ctaacgaacc cacgccttgc    10560
ctggcctatc ggcgcttgaa gaactcgtac ggtttgatca ccaaggcgat gtacgccagg  10620
accagagcga tcgtcaaaat tgcaaagacg tgataattct cattgcccag ataattggcg  10680
acggcgcaac cgactgcggg cggcaaatag ctgatcatcg tgtcccggac tgccgaatcg  10740
gcttgggacc gttgcaggaa tataacgatc aggccggcaa atatcgcgat ggtgacccaa  10800
tcataggggcg tctgcatgca tgtcctttct attcgacacc ggaatcgaac catttccggc  10860
gacgctattg cacgcactag cagtgcgcgc ggccgtcgc taggtagcgc cgcaccggat  10920
aaaccgacgt taagatgcg cggctcgatc gaaatggagt caaacgggct tgcccggccg  10980
accgaagcat ggcgccatgg cgcatgcacc gtattgtgac cacgcaaacc gcgagggtca  11040
ttcgatgcgg ttgcttgtac aggaggccat tgataatgaa gccgagaccc ggggaacct  11100
ttatgcaagt aaattcaat cgacaggctc gcaaggtcgg tgccggcaat gcgctcgcgc  11160
gggggggggc cgtgcttgcg ctgcttgga ccgcggcatg ccgggcatg gacacaacct gcgctggcgc 11220
agcgacaggc atttgagtcc gacaagtcg gtagcgagcg acaggtcgat attcgcgca  11280
cggtcgct ggaatatgac tcgcccgggc tgctgaacga ccagcggatc acggacggcg  11340
cggtggcga tgtgatcgca tcgcccgggc tggacgtgac cctagttctg cccgcgcca  11400
cgggcagt ctacctcacc ggcaatgtcg gatatgctt ttacaagcga tataccaact  11460
ttaacggcga gcagatctcg ctcaccggcg gcgcagatca gcgttcgcc tcctcgtcg  11520
tgcacggga agtcggctat cagcgccac tcaccgacct gtccagcatc ttgatccagg  11580
acaccacgcc tgcgctcaac aacacggaag aggcccggca gtacaccgcg gatatggct  11640
gcggcgcaac ctacggcctg cggcctgcgc tttcctacac ccgcaacgaa gtgcgcaaca  11700
gccttgcgca gcgccgatac gcggactcga ataccaacac ctttaccgca cagcttggcc  11760
tgacttcgcc tgcccctggg accgtggcgg tattgggcg tatgtccgac agcagctatg  11820
tccatcgcgt ccttcccggc attaccggcc aggacgggat gaagagctac gcggccggcg  11880
tccagcttga gcgctcggtg gccaaccgac tccatttcaa cggtcggtg aattacaccg  11940
aggttgaccc aaaagctgca tccaccaaag gattcaaggg cgtaggattt aacgtttccg  12000
gcgattatgc tggtgatcag tacagcctcc aattgctggc ttcacgatcg cccagccttt  12060
cactcttctt gttcgtgggt tacgagattg tgacagcggt ttcggccgaa ttcggccggg gcgacgcgcc  12120
ggctgagcga tcgcattcga atatcgctgc aaggcagccg aacctggcgc gagctcgcgt  12180
cttgcgget gctcaccaaac gtgccgattt ccggcaacga caacacctcg acgttgttcg  12240
cctcgctac cttccgggc aatcgccg tgagctttgt gctgggtgcc ggccttcagc  12300
gggcaccag caaacacgcag ctatacagtt acacagtccaa acgcatcaat ctctcgacgt  12360
cgctttcgct ctgacaaggg cctataatcat gcatatcaag aatcgcttcg tgaatatctc  12420
gacgttggcc atcgcgcgcg cgctgcccac gccggcggcg gcccgcgg gcgagatcc ccacgcggtc 12480
cgtgcccgcc ccggccgccc cggccctgc aacgccggcg gcaacacgc agaaccaggc  12540
gccgtcgacg cccgcagcgg caaccccggc gcagaccgcc gcagcccgca gcaaccgttg ccctgcagc   12600
```

FIG. 6 Sequence of insert contained in plasmid pS8 (SEQ ID NO: 1), continued.

```
aaccgcaccc gcaggttaca aaatcggcgt ggacgacgtg atcgaggccg acgtgctcgg 12660
ccagaccgac ttcaagacgc gcgccgtgt gcaggcggac gcacggtga cctgccta 12720
tctgggcgcc gtgcaggtca agggcgagac cgcgacctcg ctcgccgaaa agctggccgg 12780
gctgctgcgc gccggcggt attatgccaa gccgatcgtc agcgtcgaaa tcgtcggttt 12840
cgtcagcaac tatgtgacgg tgctgggcca ggtgaacagt tccggcctgc agccggtcga 12900
ccgggctat cacgttccg agatcatcgc ccgtgccggc cgctgcgcgc ccgaagcggc 12960
cgattcgtc gttctcaccc gcgccgatgg ctccagcgcc aagctggact acaagaagct 13020
cgcccaaggt ggcccaatg acgatccgat ggtgacgccc ggggacaagg tctttgtccc 13080
ggaagtcgag cattcctaca tttatgtca aattaacgcg cctgggtat acgcgattcg 13140
atcggacatg acgctccgtc gcgcgtggc ccagggcggt gggctttgccc ccgcaggctc 13200
cgtcaagcgt gtgaaggtca cgggacacga caatgaactc aagttgaagc tggacgatcc 13260
gattctccca ggcgacacga tcgtcatcgg cgaacgattg ttctgatctt ggcaacgatg 13320
gagcggaacg aggcccacca gtgaatatca ttcagtctct ccgcattctg tgggtgcgcc 13380
gatggatcat cctcccggcg tttctcgttt gcgttaccac tgccaccatt gtggtccagt 13440
ttctgcccga acgctacaag gccactacgc gggtggtgct cgacacgttt aagcccgatc 13500
ccgtcaccgg acaggtgatg agctcgcagt tcatgcgcgc ctatgtcgag actcagacc 13560
agctgatcga ggactatgcg accgccggtc gcgtggtcga cgaactgggc tggtgaatg 13620
atccggcgaa catctccgcg ttcaacaact cgtccgcggc tgccacggc gacatccgcc 13680
gctggctcgc caagcagatc atcgacaata ccaaggccga tgtgatggag gggagcaaca 13740
tcctcgaaat cacctattcg gacgctcgcc ccgagcgcgc ccgaggcgcg gccaacctga 13800
tccgcacctc gtccctcgcc cagtcgctcg cgccaagcg ccgccgattc ccaggccgcg accaagtcgg 13860
ccgactggta cgccagcag gccgaagctg cccggcgattc gctcgctgcg gcggtccagg 13920
cccgcaccga ttcgtgaag aagacgggca tcgtgctgac cgaaaccggc gcccacgcc gcgacctgg 13980
aaaccagaa gctccagcag atcgaggggc agacgacgac cgccacgc cggttgcca 14040
tggcccccag cggcatggc ccggcgcaga tgcagctgc ccagatcgcc cagcagatcc 14100
agcaggcagc gaccagccta ggtccgaacc acccaacttt ccaggccttg cagcggcagc 14160
gcgaagtgtt cgccaaggca gcggcggcgg acgcaggca aacgcgcgca ggcgaacggc gtatccggtc 14220
cggcacgcgg ggccatcgaa agcagcgtt acgcagctgc acgccagcgc gcgcgggttt ctcggcaatc 14280
gtcaggatgt cgacaagctt acgcagctgc gtcgccgatc agcgtgacgt ctcgctgaag caggatcagt 14340
acatgaaggc ggcacagcgc gtcgccgc ccggcctgga agcaagcagc aacgatgtcg 14400
gcatgtcgac gctcagcgaa gcatcggcgc ctattaccc aagtgccgc 14460
tcatcatcgg tggtgcagcc ggcttcgcc tcgggctcgg tctgctggtc gcgctgttcg 14520
tcgagctgct cggccgcgc gtcgtcgagcc ccgagatct ggaagttgcg atcgatgac 14580
cggtgctggg cgtgatccag agccgcgcct cgcttgccgc ccgcttcgc cgcgcccaag 14640
aaaccctcgg cgaaggtgcc gacacgacg gagcttcagt aaactcagt acgcgatgac 14700
```

FIG. 6 Sequence of insert contained in plasmid pS8 (SEQ ID NO: 1), continued.

```
cagcgaaccg ctgcccgaag gcgatcgtcc gagcgccgtg ccgaccacgc cggatacgat 14760
cggcatgctc gaataccagc tcgtcctctc cgatccgacc gggatccgag cggaagcgat 14820
ccgcgcgcta cgcacgcgca tcatgaccca gcacctccgc gagggccggc gcgcgtcgcc 14880
gatctgcgcc gcctcggcgg gatccggctg cagcttcacc gccgtcaatc tggcgacggc 14940
gctggcgcag atcggcgtta agactgcgct ggtcgatgcc aatctgcgcg atccagcat 15000
cggcgcagcc ttcggcctcg ccgccgacaa gcccggcctg gccgattatc tcgcctcggg 15060
cgatgtcgac ctcgcctcga tcatccatgc gaccccgcct gaccagtct cgatcatccc 15120
ggccgggcat gtcgagcaca gcccgcagga actgctcgcg tccgaacagt tccatgatct 15180
ggcgacgcag ctgctgccgc agttcgacat cacgatcttc gacaccacgg cgtccaacac 15240
ctgccgcgac gcgcagcgtg tcgcggctat cgccggctat gcgatcatcg tggcgcgcaa 15300
ggatgcgagc tacatccgcg acgtgaaccac gctcagccgc acgctgcgtg cagaccgcac 15360
caacgtcatc ggctgcgtac tgaacggcta ttgatttgga ccatatggca gcgaccgcga 15420
tgacgcggca gcaggagagg aagggcggtg gctattggct ggcgttgcc ggtcttgccg 15480
cgctaaccat cccgacttc atcacccctgg gtcgcgaggt ttggagtgcg gaaggcggcg 15540
tgcaggggtcc gatcgtgctc gccacgggcg cctggatgct ggcccgccag tgctcgacga 15600
tcgaggcgct acgcgccccc ggcagcgtgc tgctcggcgc gctgttcctg ctggcgacgc 15660
ttgcctttcta caccgttgga cggtgttcg acttcatcag tgtcgaaacc ttcggactgg 15720
tcgcgaccta tctggtcgtc gcctatctct attcggtgc cagggtgctc cgtgccgcct 15780
ggttcccggt gctgtgctg ttcttcctgg tgccgccgcc cggctgggcc gtcgaccgca 15840
tcaccgcacc gctcaaggag ttcgtctcct atgcggcaac tgttcgtcgg ggcctgctt cctgggtgg 15900
attatccgat cctgccgcag ggcgtgacac tgttcgtcgg ccagctggt cgtcgtgacg ctgctctaca 15960
aagatgcctg ttcgggtctg cgctcgcgt cgagcggcgtt catcgcagcg ctggtgatcc 16020
tctacatcaa gaacaagccg tcctggcgga tcatcatccc gtactgatc acctatcatc 16080
cggtggcagt ggtgaccaac gtcctgcgga agcttcctcc acgtctccac cggcatggtg atgttcgtgg 16200
tgggcgacga ggcgggccag ttgcatcttc gcgatcgact gggtgtcga gcaacttctt ctcctgcgtc 16260
tcgccctgct tgttcaaccg tgttcaaccg tgttcaaccg gtgacgtga tgcggggcag ggtgatcggcg 16320
ggagcatca tgttcaaccg gtgtgacctg ctgatcggcg gtgacgtgcg caggctgctt cgccgccgct 16380
ggcgcctcgc tcggcctgaa gccgcaccgg cggatgaccc tgctgggcg cacccaagctc 16440
gacacgctga tgcccaaggc gcgaaggcag attcggcgca tggaaggcag aggatacggg ttcgctgatc 16500
gcgccgggcgc cgaagtggcag cctgggagac aagctctaca accaggtggt cacccagacc 16560
ttctcccgcg cggaagtggt gccaccacg ccaagtgatg ctgctgatcg cctatggcaa cgcccagaco 16620
gatctactgc agctgcacgg gccgaaata tgctacccgt tctctgggctt caccgtggtg tcgcgcgctg 16680
gaaagccatg agcagaccat cccggtgacg ccgcagcag cgatcccgg tcgcgcgt cgggcgaatat 16740
acgccacca acttcaaccg caccgagcag atcctctact ggaacccgcgt agagccaggt ccagggctgg 16800
```

FIG. 6 Sequence of insert contained in plasmid pS8 (SEQ ID NO: 1), continued.

```
atcgtcgacg gtgtgctggt gcgcatctcg acggtgacgc ccgaggcgga agatggctg  16860
agcgccaatc tcgattcgc gcgagctg gtgaagacgc tcgacccgcg cgtgctgcgc  16920
ccgctgctcg ggaacgggct cacacggcag ctcggtcacc aggtctgaac cggtgccgcg  16980
cacgggcgcg cccggcaaac aaaaaggag cggcgcgggc cgccgccgct cctctcctt  17040
ctcatgcggc gccctgccct caccgctcgt gcagcgcgtc actcccgtc tcgagcacgg  17100
gcccaccag atagctgaac agggttcgct tgccggtgac gatgtccgg ctcgcgagca  17160
tccccggccg cagcggcacc tgtgcgccat gggccagcac ataccggcgc gccagcgcga  17220
tccgcgcctt gtagaccggc ggctggttct ccttcatctg caccgcctcg gggctgatgc  17280
cgccaccgt gccgggaatc atgccgtagc gggtatagg aaaggcctgc agcttcacct  17340
ttaccggcat gccgatgtgg acgaagccga tgtcgtgtt gtgaccatc acctcggcct  17400
cgagccgggc attgtcggga accaggctga ggagcggctt ggcccctcc accacgccgc  17460
cttcggtgtg gacctgcagc tgcgagacgg taccgctcac cggcgcgcgc agttcgcgga  17520
acgagctgcg cagattcgcc ttggcgacgt cctcgccgcg ggcacgcacc tcgtcctgcg  17580
ccttgaccag atcctgcagc acctgcgcc gccctcctc gcgctcttg gccgacaggc  17640
tggagacgct cagcgactgc tggccgagtt tggcgagcgt agcgcgcgcc gcgtcaggt  17700
cctgccgctc ggcgatcagc tggcgacgca tctccacgac gcgcagcttc gagacatagc  17760
ccttggcggc catcgtctcg ttcgcggcga tctgctgttc gagcagcggc agcgactgtt  17820
cgagcttccg cacctgtgcc tgcgcctcgg ccggctcgg ccggccga gacgggca ccgcgatcgg  17880
agcggccgcc ggccagcgcc gcctcgatct ggccagcgcc ggcgcgggcg agccgcgat  17940
gcgtcgccac ttcgcccggg ctggccccgg caggcgcgag gaagcggaag ccctgccgt  18000
ccagcggtc gatgatcgcc tggttgcgtg cggcgtcgag ctgggcgctg agcagcgcca  18060
cctcgcctg tgccgcctcc gccgacgaca cggtcgggtc gagcgtgatc agcaacctgg  18120
ccttggcgac cttctgccc tcgcccacca ggatgcggcg gacgatcccc gattcgggcg  18180
actggacgat cttggtctcg ccgatcggcg cgatccgcc ctgcgtcggc gcgacgactt  18240
cgaccttgcc gatcgccagc caggcggcgg tgatcgccag cccggccagc atcaccttgg  18300
cggtaagccg cgcggttgggc gaaaccggcc gctcgatgat ctccagcgcg gcaggcagga  18360
aggcggtgtc ataagcgtcg acgcgggcag gcagcacggt atcgcgcatg cggcgcgacg  18420
ggccgccgcg gcgcatcgga acaacggcgt tcatgcggca atctcccat agccgccctg  18480
gcgcggtgc agtcggcat agcgcgccgc caggcgcaac aattcgtcgt gtcggccgct  18540
ctcgacgatg cggccctgtt cgagccgtgat gatccggtcg ggcgagatg gacctgcgca  18600
cagctcctcg atcaccacga gcgtgcggcc ggtcgttcg ggtcgttcg tggccgcgg  18660
attgccgacg agcgcgggg cgatggcat tgtcatgcc tgcggcggc cgcaggatga agagttgac  18720
gcggcatcg acgatctcgg acgatctcgg tgtcatgcc gcgggctgg ccggcccgg cgcaggcgcg  18780
gccggccagc gtcgccgccg cgacacatt ctcgaacggc atggcgggt tggagagcgc  18840
                                                                18900
```

FIG. 6 Sequence of insert contained in plasmid pS8 (SEQ ID NO: 1), continued.

```
gatgtctcg cggatcgagc ggctgaacag cagattctcc tgcagcacga cgccgatctg   18960
gcgacgcagc caggcgggat cgagctgcgc cacgtcgacc tcgtcgacca gcacgcggcc   19020
gagattcggc aggttgagcc gctggagcag cttggccagc gtcgacttgc ccgagcccga   19080
cgaaccgacg atgccgagcg aggtgccccgc cggaatgtcg agcgtgatgt cgctcagcac   19140
cggcggctgg tcctcggcat agccgaagct gacattctcg aagcgaatcg caccgcgcag   19200
caccggcagc gtcgccgccg aggccggggcg cggttccacc ggatggttga gcacgtcgcc   19260
cagccgtccg accgagatgc gcacctgctg gaaatcctgc cacagctgcg ccatgcggat   19320
caccggcccg gacacgcgct gggcgaacat gttgaacgcc accagcgcgc ctacgctcat   19380
cgccgccgcg atcaccgcct tggcgccgaa gaacaggatc gccgcgaagc tcagcttcga   19440
gatcagctcg atcgccttgc tgccggtgtt ggcggtattg atcagccgct gcgacgcggc   19500
ggtatgggcg gcgagctggc gctcccagcg atttcgccag tgcggctcga ccgcggttgc   19560
cttgatcgtg tggatgccgg agacgctctc gacgagcagc gcgttgctgg cggagctctt   19620
ctcgaacttg tcctccaccc gcgcgcggag cggcccgcgcg acgctgaacg atacgatcgc   19680
ataggcgatc agcgaccaga gcacgatgcc cgagagcatc ggcgagtaga acagcatcgc   19740
ggcgaggaac acgaaggtga acagcgggtc caccatcacc gtcagcgagg cgctggtaag   19800
gaattcgcgg atcgtctcga gctgccgggac gcgggtgacg gtgtcgccca cgcggcgctt   19860
ctcgaaatag gcgagcggca gagcggcccga ccgcagcgg gtgttggaaa agcggggcac ccagctcgac   19920
gtcgatcttc tgcgtcgtct cggtgaacag gcgggtgcgg gagcacgctc agcgtgctca tgctgttgtg   19980
ccacacgaa accgccagga aggcgaaggc gagcgaaggc gagcacgctc agcgtgctca tgctgttgtg   20040
gatcagcacc ttgtcgatca cgcttctgaa caacagcggc gcggcgaggc cgagcaggtt   20100
gagcgcgagg gtgatgccga gcacctcgag gaacagcgtg cgatagcgcc ggaactgcgc   20160
ggtgaaccag gagaggccga accgcagcgg ccgtcccgcc accgcgcggg tgttgagcag   20220
caccagcgcg ccggaccaga tcgccgtccag cgcgtcccgg tcgacctgtt ccggggcatg   20280
gcccggggcgc tggatgatca cgccatgttc ggtcaggccg ccgatcacga accagccttc   20340
gggccgtcg gcgatcgcgg gcagcggctg gcgggcgagt ccgccgcgcg gcacctcgac   20400
ggccttggcg gcaccgccct gctggcgctt ggccaggagg atcaggtcgt cggcgcttgc   20460
cgcctcggca tggccaagcg cgtgccagcg ctgttcgggc gtattcgggc gtattgtgcgc   20520
gccgagcagc agcgacaaag ccaccagtcc ggattcgcgc agctccgcct cgcgctccgc   20580
cgcccatgg gccgcgagcg cgctctcgcag ggtgcctgc attcgtcgc gtgtcatttc   20640
cggaactctg cctccatggc gatactgaga gcgccatgat gaagaaggct ggtaaagact   20700
cacttaatcc tagcttttct ggtattacc cgtagctgcc gacccgattt gggacaggcc   20760
tggcttagca ggtccttaaa ctcgaccgac tataccgcga cgcgaggag gggaggatt   20820
ggcgccat cgcgcggcga aacgcgggtg cgtcgcaaca tttcgccga gtcgatccgt   20880
cgcgaatgct gcaccgcga acgcaatgac ggccgccacg caatccggct tgatcccggg   20940
cggcggatcg cgataagccg cgccacggtc gccaaaactc gccaaaataa ccgacaaaaac  21000
```

FIG. 6  Sequence of insert contained in plasmid pS8 (SEQ ID NO: 1), continued.

```
cacggcatat ggctggatat tgcagcgttt gccctgcgtt tccgtcgttc aaccgccctt    21060
cgaatcaggc aggccaagcg tgaccatgat tgatcttcct cttggaacgg cacactttgg    21120
tcgacacgga gacttccggt cgggcaattg tccgttata gtgcaatgca acaggccgaa    21180
tcggcgctg tcggcgtgca cattccggtg aggagcccg atgaggcaat gaacgtttc     21240
gaagcacagc gcgcctttga ggagcaactt cgggcgcatt cccggttac gccatctgcc    21300
gctccgtgt ggcgtcgctc gacgctgcgg atgtcctct ataccgagtt gctgctgctg    21360
gacagtctct cgatcctggc cggattccac gtcgcggcgg gcacgcgcga cggcaactgg    21420
ctgtcgctgg cgggcatcaa cgtcgggtc ttcctgctgc cgatcgtct cggcaccgcg    21480
ctcgcaagcg gcacctactc gctgaactgc ctgctctacc cggtcagcgg cgtgaagagc    21540
atcttctcgg cattcttctt ctcgatcttc gtcgtcctgc tcggcagcta cctgctgacg    21600
gccgagctgc cgctgtcccg cgtgcagctg gcggagggcg cgatcctctc gctggtcctc    21660
ctgatggtgg gccgctgat gttccgccgc cacgtccgcg cggttaccgg cggcaggctg    21720
ctcgacgaac tggtcatcat cgacggcgtc tcctcgccg tcgcgggcaa tgcggtcgcg    21780
ctcgacgcgc ggatcatcaa ccgtcgcg gtgatcgtcg cctgcaccaa gctgcatcgc    21840
ctgggcacca ccgtgatcgg gtcgacccgg caagggcatg aacatcaagg gcagagatcct cgtccccccag    21900
gggtctggg cgctgctgct tgggcgtgat cggcgtggac gcctttgacg gcctttgacg gctggtcgtc    21960
ttcaatgcgc gcgtcaacat gcccaaccgc gctgctgcg gaaggatac gctggtcgtc    22020
tcgcaggcc cgctgctgc ccgtgctgc ctgatgatcc ctgatgatcc tctcgcgatc    22080
accgtaccgg ccgtctcgcg ccgtgctgcc tgtgcgat cctgatcaag    22140
ctggagagcc cgggccggt gttgttcgcg caggatcgcg tggcgcggg caaccggctg    22200
ttcaagatca tgaagttccg ctcgatgcgc gtaacgctgt gcgacgcgaa cggcaacgtc    22260
tcggccagcc gcgacgacga tcgcatcacc aaggtcggcc gcttcatccg caagaccagc    22320
atcgacgaac tgccgcagct gctgaacgtg ctgcgccgcg acatgacgcg cgtccgcccg    22380
cggccgcatg cgctgggctc gcgcgccgcc gatcacctgt tctggaaat cgacgagcgc    22440
tactggcacc gccacacgct caagccggc atgaccggtc tggccaggt gcgcggtttc    22500
cgcgggggcga ccgatcgcg cgtcgatctg accaaccggc tccaggcaga catggaatat    22560
atcgacggat gggatatctg gcgatatctg acgatccgt tcaagacgct gcgggtgatc    22620
gtgcattcga acgcattctg atccgcgcac gacgctgggc cgcagcctcg atccgcaaat    22680
ggattgacag tccgcccgct tccgttttct cgtttgattt tcgttcggc cggtccgcgc    22740
catggggat tactgaatga aggcatcat ccttgcgggg ggcagcggga cgcgcctgta    22800
ccccgcaacg ctatcgatct cgaagcagct gcttccgtc tatgacaagc cgatgatctt    22860
ctatccgctg tcggtcgta tgctcaccgg catccgggac atcctgatta tctccaccc     22920
gcgcgactgg gagcagccct ccccaacgg gctgccgaa gcgttcatca tcggcgcgga    22980
cagctatgcc gagcagccct ccccaacgg gctgccgaa gcgttcatca tcggcgcgga    23040
tttcgtcggc aacgatccca gcgcgtgat cctgggcgac aacatctatc acggcgaaaa    23100
```

FIG. 6    Sequence of insert contained in plasmid pS8 (SEQ ID NO: 1), continued.

```
gatgggcgag cgctgccagg cagccgcagc gcaggcagcg cagggcggtg caaacgtctt 23160
cgcctatcat gtcgacgacc ccgagcgcta cggcgtggtc cgcttcgacc cggagacggg 23220
cgtcgccacc agcgtcgagg aaaagcccgg cgagcccaag tccaactggg cgatcaccgg 23280
cctgtatttc tacgacaagg acgtggtcga catcgccaag tcgatccagc cctcggcgcg 23340
cggcgaactc gagatcaccg acgtcaaccg cgttacaatg gagcgcggcg acctgcacat 23400
cacgcgcctc ggccggggct atgcctggct cgacaccggc acgcatgaca gctgcacga 23460
agccggctcg ttcgttcgca cgctcgagca tcggacgggc gtgaagatcg cctgcccgga 23520
ggaaatcgcc ttcgaaagcg gctggctcgg cgccgaagac ctgctcaagc gcgcgccgg 23580
cctcggcaag accggctatg ccgcctatct ccgcaaggtt cgcgacccag catgacccag 23640
gtccatcatc acgaactgtc cggcgtcatc gagttcacgc cgcccaaata tggcgaccac 23700
ggcgcttct tctccgaagt gttcaagcag tcggtctcg atgccgaagg cgtcgaggca 23760
cgctggtgc aggacaatca gagcttcctg ggggccccg gcacgatccg cggcctgcat 23820
ctccaggcgc gcccttcgc ccaggccaag ctggtccgcg tgttgcggg cgcgatcttc 23880
gacgtgcgg tcgacatccg tcgcggctcg gcacactatg gcaaatgggt cggcgtcgag 23940
cctcggccg agaagtggaa ccagtgctg gtcccggcg gctatgcgca cggcttcatg 24000
acgtcgttc cggattgcga gatcctctac aaggtcagcg ccaaatattc gaaggattcg 24060
gagatggcga tccgttggga cgatccgat ctcgccatcg cctggccgga catggcgtc 24120
gagccggtcc tctccgaaaa ggacgcggtc gccacgccct tgccgaatt caacaccccc 24180
ttcctctatc aggggctgag catgcagcag accttcctcg tcaccggcgg cgccggcttc 24240
atcggctcgg cggtggtgcg ccacctcgtc cgccagggcg cgcggtcat caattccgac 24300
aagctcaccct atgccggaa cccggcctcg ctgactgcga tcgagaacgc gcccaactat 24360
cgcttcgtcc atgccgacat cgccgacacc gcgacgatcc taccgctgct gcgcgaggag 24420
caggtcgatg tggtgatgca ctcgtcggg ggacgcggtc ctgtcgaact gatcgacggc 24480
cctgcgagt tcatcgagac cagtccgttg accatcctca acgcgctcga cgatcacgcc 24540
caatattggc gcgagctgga gggcgagaaa cgcgacgcgt tccgcttcca ccacatcctcc 24600
accgacgagc tgttcggcga cctgccgttc gacagcggca tcttcaccga agagacgcc 24660
tatgatcccc cctcgcccta ttcggcgtcg aaggggcga gcgaccatct ggtgcgcgcc 24720
tggggccaca cctatggcct gccggtggtg ctgtcgaact gtcgaacaa ttacgggccg 24780
ttccacttcc cgagaagct gatccgcttg accatcctca acgcgctcga cgatcacgcc 24840
ctgccggtct acggcaaggg cgagactggc cgcgactggc tgtatgtcga cgatcacgcc 24900
aaggcgctgg cgaccatcgc cggggtggtc gagacgatct gcgacctgcc cgacaagcgc 24960
cgcaacgagc ggaccaacct gcaggtggtc gaactgatca cgcttgtcac cgaccagcgc 25020
attccgctgg ccgacggtcg gccgctacgc caagtcgcgc cttcgtcac cgatcgcccc 25080
ggccatgtcc gccgtacgc gatcgacgcg accaagtcg agaccgagct gggctggaag 25140
gctgaggaga atttcgacac cggcatcgcc cggcatcgg actggtatct ggcgaacgag 25200
```

FIG. 6    Sequence of insert contained in plasmid pS8 (SEQ ID NO: 1), continued.

```
tggtggtggg gcccgatccg ctccggcaaa tatgccggcg agcggctggg gcagaccgcc   25260
tgatgcgtat cctcgtcacc gggcatgacg gccagtcgc ccagtcgctg gccgagcagg   25320
cggtgggcca cgagctggtc ttcaccacct accccgaatt cgatctctcc aagccggaga   25380
cgatcgaggc cggtgtggcg cgggtgcacc cggacctgat cgtctccgcc gccgcctaca   25440
cgcggtcga caaggcggaa agcgaaccg agctggcgat ggcgatcaaac ggcgacggtc   25500
ccggcgtgct ggcgcgcgcg ggcgcgaaga ggcgcgcgcc gatcatccac ctgtcgaccg   25560
attatgtgtt cgacggcagt ctcgaccgcc cttggcggcga ggacgatccc accggcccgc   25620
tcgggtcta tggcgcgacc aagctggccg gcgagcaggc ggtgcaggcc tcgggtgcca   25680
ccaacgccgt gatccggctg gcctgggtct acagcccgtt cggcaacaat ttcgtcaaga   25740
cgatgctccg cctcgccgag acgcgcgacg cgctgaacgt cgtggaggac cagtggggct   25800
gcccagttc ggcgctggac atcgcgaccg cgatcctgac cggcgagacc cactggcagc   25860
aggacggcgc gacgagcggc ctctaccatt tcgccggcac cggcgagacc aactgggccg   25920
acttcgcatc gacgatcttc gccgagagcg ccaagcgcgg tggcccctcg gccaccgtca   25980
ccggcattcc cagctcgggc tatccggactc cggccacgcg cccggccaat tcgcggctgg   26040
actgcaccg cttcgcggag accttcgct acgggcgcc tgcctggcag gattcgctga   26100
acgtgtact ggatcgcctg ctcggctgat gcaatgcctc cgaaaacggg gggcctcagc gccccccgcc   26160
atgctcccgt tcgcgcgccg gcaatgcctc tagcaccgcg cgctttccct taggactcag   26220
ctcgtccag ccggcgattt ccttgggcca ccgccagcac cccaaggcaca gccggatc    26278
```

FIG. 7   Sequence of insert contained in plasmid pX6 (SEQ ID NO: 54).

```
gctgcaggtc gacggatcgc cagcggcctc accatcaaact atgcaccgga tgcatcggtg      60
ggccaccgc ccggcccga ctgtcggcc ctgctggtga agacgcggcg catccagcgc         120
gaactctatc tgttcaacat cgagcggccg aaggcaggc tgcgctggct ggtccgttcc       180
gtggcgcaac cggcgatgat cccacaggac gtggccaaga tcctgcgcac accgggtacc     240
aagggcgcg gcctcgctgc ggtcaccacg ctggtccggc tcggctgtg gcggccggc         300
gccggcttgt tgcagttgct cggccgcgac atctgatcga ccggcgatcg gccgacgagc    360
gcgtcgccgg ccgatcgcat tgcatcagac ggtggccagc ggtcttcca ggtgcgcgct     420
gtcgagcgc aggcggccga tcatcagcca cagatagacc ggcagcgtat cgtcggtgaa      480
gcggaagcgg caatcgccgt cctgcgtttc ggattcgagg ccgagttgac cggtgagctc    540
gccagctcc tgctcgacct gcgccgccgt gatgtgcgcg cccggcagca gatccaccac      600
ggctttgccg ctgaaccagc catccgccga gcgcgaggcc tcgtcgatc ccggcgacgag   660
tggatcgtag cggccgccga cgaacttgcg cctggtcgag catctcgatc accgcgcgcg gcggcatgcg  720
gccctgatc tcaaggatcg cctggtccag cgcacgacgc agatgcccgg cgtcgaccgt    780
gaggcggccc tggtccaggg cttccagcgg gtggatcat gtgagtcagg cacagcagcc gcgcgaaata    840
gggcgaccc agcgcgagca ggtggatcat ctgcacctcc gattcctcca gcggggcat     900
cgaggcggtt tcgccgagcg cgatcagctc cggcgcataa ccgatcagct cctgcaggtt    960
cggcaggccg atgacgttgc ggcggatcga cggcgcgcgga gcgcgccgaa ggttcttgat   1020
cgaggcgacg cccgcgatca ccagctggac atcgctgacg cggtccgaca cgatcatatt cgtcgaggat 1080
cagcttggcg acctgctgac ggaagcgga atcgctgacg gcacaggtcg gcagttcgc cgggccgaa  1140
gatcagcacg cgtgtgcccg tgatgtcggc gcacaggtcg gcagttcgc cgggccgaa         1200
gctgcccgtc ggcaggcggt cggccaagtt cggccaggcc gtcttccagc acggcgcgga agacatcgct  1260
cgccacgccg cgatggaaca gcagcggcca ggtcgcata gctgacgata tagctggatt cgcggcgac  1320
gaaattcgcg ttcgcaccgc aggtcgcaca gcgaggtctt gccgatgcg cgctcgccat agagcacgac  1380
atcggtcagc acgtggagca cggctggcac tcgaggagat taggcgcgcc agcacgccga ggcgccggc   1440
atggctcgc tggctctcga ccggctgggt gggtgtgaag aaggtcgcca gcgcgaaccg      1500
gaagctcgac cgatcggcca ccggtcgcg gctcgtcgcg gcggcgatcc agcgccggt       1560
ggcgcgtg atctcgggc cgggaaat ccggcgacc acggccgcta tggcatcgc gatgcggcac 1620
ggcacggaag gtggaacga ggtcagcgga aacctacagc ttcttcaggt tctttcgac gatgcggcac  1680
cactgtcgca ctccagcggg aatagcgcgg aacctacagc cactccaaca cctcttaaat tcgtgcgca   1740
ccaaagaat ctccagcgc cggcgcaccc tggttcgcgc ccctgcgc cccctcctaa cgaaccacg      1800
tcggcaccga cggcgcaccc tggttcgcgc cttgaagaac tcgtacggt tgatcaccaa ggcgatgtac    1860
ccttgcctgg cctatcggcg cttgaagaac caaaattgca aagacgtgat aattctcatt gccacagaa   1920
gccaaggacca gagcgatcgt cccagcccg tgcggcgcc caaattgca aagacgtgat aattctcatt gccacagaa   1980
ttggcgacgg cgcaaccgac tgcgggcgc caggaatata acgatcaggc cggcaaatat cggcactggtg    2040
gaatcggctt gggaccgttg caggaatata acgatcaggc cggcaaatat cggcactggtg           2100
```

FIG. 7    Sequence of insert contained in plasmid pX6 (SEQ ID NO: 54), continued.

```
acccaatcat agggcgtctg catgcatgtc ctttctattc gacaccggaa tcgaaccatt 2160
tccggcgacg ctattgcacg cactagtcagt gcgcgcggcc gctcgctagg tagcgccgca 2220
ccggataaac cgacgttaag atggcgcggc tcgatcgaaa tggagtcaaa cgggcttgcc 2280
cggccgaccg aagcatggcg ccatggcca tgcaccgtat tgtgaccacg caaaccgcga 2340
gggtcattcg atgcggttgc ttgtacagga ggccattgat aatgaagccg agacccgggg 2400
gaacctttat gcaagtaaat ttcaatcgac aggctcgcaa gctcggtgcc ggcaatgcgc 2460
tcgcgcggg ggggcccgtg cttgcgctgc ttgcgaccgc ggcatggaca caacctgcgc 2520
tggcgagcg acaggcattt gagtcccgcc cctccggtag cgagcgacag gtcgatattc 2580
gcgcgacggg gtcgctggaa tatgacgaca acgtcgtgct gaacgaccag cggatcacgg 2640
acggcgcgcg tggcgatgtg atcgcatcgc ccgggctgga cgtgaccccta gtctctgccc 2700
gcgccaccgg gcagtcctac ctcaccggca atgtcggata tcgcttttac aagcgatata 2760
ccaactttaa ccggcgagcag atcctcgctca ccggcggcgc agatcagcgg ttcgctcct 2820
gcgtcgtgca cggggaagtc ggctatcagc gccacctcac cgacctgtcc agcatcttga 2880
tccaggacac cacgcctgcg ctcaacaaca cgaagaggc cggcagtac accgcggata 2940
tcggctgcgg cgcactgac ggcctgcggc ctgccgtttc ctacaccgc aacgaagtgc 3000
gcaacagcct tgccgagcgc cgatacgcgg actcgaatac caacacctt accgcacagc 3060
ttggcctgac ttccgctgcc ctggggaccg tggcggtatt tgggcgtatg tccgacagca 3120
gctatgtcca tcgcgtcctt cccggcatta cccggccaga cgggatgaag agctacgcgg 3180
ccggcgtcca gctcgagcgc tggtggcca acgactcca tttcaacggc tcggtgaatt 3240
acaccgaggt tgaccaaaag ctcgcatcca ccaaaggatt caagggcgta ggatttaacg 3300
ttttcggcga ttatgctggt gatcagtaca gctccaatt gctggcttca cgatcgcccc 3360
agccttcact tcttctgttc gtgggttacg agattgtgac agcggtttcg gcgaatgcga 3420
cgcgccgggct gagcgatcgc attcagatat cgctgcaagg cagccgaacc tgcgcgagc 3480
tccgtcttc gggctgctc accaacgtgc cgattccgg caacgacaac acctcgacgt 3540
tgttcggcctc cgctacctc cggcgaatc gccggctgag ctttgtctg ggtgccggcc 3600
ttcagcggg caccagcaaac acgcagctat acagttacag ctccaaacgc atcaatctct 3660
cgactcgct ttcgctctga caaggccgt aatcatgcat atcaagaatc gcttcgtgaa 3720
tatctcgacg ttggccatcg cgcccgcgt ggccacgccg gcctgcaacg gcggcggcgc agatcccac 3780
gccggtccgtg cccggccgg cagcggcaac gctggcaacg cgccggcgc ccgcgcgcaa acagcagaa 3840
ccggcagccg tcgacgccg cagcggcaaac ccggcgcag accgcgtgga ccgttgcccc 3900
tgcagcaacc gcaccgcag gttacaaaat ggcgtggac gacgtgatcg aggccgacgt 3960
gctcggccag accgacttca agacgcgcgc cggtcaaggg cgagacccgc acctcgctcg ccgaaaagt 4020
gccctatctg ggcgccgtgc aggtcaaggg cgagacccgg acctcgctcg ccgaaaagt 4080
ggccggctg ctgcgccgg gcgctatta tgacggtgct aacagtccg aacagttccg gcctgcagcc 4200
cggtttcgtc agcaactatg tgacggtgct aacagtccg aacagttccg gcctgcagcc 4200
```

FIG. 7 Sequence of insert contained in plasmid pX6 (SEQ ID NO: 54), continued.

```
ggtcgaccgc ggctatcacg ttccgagat catcgcccgt gccggcggcc tgcgcccga    4260
agcggccgat ttcgtcgttc tcaccgcgc cgatggctcc agcgccaagc tggactacaa   4320
gaagctcgcc caaggtggcc ccaatgacga tccgatggtg acgcccggg acaaggtctt   4380
tgtcccggaa gtcgagcatt tctacattta tggtcaaatt aacgcgcctg gcgtatacgc   4440
gattccgatcg gacatgacgc tccgtcgcgc gctggcccag ggcggtgggc ttgcccccgc   4500
aggctccgtc aagcgtgtga agtcacgcg ggatggcaat gaactcaagt tgaagctgga   4560
cgatccgatt ctcccaggcg acacgatcgt catcggcgaa cgattgtcct gatcttggca   4620
cgatggcag cggacgaggc ccaccagtga atatcattca gttcttccgc atctgtggg    4680
tgcgccgatg gatcatcctc cggcgtttc tcgtttgcgt taccactgcc accattgtgg   4740
tccagtttct gcccgaacgc tacaaggcca ctacgcggt ggtgctcgac acgtttaagc   4800
ccgatccgt caccgacag gtgatgagct cgcagttcat gcgcgcctat gtcgagactc   4860
agaccagcgt gatcgaggac tatcgacccg ccggtcgcgt ggtcgacgaa ctgggctggg   4920
tgaatgatcc ggcgaacatc tccgcgttca acaactcgtc cgcggtgcc acggcgaca    4980
tccgccgctg gctcgccaag cagatcatcg acaataccaa ggccgatgtg atggaggga   5040
gcaacatcct cgaaatcacc tattcggaca gctcgcccga gcgcgcgaa cgcatcgcca   5100
acctgatccg cacctcgttc ctcgcccagt cgctcgcgc caagcgccag gccgcgacca   5160
agtcggccga ctggtacgcc cagcaggccg aagctgcccg cgattcgctc gctgcggcgg   5220
tccagcgcg caccgattc gtgaagaaga ccggcatcgt gctgaccgaa accgcccgg    5280
acctggaaac ccagaagctc cagcagatcg agggcagca gtcgacccgc accccccgg    5340
ttgccatggc cccagcggc atgggcggcg gcctagttc cgaaccaccc aactttccag gcttgcagc   5400
agatccagca ggcagcgacc agctaggtc cggaccaccc aactttccag gcttgcagc   5460
ggcagcgcga agtgttcgcc aaggcagcgg cggggaacg cgcgcaggcg aacgcgtat   5520
cggtccggc acgcggggcc atcgaaagcg cagccaacgc ccagcgcgcg cgggttctcg   5580
gcaatcgtca ggatgtcgga aagcttacgc agctcgagcg tgacgtctcg ctgaagcagg   5640
atcagtacat gaaggcggca gtcgacgctc cgatctgcg gctggaagca agcagcaacg   5700
atgtcggcat gtcgacgcgc agcgaagcat cggcgccgga aacgcccccta acccaaag    5760
tgcgctcat catcggtggt gcagccggct ccgcgcggct tcgccctcgg gctcggcgc   5820
tgtcgtcga gctgctcggc ctcgggcgtg atccagagcc gcagccccga ggatcggaa gttcgatcg   5880
atgcaccggt gctgggcgtg atccagagcc gcgctcgct tgcccgccgc cttcgccgcg   5940
cccaagaaac cctcggcaga ggtgccgaca cgcacggagc tcagtaaaac tgatggaccc   6000
gatgaccagc gaaccgctgc ccgaaggcga tgtccgagc gccgtgccga ccacgccgga   6060
tacgatcggc atgtcgaat accagctcgt cctctccgat ccgaccggga tcgaggcgga   6120
agcgatccgc gcgctacgca cgcatcat gaccagcac ctccgcgagg gccggcgcgc   6180
gctcgcgatc tgcgccgct cggccggtgc cggtcgcagc ttcaccgccg tcaatctggc   6240
gacggcgctg gcgcagatcg gcgttaagac tgcgtggtc gatgccaatc tgcgcgatcc   6300
```

FIG. 7    Sequence of insert contained in plasmid pX6 (SEQ ID NO: 54), continued.

```
cagcatcggc gcagccttcg gcctcgccgc cgacaagccc ggcctggccg attatctcgc    6360
ctcggggcgat gtcgacctcg cctcgatcat ccatgcgacc cgcctcgacc agctctcgat   6420
catcccggcc gggcatgtcg agcacagccc gcaggaactg ctcgtccg aacagttcca     6480
tgatctggcg acgcagctgc tgcgcgagtt cgacatcacg atcttcgaca ccacggcgtc   6540
caacacctgc gccgacgcgc agcgtgtcgc gcatatcgcc ggctatgcga tcatcgtggc   6600
gcgcaaggat gcggagctaca tccgcgacgt gaacacgctc agcgcacgc tgcgtgcaga   6660
cgcaccaaac gtcatcggct gcgtactgaa cggctattga tttggaccat atggcagcga   6720
ccgcgatgac gcgcagcag gagaggaagg gcgtggcta ttggtggcc gttgccggtc      6780
ttgccgcgct aaccatcccg accttcatca cctgggtcg cgaggtttgg agtgcggaag    6840
gcgcgtgca gggtccgatc gtgctcgcca cgggcgcctg gcgtgctgct cgccagtgct    6900
cgacgatcga ggcgctacgc ctttacacc gttggacggg gcgtgctgct cgccagtgct   6960
cgacgcttgc gacctatctg gtcgtcgcct tgttcgactt catcagtgtc gaaaccttcg   7020
cgcctggtt ccggtcctg tggctgtttct atcctatt cggtcgcc gtgctccgtg        7080
accgcatcac cgcaccgctc aaggagttcg tctcctatgc gcgccccggc tggcccgtcg   7140
gggtggatta tccgatcctg cgccaggcg tgacactgtt cgtcaacggg ctgctttcct    7200
tcgtcgaaga tgcctgttcg tgcctgcgct cgctgtccag cgtcgtcgtc tatcagctgc   7260
tctacatcta catcaagaaac aagcgtccct gggctacgc cctgtcgtc gtgacgctgc    7320
tgatcccggt ggcagtggtg accaacgtcc tcggatcat cagcttcatc gcagcgctgg   7380
atcatctggg cgacgagcg gcgagagct tcttccacgt cctccaccgg agtgatgtgt    7440
tcgtggtcgc cctgctttgc atcttcgca caacggcgt tgactgggt ggtcgagcaa    7500
tgccgtggag cctgctgcgc ggaatcatgtt caaccgggt cggcgaccct gacctgctg   7560
gccgctggcg ccctcgctcgg cctgaagccg tgctacacca tggccagg tgacgttcgc   7620
aagctcgaca cgctgatgcc caaggcattc ggcgcatgga aggcagaga tggaccacc   7680
ctgatcgcgc cggcgcgcga aggcagcctg gaggacaag tctacaaca gtggtcacc    7740
cggcctttct ccgcgcgga cggtgcccaa gtgatgctgc tgatgcctta ggccaacgcc   7800
cagaccgatc tactgcagct gccacggca gaccatccg gaaatatgct acccgttctt   7860
gtggtgaaaa gccatgagca gaccaactt caaccgcacc gtgacgccgc agtgacgat    7920
gcgctgaccg ccagaacgg cgcagaacgg caatcagcag gagcagaacgc tctactggac   7980
gaatctgc cgcagaacgg caatcagcag atgctcgcgc ggctgaagag ccaggtccag    8040
ggctggatcg tgacggtgt gctggtgcgc atctcgacgg tgacgcccga gcggaagat   8100
ggctgagcg ccaatctcga tttcgcgcgc gagctggtga agacgctcga cccgcgcgtg    8160
ctgcgccgc tgctcgggaa cgggctcaca cgggctcaca gtcaccaggt ctgaaccggt    8220
gcgccacg cggcgcccc ggcaacaaaa aaggagcgg gcgggccgc gccgctcct        8280
ctccttctca tgcggcgccc tgccctcacc gctcgtgcag cgtcgtcag cccgtcacto    8340
                                                                     8400
```

FIG. 7    Sequence of insert contained in plasmid pX6 (SEQ ID NO: 54), continued.

```
gcacgggcc caccagatag ctgaacaggg ttcgcttgcc ggtgacgatg tccgcgctcg 8460
cgagcatccc cggccgcagc cggcacctgtg ggccatgggc cgccatgggc cagcacatac ccgcgcgcca 8520
gcgcgatccg cgccttgtag accggcggct ggttctccct catctgcacc cgcctcggggc 8580
tgatgcccgc caccgtgccg ggaatcatgc cgtagcgggt ataggggaag gcctgcagct 8640
tcacctttac cggcatgccg atgtggacga agccgatgtc gctgttgtcg accatcacct 8700
cggcctcgag ccgggcattg tcgggaacca ggctgaggag ggcttggcc cttccacca 8760
cgccgcttc ggtgtgggac tgcagctgcg agacggtacc gctcaccggc gcgcgcagtt 8820
cgcggaacga gctgcgcaga ttcgccttgg cgacgtcctc gccggggca cgcacctcgt 8880
cctgcgcctt gaccagatcc tgcagcacct gcgccgcgc gccctcgcgc gtcttggccg 8940
acaggctgga gacgctcagc gactgctggc cgagtttggc gagcgtagcg cgcgccgccg 9000
tcaggtcctg cgctcggccg atcagctggc gacgcatctc cacgacgcgc agcttcgaga 9060
catagcctt ggcggccatc gtctcgttcg cggcgatctg ctgttcgagc agcggcagcg 9120
actgttcgag cttccgcacc tgtgccgcac tgtgcctgcg cctcggccgc cagccgggcg 9180
gatcggagcg gccgcggcc agcgccggcc cgatctggcc cagccggcag cggccgaggc 9240
cgcgatcgt cgccacttcg cccgggctgg cggcggcagg cgcgaagccc cggaagcccc 9300
tgccgtccag cgcgtcgatg atcgcctgt tgcgtgggc gtcgagctgg ggctgagca 9360
gcgccaccctt cgcctgtgcc gcctccgccg acgacacggt cgggtcgagc gtgatcagca 9420
cctggcccct gggcgaccttc tgccccctcgc tgccccatcgc ccaccaggat gcggcgagca atccccgatt 9480
cgggcgactg gacgatcttg gtctcgggca toggcgcgat ccgccccctgc gtcggtcgca 9540
cgacttcgac cttgccgatc gccagccagg cgcggccagc cggcggtgat cgcagccccg gccagcatca 9600
ccttggcggt aagccgcgcg gtgggcgaaa cggcgcctc ccgcagcccc ccgccagcag 9660
gcaggaagc ggtgtcataa gcgtcgacgc ggccagcag cacggtatcg cgcatgcggg 9720
cgagcgggc gccgcggcgc atcggaacaa cggcagaga cgcaacaatt cgtcgtgtcg 9780
gccctgcgg cggtgcaggt cggcatagcg gccgcccagg gccgcaatct gcacgacccgc 9840
gccgctctcg acgatgcggc cctgttcgag cgtgatatc cgtcgcagc tgccaccgc 9900
gctcaggcga tgcgcgatca ccacgagcgt gccgcgcgcc gcgcgggtc gagatggcgc gcaggttgtt 9960
ctgatcagc tcctcgctct cgcatcgag gctcgtcgca gcttcgtcga acaccaggat 10020
gcggcggattg ccgacgagcg cgcgggcgat ggcgagccgc tggcgctggc cgccggaggag 10080
attgacccg cgctcgacga tctcggtgtc atagccgccgc ggctggggca ggatgaaatc 10140
atgcgcgcg gccagcgtcg gccgcgtgac gacattctcg aacgcatgg cggggttgga 10200
gagcgcgatg ttctcggaga tcgagcgggct gaacagcaga ttcttcctgca cggcgacgcc 10260
gatcggcga ccgcagcagg cgggatcgga ctgccgccacg ctgccccacg tgaccctcgt cgaccagcac 10320
gcggccgaga ttcggcaggt tgagccgctg gagcagcttg gccagcgtcg acttgcccga 10380
gcccgacgaa ccgacgatgc cgagcgaggt cgagcgaggtt gccccgcgga atgtcgagcg tgatgtcgct 10440
cagcaccggc ggctggtcct cggcatagcg cggcatagcc gaagctgaca ttctcgaagc gaatcgcacc 10500
```

FIG. 7 Sequence of insert contained in plasmid pX6 (SEQ ID NO: 54), continued.

```
gcgcagcacc ggcagcgtcg ccgccgagge cgggcgcggt tccaccggat gttgagcac     10560
gtcgcccage cgtcgaccg agatgcgcac ctgctggaaa tcctgccaca gctgcgccat    10620
gcggatcacc ggcccggaca cgcgctgggc gaacatgttg aacgccacca gcgcgcctac   10680
gctcatcgcg ccgccgatca cgcccttggc gccgaagaac aggatcgccg cgaagctcag   10740
cttcgagatc agctcgatcg cctggctgcc ggtgttggcg gtattgatca gccgctgcga   10800
cgcggggta tgggcggcga gctgcggcte tgccagttcg tgccagtgcg gctcgaccgc   10860
ggtcgccttg atcgtgtgga tgcccgagac gctctcgacg agcagcgcgt tgctgcgga   10920
gctcttctcg aacttgtcct ccaccccgcg gcggagcggc ccggcgacgc tgaacgatac   10980
gatcgcatag gcgatcagcg acacgagcac cgggtccacc agcatcggcg agtagaacag   11040
catcgcgggg aggaacacga agtgaacaga cgggtccacc atcaccgtca gcgaggcgct   11100
ggtaaggaat tcgcggatcg tctcgagctg gcggacgcgg gtgacggtgt cgcccacgcg   11160
gcgcttctcg aaataggcga gcgcagcgc cagcaggtgg tggaacagcc gggcaccag    11220
ctcgacgtcg atcttctgcg tgtctcggt gaacaggcgg gtgcggatcc agccgagcgc   11280
cacttcccac accgaaaccg ccaggaaggc gaagcgagc acgctcagcg tgctcatgct   11340
gttgtggatc agcaccttgt cgatcacgct ctggaacaaac agcggcggg cgaggccgag  11400
caggttgagc gcgagggtga tgccgagcac ctcgaggaac agcgtgcgat agcgccggaa  11460
ctgcgcggtg aaccaggaga ggccgaaccg cagcggccgt cccgccaccg gcgggtggt   11520
gagcagcacc agcgcgccgg accagatcgc accagatcgc tcccggtcga cctgttccgg 11580
ggcatggccc gggcgctgga tgatcacgcc atgttcggtc aggccgcga tcacgaacca   11640
gccttcgggc ccgtcggcga tcgcgggcag cggctggcg gcgcttggcc gcgagtccgc  11700
ctcgacggcc ttggcgcgca cgccctgctg gcgcctgctg aggaggatca ggtcgtcggc  11760
gcctgccgcc tcggcatggc ccaggcgtg gcgcagctgt tcgggcgtga tgcgatgtt    11820
gtgcgcgccg agcagcagcg acaaacgccac cagtccggat tcgcgcagct cgcctcgcg   11880
ctccgccgcc ccatgggcg cgagcgcgct ctgcagggtg gctgcattt cgtcgcgtgt   11940
cattcccgga actctgcctc catgcgata ctgagagcgc catgatgaag aaggctggta   12000
aagactcact taatcctagc tttctggta tttaccccgta gctgccgacc cgatttggga  12060
caggctggc ttagcaggtc cttaaactcg accgactata cggcgacgcc gaggaggggg  12120
aggattgggcg ccgcatcgcg cggcgaaacg cgggtcgtc gcaacatttc gcggagtcg   12180
atccgtcgcg aatgctgcac cgcgaacgc aatgacggcc gccacgcaat ccggcttgat   12240
cccgggcggc ggatcgcgat aagccgcgcc acgtcgcca aaactcgtcg aaataaccga   12300
caaaaccacg gcatatggct ggatattgca gcgtttgccc tgcgtttccg tcgttcaacc   12360
gcccttcgaa tcaggcaggc ccagcgtgac catgattgat cttccctttg gaacggcaca   12420
ctttggtcga cacggagact tccggtcggg caattgtccc gttatagtgc aatgcaacag  12480
gccgaatcgg ccgctgtcg cgtgcacatt ccgttgaggg agcccgatga ggcaatgaac   12540
gctttcgaag cacagcgcgc ctttgaggag caacttcggg cgcattcccg ggttacgcca   12600
```

FIG. 7  Sequence of insert contained in plasmid pX6 (SEQ ID NO: 54), continued.

```
tctgccgctc ccgtgtggcg tcgctcgacg ctgcggatgg tcctctatac cgagttgctg    12660
ctgctggaca gtcctctcgat cctggccgga ttccacgtcg cggcgggcac gcgcgacggc   12720
aactggctgt cgctggcggg catcaacgtc ggcgtcttcc tgtgccgat cgctctcggc     12780
accgcgctcg caagcgcac ctactcgctg aactgcctgc gctaccggt cagcggcgtg      12840
aagagcatct tctcggcatt cttcttctcg atcttcgtcg tcctgctcgg cagctacctg    12900
ctgacggccg agctgccgct gtcccgcgtg cagctgcggg agggcgcgat cctctcgctg    12960
gtcctcctga tggtgggccg cctgatgttc cgcgccacg tccgccggt taccggcggc      13020
aggctgtccg acgaactggt catcatcgac ggcgtctcgc tcgacgtcgc gggcaatgcg    13080
gtcgcgctcg acgcgcggat catcaatctc tcgccgaacc cgcgcgatcc gcaaatgctg   13140
catcgcctgg gcaccaccgt gatcgggttc gacgggtga tcgtcgcctg caccaaggag     13200
catcgcgcgg tctggcgct gctgcttcaag ggcatgaaca tcaagggcga gatcctcgtc    13260
ccccagttca atggcgtggg cgcggatcggc gtggacgcct ttgacgggaa ggatacgctg   13320
gtcgtctcgc agggcccgct caacatgccc aaccgcgcga agaagcgcgc gctcgatctc    13380
gcgatcaccg taccggccgt gctcgcgcctg cgcgcgcctga tgatcctggt ggcgatcctg   13440
atcaagctgg agagcccggg ccggtgttg ttcgcgcagg atcgtcgg cgcggcaac        13500
cggcgttca agatcatgaa gttccgctcg atgcgcgtaa cgctgtgcga cgcgaacggc     13560
aacgtctcgg ccagccgcga cgacgatcgc cgagatctgc aacgtgctgc ggcgcgactt    13620
accagcatcg acgaactgcc gcagctgctg aacgtgctg aacgtgctg gagcgtgtc      13680
ggcccgcgc cgcatgcggc gggctcgcgc gccgcgatc gggcatga ccggtcggcc       13740
gagcgtact ggcacccgcca cacgccacaag tcgcttcaag ccggtctggc ccaggtgcgc   13800
ggtttccgcg gggcgaccga tgccgcgtc gatctgacca accggctcca ggcagacatg     13860
gaatatatcg acgatggga tatctgatcc gatatcacga tcctgttcaa gacgctgcgg    13920
gtgatcgtgc attcgaacgc atttctgatcc cggcccgca gcctcgatcc gcctcgatcc   13980
gcaaatggat tgacagcgc ccggcttccg ttttctcgtt tgattccgt tgcggccggt      14040
ccgcggccatg gggattact gaatgaaggg catcatcctt gcgggggca gcgggacgcg    14100
cctgtacccc gcaacgctat cgatctgcaa gcagctgctt cccgtctatg acaagccgat   14160
gatcttctat cgcctgtcgg tgctgatgct caccggcatc cgggacaatc tgattatctc   14220
caccctcgcc gacctgcga tgttccagge gctgctgggc gacggctcgg cctttcggcat    14280
caacctcagc tatgccgcga agccctcccc caacgggctg gccgaagcgt tcatcatcgg    14340
cgcggattc gtcggcaacg atccccagcgc gctgatcctg ggcgacaaca tcatcacgg     14400
cgaaaagatg ggcgagcgct gccagcgcag ccgcagcgca gcagcgcagg gcggtgcaaa    14460
cgtcttcgcc tatcatgtcg acgaccccga gcgctacggc gtggtcgcgt tcgaccggga   14520
gacgggcgtc gccaccaagcg tcgaggaaaa ccggccgag actggcgat                14580
caccggcctg tattctacg acaaggacgt ggtcgacatc gccaagtcga tccagccctc     14640
ggcgcgggc gaactcgaga tcaccgacgt caaccgcgtt tacatggagc gcggcgacct     14700
```

FIG. 7    Sequence of insert contained in plasmid pX6 (SEQ ID NO: 54), continued.

```
gcacatcacg cgcctcggcc gcggctatgc ctggctcgac acggcacgc atgacagcct    14760
gcacgaagcc ggctcgttcg ttcgcacgct cgagcatcgg acgggcgtga agatcgcctg   14820
cccggaggaa atcgccttcg aaagcggctg gtcggcgcc gaagacctgc tcaagcgcgc    14880
cgccggcctc ggcaagaccg gctatgccgc ctatctccgc aaggttgcga ccgcagcatg   14940
accaggtcc atcatcacga actgtccggc gtcatcgagt tcacgccgcc caaatatggc    15000
gaccaccgcg gctccttctc cgaagtgttc aagcagtcgg tgctcgatgc cgaaggcgtc   15060
gaggcacgct gggtgcagga caatcagage ttcctcggcgg cccgggcac gatccggcgg   15120
ctgcatctcc aggcgcgcc cttcgcccag gccaagctgg tccgcgtgtt gcgcgcgcg    15180
atcttcgacg tcgcggtcga catccgtcgc ggctcgccca cctatggcaa atgggtcggc   15240
gtcgagctct cggccgagaa gtggaaccag ctgctggtcc ccgccggcta tgccacggc    15300
ttcatgacgc tcgttccgga ttgcgagatc tcctacaagg tcagcgccaa atattcgaag   15360
gattcggaga tggcgatccg ttgggacgat cccgatctcg ccatccctg gccggacatc    15420
gggtcgagc cggtcctctc cgaaaaggac gcggtcgcca cgccttcgc cggcggcgcc    15480
accccttct tctatcaggg ctgagccatg cagcagacct tcctcgtcac cggcggcgcc    15540
ggcttcatcg gctcggcggt ggtgccgcac ctcgtccgcc agggcgcgcg cgtcatcaat   15600
ctcgacaage tcaacctatgc cggcaaccog gcctcgctga ctgcgatcga gaacgcgcc    15660
aactatcgct tcgtccatgc cgacatcgcc gacaccggga cgatcctacc gctgctgcgc   15720
gaggagcagg tcgatgtggt gatgcacctc gcgagccgaga gccatgtcga tgctcgatc    15780
gacgccctg gcgagttcat cgagaccaat gtcgtcggca ccttcaagct gctccagtcg   15840
gcgctgcaat attggcgcga ctggagggc gctggagggc gagaaacgcg acgcgttccg cttccaccac   15900
atctccaccg acgaagtgtt cgggcgactg ccgttcgaca gcgcatctt caccgaagag   15960
acgccctatg atccctcctc gccctattcg gcgtcgaagg cggcgagcga ccatctggtg   16020
cgccctggg gccacaccta tggcctgccg gtggtgctgt cgaactgctc gaacaattac   16080
gggccgttcc acttccccga gaagctgatc cggttgacca tcctcaacgc gctcgaggc    16140
aagccggctgc cggtctacgg caaggcgag aatatccgcg actgtgtta tgtcgacgat   16200
cacgccaagg cgctggcgac catcgccacc acgggcaagg tcggccagag cctgctcgac   16260
ggcgccgca acgagcggac cgctcggcga cggtcgcaaa cgccgcgaa cgatctcgac cctgtcgac   16320
cagcgcattc cgctcggcga cgtcaccgga cgtcaccgga cgccgcgaac tgatcacctt cgtcaccgat   16380
cgccccgcc atgcgcggcg ctacgcgatc gacacggcc agctcgagac cgagctgggc   16440
tggaaggctg aggagaattt cgacaccggg atcgccgca ggcaaatatg cggggggcag   16500
aacgagtggt ggtggggccc gatcgctcc ggcaccggc atgacgggca cgctggccgc   16560
acggcctgat gcgtatccto gtcaccggcc ctggtcttca ccacctaccc cgaattcgat   16620
agcaggcggt gggccacgag ctggtcgcgg gtggcgggg cgggcgggt tgcacccgga   16680
cggagacgat cgaggccggt gtggcggccgg ctggcgggg tgggggccaagg   16740
cctacacggc ggtcgacaag gccgaaagcg accccgagct ggccagcagc atcaacggcg   16800
```

FIG. 7  Sequence of insert contained in plasmid pX6 (SEQ ID NO: 54), continued.

```
acggtccgg cgtgctggcg cgcgggcg cgaagatcgg cgcgccgatc atccacctgt 16860
cgaccgatta tgtgttcgac ggcagtctcg acgccctttg acgcgaggac gatcccaccg 16920
gcccgtcgg cgtctatggc gcgaccaagc tggccggcga gcaggcggtg caggcctcgg 16980
gtgccaccaa cgccgtgatc cggctggcct gggtctacag ccgttcggc aacaatttcg 17040
tcaagacgat gctccgcctc gccgagacgc gcgacgcgct gaacgtcgtg gaggaccagt 17100
ggggctgccc cagttcggcg ctgacatcg cgacgcgat cctgacggtg gtcgggcact 17160
ggcagcagga cggcgacg acggcctct accattcgc cggcaccggc gagaccaact 17220
gggccgactt cgcatcgacg atcttgccg agagcgcaa gcgcggtggc ccctcggcca 17280
ccgtcacgg cattccagc tcgggctatc cgactccggc cacgcgccg gccaattcgc 17340
ggctggactg caccgcctc gcggagacct tcggctaccg ggcgcctgcc tggcaggatt 17400
cgctgaacgt cgtactggat cgctgctcg gctgatccga acggggggc ctcagcgccc 17460
cccgccatgc tcccgttcgc gcgccggcaa tgcctctagc acgcgcgct ttcccttagg 17520
actcagttcg ctccagccgg cgattcctt gggcgacgc cagcaccca ggcacagccg 17580
gatctccatg tcgaggcggc agaccttgcg acaggcgat tccagcccg cggcgcaa 17640
gcgcgagaac agccccatca gcgcttgaag gcgcttggc tcttcgggc gaacttgcg 17700
aggccggtga tcaccgggt cggcgcatag tcgcggatca ggccctttcac ccggtgcagc 17760
gcggtgcgct tgtgtcgcg cgagacgcgc cttccaacgc acgaagttcg aatagccgcg 17820
accctcggta tcctctctg cgctgtagta cgctgctagc agcgagttgc gcgatgtt 17880
cggcggcgtc tgcagcggga agggctggcc gtgccacgac ttgcccgaga cgcggaagat 17940
cgcgaggcga ttgaacttgg gcgtgatgct ggaaacgcac ctggtcgcat cctcgtccca 18000
cagctccagg tcgccgcccc attcctctg ccagtctggc gtgcagtaat agatgcagtt 18060
gatctgctgg ctgagcttct tgttggggtg gcgcgaggca tcgatgtgga gcatcagccg 18120
ccgcccgag cggtcgagt gcaggccgca gccataatgg ttggatccg gcagcaggtg 18180
cttgtgccg ctcagccggt cgaggaagtt cgagaagatg cccgactgaa actgcatcat 18240
catcaggcgg acgagcggcg gaaactgctc ctcgtccgag gtcgtcacct ttcgatcttg 18300
cgatcaccgc tgtcgcgct atcgcccggc ccttccaggc gccagttgac gtcgtccagc 18360
ttcgggaagg catcccgag ccgccgcgcc acgtcgtcgg gcaggaaatt gtcgatcgcg 18420
acatgctcat agggctcggc gttcaggaag cgatcatgat attcgtccgc gagcgcatat 18480
agcttctcgc gcgtgaagaa gaagacgca gcgatcataa acgattcacc gcaatcgcgt 18540
ccccgaaga gcgatcctt atccgaacca cgatcggctt gaccaggcgg 18600
gcacagcacc gtaacactta gcgatccggc cggacatcgg gtgcgcaccg catgtcccca cagaatcgcg 18660
ataccgaatt cgcggaagcg ccggccctgc ggcgacatcg ctgcggatct tgaacatatt gatgatgtcg 18720
ccggcgcca ccggcccca ccagcttgcc cttgatccgg ttgttacat tctcgccgtg caccacctgc 18780
atgtcggaaa ccagttgcgg gcttgctcgg cacctggcgg atcgtccaat ctctcgccag ctcgtggtgc 18840
agccatagcg gcttgctcgg cacctggcgg atgtccaact                                  18900
```

FIG. 7 Sequence of insert contained in plasmid pX6 (SEQ ID NO: 54), continued.

```
ggcttggcc agatcgtctc gatcccggcc acgtctttct cgaccagcga ggtgaacggg    18960
ctgctgtgat cgctggcggt gtagagttgc ccgccccgca tcgcgatgcc gtggggaag    19020
ttcagcacgg tctgcgccgg cgcttccttg gcggcgtcct gcaccgcgc gacgaaatcg    19080
ctcgacaccg catcatcatt gtccagccgc gtggtgacga tcagcgtctc gcccgccgtc    19140
gcgagtgccc gcacgtctc ggcgatcatc gccttgtcga acatcgccac atagcgtggg    19200
gtaaaattga agatctggcg atcgcgtccg atccgctcgc ggaattcaac cggcgtatcc    19260
ttgtcgaaat agatcagcca gtggaagttg cgtcggttg cgtccggtct ggcccgcgat    19320
cagaactgct cgaacaggcc gaaacggcgt tccagccagc ggcgcagagt gcgaatcgcc    19380
acctcgtc ccgggctggc gatgttgaag cgagtcagga tcacgtggag catggggttg    19440
atcagccctt gttgcggaa ggaatggcgc gggcacggc gaccggcat gccaggaacc    19500
gggagcggcg cttcgcgaca tggcggagct tcgccctgaa tggcacgcgc tgcacggctg    19560
ctagcccct ttattgccgt tcaactgctt cggttaaggg atattccgga gcccggcaac    19620
cggcgattgc tgcgctgcgc aatgaacggc gccgccgt ggtgccaag ggcgcgccaa    19680
tccacaccig ccgggccggc gatccgcgc gccaaagcgcc gccaacgcat tcgcaaggct    19740
tgcgaaataa atggcttgcc cctacccgag cccggtgtcg cccctcgtc ccgacacgat    19800
cgccaccgg ctggcgcttc gccgtttcgc gatcgcctgc atgtcgacca tgtcggcgct    19860
catcaagatg tccgaactgc gggcgcctc gctgatcgag acgatgtttc accgccagct    19920
ctcgctgttg cccttgtca cctgggt cacgctgggg cccggcctca agtcgctcag    19980
gaccgcgcgg ttcgccgcgc atgtctggcg caccgcgggtg ggacttaccg gcatgatctt    20040
caccttcggc gcggtgatcc tgctgccgct cgccgaagcg cagacccttcc agttcaccgt    20100
ccccatcttc gcgacgctgc tcgggcgcgt gatcctaggc cgccgacgc gctggcaccg    20160
ctggagcgcg gtgatcctcg ggttcgtcgg cgtgcttatc gtcgtccagc cgggcacga    20220
ggcgatcccg gtgttcggtg cgttcgtcgg cctgatggcg ctgttcg tgccatcgt    20280
cgcgatcacg ctccgcacga tcgggaagac cgaaagcgcc ggcaccacgg tgtctggtt    20340
ctcgctgttg tcggtgccga tgctggccgc aatctatgcc ttccactaca agccccatga    20400
tgccgagacc tgggccatcc tgatcgccac gggctggtcc ggcggcgtcg gccagctcgc    20460
gctgaccggg gcgatggcgt tcgctcccgt gtcggcagtg gtgcgatgg actattcggg    20520
gctgctctgg gcgacgctct atggctggct gctgttcggc cggcctgcga ccttttccac    20580
ctggctcggc gcgccggtga tcatcgccag cggcctgtac atcgtctatc gcgagcagaa    20640
gctgggcgcc ggccaggta gctacggca aacgccacta tgaggttgtt ggcgggcatc    20700
gccacccgcc gctcgaacac cagcccgtgc gcttccgcg ccgcacgac atcgcccagc    20760
aaccgcaggc cccaggcgg                                                20779
```

SPHINGOMONAS STRAINS PRODUCING GREATLY INCREASED YIELD OF PHB-DEFICIENT SPHINGAN (DIUTAN)

CROSS-REFERENCE TO RELATED APPLICATIONS

This application is a continuation application of U.S. application Ser. No. 13/733,933, which is a divisional application of U.S. application Ser. No. 12/533,649 filed Jul. 31, 2009, which are hereby incorporated by reference in their entireties.

SEQUENCE LISTING

The sequence listing in the file named "68492o705000.txt" having a size of 179,295 bytes that was created Jul. 31, 2009 is hereby incorporated by reference in its entirety.

BACKGROUND

Field of the Art

This application generally relates to the construction of PHB-deficient *Sphingomonas* strains that produce high yields of diutan with improved filterability. In another aspect, this application relates to diutan produced from PHB-deficient *Sphingomonas* strains that produce high yields of diutan with improved filterability.

Description of Related Art

A number of bacteria of the genus *Sphingomonas* produce polysaccharides called sphingans that have related structures with a generally conserved tetrasaccharide backbone structure and different side chains (ref. no. 1, 6, 7, 8, 10). The sphingans gellan, welan, rhamsan and diutan are produced commercially for use in food, oilfield or personal care applications. The value of sphingan polysaccharides lies in their abilities to modify the rheology of aqueous solutions, i.e., to thicken liquids, suspend solids, stabilize emulsions, or form gels and films.

Sphingans are structurally related to one another, but are not identical. Common members of the genus *Sphingomonas* and the sphingans they produce include *Sphingomonas elodea* ATCC 31461, which produces gellan (S-60); *Sphingomonas* sp. ATCC 31555, which produces welan (S-130); *Sphingomonas* sp. ATCC 31961, which produces rhamsan (S-194); *Sphingomonas* sp. ATCC 53159, which produces diutan (S-657); *Sphingomonas* sp. ATCC 31554, which produces an as yet unnamed polysaccharide (S-88); *Sphingomonas* sp. ATCC 31853, which produces an as yet unnamed polysaccharide (S-198); *Sphingomonas* sp. ATCC 21423, which produces an as yet unnamed polysaccharide (S-7); *Sphingomonas* sp. ATCC 53272, which produces an as yet unnamed polysaccharide (NW-11); *Sphingomonas* sp. FERM-BP2015 (previously *Alcaligenes latus* B-16), which produces alcalan (Biopolymer B-16) and the like. A description of the Sphingomonads and the polysaccharides they produce can be found, for example, in U.S. Pat. Nos. 4,377,636; 4,326,053; 4,326,052 and 4,385,123 (for ATCC 31461 and its S-60 polysaccharide); in U.S. Pat. No. 4,342,866 (for ATCC 31555 and S-130); in U.S. Pat. No. 4,401,760 (for ATCC 31961 and S-194); in U.S. Pat. No. 5,175,278 (for ATCC 53159 and S-657); in U.S. Pat. Nos. 4,331,440 and 4,535,153 (for ATCC 31554 and S-88); in U.S. Pat. No. 4,529,797 (for ATCC 31853 and S-198); in U.S. Pat. No. 3,960,832 (for ATCC 21423 and S-7); in U.S. Pat. No. 4,874,044 (for ATCC 53272 and NW-11); in U.S. Pat. No. 5,175,279 (for FERM BP-2015 and B-16), each of which is incorporated by reference herein in its entirety to the extent that they are not inconsistent with the disclosure herein.

One particular sphingan, diutan (also known as heteropolysaccharide S-657), is prepared by fermentation of strain *Sphingomonas* sp. ATCC 53159 (ref. no. 17). Diutan exhibits unique rheological properties in aqueous solutions including high thermal stability, superior suspension properties, and the ability to generate high viscosity at low concentrations. The diutan polysaccharide imparts significant pseudoplasticity to polar solvents such as water, such that diutan can act as a rheological modifier that is capable of particle suspension, friction reduction, emulsion and foam stabilization, filter cake deposition and filtration control. Consequently, diutan has found industrial utility as a rheological modifier in a variety of contexts, including cementitious systems as disclosed in U.S. Pat. No. 6,110,271, which is incorporated herein by reference in its entirety to the extent that it is not inconsistent with the disclosure herein.

Diutan consists of a repeat unit with a backbone comprised of [→4)-α-L-rhamnose-(1→3)-β-D-glucose-(1→4)-β-D-glucuronic acid-(1→4)-β-D-glucose-(1→] and a two-sugar L-rhamnose side-chain attached to the (1→4) linked glucose residues (ref. no. 2, 7). Two O-acetyl groups are attached per repeat unit to the 2' and 6' positions of the (1→3) linked glucose (ref. no. 4).

Progress has been made in elucidating the genetics and biochemistry underlying biosynthesis of diutan and other sphingans. Genes for biosynthesis of sphingans S-88, S-7, and gellan have been identified (ref. no. 5, 12, 13, 15). Genes for several glycosyl transferases of the backbone structure have been analyzed biochemically (ref. no. 11, 14), as have genes gelC and gelE, potentially involved in chain length determination (ref. no. 9). Several of the genes for synthesis of sugar nucleotide precursors have also been elucidated (ref. no. 12). The genetics and biochemistry of polymerization, secretion and control of polysaccharide molecular length are less defined.

A cluster of genes involved in biosynthesis of diutan has been identified that includes genes for glycosyl transferases, genes encoding enzymes for synthesis of a precursor molecule dTDP rhamnose, and genes for secretion of the polysaccharide (ref. no. 3). Plasmids, e.g., pS8 and pX6, containing some of the genes in the aforementioned cluster, were shown to increase the yield of diutan by about 10%, and one plasmid in particular (pS8) was found to significantly improve the rheological properties of diutan from the wild-type strain (ref. no. 18).

Growth conditions typically used for producing diutan and other sphingans also promote production of the internal storage polymer polyhydroxybutyrate ("PHB"), which is generally regarded as an undesirable side-product and is difficult to remove during sphingan preparation. The PHB can form small insoluble particles that interfere with clarity and filterability, limiting the usefulness of the sphingans. For example, the turbidity imparted by PHB particles can limit applicability for household and personal care products in which appearance is critical for consumer acceptance. Moreover, certain oilfield uses require filterability; however, the PHB particles can plug small pores in oil field rock formations, preventing the flow of the sphingan solution and/or the return flow of the crude oil after treating the well. Finally, as PHB synthesis and sphingan synthesis compete for the available carbon source, PHB synthesis can have some adverse effect on sphingan yield.

Accordingly, attempts have been made to eliminate PHB production in sphingan-producing strains. Ref. no. 26 describes a strain of *Sphingomonas elodea* (a gellan-producing species) that was isolated following chemical mutagenesis. This strain, called LPG-2, has decreased PHB production, but produces gellan of inconsistent quality and yield.

A more targeted approach to eliminating PHB production was undertaken by deletion of a gene required for PHB synthesis, the phaC gene (ref. no. 20). Precise deletion of phaC from a diutan producing strain (ATCC 53159) reproducibly resulted in poor growth and severely reduced diutan productivity (strains NPD3 and NPD6). These strains exhibit increased carbohydrate hydrolysis and accumulation of organic acids, suggesting a critical role for phaC in maintaining normal cellular metabolism. Derivatives with less impaired diutan productivity were subsequently isolated. Two independent derivatives, PDD3 and PDD6, have uncharacterized spontaneous mutation(s) and remain PHB-deficient (ATCC deposit nos. PTA-4865 and PTA-4866, respectively). Though recovery of up to 90% of total diutan yield has been reported (ref. no. 20), this yield was only obtained following a greatly increased culture growth time and has not been consistently reproducible. Under standard growth conditions, diutan productivity and yield by these strains is only approximately half of wild-type levels.

SUMMARY

In view of the foregoing, there is a need to overcome the low sphingan productivity that is characteristic of PHB-deficient strains. The present disclosure addresses this need in the art by providing a genetically modified strain of *Sphingomonas* which not only lacks PHB production but also provides surprisingly high diutan productivity. Unexpectedly, the plasmids pS8 and pX6—which give only modest improvement in diutan productivity in PHB-producing strain—are now shown to greatly improve diutan productivity in a PHB-deficient strain. The great improvement in diutan productivity was particularly surprising because the plasmids contain genes involved in diutan biosynthesis and are not known to contain any genes that would offset the metabolic deficiency of a PHB-deficient strain. Certain embodiments of these genetically modified strains, described infra, fully overcome the poor yield and low productivity of PHB-deficient strains, while simultaneously attaining the desired filterability and clarity of PHB-deficient sphingans.

Certain embodiments encompass a mutant strain of the genus *Sphingomonas* having a genetic modification that reduces, or, preferably, substantially or entirely eliminates the production of PHB. In exemplary embodiments, the genetic modification inactivates the phaA gene, phaB gene, phaC gene, or any combination thereof. In another exemplary embodiment, the genetic modification to impair PHB synthesis is obtained by screening or selection for a PHB-deficient organism. The genetic modification that impairs PHB synthesis can reduce or completely eliminate PHB production, and can optionally be conditional, such as conditional induction, suppression, overexpression, knock-out, etc. of a gene involved in PHB synthesis, a gene that suppresses PHB synthesis, or any combination thereof. Optionally, a mutant strain of the genus *Sphingomonas* having a genetic modification that reduces, or, preferably, substantially or entirely eliminates the production of PHB also includes at least one additional genetic modification that suppresses the poor growth and/or poor diutan productivity of such strains. In an exemplary embodiment, the additional genetic modification can include at least one of the suppressor mutations contained in strains PDD3, PDD6, or both, or a variant of such suppressor mutation(s).

Certain embodiments encompass a method of increasing sphingan production in a host organism, such as an organism of the genus *Sphingomonas*. Exemplary methods of increasing sphingan production include increasing the expression in the host organism of at least one gene involved in sphingan synthesis. Such genes can be involved in sphingan synthesis, secretion, polymerization, synthesis of precursors, control of polysaccharide molecular length, etc. For example, additional copies of at least one gene involved in sphingan production can be introduced on an extrachromosomal element (such as a plasmid) or can be integrated into the host genome, or both. Such genes can be derived from the host strain or can be homologs derived from another species or strain. Homologs can include functional, structural, or sequence homologs of a gene involved in sphingan production or of a gene having an enzymatic activity the same as or similar to a gene involved in sphingan synthesis. In exemplary embodiments, the genes can be obtained by screening or selection for a *Sphingomonas* strain having increased sphingan production. Exemplary methods of increasing sphingan production also include introduction of genes involved in sphingan production having modified (non-native) sequences, such as modified promoter or enhancer elements, expression-optimized sequences, etc. Additionally, the native chromosomal copy of at least one gene involved in sphingan synthesis can optionally be deleted, or be replaced by any of the foregoing.

In certain embodiments, an extrachromosomal or integrated sequence element containing at least one gene, such as all of the genes that are contained in the insert in plasmid pS8 and/or pX6, or homolog(s) thereof, can be introduced into a *Sphingomonas* strain. For example, the at least one gene can include dpsS, dpsG, dpsR, dpsQ, dpsI, dpsK, dpsL, dpsJ, dpsF, dpsD, dpsC, dpsE, dpsM, dpsN, atrD, atrB, dpsB, rmlA, rmlC, rmlB, rmlD, orf7, orf6, orf5, or any combination thereof. In certain exemplary embodiments, the gene(s) include at least one gene encoding a sphingan biosynthetic enzyme, such as a dpsG polymerase. In another exemplary embodiment, such genes encoding a sphingan biosynthetic enzyme can include a dpsG polymerase and a glucose-1-phosphate thymidylyltransferase gene; a dTDP-6-deoxy-D-glucose-3-5-epimerase gene; a dTDP-D-glucose-4,6-dehydratase gene; and a dTDP-6-deoxy-L-mannose-dehydrogenase gene. In another exemplary embodiment, such genes encoding a sphingan biosynthetic enzyme can include a dpsG polymerase and a rhamnosyl transferase IV gene; a beta-1,4-glucuronosyl transferase II gene; a glucosyl isoprenylphosphate transferase I gene; and a glucosyl transferase III gene. In another exemplary embodiment, such a gene encoding a sphingan biosynthetic enzyme can include a dpsG polymerase and one or more of the polysaccharide export genes dpsD, dpsC, and dpsE. In another exemplary embodiment, such a gene encoding a sphingan biosynthetic enzyme can include a rhamnosyl transferase IV gene; a beta-1,4-glucuronosyl transferase II gene; a glucosyl isoprenylphosphate transferase I gene; glucosyl transferase III gene; a glucose-1-phosphate thymidylyltransferase gene; a dTDP-6-deoxy-D-glucose-3-5-epimerase gene; a dTDP-D-glucose-4,6-dehydratase gene; and a dTDP-6-deoxy-L-mannose-dehydrogenase gene. In another exemplary embodiment, such a sphingan biosynthetic enzyme can be selected from the group consisting of a gene encoding a polymerase; lyase; rhamnosyl transferase IV; beta-1,4-glucuronosyl transferase II; glucosyl transferase III; polysaccharide export protein; secretion protein; glucosyl-isoprenylphosphate transferase I; glucose-1-phosphate thymidylyltransferase; dTDP-6-deoxy-D-glucose-3-5-epimerase; dTDP-D-glucose-4,6-dehydratase; dTDP-6-deoxy-L-mannose-dehydrogenase, and any combination thereof. In certain embodiments, any combination of the foregoing genes or homologs thereof can be introduced into a *Sphingomonas* strain. In one exemplary embodiment, the *Sphingomonas* strain is a diutan-producing strain, such as ATCC 53159, or a PHB-deficient derivative thereof, such as a phaC deletion strain, such as NPD3, NPD6, PDD3, or PDD6. In another exemplary embodiment, the *Sphingomonas* strain is derived from *Sphingomonas elodea* ATCC 31461, *Sphingomonas* sp. ATCC 31555, *Sphingomonas* sp. ATCC 31961, *Sphingomonas* sp. ATCC 53159, *Sphingomonas* sp. ATCC 31554, *Sphingomonas* sp. ATCC 31853, *Sphingomonas* sp. ATCC 21423, *Sphingomonas* sp. ATCC 53272, *Sphingomonas* sp. FERM-BP2015, or a PHB-deficient derivative, such as a phaC deletion strain of any of the foregoing, or a phaC deletion strain bearing further mutation(s) that improve growth or sphingan productivity. In an exemplary embodiment, the phaC deletion strain is derived from a gellan-producing strain, such as LPG-2 (ref. no. 26), NPG-1, NPG-2, NPG-3, PDG-1, PDG-3 (ref. no. 20) or a derivative thereof.

In exemplary embodiments, a gene involved in sphingan synthesis can be derived from a homolog of a gene contained in plasmids pS8 or pX6. Such a homolog can be a *Sphingomonas* homolog, i.e., derived from an organism of the genus *Sphingomonas*. Exemplary organisms from which *Sphingomonas* homologs can be derived include *Sphingomonas elodea* ATCC 31461, *Sphingomonas* sp. ATCC 31555, *Sphingomonas* sp. ATCC 31961, *Sphingomonas* sp. ATCC 53159, *Sphingomonas* sp. ATCC 31554, *Sphingomonas* sp. ATCC 31853, *Sphingomonas* sp. ATCC 21423, *Sphingomonas* sp. ATCC 53272, *Sphingomonas* sp. FERM-BP2015, or any combination thereof. In another exemplary embodiment, a gene involved in sphingan synthesis can encode a polypeptide having at least about 70% sequence identity, such as about 75%, about 80%, about 85%, about 90%, about 91%, about 92%, about 93%, about 94%, about 95%, about 96%, about 97%, about 98%, about 99%, or about 100% sequence identity, to a polypeptide sequence of SEQ ID NO: 3, 5, 7, 9, 11, 13, 15, 17, 19, 21, 23, 25, 27, 29, 31, 33, 35, 37, 39, 41, 43, 45, 47, 49, 51, or 53. In another exemplary embodiment, a gene involved in sphingan synthesis can be encoded by a polynucleotide having at least about 60% sequence identity, such as about 65%, about 70%, about 75%, about 80%, about 85%, about 90%, about 91%, about 92%, about 93%, about 94%, about 95%, about 96%, about 97%, about 98%, about 99%, or about 100% sequence identity, to a polynucleotide sequence of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

Certain embodiments of the present compositions include a diutan, particularly a PHB-deficient diutan, exhibiting an improvement (relative to diutan produced from a wild-type strain) in a number of different viscosity measurements. Among these are: i) an intrinsic viscosity of greater than about 150, preferably higher than about 155, more preferably higher than about 160 dL/g; ii) a sea water 3 rpm viscosity greater than about 35, such as greater than about 37, such as greater than about 40, such as greater than about 42, such as greater than about 45, such as greater than about 47, such as greater than about 50 dial reading; iii) a sea water 0.3 rpm viscosity greater than about 35,000, such as greater than about 39,000, such as greater than about 40,000, such as greater than about 42,000, such as greater than about 45,000, such as greater than about 48,000, such as greater than about 50,000, such as greater than about 54,000 centipoise (cP); and a PEG low shear rate viscosity greater than about 3500, such as greater than about 3700, such as greater than about 3900, such as greater than about 4000, such as greater than about 4200, such as greater than about 4500, such as greater than about 4700, such as greater than about 5000, such as greater than about 5200, such as greater than about 5500, such as greater than about 5700, such as greater than about 6000 cP.

Certain embodiments of the present strains include a mutant strain of the genus *Sphingomonas* that is able to produce PHB-deficient diutan at a rate of at least about 0.10 g/L/hr, such as at least about 0.11 g/L/hr, such as at least about 0.12 g/L/hr, such as at least about 0.13 g/L/hr, such as at least about 0.14 g/L/hr, such as at least about 0.15 g/L/hr, such as at least about 0.2 g/L/hr, and/or a yield of PHB-deficient diutan of at least about 12 g/L, such as at least about 15 g/L, such as at least about 16 g/L, such as at least about 17 g/L, such as at least about 18 g/L, such as at least about 19 g/L, such as at least about 20 g/L, such as at least about 21 g/L. For example, certain embodiments can include a mutant strain of the genus *Sphingomonas* able to produce PHB-deficient diutan at a rate of between about 0.15 g/L/hr and about 0.60 g/L/hr, such as between about 0.16 g/L/hr and about 0.5 g/L/hr, such as between about 0.17 g/L/hr and about 0.4 g/L/hr, such as between about 0.18 g/L/hr and about 0.35 g/L/hr, such as between about 0.19 g/L/hr and about 0.3 g/L/hr, such as between about 0.2 g/L/hr and 0.25 g/L/hr, such as between about 0.21 g/L/hr and about 0.22 g/L/hr. Additionally, certain embodiments can include a mutant strain of the genus *Sphingomonas* able to produce a yield of PHB-deficient diutan between about 12 g/L and about 30 g/L, such as between about 13 g/L and about 25 g/L, such as between about 14 g/L and about 22 g/L, such as between about 19 g/L and about 21 g/L.

Certain embodiments of the present strains include a mutant strain of the genus *Sphingomonas* containing a genetic modification that substantially or entirely eliminates the production of PHB and a genetic modification that results in increased production of a sphingan, wherein the mutant strain of the genus *Sphingomonas* increases the rate of production or yield of PHB-deficient diutan by at least about 50%, such as by at least about 60%, such as by at least about 70%, such as by at least about 80%, such as by at least about 90%, such as by at least about 100%, such as by at least about 110%, such as by at least about 120%, such as by at least about 120%, such as by at least about 130%, such as by at least about 140% relative to a congenic strain containing the genetic modification that substantially or entirely eliminates the production of PHB and lacking the genetic modification that increases the production of a sphingan. For example, the increase in the rate of production or yield of PHB-deficient diutan can be between about 50% and about 200%, such as between about 60% and about 190%, such as between about 70% and about 180%, such as between about 80% and about 170%, such as between about 90% and about 160%, such as between about 100% and about 150%, such as between about 110% and about 140%, such as between about 120% and about 130%.

In certain embodiments, one or more copies of specific DNA sequences are introduced within certain *Sphingomonas* strains to provide increased biosynthetic production of high viscosity diutan polysaccharide that is essentially free of PHB. The engineered bacteria containing such genes for increased production produce significantly greater amounts of PHB-deficient diutan polysaccharide compared to non-engineered bacteria and create diutan with the aforementioned resultant high viscosity properties.

The DNA can be delivered into bacteria of the genus *Sphingomonas* in multiple copies (via plasmid, other known manner) or increased expression of the genes via a suitable method, e.g., coupling to a stronger promoter. After insertion of the DNA into the target bacteria, the production of diutan can be determined by fermenting the engineered bacteria and comparing the yield in terms of amount produced and quality produced. Increased production and viscosity can both be determined by comparison with other diutan-producing strains.

*Sphingomonas* strains, such as the genetically modified strains described herein, can be used to produce sphingans, such as diutan, by fermentation. Generally, a suitable medium for fermentation is an aqueous medium which contains a source of carbon (for example, carbohydrates including glucose, lactose, sucrose, maltose or maltodextrins), a nitrogen source (for example, inorganic ammonium, inorganic nitrate, urea, organic amino acids or proteinaceous materials, such as hydrolyzed yeast, soy flour or casein, distiller's solubles or corn steep liquor), and inorganic salts. A wide variety of fermentation media will support the production of diutan according to the present invention. One of ordinary skill in the art can readily determine an appropriate media formulation.

Carbohydrates can be included in the fermentation broth in varying amounts—usually between about 1 and 10% by weight (preferably 2-8%) of the fermentation medium. The carbohydrates can be added prior to fermentation or, alternatively, during fermentation. The amount of nitrogen can, for example, range from about 0.01% to about 0.4% by weight of the aqueous medium. A single carbon source or nitrogen source can be used, as well as mixtures of these sources. Among the inorganic salts which are useful in fermenting *Sphingomonas* bacteria are salts which contain sodium, potassium, ammonium, nitrate, calcium, phosphate, sulfate, chloride, carbonate and similar ions. Trace metals, such as magnesium, manganese, cobalt, iron, zinc, copper, molybdenum, iodide and borate, can also be advantageously included in the broth.

In certain embodiments of the present method, *Sphingomonas* strains undergo fermentation. Fermentation can be carried out, for example, at temperatures between about 25 degrees C. and 40 degrees C., preferably between about 27 degrees C. and 35 degrees C. An inoculum can be prepared by standard methods of volume scale-up, including shake flask cultures and small-scale submerged stirred fermentation. The medium for preparing an inoculum can be the same as the production medium or can be any one of several standard media well-known in the art, such as Luria broth or YM medium. More than one seed stage can be used to obtain the desired volume for inoculation. Typical inoculation volumes range from about 0.5% to about 10% of the total final fermentation volume.

Certain embodiments of the present methods include agitation of the fermentation medium. In some embodiments, an agitator is contained within a fermentation vessel, whereby the contents of the agitation vessel are mixed. The vessel also can have automatic pH and foaming controls. The production medium can be added to the vessel and sterilized in place, e.g., by heating. Alternatively, the media can be sterilized separately before addition. A previously grown seed culture can be added to the cooled medium (typically at the preferred fermentation temperature of about 27 degrees to about 35 degrees C.), and the stirred culture can be fermented for about 48 to about 110 hours, producing a high viscosity broth. The sphingan, such as diutan, can be recovered from the broth by, for example, a standard method of precipitation with an alcohol, generally isopropanol.

BRIEF DESCRIPTION OF THE DRAWINGS

FIG. 1 shows greatly improved diutan productivity of PHB-deficient strains bearing plasmids pX6 and pS8 relative to PHB-deficient strains without the plasmids.

FIG. 2 shows greatly improved diutan yield from PHB-deficient strains bearing plasmids pX6 and pS8 relative to PHB-deficient strains without the plasmids.

FIG. 3A illustrates poor filterability of a PHB-containing diutan preparation (0.04% S657/pS8 diutan in seawater). FIG. 3B illustrates poor filterability of an independent PHB-containing diutan preparation (0.04% S657/pS8 diutan in seawater).

FIG. 4A illustrates improved filterability of a PHB-deficient diutan preparation (0.04% PDD3/pS8 diutan in seawater). FIG. 4B illustrates improved filterability of a PHB-deficient diutan preparation (0.04% PDD3/pS8 diutan in seawater). FIG. 4C illustrates improved filterability of a PHB-deficient diutan preparation (0.04% PDD3/pS8 diutan in seawater).

FIG. 5 presents a map showing the inserts contained in plasmids pS8 and pX6.

FIG. 6 shows the insert sequence contained in plasmid pS8 (SEQ ID NO: 1).

FIG. 7 shows the insert sequence contained in plasmid pX6 (SEQ ID NO: 54).

DETAILED DESCRIPTION

Two PHB-deficient bacterial strains derived from *Sphingomonas* sp. ATCC 53159 (S657) were previously developed and designated PDD3 and PDD6 (see ref. no. 20). These strains exhibit approximately half of the diutan productivity of the wild-type strain (S657). The plasmid pS8 contains several genes involved in diutan biosynthesis in a multicopy plasmid and has been used to enhance diutan productivity and rheology (ref. no. 18). See also refs. no. 21-23 which describe the use of plasmid mediated gene amplification to increase polysaccharide yield (DNA segments and methods for increasing polysaccharide production).

As is shown in greater detail below, applicants have now shown that introduction of the plasmids pX6 and pS8—which contain multiple genes involved in diutan biosynthesis, but are not known to contain any genes that would offset the metabolic deficiency of a PHB-deficient strain—into PHB-deficient mutants PDD3 and PDD6 results in an unexpected significantly improved productivity (g/L/hr) and dry weight yield (g/L) of the PDD strains (70% to >100% increase) relative to the PHB-deficient strains without the introduced plasmids. The PHB-deficient strains produced fewer cells and no PHB, thus, more of their dry weight yield is diutan polysaccharide. Due to their increased productivity, these strains can be used for more economical production of PHB-deficient diutan than strains lacking these genetic modifications. Moreover, a clarified diutan produced from such strains exhibits improved filterability and clarity due to the absence of PHB particles relative to PHB-containing diutan. Such PHB-deficient diutan can be particularly desirable in a variety of applications, including household and personal care products, cementitious systems, for enhanced oil recovery, fracturing, well bore clean-up and other 'pay zone' applications, or any other application involving particle suspension, friction reduction, emulsion and foam stabilization, filter cake deposition and filtration control, or modification of the rheology of aqueous solutions (such as to thicken liquids, suspend solids, stabilize emulsions, or form gels and films, etc.). Additionally, upon acid hydrolysis, the PHB-deficient diutan leaves little to no residue as compared to PHB-containing diutan. The low acid hydrolysis residue renders the PHB-deficient diutan particularly suitable in oil field applications, such as fracturing, in which a viscosifying fluid is degraded after fracturing the formation, so the return flow of oil is maximized. Unlike the PHB-containing diutan, which contains PHB particles that would plug the pores in the rock formation, PHB-deficient diutan would not plug the pores in the formation, leading to improved oil yield.

In one exemplary embodiment of the present strains, a plasmid containing the relevant DNA sequence is inserted into a recipient *Sphingomonas* bacterium and replicates in the recipient cell, typically giving one or several (at least two and usually 4-10) copies of the DNA segment that result in increased production of high viscosity diutan polysaccharide relative to a strain lacking the DNA sequence. Alternatively or in addition to insertion of a plasmid-borne DNA sequence, DNA sequences that integrate into the bacterial chromosome can also be used. The use of conjugation or mobilization to transfer DNA into recipient bacteria is generally effective. Electroporation or chemical transformation of competent cells with purified DNA can also be used. Other vectors or bacteriophages can be used to transfer DNA into the host cell. Maintaining the DNA segments on plasmids (or other well known delivery vectors) in the recipient diutan-producing *Sphingomonas* is not necessary. It is routine to introduce additional copies of a DNA segment into the bacterial chromosome so that the segments are replicated each generation by the same mechanism that replicates the bacterial DNA. Alternative to or in conjunction with methods that increase the copy number of a DNA sequence, increased gene expression can be achieved by using stronger promoter elements.

The following terms shall be used throughout the specification in connection with the present invention and have the meaning indicated:

The term "*Sphingomonas*" is used throughout the specification to refer to strains of gram-negative bacteria from the genus *Sphingomonas*.

The term "inserted" is used throughout the specification to describe the process and outcome of transferring DNA into a *Sphingomonas* strain. Such isolated DNA can be introduced first into, as one non-limiting possibility, a desired plasmid (such as pLAFR3), by well-known techniques in the art, and then transferred, for example, by conjugation or mobilization into a recipient *Sphingomonas* bacterium.

The term "gene amplification" is used to refer to either increased copies of genes, for example, by cloning the target genes on a multicopy plasmid (such as from 4 to 10 copies) or by insertion of multiple copies (such as from 4 to 10) of the genes into the bacterial genome, or alternatively, increased expression of genes by modification of promoter elements to increase gene expression. Both of these methods and others can result in increased amounts of the encoded proteins.

The term "biosynthesis" is used throughout the specification to describe the biological production or synthesis of a sphingan by *Sphingomonas* bacteria.

Cloning of DNA in the present invention relies on general techniques and methods which have become standard in the art. It is noted that any number of methods can be used to clone DNA segments according to the present invention, and the present invention is not limited, for example, to the use of plasmid cloning vectors. For example, DNA fragments can be cloned by insertion into a bacteriophage vector. In certain embodiments of the present methods, cloned DNA sequences are introduced to a *Sphingomonas* strain via a plasmid or other delivery vector.

The term "ectopic promoter" is used to refer to a non-native promoter, i.e., a promoter with some sequence difference(s) relative to the native promoter. Such a promoter can be, for example, a strong promoter which drives a measurably increased level of transcription relative to the native promoter. An ectopic promoter can also be a regulated promoter, whereby gene expression is increased or decreased in response to some factor, such as a small molecule, temperature, presence of a gene product, etc. Suitable promoters for a particular use are well known in the art.

The term "genetic modification" is used throughout the specification to refer to a genetic change. Generally, a genetically modified organism, such as a *Sphingomonas* strain, is described with reference to a "parent" strain which does not contain the genetic modification. Exemplary genetic modifications include those that increase, decrease, or abolish the expression of a gene. Such changes include modification of chromosomal and extrachromosomal genetic material. Exemplary genetic modifications include introduction of a plasmid, deletion or substitution of a chromosomal sequence. For example, a chromosomal gene can be inactivated by a targeted deletion of part or all of the coding sequence and/or regulatory element (e.g., as described in ref. no. 20), or genetic screen, optionally including mutagenesis (e.g., as described in ref. no. 26). Chromosomal genetic modification can also involve a targeted replacement, e.g., to replace a native gene promoter with an inducible promoter, regulated promoter, strong promoter, etc. Chromosomal gene modification can also involve gene amplification, i.e., introduction of at least one additional copy of at least one gene. Extrachromosomal genetic material can be introduced, for example, on a plasmid, which can be single-copy, multi-copy, or high-copy, as is well known in the art. Genetic modification can be coupled to a selectable marker, such as an antibiotic resistance gene, which helps ensure that the genetic modification is retained.

The term "essentially free of PHB" is used throughout the specification to refer to a composition, such as a sphingan (e.g., diutan), having a greatly reduced PHB content when compared to a similar composition prepared from a wild-type or PHB-containing strain. Great reduction can be at least a 90% reduction, 95% reduction, 99% reduction, 99.5% reduction, etc. in PHB content (where PHB content is expressed as a fraction of the dry weight of the sphingan composition). Suitable assays for measuring PHB content include the 15% HCl solubility and residue test, HPLC, gas chromatography, and gas chromatography coupled to mass spectrometry (GC-MS). In certain embodiments of the present compositions, a clarified (e.g., cellulase clarified) diutan preparation that is essentially free of PHB can yield less than approximately 1%, such as less than approximately 0.5%, such as less than approximately 0.1%, residue in a 15% HCl solubility and residue test.

The term "PHB-deficient diutan" is used throughout the specification to refer to a diutan produced from a PHB-deficient strain, such as strain bearing a genetic modification inactivates the phaA gene, phaB gene, phaC gene, or any combination thereof.

The term "phaC gene" is used throughout the specification to refer to a phaC gene of a *Sphingomonas* strain. Examples of phaC gene sequences are provided in (ref. no. 20); however, other phaC gene orthologs are also encompassed except where the context indicates otherwise.

When an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed.

The term "a" or "an" as used herein means "one" or "one or more".

The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Where particular values are described in the application and claims, unless otherwise stated, the term "about" means within an acceptable error range for the particular value.

Unless otherwise indicated, all numbers expressing quantities of ingredients, properties such as molecular weight, reaction conditions, and so forth used in the specification and claims are to be understood as being modified in all instances by the term "about" Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Except wherein indicated otherwise, all measurements and protocols are conducted at standard temperature and pressure, i.e., approximately 20° C. and approximately 1 atmosphere. Except where indicated otherwise, "sea water 3 rpm viscosity," "sea water 0.3 rpm viscosity," and "low shear rate viscosity in the presence of polyethylene glycol" are measured as described in Example 2 below.

The invention will now be described in more detail with respect to the following, specific, non-limiting examples.

EXAMPLES

Example 1

Production of Diutan

This example described an increased yield of PHB-deficient diutan produced from several genetically modified *Sphingomonas* strains.

Methods

The plasmids pS8 and pX6 were transferred into PHB-deficient *Sphingomonas* strains PDD3 and PDD6 by triparental conjugal mating as described previously (ref. no. 3) and which is well known in the art. Strains PDD3, PDD6, 5657, and S657/pS8 are as described previously (ref. nos. 17, 18, and 20). Strains PDD3/pS8, PDD6/pS8, PDD3/pX6, PDD6/pX6, PDD3, PDD6, S657, and S657/pS8 were grown in 15 L volumes in 20 L Applikon fermentors with agitation and aeration. For the plasmid containing strains, the antibiotic tetracycline at 5 mg/L was added throughout the fermentation to ensure retention of the plasmid. KOH was added as needed to control pH. Two seed stages were used with 1% to 6% inoculum transfers. The fermentation media contained corn syrup as carbohydrate source, an assimilable nitrogen source, and salts.

At the end of the fermentation, each broth was treated by introduction of glucoamylase enzyme to hydrolyze any remaining oligosaccharides from the corn syrup. The viscosities of the fermentation broths were measured via a Brookfield® viscometer run at 60 rpm with a spindle #4. The diutan gums produced were then precipitated from an aliquot of broth with two volumes of isopropyl alcohol. The diutan fibers were collected on a filter and dried. For some strains, multiple replicates were prepared, and the results presented below are the average values across these replicates.

Results

The presence of a plasmid containing genes involved in diutan synthesis (pX6 or pS8, see FIG. 5) greatly improved the diutan production by PHB-deficient strains compared to the parent PHB-deficient strains PDD3 and PDD6. Diutan productivity of PHB-deficient strains was greatly improved by between 70% and 142% (FIG. 1 and Table 1B) relative to the parental strains. This increased productivity was much greater than for the wild-type (S657) strain with the introduced pS8 plasmid, which demonstrated increased productivity by only 33%. Three of the four PHB-deficient, plasmid-containing strains had higher productivity than the wild-type (S657) strain, and strain PDD3/pX6 had productivity essentially equal to S657/pS8. Diutan yield of PHB-deficient strains bearing these plasmids was also greatly improved by between 53% and 90% (FIG. 2 and Table 1B) relative to the parental strains. This increase was much greater than for the wild-type (S657) strain with the introduced pS8 plasmid, which only increased diutan yield by 18%.

Consistent with these results, the PHB-deficient strains also exhibited increases in final broth viscosity due to introduction of the plasmids, indicating greater diutan content. The PHB-deficient, plasmid-containing strains also had lower cell density (measured by $OD_{600}$) than the wild-type strain with or without plasmid pS8 (Table 1B), indicating that the unclarified products from these strains are expected to contain a higher proportion of diutan (due to the presence of fewer bacterial cells). Due to the higher purity of the diutan produced from PHB-deficient, plasmid containing strains (both due to lower cell content and absence of PHB), the extent of productivity and yield improvement in these strains compared to wild-type strains is likely to be even greater than these measurements indicate.

TABLE 1A

Final culture conditions.

| Strain | PHB | Replicates (n) | Final Cell Density ($OD_{600}$) | Final Broth Viscosity (cP) |
| --- | --- | --- | --- | --- |
| S657 (wild-type) | + | 2 | 8.22 | 3000 |
| S657/pS8 | + | 2 | 5.84 | 3775 |
| PDD3 | − | 1 | 3.80 | 3000 |
| PDD3/pX6 | − | 1 | 4.14 | 3650 |
| PDD3/pS8 | − | 3 | 3.50 | 4158 |
| PDD6 | − | 1 | 4.15 | 2500 |

TABLE 1A-continued

Final culture conditions.

| Strain | PHB | Replicates (n) | Final Cell Density (OD$_{600}$) | Final Broth Viscosity (cP) |
|---|---|---|---|---|
| PDD6/pX6 | − | 2 | 3.73 | 3125 |
| PDD6/pS8 | − | 3 | 3.74 | 3783 |

TABLE 1B

Diutan productivity and yield.

| Strain | PHB | Productivity (g/L/hr) | Percent Change Over S657 (wild-type) | Percent Change over PHB-deficient parent | Yield* (g/L) | Percent Change Over S657 (wild-type) | Percent Change over PHB-deficient parent |
|---|---|---|---|---|---|---|---|
| S657 (wild-type) | + | 0.153 | | | 17.5 | | |
| S657/pS8 | + | 0.203 | +33% | | 20.7 | +18% | |
| PDD3 | − | 0.082 | −46% | | 11.4 | −35% | |
| PDD3/pX6 | − | 0.197 | | +140% | 20.9 | | +83% |
| PDD3/pS8 | − | 0.177 | | +116% | 21.7 | | +90% |
| PDD6 | − | 0.067 | −56% | | 9.4 | −46% | |
| PDD6/pX6 | − | 0.114 | | +70% | 14.4 | | +53% |
| PDD6/pS8 | − | 0.162 | | +142% | 17.3 | | +84% |

*Total dry weight of unclarified precipitate (dry weight yield).

Example 2

Diutan Analysis

The diutan samples produced in the method of Example 1 were analyzed for uses as oilfield additives for oil recovery and for uses requiring good suspension and stabilization (such as for cement additives for water retention and quick set-up).

Methods

The oilfield industry relies on a "sea water viscosity" (SWV) test as an indicator of acceptable performance for rheology modifiers in oil recovery. This test indicates whether a rheology modifier can sufficiently increase viscosity in briny conditions of sea water, such as those encountered in seabed oil recovery. Typically, a sea water viscosity test employs synthetic seawater produced by mixing 419.53 grams of sea salt (ASTM D-1141-52) per 9800 grams of deionized water. For a seawater viscosity test, a rheology modifier is dispersed in synthetic seawater by vigorous mixing (e.g., 35 minutes at approximately 11,500 rpm in a Fann Multimixer (Model 9B5, part number N5020)). The sample is cooled to approximately 25° C. before the viscosity is measured. For a 3-rpm viscosity test, the sample is placed on the Fann sample platform (Fann model 35 A; Torsion spring MOC 34/35 F0.2b; Bob B1; Rotor R1) and the speed is adjusted to 3 rpm by turning the motor to low speed and setting the gearshift in the middle position. The reading is then allowed to stabilize, and the shear stress value is read from the dial and recorded as the SWV 3 rpm dial reading (DR). For the 0.3-rpm reading, a Brookfield viscometer is used (Brookfield LV DV-II or DV-III viscometer, with LV-2C spindle) to measure the viscosity. The speed of the spindle is set to 0.3 rpm, and the spindle is allowed to rotate at least 6 minutes before the viscosity is recorded as the SWV-0.3 rpm reading and expressed in centipoises (cP).

The LSRV test (a low shear rate viscosity using polyethylene glycol as dispersant as described below) is a general test for viscosity at a low shear rate. Typically, the higher the viscosity the better a sample is at stabilization and suspension. For example, in a cementitious application, a higher viscosity in the LSRV test indicates that a diutan should help suspend particulates in the cement more effectively, giving a more homogeneous cement/concrete, thus, providing better strength and durability. The LSRV test measures the viscosity of a 0.25% solution of biogum in Synthetic Tap Water (STW). STW is prepared by adding 10.0 grams NaCl and 1.47 grams CaCl$_2$.2H$_2$O to 10 liters of deionized water. For the viscosity measurement, 0.75 grams of biogum is added to 4.5 grams Polyethylene Glycol 200 (CAS 25322-68-3) in a 400-mL beaker and thoroughly dispersed. Then, 299 grams of STW are added to the beaker and mixed for approximately 4 hours using a low-pitched, propeller-style stirrer at 800±20 rpm. After the 4-hr mixing time, the beaker is placed in a 25° C. water bath and allowed to sit undisturbed for approximately 30 minutes. The viscosity is then measured using a Brookfield LV viscometer equipped with a 2.5+ torque spring (or equivalent instrument, such as Model DVE 2.5+) at 3 rpm using the LV 1 spindle after allowing the spindle to rotate for 3 minutes and expressed in centipoises (cP).

Results

The diutan samples produced in Example 1 above were analyzed to determine suitability for use in cement and oilfield applications (Table 2). Utility for stabilization and suspension, such as for cement additives for water retention and quick set-up, was evaluated by low shear rate viscosity (LSRV) testing. Suitability for oil recovery was evaluated using sea water viscosity (SWV) tests at 0.3 rpm and 3 rpm as an indicator of the effectiveness of a gum to increase viscosity in brines.

In the LSRV test, diutan produced from PHB-deficient strain PDD3 containing either plasmid performed better than or about equal to the wild-type strain bearing pS8, with greater improvement observed for PDD3/pX6 than for PDD3/pS8 (Table 2). In the SWV test at 0.3 rpm, diutan produced from plasmid-containing PHB-deficient strains derived from PDD3 performed better than wild-type strains bearing pS8. In the SWV test at 3 rpm, either PHB-deficient strain bearing pS8 performed essentially equally to the wild-type strains bearing pS8. Together, these results indicate that a PDD3/pS8 diutan is particularly suitable for oilfield applications and cement applications.

TABLE 2

Rheology of unclarified PHB-deficient diutan.

| Strain | PHB | Diutan Productivity | n | LSRV (centipoise) | n | SWV 0.3 rpm (centipoise) | n | SWV 3 rpm (dial reading) |
|---|---|---|---|---|---|---|---|---|
| S657 | + | ++ | 1 | 5110 | 2 | 37,400 | 2 | 40.0 |
| S657/pS8 | + | +++ | 1 | 6610 | 2 | 48,600 | 2 | 56.5 |
| PDD3 | − | + | 1 | 3160 | — | nt. | — | nt. |
| PDD3/pX6 | − | +++ | 1 | 6910 | 1 | 54,400 | 1 | 45.5 |
| PDD3/pS8 | − | +++ | 2 | 6198 | 3 | 51,867 | 2 | 57.0 |
| PDD6 | − | + | 1 | 3020 | — | nt. | — | nt. |
| PDD6/pX6 | − | +++ | 2 | 5188 | 2 | 41,600 | 1 | 43.0 |
| PDD6/pS8 | − | +++ | — | nt. | 1 | 38,400 | 1 | 57.0 | nt.: Not tested.

Example 3

Low Acid Residue of PHB-Deficient Diutan

Methods

The indicated strains were grown in 1000 gallon fermentors and in multiple Applikon® fermentors to prepare larger samples for testing and analysis. After the fermentations had finaled, the broths were either left untreated or enzyme clarified using one of two methods.

The first method, clarification with a cellulase, CELLUCLAST™ ("Clarified") was as follows: First, the broth temperature was adjusted to 50° C. Next, the pH was adjusted to between 5.0 and 5.4. CELLUCLAST™ enzyme (1 g/L) was then added, and the broth was incubated for two hours. Stock solutions of EDTA and Lysozyme in distilled water were then sequentially added to the broth to a final concentration of 0.25 g/L EDTA and 0.05 g/L Lysozyme, and the broth incubated for one hour. The pH was then adjusted to 8.0 to 8.5. Protex 6 L protease was then added to the broth at a final concentration of 0.5 g/L and the broth was incubated for two hours. Finally, the diutan gum was precipitated by addition of three volumes of isopropyl alcohol, dried, and milled.

The second enzyme clarification ("Treated") was similar to the first method, except the initial pH adjustment and the addition of CELLUCLAST™ enzyme were omitted.

Dried diutan samples were analyzed using the 15% HCl Solubility and Residue Test, as follows: 1.6 grams of a sample is rehydrated in 253 ml Synthetic Tap Water (typically 1 hr mixing at 1000 rpm). The mixing speed was then decreased to 500 RPM, and 147 mL of concentrated HCl (37%) is added to the rehydrated sample and mixed for 10 minutes. The sample container was then sealed and incubated at 150 degrees F. for twenty-four hours. The sample was again mixed, then a 100 gram aliquot was removed. The aliquot was quantitatively transferred to a Gelman filter apparatus containing a 0.5 micron filter. The filter was dried, cooled, and weighed prior to filtration and again after filtration. The weight of residue was reported as a percentage of the dry weight of polymer in the 100 gram aliquot (dry weight is determined by drying a sample of the same starting material).

Results

The acid residue test measures the amount of insoluble material that remains in a sample after acid hydrolysis. Low acid residue is preferred for certain uses, for example, an oilfield use in which the diutan is removed by acid hydrolysis and any insoluble residue has the potential to clog pores in the formation. This residue test also provides an indirect indication of the amount of PHB in a diutan preparation because the acid residue of a wild-type diutan is predominantly PHB. For a PHB-deficient diutan, the acid residue indicates an upper bound for the PHB content.

Results of the acid residue test are provided in Table 3, with residue indicated as a percentage of the starting sample material. Unlike the PHB-containing strains, which contained between 1.8 wt % and 6.8% wt % acid residue, the clarified PHB-deficient strain produced only 0.05 wt % acid residue. These results confirmed that the PHB-deficient strain produced diutan that would not damage an oilfield formation and, moreover, that the PHB-deficient diutan contains less than 0.05% PHB by weight.

TABLE 3

Low acid residue of clarified PHB-deficient diutan.

| Strain | PHB | Weight Percentage Residue |
| --- | --- | --- |
| S657/pS8 (Treated) | + | 1.80% |
| S657 (untreated) | + | 6.78% |
| S657/pS8 (untreated) | + | 2.98% |
| PDD3/pS8 (Clarified) | − | 0.05% |

Example 4

Confirmation that PHB is Absent from PHB-Deficient Diutan

Methods

The analytical method measured the PHB content of diutan preparations and can also be used to measure the PHB content of other polysaccharides. In this method, the diutan is digested with an aqueous hypochlorite solution leaving the PHB intact; the PHB polymer is then hydrolyzed, then esterified to the propyl ester; and finally, the resulting ester is measured by gas chromatography with flame ionization detection. The instrument used was the Hewlett Packard Model 6890 Gas Chromatograph System equipped with a HP model 7673 auto injector, flame ionization detector, and Hewlett Packard HP 5MS column (30 m×250 μm×0.25 μm nominal id).

The detailed protocol is as follows. Approximately 35-40 mg of each diutan sample was weighed into a glass centrifuge tube, in duplicate and the weight recorded to the nearest 0.1 mg. Approximately 5 mL of approximately 5% sodium hypochlorite (JT Baker Cat #4616 or equivalent) was then added to each tube and the tubes vortexed. Samples were then incubated at approximately 37° C. for 12-18 hours, resulting in hypochlorite digestion. Tubes were then centrifuged at approximately 8000 rpm for approximately 40 minutes, and the hypochlorite supernatants were removed with a disposable pipette and discarded. Samples were then washed twice by addition of 5 mL deionized water with centrifugation and supernatant removal as in the previous step. Samples were then evaporated to dryness under reduced pressure using a vacuum oven, optionally with heating to accelerate the drying process. 2.0 mL of internal standard solution (0.513 mg/mL propyl benzoate, Aldrich Cat #30,700-9 or equivalent, in 1,2-dichloroethane, Aldrich Cat #15,478-4 or equivalent) was then added to each dry sample, followed by 1.0 mL of 20% (vol/vol) HCl (EM Science Cat # HX0603P-1 or equivalent) in n-propanol (Aldrich Cat #29,328-8 or equivalent). Samples were then sealed with polytetrafluoroethylene film (Teflon tape or equivalent), capped tightly, and incubated at approximately 100° C. for 3 hours with vortexing approximately every 30 minutes. Samples were then cooled to room temperature. An aqueous extraction was then performed by addition of 2 mL deionized water to each tube, vortexing for 10-20 seconds, allowing the phases to separate, and removal of the aqueous (top) phase. The aqueous extraction was repeated a second time, then the organic (lower) phase was transferred to a GC vial. Calibration standards containing between 0.2 and 10.0 mg/ml sodium 3-hydroxybutyrate (ICN Biomedical Cat #100964 or equivalent) were also prepared by the same method starting with the step of evaporation to dryness, i.e., the sodium hypochlorite digestion was omitted. Each sample and calibration standard was then analyzed using the Hewlett Packard Model 6890 Gas Chromatograph System.

The Hewlett Packard Model 6890 Gas Chromatograph System was operated with the following parameters: Sample Inlet: GC; Injection Source: GC ALS; Mass Spectrometer: Disabled; OVEN: Initial temp.: 50 C (On); Maximum temp.: 325 C; Initial time: 2.00 min; Equilibration time: 0.50 min; Ramp #1 Rate 7.00, Final temp. 120 C, Final time 0.00; Ramp #2 Rate 18.00, Final temp., 280 C, Final time 2.00; Ramp #3 Rate 0.0 (Off); Post temp: 0 C; Post time: 0.00 min; Run time: 22.89 min; BACK INLET: Mode: Split; Initial temp: 275 C (On); Pressure: 12.96 psi (On); Split ratio: 10:1; Split flow: 11.0 mL/min; Total flow: 13.1 mL/min; Gas saver: On; Saver flow: 20.0 mL/min; Saver time: 2.00 min; Gas type: Helium; COLUMN 2; Capillary Column; Model Number: HP 19091S-433; HP-5MS 5% Phenyl Methyl Siloxane; Max temperature: 325 C; Nominal length: 30.0 m; Nominal diameter: 250.00 um; Nominal film thickness: 0.25 um; Mode: constant flow; Initial flow: 1.1 mL/min; Nominal init pressure: 12.97 psi; Average velocity: 27 cm/sec; Inlet: Back Inlet; Outlet: Back Detector; Outlet pressure: ambient; BACK DETECTOR (FID); Temperature: 280 C (On); Hydrogen flow: 40.0 mL/min (On); Air flow: 450.0 mL/min (On); Mode: Constant makeup flow; Makeup flow: 15.0 mL/min (On); Makeup Gas Type: Helium; Flame: On; Electrometer: On; Lit offset: 2.0; SIGNAL 1; Data rate: 20 Hz; Type: back detector; Save Data: On; Start Save Time: 4.00 min; Stop Save Time: 22.00 min; Zero: 0.0 (Off); Range: 0; Fast Peaks: Off; Attenuation: 0; POST RUN: Post Time: 0.00 min; Front Injector: No parameters specified; BACK INJECTOR: Sample Washes: 0; Sample Pumps: 2; Injection Volume: 1.0 microliters; Syringe Size: 10.0 microliters; Nanoliter Adapter: Off; PostInj Solvent A Washes: 5; PostInj Solvent B Washes: 5; Viscosity Delay: 0 seconds; Plunger Speed: Fast; PreInjection Dwell: 0.00 minutes; PostInjection Dwell: 0.00 minutes.

A standard curve was fitted to the calibration standards by linear regression analysis using multilevel calibration with internal standard, resulting in the equation:

$$y = mx + b$$

Where:

$$y = \frac{\text{Area } PHB}{\text{Area } Istd} = \text{Area ratio}$$

$$x = \frac{\text{Amount } PHB}{\text{Amount } Istd} = \text{Amount ratio}$$

$Istd$. is the internal standard $m$ = slope $b$ = y-intercept

PHB content of the samples was then calculated using the following equation:

$$\text{Amount } PHB = \frac{(\text{Area } PHB/\text{Area } Istd) - b}{m} \times \text{Amount } Istd$$

Results

The presence or absence of PHB was confirmed using gas chromatography (GC). Diutan samples from strain S657/pS8 contained an average of 4.0% PHB by weight (Table 4). In contrast, PHB was undetectable in four samples from each of two independent diutan preparations from strain PDD3/pS8 (Table 4). These results indicated that strain PDD3/pS8 produced diutan containing less than approximately 0.05% PHB by weight (the estimated detection limit of the method).

As discussed above, abolition of PHB production by deletion of the phaC gene resulted in severe metabolic deficiency, poor growth, and greatly impaired diutan productivity. These results provide further confirmation of the unexpected finding that the diutan productivity and yield of a phaC deletion strain can be greatly enhanced by introduction of a plasmid containing genes involved in diutan synthesis, even though PHB production has not been detectably restored.

TABLE 4

Confirmation of absence of PHB by Gas Chromatography.

| Strain | Sample Weight (mg) | Calculated PHB (mg) | Wt % PHB |
|---|---|---|---|
| S657/pS8 | 39.8 | 1.68 | 4.22 |
|  | 39.8 | 1.65 | 4.16 |
|  | 36.0 | 1.39 | 3.86 |
|  | 36.0 | 1.36 | 3.79 |
| PDD3/pS8 (Preparation #1) | 33.1 | n.d. | n.d. |
|  | 33.1 | n.d. | n.d. |
|  | 38.0 | n.d. | n.d. |
|  | 38.0 | n.d. | n.d. |
| PDD3/pS8 (Preparation #2) | 38.5 | n.d. | n.d. |
|  | 38.5 | n.d. | n.d. |
|  | 38.0 | n.d. | n.d. |
|  | 38.0 | n.d. | n.d. | n.d.: Not detected. The limit of detection was 0.05% by weight.

Example 5

Diutan Filterability for Enhanced Oil Recovery Applications

Methods

Diutan fermentation broths were clarified with cellulase and recovered as described in Example 3.

Filterability studies were performed on 0.04% diutan rehydrated in seawater. The diutan solution was passed through a 47 mm diameter NUCLEPORE™ filter (track-etched polycarbonate membranes having stringently controlled pore size, available from Whatman, Inc., Piscataway, N.J.) of the indicated pore size using a flow pressure of 20 psi. The time for each 200 ml of the diutan solution (1 or 2 liters total) to flow through the filter was measured with a graduated cylinder and a stop watch.

Results

In this example, the filterability of enzyme-clarified, rehydrated products from the PDD3/pS8 strain were compared to enzyme-clarified, rehydrated products from the 5657/pS8 strain. Enzyme-clarified diutan preparations were filtered through NUCLEPORE™ filters of the indicated sizes, and the volume filtered is shown as a function of time (FIGS. 3A-3B and 4A-4C). Clogging of filters is indicated by lines tending towards vertical on the graphs, showing that little additional volume was passing through the filter as time passed. Two preparations containing PHB made from strain S657/pS8 were poorly filterable, clogging filters of 5 microns (FIG. 3A) and 3 microns (FIG. 3B) before one liter could be filtered. In contrast, PHB-deficient diutan preparations made from strain PDD3/pS8 showed improved filterability. Two out of three preparations were filterable at 3 microns (FIG. 4A and FIG. 4C), while the third was filterable at 5 microns (FIG. 4B). Together, these results indicated that the PHB-deficient strains produced diutan with improved filterability.

Example 6

Description of Plasmids pS8 and pX6

The plasmids pS8 and pX6 are as previously described in U.S. Publication No. 2008/0319186. In brief, these plasmids were obtained by screening an ATCC 53159 genomic sequence library (in cosmid cloning vector pLAFR3) for clones able to restore polysaccharide production in the nonmucoid mutant (GPS2) of *S. elodea* ATCC 31461 or a nonmucoid mutant of *Xanthomonas campestris*. Plasmid inserts were end-sequenced and/or shotgun sequenced. A map showing the genes contained in complementing plasmids is shown in FIG. 5. The pS8 insert DNA sequence is provided as SEQ ID NO: 1 (FIG. 6), and the pX6 insert DNA sequence is provided as SEQ ID NO: 54 (FIG. 7). Predicted gene functions were designated based on homology to other genes in public databases. Genes contained in plasmid pS8 and pX6 and their predicted functions are listed in Tables 5 and 6, respectively. Pursuant to the Budapest Treaty for the International Recognition of the Deposit of Microorganisms, strains of *E. coli* containing plasmids pS8 and pX6 have been deposited with the Patent Depository at the American Type Culture Collection at 10801 University Boulevard, Manassas, Va. 20110, and are available as deposit numbers PTA-10102 (deposit date Jun. 2, 2009) and PTA-10103 (deposit date Jun. 2, 2009), respectively.

Plasmid pS8 contains the genes dpsS, dpsG, dpsR, dpsQ, dpsI, dpsK, dpsL, dpsJ, dpsF, dpsD, dpsC, dpsE, dpsM, dpsN, atrD, atrB, dpsB, rmlA, rmlC, rmlB, rmlD, and orf7. Plasmid pX6 contains the genes dpsJ, dpsF, dpsD, dpsC, dpsE, dpsM, dpsN, atrD, atrB, dpsB, rmlA, rmlC, rmlB, rmlD, orf7, orf6, and orf5. Based on their homology to known genes, many of the genes contained in these plasmids are predicted to be involved in diutan production. The genes in the genomic region from which plasmids pS8 and pX6 were derived (FIG. 5) include genes that encode the transferases for the four sugars of the diutan backbone and the four genes for dTDP-rhamnose synthesis. Genes for secretion of the polysaccharide, dpsD, dpsC, and dpsE, were identified based on homology to genes for biosynthesis of other polysaccharides. Two genes, atrB and atrD, encode proteins homologous to proteins involved in protein secretion. Two genes, dpsG and dpsR, putatively encode a polymerase and a lyase, respectively. Two genes, dpsM, and dpsN, encode polysaccharide attachment proteins. The insert in plasmid pX6 contained 17 genes including gene dpsB encoding transferase I (which initiates the first step in diutan synthesis), genes for secretion and four genes for dTDP-rhamnose synthesis, but lacks the genes for transferases II, III and IV and the putative genes for polymerase and lyase. Plasmid pS8 contains 20 genes of the dps gene cluster, including genes for all four backbone sugar transferases, the four genes for dTDP-rhamnose synthesis, and genes for secretion of the polysaccharide, including the putative genes for polymerase and lyase, but lacks the genes of unknown function, orf5, orf6, and orf7.

TABLE 5

Genes contained in plasmid pS8. Start and end coordinates are relative to the pS8 insert sequence contained in SEQ ID NO: 1.

| Start | End | Gene Name | Description | SEQ ID NO DNA | SEQ ID NO Amino Acid |
|---|---|---|---|---|---|
| 2* | 1054 | dpsS | (partial) homologous to gelS | 2 | 3 |
| 2738 | 1113 | dpsG | putative polymerase | 4 | 5 |
| 4895 | 2898 | dpsR | putative lyase | 6 | 7 |
| 5093 | 6031 | dpsQ | putative rhamnosyl transferase IV | 8 | 9 |
| 7082 | 6111 | dpsI | unknown | 10 | 11 |
| 7121 | 8167 | dpsK | beta-1,4-glucuronosyl transferase II | 12 | 13 |
| 8164 | 9030 | dpsL | glucosyl transferase III | 14 | 15 |
| 10467 | 9079 | dpsJ | unknown | 16 | 17 |
| 11076 | 12374 | dpsF | unknown | 18 | 19 |
| 12389 | 13306 | dpsD | polysaccharide export protein | 20 | 21 |
| 13341 | 14687 | dpsC | polysaccharide export protein | 22 | 23 |
| 14687 | 15394 | dpsE | polysaccharide export protein | 24 | 25 |
| 15405 | 16286 | dpsM | polysaccharide attachment | 26 | 27 |
| 16270 | 16968 | dpsN | polysaccharide attachment | 28 | 29 |
| 18454 | 17060 | atrD | secretion protein | 30 | 31 |
| 20637 | 18451 | atrB | secretion protein | 32 | 33 |
| 21229 | 22641 | dpsB | glucosyl-isoprenylphosphate transferase I | 34 | 35 |
| 22757 | 23635 | rmlA | glucose-1-phosphate thymidylyltransferase | 36 | 37 |
| 23632 | 24198 | rmlC | dTDP-6-deoxy-D-glucose-3-5-epimerase | 38 | 39 |
| 24202 | 25263 | rmlB | dTDP-D-glucose-4,6-dehydratase | 40 | 41 |
| 25263 | 26129 | rmlD | dTDP-6-deoxy-L-mannose-dehydrogenase | 42 | 43 |
| 26277 | 26146 | orf7 | (partial) unknown function | 44 | 45 |

*First in-frame codon; the start codon is not present.

TABLE 6

Genes contained in plasmid pX6. Start and end coordinates are relative to the pX6 insert sequence contained in SEQ ID NO: 54.

| Start | End | Gene Name | Description | SEQ ID NO DNA | SEQ ID NO Amino Acid |
|---|---|---|---|---|---|
| 1 | 336 | dpsL | (partial) glucosyl transferase III | 46 | 47 |
| 1773 | 385 | dpsJ | unknown | 16 | 17 |
| 2382 | 3680 | dpsF | unknown | 18 | 19 |
| 3695 | 4612 | dpsD | polysaccharide export protein | 20 | 21 |
| 4647 | 5993 | dpsC | polysaccharide export protein | 22 | 23 |
| 5993 | 6700 | dpsE | polysaccharide export protein | 24 | 25 |
| 6711 | 7592 | dpsM | polysaccharide attachment | 26 | 27 |
| 7576 | 8274 | dpsN | polysaccharide attachment | 28 | 29 |
| 9760 | 8366 | atrD | secretion protein | 30 | 31 |
| 11943 | 9757 | atrB | secretion protein | 32 | 33 |
| 12535 | 13947 | dpsB | glucosyl-isoprenylphosphate transferase I | 34 | 35 |
| 14063 | 14941 | rmlA | glucose-1-phosphate thymidylyltransferase | 36 | 37 |
| 14938 | 15504 | rmlC | dTDP-6-deoxy-D-glucose-3-5-epimerase | 38 | 39 |
| 15508 | 16569 | rmlB | dTDP-D-glucose-4,6-dehydratase | 40 | 41 |
| 16569 | 17435 | rmlD | dTDP-6-deoxy-L-mannose-dehydrogenase | 42 | 43 |

TABLE 6-continued

Genes contained in plasmid pX6. Start and end coordinates are relative to the pX6 insert sequence contained in SEQ ID NO: 54.

| Start | End | Gene Name | Description | SEQ ID NO | |
|---|---|---|---|---|---|
| | | | | DNA | Amino Acid |
| 18288 | 17452 | orf7 | unknown function | 48 | 49 |
| 19433 | 18618 | orf6 | unknown function | 50 | 51 |
| 19751 | 20683 | orf5 | unknown function | 52 | 53 |

REFERENCES

The entire disclosure of each patent, publication or other reference cited anywhere herein is hereby incorporated by reference in its entirety to the extent that they are not inconsistent with the disclosure herein.

Numbered citations in the text above refer to the list below.

Non-Patent Literature

1. Campana, S., J. Ganter, M. Milas, and M. Rinaudo. 1992. On the solution properties of bacterial polysaccharides of the gellan family. Carbohydr. Res. 231: 31-38.
2. Chowdhury, T. A., B. Lindberg, U. Lindquist, and J. Baird. 1987. Structural studies of an extracellular polysaccharide, S-657, elaborated by *Xanthomonas* ATCC 53159. Carbohydr. Res. 164: 117-122.
3. Coleman R. J., N. E. Harding, and Y. N. Patel. 2008. Identification and organization of genes for diutan polysaccharide synthesis from *Sphingomonas* sp. ATCC 53159. J. Ind. Microbiol. Biotechnol. 35: 263-274.
4. Diltz, S. and S. G. Zeller. 2001. Location of O-acetyl groups in S-657 using the reductive-cleavage method. Carbohydr. Res. 331: 265-270.
5. Harding, N. E., Y. N. Patel, and R. J. Coleman. 2004. Organization of Genes Required for Gellan Polysaccharide Biosynthesis in *Sphingomonas elodea* ATCC 31461 J. Ind. Microbiol. Biotechnol. 31: 70-82.
6. Kang, K. S. and D. J. Pettitt. 1993. Xanthan, gellan, welan, and rhamsan, p. 341-398. In R. L. Whistler and J. N. BeMiller (ed.), Industrial gums: polysaccharides and their derivatives, 3$^{rd}$ edition. Academic Press, Inc., New York.
7. Lee E. J. and R. Chandrasekaran. 1991. X-ray and computer modeling studies on gellan-related polymers: molecular structures of welan, S-657, and rhamsan. Carbohydr. Res. 214: 11-24.
8. Moorehouse, R. 1987. Structure/property relationships of a family of microbial polysaccharides, p. 187-206. In M. Yalpani (ed.), Industrial polysaccharides: genetic engineering. Structure/property relations and applications. Elsevier Science Publishers BV, Amsterdam.
9. Moreira, L. M., K. Hoffmann, H. Albano, A. Becker, K. Niehaus and I. Sa-Correia. 2004. The gellan gum biosynthetic genes gelC and gelE encode two separate polypeptides homologous to the activator and the kinase domains of tyrosine autokinases. J. Mol. Microbiol. Biotechnol. 8: 43-57
10. Pollock, T. J. 1993. Gellan-related polysaccharides and the genus *Sphingomonas*. J. Gen. Microbiology. 139: 1939-1945.
11. Pollock, T. J., W. VanWorkum, L. Thorne, M. J. Mikolajczak, M. Yamazaki, J. W. Kijne, and R. W. Armentrout. 1998. Assignment of biochemical functions to glycosyl transferase genes which are essential for biosynthesis of exopolysaccharides in *Sphingomonas* strain S88 and *Rhizobium leguminosarum*. J. Bacteriology. 180: 586-593.
12. Sa-Correia I., A. M. Fialho, P. Videira, L. M. Moreira, A. R. Marques and H. Albano. 2002. Gellan gum biosynthesis in *Sphingomonas paucimobilis* ATCC 31461: Genes, enzymes and exopolysaccharide production engineering. J. Ind. Microbiol. Biotechnol. 29: 170-176.
13. Thorne, L., M. J. Mikolajczak, R. W. Armentrout, and T. J. Pollock. 2000. Increasing the yield and viscosity of exopolysaccharides secreted by *Sphingomonas* by augmentation of chromosomal genes with multiple copies of cloned biosynthetic genes. J. Ind. Microbiol. Biotechnol. 25: 49-57.
14. Videira P., A. Fialho, R. A. Geremia, C. Breton and I. Sa-Correia. 2001. Biochemical characterization of the β-1,4-glucuronosyltransferase GelK in the gellan gum-producing strain *Sphingomonas paucimobilis* ATCC 31461. Biochem. J. 258: 457-464.
15. Yamazaki, M., L. Thorne, M. Mikolajczak, R. W. Armentrout, and T. J. Pollock. 1996. Linkage of genes essential for synthesis of a polysaccharide capsule in *Sphingomonas* strain S88. J. Bacteriology. 178: 2676-2687.

Patent Literature

16. Harding, N. E., Y. N. Patel, and R. J. Coleman. 2006. Targeted gene deletions for polysaccharide slime formers. U.S. Publication Number 2006/0199201.
17. Peik, J. A., S. M. Steenbergen, G. T. Veeder. 1992. Heteropolysaccharide S-657. U.S. Pat. No. 5,175,278.
18. Harding, N. E., Y. N. Patel, R. Coleman, and S. Matzke. 2008. High Viscosity Diutan Gums. U.S. Publication Number 2008/0319186.
19. Dial, H. D., C. B. Skaggs, and W. G. Rakitsky. 2000. Stable suspension of hydrocolloids. U.S. Pat. No. 6,221,152.
20. Bower; S., E. Burke, N. E. Harding, Y. N. Patel, J. C. Schneider, D. Meissner, N. A. Morrison, R. Bezanson. 2006. Mutant bacterial strains of the genus *sphingomonas* deficient in production of polyhydroxybutyrate and a process of clarification of sphingans and compositions thereof. U.S. Publication Number 2006/0121578.
21. Pollock, T. J., M. Yamazaki, L. Thorne, M. Mikolajczak, and R. W. Armentrout. 1998. DNA segments and methods for increasing polysaccharide production. U.S. Pat. No. 5,854,034.
22. Pollock, T. J., M. Yamazaki, L. Thorne, M. Mikolajczak, and R. W. Armentrout. 1999. DNA segments and methods for increasing polysaccharide production. U.S. Pat. No. 5,985,623.
23. Pollock, T. J., M. Yamazaki, L. Thorne, M. Mikolajczak, and R. W. Armentrout. 2001. DNA segments and methods for increasing polysaccharide production. U.S. Pat. No. 6,284,516.
24. Pollock, T. J. 2004. Production of modified polysaccharide S-7. U.S. Pat. No. 6,709,845.
25. Bower, S., E. Burke, N. E. Harding, Y. N. Patel, J. C. Schneider, D. Meissner, N. A. Morrison, and R. Bezanson. 2008. Mutant bacterial strains of the genus *sphingomonas* deficient in production of polyhydroxybutyrate and a process of clarification of sphingans and compositions thereof. U.S. Publication Number 2008/0268527.

26. Baird, J. K., and J. M. Cleary. 1994. *P. elodea* mutants are produced which produce gellan gum broth which contains no detectable amount of poly-β-hydroxy-butyrate (PHB). U.S. Pat. No. 5,300,429.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. A method of producing a sphingan essentially free from polyhydroxybutyrate (PHB), said method comprising, culturing a mutant strain of the genus *Sphingomonas* under conditions that facilitate production of the sphingan, wherein the mutant strain comprises: at least one genetic modification that substantially or entirely eliminates a production of polyhydroxybutyrate (PHB) and at least one genetic modification that results in increased production of a sphingan, wherein said genetic modification resulting in increased production of a sphingan comprises a genetic modification that increases the expression of at least one gene involved in sphingan synthesis, wherein said at least one gene involved in sphingan synthesis is selected from the group consisting of the genes contained in the plasmid contained in strain ATCC PTA-10102 and the plasmid contained in strain ATCC PTA-10103; whereby the mutant strain of the genus *Sphingomonas* produces an increased production of the sphingan that is essentially free of PHB relative to a congenic strain containing the at least one genetic modification that substantially or entirely eliminates the production of PHB and lacking the at least one genetic modification that results in increased production of a sphingan.

2. The method of claim 1, wherein the sphingan is selected from the group consisting of diutan, S-7, gellan, S-88, welan, rhamsan, S-198, NW-11, and alcalan.

3. The method of claim 1, wherein the sphingan is diutan.

4. The method of claim 1, wherein when the at least one gene involved in sphingan synthesis is selected from the genes contained in the plasmid contained in strain ATCC PTA-10102 then said at least one gene involved in sphingan synthesis is selected from the group consisting of *Sphingomonas* genes dpsS, dpsG, dpsR, dpsQ, dpsI, dpsK, dpsL, dpsJ, dpsF, dpsD, dpsC, dpsE, dpsM, dpsN, atrD, atrB, dpsB, rmlA, rmlC, rmlB, rmlD and orf7, and when the at least one gene involved in sphingan synthesis is selected from the genes contained in the plasmid contained in strain ATCC PTA-10103 then said at least one gene involved in sphingan synthesis is selected from the group consisting of *Sphingomonas* genes dpsJ, dpsF, dpsD, dpsC, dpsE, dpsM, dpsN, atrD, atrB, dpsB, rmlA, rmlC, rmlB, rmlD, orf7, orf6, and orf5.

5. The method of claim 1, wherein the at least one genetic modification that results in increased production of a sphingan is selected from the group consisting of: (i) an operable linkage of at least one gene involved in sphingan synthesis to an ectopic promoter; (ii) an increased number of copies per bacterial chromosome of at least one gene involved in sphingan synthesis; and (iii) any combination thereof, wherein each of said at least one gene involved in sphingan synthesis are contained in a bacterial chromosome or extrachromosomal element.

6. The method of claim 1, wherein the at least one genetic modification that substantially or entirely eliminates the production of PHB is a mutation that constitutively or conditionally inactivates or deletes a gene selected from the group consisting the phaA gene, the phaB gene, and the phaC gene or a combination thereof.

7. The method of claim 1, wherein the at least one genetic modification that substantially or entirely eliminates the production of PHB is an insertion or deletion that inactivates the phaC gene.

8. The method of claim 3, wherein the mutant strain of the genus *Sphingomonas* increases the rate of production or yield of diutan by at least about 50% relative to a congenic strain containing the at least one genetic modification that substantially or entirely eliminates the production of PHB and lacking the at least one genetic modification that results in increased production of diutan.

9. The method of claim 1, further comprising isolating the sphingan from the culture, wherein the sphingan produced from the mutant strain of the genus *Sphingomonas* is clarified to yield less than 0.5% residue in a 15% HCl solubility and residue test, or less than 0.1 wt % PHB when measured using gas chromatography.

10. The method of claim 3, wherein the mutant strain of the genus *Sphingomonas* is able to produce diutan at a rate of at least about 0.15 g/L/hr or a yield of diutan of at least about 12 g/L.

11. The method of claim 3, wherein the mutant strain of the genus *Sphingomonas* is able to produce diutan at a rate of at least about 0.2 g/L/hr or a yield of diutan of at least about 15 g/L.

12. The method of claim 3, further comprising isolating the diutan from the culture, and dehydrating the diutan, wherein when rehydrated as one liter of 0.04% diutan in seawater can pass through a polycarbonate membrane filter in less than five minutes at a flow pressure of approximately 20 psi; wherein the polycarbonate membrane filter is approximately 47 mm in diameter and has a pore size of approximately 3 microns.

13. The method of claim 3, further comprising isolating the diutan from the culture, and clarifying the diutan to exhibit a sea water 3 rpm viscosity of at least about 40 dial reading, a sea water 0.3 rpm viscosity of at least about 37,000 cp, or a low shear rate viscosity in the presence of polyethylene glycol dispersant of at least about 3,500 cp.

14. A method of producing a sphingan essentially free from polyhydroxybutyrate (PHB), said method comprising, culturing a mutant strain of the genus *Sphingomonas* under conditions that facilitate production of the sphingan, wherein the mutant strain comprises: at least one genetic modification that substantially or entirely eliminates a production of polyhydroxybutyrate (PHB) and at least one genetic modification that results in increased production of a sphingan, wherein said genetic modification resulting in increased production of a sphingan comprises a genetic modification that increases the expression of at least one gene involved in sphingan synthesis, wherein said at least one gene involved in sphingan synthesis is selected from the group consisting of the genes-contained in the insert in plasmids pS8 (SEQ ID NO: 1) and pX6 (SEQ ID NO: 54); whereby the mutant strain of the genus *Sphingomonas* produces an increased production of the sphingan that is essentially free of PHB relative to a congenic strain containing the at least one genetic modification that substantially or entirely eliminates the production of PHB and lacking the at least one genetic modification that results in increased production of a sphingan.

15. The method of claim 14, wherein the sphingan is selected from the group consisting of diutan, S-7, gellan, S-88, welan, rhamsan, S-198, NW-11, and alcalan.

16. The method of claim 14, wherein the sphingan is diutan.

17. The method of claim 14, wherein when the at least one gene involved in sphingan synthesis is selected from the genes contained in the plasmid contained in strain ATCC PTA-10102 then said at least one gene involved in sphingan synthesis is selected from the group consisting of *Sphingomonas* genes dpsS, dpsG, dpsR, dpsQ, dpsl, dpsK, dpsL, dpsJ, dpsF, dpsD, dpsC, dpsE, dpsM, dpsN, atrD, atrB, dpsB, rmlA, rmlC, rmlB, rmlD and orf7, and when the at least one gene involved in sphingan synthesis is selected from the genes contained in the plasmid contained in strain ATCC PTA-10103 then said at least one gene involved in sphingan synthesis is selected from the group consisting of *Sphingomonas* genes dpsJ, dpsF, dpsD, dpsC, dpsE, dpsM, dpsN, atrD, atrB, dpsB, rmlA, rmlC, rmlB, rmlD, orf7, orf6, and orf5.

18. The method of claim 14, wherein the at least one genetic modification that results in increased production of a sphingan is selected from the group consisting of: (i) an operable linkage of at least one gene involved in sphingan synthesis to an ectopic promoter; (ii) an increased number of copies per bacterial chromosome of at least one gene involved in sphingan synthesis; and (iii) any combination thereof, wherein each of said at least one gene involved in sphingan synthesis are contained in a bacterial chromosome or extrachromosomal element.

19. The method of claim 14, wherein the at least one genetic modification that substantially or entirely eliminates the production of PHB is a mutation that constitutively or conditionally inactivates or deletes a gene selected from the group consisting the phaA gene, the phaB gene, and the phaC gene or a combination thereof.

20. The method of claim 14, wherein the at least one genetic modification that substantially or entirely eliminates the production of PHB is an insertion or deletion that inactivates the phaC gene.

21. The method of claim 16, wherein the mutant strain of the genus *Sphingomonas* is able to produce diutan at a rate of at least about 0.15 g/L/hr or a yield of diutan of at least about 12 g/L.

22. The method of claim 16, wherein the mutant strain of the genus *Sphingomonas* is able to produce diutan at a rate of at least about 0.2 g/L/hr or a yield of diutan of at least about 15 g/L.

23. The method of claim 16, wherein the mutant strain of the genus *Sphingomonas* increases the rate of production or yield of diutan by at least about 50% relative to a congenic strain containing the at least one genetic modification that substantially or entirely eliminates the production of PHB and lacking the at least one genetic modification that results in increased production of diutan.

24. The method of claim 16, further comprising isolating the sphingan from the culture, wherein the sphingan produced from the mutant strain of the genus *Sphingomonas* is clarified to yield less than 0.5% residue in a 15% HCl solubility and residue test, or less than 0.1 wt % PHB when measured using gas chromatography.

25. The method of claim 16, further comprising isolating the diutan from the culture, and dehydrating the diutan, wherein when rehydrated as one liter of 0.04% diutan in seawater can pass through a polycarbonate membrane filter in less than five minutes at a flow pressure of approximately 20 psi; wherein the polycarbonate membrane filter is approximately 47 mm in diameter and has a pore size of approximately 3 microns.

26. The method of claim 16, further comprising isolating the diutan from the culture, and clarifying the diutan to exhibit a sea water 3 rpm viscosity of at least about 40 dial reading, a sea water 0.3 rpm viscosity of at least about 37,000 cp, or a low shear rate viscosity in the presence of polyethylene glycol dispersant of at least about 3,500 cp.

* * * * *

SEQUENCE LISTING

```
<160> NUMBER OF SEQ ID NOS: 54

<210> SEQ ID NO 1
<211> LENGTH: 26278
<212> TYPE: DNA
<213> ORGANISM: Sphingomonas sp. ATCC53159

<400> SEQUENCE: 1
gatcaacggc gccttgctcg gacggcacaa attcgtcctg gtcaatgtgt ccacggtcgc      60
ctcttcgata ctgttccagc tgttcccgct tgtcgtcgcc tggatgatcg gcccggacct     120
gcgaacgctg ctgatcgccg cgctcgttgg ccgggcggtt ccgatgatcg gcatgctgcc     180
cgcgctgtat cgaaaccttt tgcgcggcaa cacgccgcgt tttcacgcca gcgaggcgcg     240
cttcctgata ggctatggcg ggtgggcctc gctcacgacc gtggtagcga ccgtgctcat     300
gatggcggac cgcttcctga ttggcgcact tcttgggccc gtcgccgtga ccatctacac     360 ggccccctg caactcgcac agcgcgtatc gctgctgccc tccgcactgt ccgccgcgct     420
gttcccgcgc ctgcccagcg cgacgccggc ggagcgcatg gcgcttcaga tccgctcgct     480
gtcgctgatc atgggcggcc ttaccgggat gatcggcggc ggactattgc tggccgcgcc     540
gtttctcgat ctctggatcg gcaagtcgct cggccatgcg ggaacgccgg tcgcgctctt     600
cctgttcttc ggcgcatggt ggaatgcgct ggcgatcatt tcgttcagcg gcctgcaggc     660
gagcggacgg ccgaaagcga gcgcgatcgt ccagggggca gagctgctac ccgtgttgat     720
cgcgctgtat gcagggatcc gatggggcgg cgtgaccggc gccgcagcgg tctttctggg     780
acgctccgcc ctggatttcg tcctgttgac ctggcaggca ggcctgctcc gccagacggt     840
gaagcaagta tccgtatgcg gcgccgttct caccgtcgcg atgctcgtgg gcgcgaccta     900
tcgctattcg gtgccgctct ggtgcgtact cagcgcctgc tgcctggtcg cgctggcagc     960
ctgctcctgg tggacattgg cgcgccagga caaggcactg ctgattggac gattgagccg    1020
aattctacca aagcagcggc aactcgacct atagcctttc cgcaatgcac cgatggacca    1080
caccaacccg ttttaattga cacacacaaa tgctacaccg acaaagacac aggccgagag    1140
cgatatagaa gcgctatgcc tagccccagc gtcataaaga tgaacgggtc attgtcacct    1200
tgcgacagga ctgaccgcgt atttaaaaga acagccagga aagttgctac ggcgagctca    1260
agcgggtagc catctccgct catcttaaga ccacgaaacg cgagcaaaat cattaacgta    1320
atcatcgtgc cgtatagcga aacaaaaccc agcaagccgt aatcagccgc tacgacagg     1380 aaaccactgt cgatcgatag gaagccttgc tgattacgcc acccgacagc gccagcaccc    1440
tctcccgggc catagccgaa gaaagggcgg cgagcgatgg caggcacgcc caagcgaaac    1500
tgctcctgcc tgccttgatt gctaagttga gaagcgcctc caccgagaac acggttgtgg    1560
acggcaggca cgaacatgac cgccagcgac agcgccacca tcaaggcggg atacgtcaac    1620
gtcagcgaaa tgccgacaag cccgcccttt gtggtccgcc accgccgaat tgcccaaata    1680
agcaaataca cggtatgcgc caccaatccc cccaccattg ccagtcgaga accgctaaga    1740
```

```
aatccggacg caactacaag aaaatcgaag aaaatccaaa atgccaatct ccctacgcca      1800
cgggaattcg ctatacggtg cagcacgaaa ggaatcgtca aagccgtcaa ctctccccag      1860
acaagcggac tgctgaaagt cgtcaaaacg cggtaagtac cccggaaacc gggcgtaagc      1920
actacggtaa gaaactgctc atcaacgcgc aggaagctcg gaatcgagta ggcccagagg      1980
acgtgcttca cccggaactc cagcacgcca atcgccatca gcacgcccac gcaccaaaac      2040
aagcgcgtaa cccaccactc cggggtgcgc gtgtcggtcc cgatcagcca tagcgagatg      2100
aatgccatcg gcgtcaccgt cagaacgatg ccaatcaacc gcggaattgt ttgcgaggcc      2160
gctggggtcg caatggaggc gacgatctgg accataatga aggcaagcaa tagtcgcgat      2220
gggatcggcg ccgcccgcat aatcgccgcc atctcggatc gaaacttttt cgagaccgaa      2280
agcgagatca tgagcgtgag caatgcgatc gaaccgatca tccgcctgat cgagatccaa      2340
ggcaaaccac caacgctgag cgcaagatag ttcggccaca cgagcgccgc caccatatag      2400
gcgaggtata gttttgccag caggcgagta ggcgcctgcc gcgcctcggg tagcgcccag      2460
atcactacga gcgccatcag aacgaggggc acggccggga tcgccagcat ctggagcggc      2520
agaactgcgg cgagcaggcc gtagactgcg gcaagaaaca tcacgctgac cagcagaacg      2580
gtacgccgcg ccgcgatcgt cacgcctgat cgctcggctt tgtagacggg cagtaccggg      2640
atcgctggct ttgtcagaaa ccgaaccagt cgcaacctgc gaagccgctg catcgctccg      2700
tggaaggccg ggcgacgaaa cgccgaggta gtcgtcatct gcaagtcccc aacaagtccc      2760
caagaggcgc tgccgctcgc atgatcgaag ggttcgcgaa aagcaaggtc gatacgccgc      2820
actccctgcg atgtgccgcc ggatcgcagg agggcacggg cggcgccggc gcaaggccgc      2880
tcaccgcccg ccccgctca ggcgcggtac aggttgtact gatccgccgt agcgctcagt      2940
gtcgccgcgc tgcggattgc gcccatcgcc ccgcggtca tcatgtcgac accgatcttg      3000
ctgacgagcg cgatctgcga ggacgcggca gtacctatag acagcgtact gcccaccgtg      3060
gccaccgtcg caagcggcgt tgccgtgcta gcggcgccgg cacccgccag cagcgcagcg      3120
gcctgcgcgg ccgcgccggt gacgaggctg tccttgaccg tcgccgccgc gctggcgctc      3180
gacgcggtca ccagcgcctg cacctgggcg gcgctgatcg cgccatcgcg gatctcgatg      3240
tcgccgaccg ttccgctgaa tgcggtcgag aacgggctgc cgacatacag cccccaggat      3300
tcggcgggcc gggtcgtgcc ggtcatcgtc gctgtgccgc gttgcatgcc gtctacgtac      3360
agaatcgcgg ttttccgcgt gctgtcgtag gtcagggcga tcttgtgtgt ggcagcatca      3420
agcagcttgg cgccgctcgt caccattgtc tggctgacgc ccgcggcgtt gcgcatggtg      3480
aagctcagtt ccccattggc ctgcagcgaa accgaccagc tctggaagat gccaagaatt      3540
tgcccggccg tggccgtagc cgagtcccgc ttgaggtcga agctgagcgt gaacgccgac      3600
aatgcgtaaa tctgccgcga atagctccgg tttagttcca cccccgtgcc cgtcgagacg      3660
tggaaggcgc tgcccacgac cgccgacacg tccaccgcct ttgtcgtctg gccggtattc      3720
cagtgcgaaa ggtccacgac gccgctgttg ctgaacgaca gatcgagcag cagcgacgga      3780
tttgccgcct tcgcagtcga cagttcggta gtcacctgag cggcagcagc gctcgacacg      3840
ggcggctggt acccgacgcc gggaacgatc aaatcgctga gccgcgccgt agccccatcg      3900
ttgaggccat agatcttgcg gatcgttgcc gagtcactcg tcagcgtacg attgcctgtc      3960
tgcacgatat tgctcgagga gcttgtgacg gtgatcaggt ccgcaacatt gttcttgatc      4020
gtcgcgccat tggttttgtc gaggcgaatc caaaatgatg tgccatccac ttgcgatatc      4080
acgctattgg attcgatatt gacattaacg ccgttaacaa cgttgatacc gtggtaataa      4140
```

```
ccattcagat agataagatt gtttttgatg tttacattga catagggaag attaccggcc    4200
tcgtcattca tgaaaatccc ttgcgcgcca gagcccgcgc cctgcatgat gacgttattg    4260
gagatggtga tgttggtatt gcccttgacc ttgcccgccg tgaagaactg aatggcgtcg    4320
ggatgttcgg tgcccacggg aaacaggttc gtgaacgaat ttccgtcgat gacaagattg    4380
ttcatctcag tgaagttcgt atgatcgcgc cggttgtcgt ggaagctgct gttctggacc    4440
accatgccat cgacgttgta ggcctcaagg cccagaccga agtggtcgat agacgaattc    4500
tgcatcgtca ccgacgtgct gttgcgcacg aacaagcccg ccccttcga gagcgaaggg    4560 tcaccagtgc cgccgctgaa ccgcacgccg tccaaaacga tgttggccga accctggatc    4620
gtattcagtc gattccagtc atcggcgggc ttgtaatcgg tcgcagcgac catgtttttg    4680
acggtaacgt tgctactgtt cccgatcacc agcttttgga tattgaccgg gttcgacgag    4740
tcgagcgact caattgtcac catgctggta acgtcttgg tcattacagt gagatctgtg    4800
tagaccccgg cggcaagctt gatggtttcg ccacccttcg ccgccgcgat tgcagcattc    4860
aactccgtct gattcttgac aatgatatcc ggcatgttga cttacccgt acgcacgaac    4920 ccgggccgat attgaccctt ccattgtcat aaataccaga acagccatga aatttgctcg    4980
aagggataca gttaagaact cccttctacg gggccgcatg ccgggcccat gcacgcccga    5040
ctttcgccgg caccgtctcg acggcgcaac acagtgcagc tactagggtg cgatgcagat    5100
gctcccaacg cccgatgtca gcatactcgt ggtcgctttc aactcgaccg agtatatcga    5160
agactgcctg cgcggcatcg ccgaaggagc gggcaagacc ccccacgaag ttctgctgat    5220
cgacaatggc gacgggcgaa ccgaagcgct ggtccggcag cggttccacc acgtccgcat    5280
cgttcccagt gagggcaata ttggtttcgg ggccggcaat aatcgcctgg cagcgcaggc    5340
tgccggcccg ctcctgctgc tcgtcaaccc cgatgccatt cccagcccg cgcaatcga    5400 tcagttggtc acctttgcca aacagcatcc cgaggcggcg catggggcg ccgttccta    5460 ctcgcccagc ggcgatctag aacccgcaaa tttcatgtcc ctgccgacgc ccgccgactt    5520
tctgacggcg attttcaacg cgcgtgcgct acgcagcggc gggctgcaag aaggcgcgac    5580
cacccccgga gcggtcgagg tgttgaatgg cggcttcatg atggtacgca ccgatgtctg    5640
gcaggcgatc ggcggttttg acgagagctt ttttctttat tcggaagaga tcgatctctt    5700
ccagcgaatc cgcacgttgg ggcacaaggt gctcgtcgac ccctcggtca aagtggtaca    5760
caatacgggg agtggtcagt cgatgtccca gaaccgcctg atgtatctca cgaccgggcg    5820
catgcactat gcgcgaaagc attttggcgc actcggcacc cttgccaccg ggtgcgcgct    5880
ttggctgatc gccgccaaat acacgttggt cggggcggca ctctggcgcc tgtcgccgcg    5940
gacgggcacg cgatacaaag agctgagcaa cgggtggcgt gccgtattta gcaatcctgg    6000
ccgatggtgg agcggctatc cgcgtcgcta aaagtccagc tcccccccc ctaaaggcgc    6060 cgttgggagg cggacgcatc gttgcaacaa cgcgcccgcc tttcagacct tcagttcccc    6120
gccggcgttg cgccgctgcc gcgaagctgc ggcggtgcgc tgtagccggc ctgatatttc    6180
acggtttccc gcgccttctt caggcggtcg ttgagctgtg cgtcagccgc cttgccgaag    6240
cgctcggtac gcagcccgct gagcgcgatc tcgcgcgcct ggtcggccgg caccggcagc    6300
accgtggtcg acgtgatgat attgcgggtc agtccctgct gggtcggcag gatgaacatc    6360
tcctgtgccg gcagcgacgc gatcttggca gcgatttccg gcggcagcgc agcggtgtcg    6420
atctgcgacg gcgcgcgacg gaactggaca ttgtccgccg agagcttggc ggttagctgg    6480
```

```
tccagcgtct tcagcggcgc gaattgcttg agctttgcgg ccgagctcgg cggagcgaag      6540
acgacctgat cgatcgcgta gatcttgcgc tgcgcgaacc gctccggatg cgcggcctga      6600
tatttctcga tctcggcatc ggtcggctgg gcgatgccgc cggcgatctt gtcgcgcagc      6660
atggcggtga ggatcagctc gtcggcccgg cgctcctgga tcaggaaggc aggcgtcttg      6720
tccagcttct gctcgcgggc gaccttggcg aggatcttgc gctcgatgat gcgctgcagc      6780
gccagctgct cggccagctt gcgatcggtc cccggggta cctgggaggc ctgcagttcg       6840
gcattcagct cgaagacggt gatttcttcg ccatcgacgc tggcgaccac ctgccccttg      6900
tcgagcttgc cgcccttgcc gccacatccg gagacggcca cgcggccgc agccaccgcc       6960 gtaaccaggt acaatttctt catgaagacc tccccgccgg cacggaattg cgcacggcac      7020
aaacttctac ttgaacctat tcggacgggc gggcatccgc aatagcgttg gcagtgcagc      7080
atggttctaa gcggagccag gcggcaacaa gggggacgag atggcagaag cgaacgcggt      7140
agatggaaag gcctccaagc cgctgaaaat gtgccttgca gcgtcgggcg gcggccatct      7200
ccggcaaatc ctcgatctgg aatcggtgtg gcgcgaacac gattatttct tcgttactga      7260
agataccgcg ctcggccgga gccttgccga aaacatccc gtcgaactgg tggagcacta       7320
tgcgctcggc caggccaagc tgggccatcc cttgcgcatg ctgggcggcg catggcgcaa      7380
cctgcgccag agccttcga tcctgcgccg gcacaagccg gatgtggtga tttccaccgg       7440
cgcgggcgca gtctatttca ccgcgctgct cgccaaactg tcgggcgcca agttcgtcca      7500
tatcgaaagc ttcgcgcgct tcgaccaccc gtctgccttc ggcaagatgg tgaagggcat      7560
cgcgacggtg acgatcgtcc agtcggcggc gctgaaagaa acctggcctg atgccgagct      7620
gttcgatccg ttccgcctgc tcgatacacc gcgcccgccc aagcaggcgc taatcttcgc      7680
gacggtcggc gccaccctgc ccttcccgcg gctggtgcag gcagtgctcg acctgaagcg      7740
cgccggcggg ctgccgggca agctgatcct gcaatatggc gaccaggacc tgcccgatcc      7800
cggcatcccc gacgtcgaga tccgccgtac catcccgttc gacgatctgc agctgctgct      7860
gcgcgatgcg gatatggtga tatgccacgg cggcaccgga tcgctggtca cggcgctgcg      7920
cgccggctgc cgggtcgtcg ccttttccgcg ccgccacgat ctgggcgagc attatgacga     7980
tcaccaggaa gagatcgccc agaccttcgc cgaccggggc ctgctccagg cggtgcgcga      8040
cgagcgccag ctcggcgccg ctgtggaagc ggccaaggca accgagccgc agctggcgac      8100
caccgaccac acggccctcg cggcgcggct gcgccagctg ctggcgcagt ggagtgccaa      8160
gcgatgagca cgccccggat cagcgtcgtc atcccgcact ataacgatcc gcaatccttg      8220
cggctctgcc tggatgcgct ggagcggcag acgatcggtc gcgacgcgtt cgagatcatc      8280
gtcggcgaca acaattcgcc ctgtgggctc gcggcggtgg aggcggcggt cgccggacgt      8340
gcgcggatcg tgaccattct ggaaaagggg gcgggccccg cgcgcaacgg ggcggcagcc      8400
gcagcgcgtg gcgagatcct cgcctttacc gacagtgact gcgtggtgga gcccggctgg      8460
ctggcgggcg gcacgaccag ggtcgcgcct ggccgtttca tcggcgggca catgtatgtg      8520
cgcaagcccg aagggccgcc gaacggcgcc gaggcgctgg agatggcgct ggcgttcgac      8580
aatgaaggct atgtgcggcg cacccagttc acggtcaccg caaacctgtt cgtgatcgcg      8640
gccgatttcg aacgggtcgg cggcttccgc gttggcgtgt ccgaggatct ggaatggtgc      8700 caccggggcga tcgccagcgg cctcaccatc aactatgcac cggatgcatc ggtgggccac      8760 ccgcccggc ccgactggtc ggccctgctg gtgaagacgc ggcgcatcca gcgcgaactc       8820
tatctgttca acatcgagcg gccgaagggc aggctgcgct ggctggtccg ttccgtggcg      8880
```

```
caaccggcga tgatcccaca ggacgtggcc aagatcctgc gcacaccggg taccaagggc    8940
gcgcgcctcg ctgcggtcac cacgctggtc cggctgcggc tgtggcgcgg cggcgccggc    9000
ttgttgcagt tgctcggccg cgacatctga tcgaccggcg atcggccgac gagcgcgtcg    9060
ccggccgatc gcattgcatc agacggtggc cagcgcgtct tccagcgtgc cgctgtcgag    9120
ccgcaggcgg ccgatcatca gccacagata gaccggcagc gtatcgtcgg tgaagcggaa    9180
gcggcaatcg ccgtcctgcg tttcggattc gaggccgagt tgaccggtga gctcgcccag    9240
ctcctgctcg acctgcgccg ccgtgatgtg cgcgcccggc agcagatcca ccacggcttg    9300
gccgctgaac cagccatccg ccgagcgcga ggcctcgccc agcgccgcga cgagtggatc    9360
gtagcggccg ccgacgaact tgcgcatctc gatcaccgcg cgcggcggca tgcggccctc    9420
gatctcaagg atcgcctggt cgagcgcacg acgcagatgc ccggcgtcga ccgtgaggcg    9480
gccctggtcc agggcttcca gcgcggaatg gtggcacagc agccgcgcga aatagggcga    9540
ccccagcgcg agcaggtgga tcatgtgagt caggtccgga tcgaagcgaa cgcccgaggc    9600
ggtttcgccg agcgcgatca tctcctgcac ctccgattcc tccagccggg gcatcggcag    9660
gccgatgacg ttgcggcgga tcgacggcgc ataaccgatc agctcctgca ggttcgaggc    9720
gacgcccgcg atcaccagct ggacgcgcgc cgaacggtcc gacaggttct tgatcagctc    9780
ggcgacctgc tgacggaagg cggaatcgct gacgcgatca tattcgtcga ggatgatcag    9840
cacgcgtgtg cccgtgatgt cggcgcacag gtcggccagt tcgccgggcc cgaagctgcc    9900
cgtcggcagg cggtcggcca agttgccgcc gctctccgcc tcgccggcgt tgggcgccac    9960
gccgcgatgg aacagcagcg gcacgtcttc cagcacggcg cggaagacat cgctgaaatt    10020
cgcgttcgca ccgcaggtcg catagctgac gatatagctg gattcgcggg cgacatcggt    10080
cagcacgtgg agcagcgagg tcttgccgat gccgcgctcg ccatagagca cgacatggct    10140
gcgctggctc tcgatcgagg agattaggcg cgccagcacg ccgaggcgcc cggcgaagct    10200
cgaccgatcg gccaccggct gggtgggtgt gaagaaggtc gccagcgcga accgggcgcg    10260
cgtgatctcg cggcgctcgt cgcggcggcg atccagcggg cggtccagcg cggaggcacg    10320
gaaggttggg aaatccgggc gaccacggcc gctatgggca tcgcgatgcg gcaccactgt    10380
cgcagtcagc gggaaatagc cctcttcttc aggttcttct cgacggccga acggccacaa    10440
gaatctcagc gcggaaccta cagccactcg aacacctctt aaattcgtgc gccatcggca    10500
ccgacggcgc accctggttc gcgccccctg gcgcccccctc ctaacgaacc cacgccttgc    10560
ctggcctatc ggcgcttgaa gaactcgtac ggtttgatca ccaaggcgat gtacgccagg    10620
accagagcga tcgtcaaaat tgcaaagacg tgataattct cattgcccag ataattggcg    10680
acggcgcaac cgactgcggg cggcaaatag ctgatcatcg tgtcccggac tgccgaatcg    10740
gcttgggacc gttgcaggaa tataacgatc aggccggcaa atatcgcgat ggtgacccaa    10800
tcatagggcg tctgcatgca tgtccttcct attcgacacc ggaatcgaac catttccggc    10860
gacgctattg cacgcactag cagtgcgcgc ggccgctcgc taggtagcgc cgcaccggat    10920
aaaccgacgt taagatggcg cggctcgatc gaaatggagt caaacgggct tgcccggccg    10980
accgaagcat ggcgccatgg cgcatgcacc gtattgtgac cacgcaaacc gcgagggtca    11040
ttcgatgcgg ttgcttgtac aggaggccat tgataatgaa gccgagaccc ggggggaacct    11100
ttatgcaagt aaatttcaat cgacaggctc gcaagctcgg tgccggcaat gcgctcgcgc    11160
ggggggggcc cgtgcttgcg ctgcttgcga ccgcggcatg gacacaacct gcgctggcgc    11220
```

```
agcgacaggc atttgagtcc cgcccctccg gtagcgagcg acaggtcgat attcgcgcga    11280
cggggtcgct ggaatatgac gacaacgtcg tgctgaacga ccagcggatc acggacggcg    11340
cgcgtggcga tgtgatcgca tcgcccgggc tggacgtgac cctagttctg ccccgcgcca    11400 ccggcagct ctacctcacc ggcaatgtcg gatatcgctt ttacaagcga tataccaact    11460
ttaaccgcga gcagatctcg ctcaccggcg gcgcagatca gcggttcgcc tcctgcgtcg    11520
tgcacgggga agtcggctat cagcgccacc tcaccgacct gtccagcatc ttgatccagg    11580
acaccacgcc tgcgctcaac aacaccgaag aggcccggca gtacaccgcg gatatcggct    11640
gcggcgcgac ctacgcctg cggcctgccg tttcctacac ccgcaacgaa gtgcgcaaca    11700
gccttgccga gcgccgatac gcggactcga ataccaacac ctttaccgca cagcttggcc    11760
tgacttcgcc tgccctgggg accgtggcgg tatttgggcg tatgtccgac agcagctatg    11820
tccatcgcgt ccttcccggc attaccggcc aggacgggat gaagagctac gcggccggcg    11880
tccagctcga gcgctcggtg gccaaccgac tccatttcaa cggctcggtg aattacaccg    11940
aggttgaccc aaagctcgca tccaccaaag gattcaaggg cgtaggattt aacgtttccg    12000
gcgattatgc tggtgatcag tacagcctcc aattgctggc ttcacgatcg ccccagcctt    12060
cacttcttct gttcgtgggt tacgagattg tgacagcggt ttcggcgaat gcgacgcgcc    12120
ggctgagcga tcgcattcag atatcgctgc aaggcagccg aacctggcgc gagctcgcgt    12180
cttcgcggct gctcaccaac gtgccgattt ccggcaacga caacacctcg acgttgttcg    12240
cctccgctac cttccggccg aatcgccggc tgagctttgt gctgggtgcc ggccttcagc    12300
ggcgcaccag caacacgcag ctatacagtt acagctccaa acgcatcaat ctctcgacgt    12360
cgctttcgct ctgacaaggg ccgtaatcat gcatatcaag aatcgcttcg tgaatatctc    12420
gacgttggcc atcgccgccg cgctggccac gccggcggcg gcgcagatcc ccacgcggtc    12480
cgtgcccgcg ccggcccgcc cgcggcctgc aacgccgccg gcgcaacagc agaaccaggc    12540
gccgtcgacg cccgcagcgg caaccccggc gcagaccgcc gcaaccgttg ccccctgcagc    12600 aaccgcaccc gcaggttaca aaatcggcgt ggacgacgtg atcgaggccg acgtgctcgg    12660
ccagaccgac ttcaagacgc gcgcccgtgt gcaggcggac ggcacggtga ccctgcccta    12720
tctgggcgcc gtgcaggtca agggcgagac cgcgacctcg ctcgccgaaa agctggccgg    12780
gctgctgcgc gccggcggct attatgccaa gccgatcgtc agcgtcgaaa tcgtcggttt    12840
cgtcagcaac tatgtgacgg tgctgggcca ggtgaacagt tccggcctgc agccggtcga    12900
ccgcggctat cacgttcgg agatcatcgc ccgtgccggc ggcctgcgcc ccgaagcggc    12960
cgatttcgtc gttctcaccc cgcccgatgg ctccagcgcc aagctggact acaagaagct    13020
cgcccaaggt ggccccaatg acgatccgat ggtgacgccc ggggacaagg tctttgtccc    13080
ggaagtcgag catttctaca tttatggtca aattaacgcg cctggcgtat acgcgattcg    13140
atcggacatg acgctccgtc gcgcgctggc ccagggcggt gggcttgccc ccgcaggctc    13200
cgtcaagcgt gtgaaggtca cgcgggatgg caatgaactc aagttgaagc tggacgatcc    13260
gattctccca ggcgacacga tcgtcatcgg cgaacgattg ttctgatctt ggcaacgatg    13320
gcagcggacg aggcccacca gtgaatatca ttcagttctt ccgcattctg tgggtgcgcc    13380
gatggatcat cctcccggcg tttctcgttt gcgttaccac tgccaccatt gtggtccagt    13440
ttctgcccga acgctacaag gccactacgc gggtggtgct cgacacgttt aagcccgatc    13500
ccgtcaccgg acaggtgatg agctcgcagt tcatgcgcgc ctatgtcgag actcagaccc    13560
agctgatcga ggactatgcg accgccggtc gcgtggtcga cgaactgggc tgggtgaatg    13620
```

```
atccggcgaa catctccgcg ttcaacaact cgtccgcggc tgccaccggc gacatccgcc   13680
gctggctcgc caagcagatc atcgacaata ccaaggccga tgtgatggag gggagcaaca   13740
tcctcgaaat cacctattcg gacagctcgc ccgagcgcgc cgaacgcatc gccaacctga   13800
tccgcacctc gttcctcgcc cagtcgctcg ccgccaagcg ccaggccgcg accaagtcgg   13860
ccgactggta cgcccagcag gccgaagctg cccgcgattc gctcgctgcg gcggtccagg   13920
cccgcaccga tttcgtgaag aagaccggca tcgtgctgac cgaaaccggc gccgacctgg   13980
aaacccagaa gctccagcag atcgaggggc agacgacgac cgccaccgcc ccggttgcca   14040
tggcccccag cggcatgggc ccggcgcaga tgcagctcgc ccagatcgac cagcagatcc   14100
agcaggcagc gaccagccta ggtccgaacc acccaacttt ccaggccttg cagcggcagc   14160
gcgaagtgtt cgccaaggca gcggcggcgg aacgcgcgca ggcgaacggc gtatccggtc   14220
cggcacgcgg ggccatcgaa agcgcagcca acgcccagcg cgcgcgggtt ctcggcaatc   14280
gtcaggatgt cgacaagctt acgcagctgc agcgtgacgt ctcgctgaag caggatcagt   14340
acatgaaggc ggcacagcgc gtcgccgatc tgcggctgga agcaagcagc aacgatgtcg   14400
gcatgtcgac gctcagcgaa gcatcggcgc cggaaacgcc ctattacccc aaggtgccgc   14460
tcatcatcgg tggtgcagcc ggcttcggcc tcgggctcgg tctgctggtc gcgctgctcg   14520
tcgagctgct cggccgccgc gtccgcagcc ccgaggatct ggaagttgcg atcgatgcac   14580
cggtgctggg cgtgatccag agccgcgcct cgcttgccgc ccgccttcgc cgcgcccaag   14640
aaaccctcgg cgaaggtgcc gacacgcacg gagcttcagt aaactgatgg acgcgatgac   14700
cagcgaaccg ctgcccgaag gcgatcgtcc gagcgccgtg ccgaccacgc cggatacgat   14760
cggcatgctc gaataccagc tcgtcctctc cgatccgacc gggatcgagg cggaagcgat   14820
ccgcgcgcta cgcacgcgca tcatgaccca gcacctccgc gagggccggc gcgcgctcgc   14880
gatctgcgcc gcctcggcgg gatccggctg cagcttcacc gccgtcaatc tggcgacggc   14940
gctggcgcag atcggcgtta agactgcgct ggtcgatgcc aatctgcgcg atcccagcat   15000
cggcgcagcc ttcggcctcg ccgccgacaa gcccggcctg gccgattatc tcgcctcggg   15060
cgatgtcgac ctcgcctcga tcatccatgc gacccgcctc gaccagctct cgatcatccc   15120
ggccgggcat gtcgagcaca gcccgcagga actgctcgcg tccgaacagt tccatgatct   15180
ggcgacgcag ctgctgcgcg agttcgacat cacgatcttc gacaccacgg cgtccaacac   15240
ctgcgccgac gcgcagcgtg tcgcgcatat cgccggctat gcgatcatcg tggcgcgcaa   15300
ggatgcgagc tacatccgcg acgtgaacac gctcagccgc acgctgcgtg cagaccgcac   15360
caacgtcatc ggctgcgtac tgaacggcta ttgatttgga ccatatggca gcgaccgcga   15420
tgacgcggca gcaggagagg aagggcggtg gctattggct ggccgttgcc ggtcttgccg   15480
cgctaaccat cccgaccttc atcaccctgg gtcgcgaggt ttggagtgcg aaggcggcg   15540 tgcagggtcc gatcgtgctc gccacgggcg cctggatgct ggcccgccag tgctcgacga   15600
tcgaggcgct acgccgcccc ggcagcgtgc tgctcggcgc gctgttcctg ctggcgacgc   15660
ttgccttcta caccgttgga cgggtgttcg acttcatcag tgtcgaaacc ttcggactgg   15720
tcgcgaccta tctggtcgtc gcctatctct atttcggtgc cagggtgctc cgtgccgcct   15780
ggttcccggt gctgtggctg ttcttcctgg tgccgccgcc cggctgggcc gtcgaccgca   15840
tcaccgcacc gctcaaggag ttcgtctcct atgcggcaac gggcctgctt tcctgggtgg   15900
attatccgat cctgcgccag ggcgtgacac tgttcgtcgg cccctatcag ctgctcgtcg   15960
```

| | | | | | |
|---|---|---|---|---|---|
| aagatgcctg | ttcgggtctg | cgctcgctgt | ccagcctggt | cgtcgtgacg | ctgctctaca | 16020 |
| tctacatcaa | gaacaagccg | tcctggcgct | acgcggcgtt | catcgcagcg | ctggtgatcc | 16080 |
| cggtggcagt | ggtgaccaac | gtcctgcgga | tcatcatcct | ggtactgatc | acctatcatc | 16140 |
| tgggcgacga | ggcggcgcag | agcttcctcc | acgtctccac | cggcatggtg | atgttcgtgg | 16200 |
| tcgccctgct | ttgcatcttc | gcgatcgact | gggtggtcga | gcaacttctt | ctcctgcgtc | 16260 |
| ggaggcatca | tgttcaaccg | gcgtgacctg | ctgatcggcg | caggctgctt | cgccgccgct | 16320 |
| ggcgcctcgc | tcggcctgaa | gccgcaccgg | cggatggacc | tgctgggcgg | caccaagctc | 16380 |
| gacacgctga | tgcccaaggc | attcggcgca | tggaaggcag | aggataccgg | ttcgctgatc | 16440 |
| gcgccggcgc | gcgaaggcag | cctggaggac | aagctctaca | accaggtggt | cacccgcgcc | 16500 |
| ttctcccgcg | cggacggtgc | ccaagtgatg | ctgctgatcg | cctatggcaa | cgcccagacc | 16560 |
| gatctactgc | agctgcaccg | gccggaaata | tgctacccgt | tcttcggctt | caccgtggtg | 16620 |
| gaaagccatg | agcagaccat | cccggtgacg | ccgcaggtga | cgatcccggg | tcgcgcgctg | 16680 |
| accgccacca | acttcaaccg | caccgagcag | atcctctact | ggacccgcgt | cggcgaatat | 16740 |
| ctgccgcaga | acggcaatca | gcagatgctc | gcgcggctga | agagccaggt | ccagggctgg | 16800 |
| atcgtcgacg | gtgtgctggt | gcgcatctcg | acggtgacgc | ccgaggcgga | agatggcctg | 16860 |
| agcgccaatc | tcgatttcgc | gcgcgagctg | gtgaagacgc | tcgacccgcg | cgtgctgcgc | 16920 |
| ccgctgctcg | ggaacgggct | cacacggcag | ctcggtcacc | aggtctgaac | cggtgcgccg | 16980 |
| cacgcggcgc | ccccggcaac | aaaaaaggag | cggcgcgggc | cgccgccgct | ccctctcctt | 17040 |
| ctcatgcggc | gccctgccct | caccgctcgt | gcagcgcgtc | actccccgtc | tcgagcacgg | 17100 |
| gccccaccag | atagctgaac | agggttcgct | tgccggtgac | gatgtccgcg | ctcgcgagca | 17160 |
| tccccggccg | cagcggcacc | tgtgcgccat | gggccagcac | ataccccgcgc | gccagcgcga | 17220 |
| tccgcgcctt | gtagaccggc | ggctggttct | ccttcatctg | caccgcctcg | gggctgatgc | 17280 |
| ccgccaccgt | gccgggaatc | atgccgtagc | gggtataggg | aaaggcctgc | agcttcacct | 17340 |
| ttaccggcat | gccgatgtgg | acgaagccga | tgtcgctgtt | gtcgaccatc | acctcggcct | 17400 |
| cgagccgggc | attgtcggga | accaggctga | ggagcggctt | ggccccttcc | accacgccgc | 17460 |
| cttcggtgtg | gacctgcagc | tgcgagacgg | taccgctcac | cggcgcgcgc | agttcgcgga | 17520 |
| acgagctgcg | cagattcgcc | ttggcgacgt | cctcgccgcg | ggcacgcacc | tgtcctgcg | 17580 |
| ccttgaccag | atcctgcagc | acctgcgccc | gcgcctcctc | gcgcgtcttg | gccgacaggc | 17640 |
| tggagacgct | cagcgactgc | tggccgagtt | tggcgagcgt | agcgcgcgcc | gccgtcaggt | 17700 |
| cctgccgctc | ggcgatcagc | tggcgacgca | tctccacgac | gcgcagcttc | gagacatagc | 17760 |
| ccttggcggc | catcgtctcg | ttcgcggcga | tctgctgttc | gagcagcggc | agcgactgtt | 17820 |
| cgagcttccg | cacctgtgcc | tgcgcctcgg | ccgcggccga | gacggcggca | ccgcgatcgg | 17880 |
| agcggccgcc | ggccagcgcc | gcctcgatct | ggcccagccg | ggcgcgggcg | aggccgcgat | 17940 |
| gcgtcgccac | ttcgcccggg | ctggcggcgg | caggcgcgac | gaagcggaag | cccctgccgt | 18000 |
| ccagcgcgtc | gatgatcgcc | tggttgcgtg | cggcgtcgag | ctgggcgctg | agcagcgcca | 18060 |
| ccttcgcctg | tgccgcctcc | gccgacgaca | cggtcgggtc | gagcgtgatc | agcacctggc | 18120 |
| ccttggcgac | cttctgcccc | tcgcccacca | ggatgcggcg | gacgatcccc | gattcgggcg | 18180 |
| actggacgat | cttggtctcg | ccgatcggcg | cgatccgccc | ctgcgtcggc | gcgacgactt | 18240 |
| cgaccttgcc | gatcgccagc | caggcggcgg | tgatcgccag | cccggccagc | atcaccttgg | 18300 |
| cggtaagccg | cgcggtgggc | gaaaccggcc | gctcgatgat | ctccagcgcg | gcaggcagga | 18360 |

```
aggcggtgtc ataagcgtcg acgcgggcag gcagcacggt atcgcgcatg cgggcgagcg    18420
ggccgccgcg gcgcatcgga acaacggcgt tcatgcggca atctcccat agccgccctg     18480
gcggcggtgc aggtcggcat agcggccgcc caggcgcaac aattcgtcgt gtcggccgct    18540
ctcgacgatg cggccctgtt cgagcgtgat gatccggtcg cagctgcgca ccgcgctcag    18600
gcgatgcgcg atcaccacga gcgtgcggcc ggccgagatg gcgcgcaggt tgttctggat    18660
cagctcctcg ctctcggcat cgagcgccga ggtcgcttcg tcgaacacca ggatgcgcgg    18720
attgccgacg agcgcgcggg cgatggcgag ccgctggcgc tggccgccgg agagattgac    18780
gccgcgctcg acgatctcgg tgtcatagcc gcgcggctgg cgcaggatga atcatgcgc    18840
gccggccagc gtcgccgccg cgacgacatt ctcgaacggc atggcggggt tggagagcgc    18900
gatgttctcg cggatcgagc ggctgaacag cagattctcc tgcagcacga cgccgatctg    18960
gcgacgcagc caggcgggat cgagctgcgc cacgtcgacc tcgtcgacca gcacgcggcc    19020
gagattcggc aggttgagcc gctggagcag cttggccagc gtcgacttgc ccgagcccga    19080
cgaaccgacg atgccgagcg aggtgcccgc cggaatgtcg agcgtgatgt cgctcagcac    19140
cggcggctgg tcctcggcat agcggaagct gacattctcg aagcgaatcg caccgcgcag    19200
caccggcagc gtcgccgccg aggccgggcg cggttccacc ggatggttga gcacgtcgcc    19260
cagccgctcg accgagatgc gcacctgctg gaaatcctgc cacagctgcg ccatgcggat    19320
caccggcccg gacacgcgct gggcgaacat gttgaacgcc accagcgcgc ctacgctcat    19380
cgcgccgccg atcaccgcct tggcgccgaa gaacaggatc gccgcgaagc tcagcttcga    19440
gatcagctcg atcgcctggc tgccggtgtt ggcggtattg atcagccgct gcgacgcggc    19500
ggtatgggcg gcgagctggc gctcccagcg attctgccag tgcggctcga ccgcggtcgc    19560
cttgatcgtg tggatgcccg agacgctctc gacgagcagc gcgttgctgg cggagctctt    19620
ctcgaacttg tcctccaccc gcgcgcggag cggcccggcg acgctgaacg atacgatcgc    19680
ataggcgatc agcgacacga gcacgatgcc cgagagcatc ggcgagtaga acagcatcgc    19740
ggcgaggaac acgaaggtga acagcgggtc caccatcacc gtcagcgagg cgctggtaag    19800
gaattcgcgg atcgtctcga gctggcggac gcgggtgacg gtgtcgccca cgcggcgctt    19860
ctcgaaatag gcgagcggca gcgccagcag gtggtggaac agccgggcac ccagctcgac    19920
gtcgatcttc tgcgtcgtct cggtgaacag gcgggtgcgg atccagccga gcgccacttc    19980
ccacaccgaa accgccagga aggcgaaggc gagcacgctc agcgtgctca tgctgttgtg    20040
gatcagcacc ttgtcgatca cgctctggaa caacagcggc gcggcgaggc cgagcaggtt    20100
gagcgcgagg gtgatgccga gcacctcgag gaacagcgtg cgatagcgcc ggaactgcgc    20160
ggtgaaccag gagaggccga accgcagcgg ccgtcccgcc accgcgcggg tggtgagcag    20220
caccagcgcg ccggaccaga tcgcgtccag cgcgtcccgg tcgacctgtt ccggggcatg    20280
gcccgggcgc tggatgatca cgccatgttc ggtcaggccg ccgatcacga accagccttc    20340
gggcccgtcg gcgatcgcgg gcagcggctg gcgggcgagt ccgccgcgcg gcacctcgac    20400
ggccttggcg cgcacgccct gctggcgctt ggccaggagg atcaggtcgt cggcgcttgc    20460
cgcctcggca tgcccagcg cgtggcgcag ctgttcgggc gtgatggcga tgttgtgcgc    20520
gccgagcagc agcgacaacg ccaccagtcc ggattcgcgc agctccgcct cgcgctccgc    20580
cgccccatgg gccgcgagcg cgctctgcag ggtggcctgc atttcgtcgc gtgtcatttc    20640
cggaactctg cctccatggc gatactgaga gcgccatgat gaagaaggct ggtaaagact    20700
```

```
cacttaatcc tagcttttct ggtatttacc cgtagctgcc gacccgattt gggacaggcc    20760
tggcttagca ggtccttaaa ctcgaccgac tataccgcga cgccgaggag ggggaggatt    20820
ggcgccgcat cgcgcggcga aacgcgggtg cgtcgcaaca tttcgccgga gtcgatccgt    20880
cgcgaatgct gcaccgcga acgcaatgac ggccgccacg caatccggct tgatcccggg    20940
cggcggatcg cgataagccg cgccacggtc gccaaaactc gtcgaaataa ccgacaaaac    21000
cacggcatat ggctggatat tgcagcgttt gccctgcgtt tccgtcgttc aaccgccctt    21060
cgaatcaggc aggcccagcg tgaccatgat tgatcttcct cttggaacgg cacactttgg    21120
tcgacacgga gacttccggt cgggcaattg tcccgttata gtgcaatgca acaggccgaa    21180
tcggccgctg tcggcgtgca cattccgttg agggagcccg atgaggcaat gaacgctttc    21240
gaagcacagc gcgcctttga ggagcaactt cgggcgcatt cccgggttac gccatctgcc    21300
gctcccgtgt ggcgtcgctc gacgctgcgg atggtcctct ataccgagtt gctgctgctg    21360
gacagtctct cgatcctggc cggattccac gtcgcggcgg gcacgcgcga cggcaactgg    21420
ctgtcgctgg cgggcatcaa cgtcggcgtc ttcctgctgc cgatcgctct cggcaccgcg    21480
ctcgcaagcg gcacctactc gctgaactgc ctgcgctacc cggtcagcgg cgtgaagagc    21540
atcttctcgg cattcttctt ctcgatcttc gtcgtcctgc tcggcagcta cctgctgacg    21600
gccgagctgc cgctgtcccg cgtgcagctg gcggagggcg cgatcctctc gctggtcctc    21660
ctgatggtgg gccgcctgat gttccgccgc cacgtccgcg cggttaccgg cggcaggctg    21720
ctcgacgaac tggtcatcat cgacggcgtc tcgctcgacg tcgcgggcaa tgcggtcgcg    21780
ctcgacgcgc ggatcatcaa tctctcgccg aacccgcgcg atccgcaaat gctgcatcgc    21840
ctgggcacca ccgtgatcgg gttcgaccgg gtgatcgtcg cctgcaccaa ggagcatcgc    21900
gcggtctggg cgctgctgct caagggcatg aacatcaagg gcgagatcct cgtccccag    21960 ttcaatgcgc tgggcgcgat cggcgtggac gcctttgacg ggaaggatac gctggtcgtc    22020
tcgcagggcc cgctcaacat gcccaaccgc gcgaagaagc gcgcgctcga tctcgcgatc    22080
accgtaccgg ccgtgctcgc gctggcgccg ctgatgatcc tggtggcgat cctgatcaag    22140
ctggagagcc cgggcccggt gttgttcgcg caggatcgcg tcggccgcgg caaccggctg    22200
ttcaagatca tgaagttccg ctcgatgcgc gtaacgctgt gcgacgcgaa cggcaacgtc    22260
tcggccagcc gcgacgacga tcgcatcacc aaggtcggcc gcttcatccg caagaccagc    22320
atcgacgaac tgccgcagct gctgaacgtg ctgcgcggcg acatgagcgt cgtcggcccg    22380
cggccgcatg cgctgggctc gcgcgccgcc gatcacctgt tctgggaaat cgacgagcgc    22440
tactggcacc gccacacgct caagccgggc atgaccggtc tggcccaggt gcgcggtttc    22500
cgcggggcga ccgatcgccg cgtcgatctg accaaccggc tccaggcaga catggaatat    22560
atcgacggat gggatatctg gcgcgatatc acgatcctgt tcaagacgct gcgggtgatc    22620
gtgcattcga acgcattctg atccgcgcac gacgctgggc cgcagcctcg atccgcaaat    22680
ggattgacag cggcccggct tccgtttcct cgtttgattt tcgttgcggc cggtccgcgc    22740 catggggat tactgaatga agggcatcat ccttgcgggg ggcagcggga cgcgcctgta    22800
ccccgcaacg ctatcgatct cgaagcagct gcttcccgtc tatgacaagc cgatgatctt    22860
ctatccgctg tcggtgctga tgctcaccgg catccgggac atcctgatta tctccacccc    22920
gcgcgacctg ccgatgttcc aggcgctgct gggcgacggc tcggccttcg gcatcaacct    22980
cagctatgcc gagcagccct cccccaacgg gctggccgaa gcgttcatca tcggcgcgga    23040
tttcgtcggc aacgatccca gcgcgctgat cctgggcgac aacatctatc acggcgaaaa    23100
```

```
gatgggcgag cgctgccagg cagccgcagc gcaggcagcg cagggcggtg caaacgtctt    23160
cgcctatcat gtcgacgacc ccgagcgcta cggcgtggtc gcgttcgacc cggagacggg    23220
cgtcgccacc agcgtcgagg aaaagccggc cgagcccaag tccaactggg cgatcaccgg    23280
cctgtatttc tacgacaagg acgtggtcga catcgccaag tcgatccagc cctcggcgcg    23340
cggcgaactc gagatcaccg acgtcaaccg cgtttacatg gagcgcggcg acctgcacat    23400
cacgcgcctc ggccgcggct atgcctggct cgacaccggc acgcatgaca gcctgcacga    23460
agccggctcg ttcgttcgca cgctcgagca tcggacgggc gtgaagatcg cctgcccgga    23520
ggaaatcgcc ttcgaaagcg gctggctcgg cgccgaagac ctgctcaagc gcgccgccgg    23580
cctcggcaag accggctatg ccgcctatct ccgcaaggtt gcgaccgcag catgacccag    23640
gtccatcatc acgaactgtc cggcgtcatc gagttcacgc cgcccaaata tggcgaccac    23700
cgcggcttct tctccgaagt gttcaagcag tcggtgctcg atgccgaagg cgtcgaggca    23760
cgctgggtgc aggacaatca gagcttctcg gcggccccgg gcacgatccg cggcctgcat    23820
ctccaggcgc cgcccttcgc ccaggccaag ctggtccgcg tgttgcgcgg cgcgatcttc    23880
gacgtcgcgt cgacatccg tcgcggctcg cccacctatg gcaaatgggt cggcgtcgag    23940
ctctcggccg agaagtggaa ccagctgctg gtccccgccg gctatgcgca cggcttcatg    24000 acgtcgttc cggattgcga gatcctctac aaggtcagcg ccaaatattc gaaggattcg    24060
gagatggcga tccgttggga cgatcccgat ctcgccatcg cctggccgga catcggcgtc    24120
gagccggtcc tctccgaaaa ggacgcggtc gccacgccct tcgccgaatt caacacccccc    24180 ttcttctatc agggctgagc catgcagcag accttcctcg tcaccggcgg cgccggcttc    24240
atcggctcgg cggtggtgcg ccacctcgtc cgccagggcg cgcgcgtcat caatctcgac    24300
aagctcacct atgccggcaa cccggcctcg ctgactgcga tcgagaacgc gcccaactat    24360
cgcttcgtcc atgccgacat cgccgacacc gcgacgatcc taccgctgct gcgcgaggag    24420
caggtcgatg tggtgatgca cctcgccgcc gagagccatg tcgatcgctc gatcgacggc    24480
cctggcgagt tcatcgagac caatgtcgtc ggcaccttca agctgctcca gtcggcgctg    24540
caatattggc gcgagctgga gggcgagaaa cgcgacgcgt tccgcttcca ccacatctcc    24600
accgacgaag tgttcggcga cctgccgttc gacagcggca tcttcaccga agagacgccc    24660 tatgatcccct cctcgcccta ttcggcgtcg aaggcggcga cgaccatct ggtgcgcgcc    24720 tggggccaca cctatggcct gccggtggtg ctgtcgaact gctcgaacaa ttacgggccg    24780
ttccacttcc ccgagaagct gatcccgttg accatcctca acgcgctcga gggcaagccg    24840
ctgccggtct acggcaaggg cgagaatatc cgcgactggc tgtatgtcga cgatcacgcc    24900
aaggcgctgg cgaccatcgc caccaccggc aaggtcggcc agagctacaa tgtcggcggc    24960
cgcaacgagc ggaccaacct gcaggtggtc gagacgatct gcgacctgct cgaccagcgc    25020
attccgctgg ccgacggtcg caagcgccg gaactgatca ccttcgtcac cgatcgcccc    25080
ggccatgacc gccgctacgc gatcgacgcg accaagctcg agaccgagct gggctggaag    25140
gctgaggaga atttcgacac cggcatcgcc gcgacgatcg actggtatct ggcgaacgag    25200
tggtggtggg gccgatccg ctccggcaaa tatgccggcg agcggctggg gcagaccgcc    25260
tgatgcgtat cctcgtcacc gggcatgacg gccaggtcgc ccagtcgctg gccgagcagg    25320
cggtgggcca cgagctggtc ttcaccacct accccgaatt cgatctctcc aagcggaga    25380 cgatcgaggc cggtgtggcg cgggtgcacc cggacctgat cgtctccgcc gccgcctaca    25440
```

```
cggcggtcga caaggcggaa agcgaacccg agctggcgat ggcgatcaac ggcgacggtc   25500
ccggcgtgct ggcgcgcgcg ggcgcgaaga tcggcgcgcc gatcatccac ctgtcgaccg   25560
attatgtgtt cgacggcagt ctcgaccgcc cttggcgcga ggacgatccc accggcccgc   25620
tcggcgtcta tggcgcgacc aagctggccg gcgagcaggc ggtgcaggcc tcgggtgcca   25680
ccaacgccgt gatccggctg gcctgggtct acagcccgtt cggcaacaat ttcgtcaaga   25740
cgatgctccg cctcgccgag acgcgcgacg cgctgaacgt cgtggaggac cagtggggct   25800
gccccagttc ggcgctggac atcgcgaccg cgatcctgac ggtggtcggg cactggcagc   25860
aggacggcgc gacgagcggc ctctaccatt tcgccggcac cggcgagacc aactgggccg   25920
acttcgcatc gacgatcttc gccgagagcg ccaagcgcgg tggcccctcg ccaccgtca   25980 ccggcattcc cagctcgggc tatccgactc cggccacgcg cccggccaat tcgcggctgg   26040
actgcacccg cttcgcggag accttcggct accgggcgcc tgcctggcag gattcgctga   26100
acgtcgtact ggatcgcctg ctcggctgat ccgaaacggg gggcctcagc gcccccccgcc  26160 atgctcccgt tcgcgcgccg gcaatgcctc tagcaccgcg cgctttccct taggactcag   26220
ctcgctccag ccggcgattt ccttgggcga ccgccagcac cccaggcaca gccggatc     26278

<210> SEQ ID NO 2
<211> LENGTH: 1053
<212> TYPE: DNA
<213> ORGANISM: Sphingomonas sp. ATCC53159

<400> SEQUENCE: 2
atcaacggcg ccttgctcgg acggcacaaa ttcgtcctgg tcaatgtgtc cacggtcgcc     60
tcttcgatac tgttccagct gttcccgctt gtcgtcgcct ggatgatcgg cccggacctg    120
cgaacgctgc tgatcgccgc gctcgttggc cgggcggttc cgatgatcgg catgctgccc    180
gcgctgtatc gaaaccttt gcgcggcaac acgccgcgtt tcacgccag cgaggcgcgc     240 ttcctgatag gctatggcgg gtgggcctcg ctcacgaccg tggtagcgac cgtgctcatg    300
atggcggacc gcttcctgat tggcgcactt cttgggcccg tcgccgtgac catctacacg    360 gccccctgc aactcgcaca gcgcgtatcg ctgctgccct ccgcactgtc cgccgcgctg    420
ttcccgcgcc tgcccagcgc gacgccggcg gagcgcatgg cgcttcagat ccgctcgctg    480
tcgctgatca tgggcggcct taccgggatg atcggcggcg gactattgct ggccgcgccg    540
tttctcgatc tctggatcgg caagtcgctc ggccatgcgg gaacgccggt cgcgctcttc    600
ctgttcttcg gcgcatggtg gaatgcgctg gcgatcattt cgttcagcgg cctgcaggcg    660
agcggacggc cgaaagcgag cgcgatcgtc caggggcag agctgctacc cgtgttgatc    720
gcgctgtatg cagggatccg atggggcggc gtgaccggcg ccgcagcggt ctttctggga   780
cgctccgccc tggatttcgt cctgttgacc tggcaggcag gcctgctccg ccagacggtg    840
aagcaagtat ccgtatgcgg cgccgttctc accgtcgcga tgctcgtggg gcgcgaccta   900
cgctattcgg tgccgctctg gtgcgtactc agcgcctgct gcctggtcgc gctggcagcc   960
tgctcctggt ggacattggc gcgccaggac aaggcactgc tgattggacg attgagccga  1020
attctaccaa gcagcggca actcgaccta tag                                1053

<210> SEQ ID NO 3
<211> LENGTH: 350
<212> TYPE: PRT
<213> ORGANISM: Sphingomonas sp. ATCC53159

<400> SEQUENCE: 3
```

```
Ile Asn Gly Ala Leu Leu Gly Arg His Lys Phe Val Leu Val Asn Val
 1               5                  10                  15

Ser Thr Val Ala Ser Ser Ile Leu Phe Gln Leu Phe Pro Leu Val Val
            20                  25                  30

Ala Trp Met Ile Gly Pro Asp Leu Arg Thr Leu Leu Ile Ala Ala Leu
        35                  40                  45

Val Gly Arg Ala Val Pro Met Ile Gly Met Leu Pro Ala Leu Tyr Arg
    50                  55                  60

Asn Leu Leu Arg Gly Asn Thr Pro Arg Phe His Ala Ser Glu Ala Arg
65                  70                  75                  80

Phe Leu Ile Gly Tyr Gly Gly Trp Ala Ser Leu Thr Thr Val Val Ala
                85                  90                  95

Thr Val Leu Met Met Ala Asp Arg Phe Leu Ile Gly Ala Leu Leu Gly
            100                 105                 110

Pro Val Ala Val Thr Ile Tyr Thr Ala Pro Leu Gln Leu Ala Gln Arg
        115                 120                 125

Val Ser Leu Leu Pro Ser Ala Leu Ser Ala Ala Leu Phe Pro Arg Leu
    130                 135                 140

Pro Ser Ala Thr Pro Ala Glu Arg Met Ala Leu Gln Ile Arg Ser Leu
145                 150                 155                 160

Ser Leu Ile Met Gly Gly Leu Thr Gly Met Ile Gly Gly Leu Leu
                165                 170                 175

Leu Ala Ala Pro Phe Leu Asp Leu Trp Ile Gly Lys Ser Leu Gly His
            180                 185                 190

Ala Gly Thr Pro Val Ala Leu Phe Leu Phe Gly Ala Trp Trp Asn
        195                 200                 205

Ala Leu Ala Ile Ile Ser Phe Ser Gly Leu Gln Ala Ser Gly Arg Pro
    210                 215                 220

Lys Ala Ser Ala Ile Val Gln Gly Ala Glu Leu Leu Pro Val Leu Ile
225                 230                 235                 240

Ala Leu Tyr Ala Gly Ile Arg Trp Gly Gly Val Thr Gly Ala Ala Ala
                245                 250                 255

Val Phe Leu Gly Arg Ser Ala Leu Asp Phe Val Leu Leu Thr Trp Gln
            260                 265                 270

Ala Gly Leu Leu Arg Gln Thr Val Lys Gln Val Ser Val Cys Gly Ala
        275                 280                 285

Val Leu Thr Val Ala Met Leu Val Gly Ala Thr Tyr Arg Tyr Ser Val
    290                 295                 300

Pro Leu Trp Cys Val Leu Ser Ala Cys Cys Leu Val Ala Leu Ala Ala
305                 310                 315                 320

Cys Ser Trp Trp Thr Leu Ala Arg Gln Asp Lys Ala Leu Leu Ile Gly
                325                 330                 335

Arg Leu Ser Arg Ile Leu Pro Lys Gln Arg Gln Leu Asp Leu
            340                 345                 350

<210> SEQ ID NO 4
<211> LENGTH: 1626
<212> TYPE: DNA
<213> ORGANISM: Sphingomonas sp. ATCC53159

<400> SEQUENCE: 4
atgacgacta cctcggcgtt tcgtcgcccg gccttccacg gagcgatgca gcggcttcgc        60
aggttgcgac tggttcggtt tctgacaaag ccagcgatcc cggtactgcc cgtctacaaa      120
```

```
gccgagcgat caggcgtgac gatcgcggcg cggcgtaccg ttctgctggt cagcgtgatg      180
tttcttgccg cagtctacgg cctgctcgcc gcagttctgc cgctccagat gctggcgatc      240
ccggccgtgc ccctcgttct gatggcgctc gtagtgatct gggcgctacc cgaggcgcgg      300
caggcgccta ctcgcctgct ggcaaaacta tacctcgcct atatggtggc ggcgctcgtg      360
tggccgaact atcttgcgct cagcgttggt ggtttgcctt ggatctcgat caggcggatg      420
atcggttcga tcgcattgct cacgctcatg atctcgcttt cggtctcgaa aaagtttcga      480
tccgagatgg cggcgattat gcgggcggcg ccgatcccat cgcgactatt gcttgccttc      540
attatggtcc agatcgtcgc ctccattgcg accccagcgg cctcgcaaac aattccgcgg      600
ttgattggca tcgttctgac ggtgacgccg atggcattca tctcgctatg ctgatcggga      660
accgacacgc gcaccccgga gtggtgggtt acgcgcttgt tttggtgcgt gggcgtgctg      720
atggcgattg gcgtgctgga gttccgggtg aagcacgtcc tctgggccta ctcgattccg      780
agcttcctgc gcgttgatga gcagtttctt accgtagtgc ttacgcccgg tttccggggt      840
acttaccgcg ttttgacgac tttcagcagt ccgcttgtct ggggagagtt gacggctttg      900
acgattcctt tcgtgctgca ccgtatagcg aattcccgtg gcgtagggag attggcattt      960
tggattttct tcgattttct tgtagttgcg tcccggattc ttagcggttc tcgactggca     1020 atggtgggg gattggtggc gcataccgtg tatttgctta tttgggcaat tcggcggtgg     1080
cggaccacaa agggcgggct tgtcggcatt tcgctgacgt tgacgtatcc cgccttgatg     1140
gtggcgctgt cgctggcggt catgttcgtg cctgccgtcc acaaccgtgt tctcggtgga     1200
ggcgcttctc aacttagcaa tcaaggcagg caggagcagt ttcgcttggg cgtgcctgcc     1260
atcgctcgcc gccctttctt cggctatggc ccgggagagg gtgctggcgc tgtcgggtgg     1320
cgtaatcagc aaggcttcct atcgatcgac agtggtttcc tgtccgtagc ggctgattac     1380
ggcttgctgg gttttgtttc gctatacggc acgatgatta cgttaatgat tttgctcgcg     1440
tttcgtggtc ttaagatgag cggagatggc tacccgcttg agctcgccgt agcaactttc     1500
ctggctgttc ttttaaatac gcggtcagtc ctgtcgcaag gtgacaatga cccgttcatc     1560
tttatgacgc tggggctagg catagcgctt ctatatcgct tcggcctgt gtctttgtcg     1620 gtgtag                                                                 1626
```

<210> SEQ ID NO 5
<211> LENGTH: 541
<212> TYPE: PRT
<213> ORGANISM: Sphingomonas sp. ATCC53159

<400> SEQUENCE: 5

```
Met Thr Thr Thr Ser Ala Phe Arg Arg Pro Ala Phe His Gly Ala Met
1               5                   10                  15

Gln Arg Leu Arg Arg Leu Arg Leu Val Arg Phe Leu Thr Lys Pro Ala
            20                  25                  30

Ile Pro Val Leu Pro Val Tyr Lys Ala Glu Arg Ser Gly Val Thr Ile
        35                  40                  45

Ala Ala Arg Arg Thr Val Leu Leu Val Ser Val Met Phe Leu Ala Ala
    50                  55                  60

Val Tyr Gly Leu Leu Ala Ala Val Leu Pro Leu Gln Met Leu Ala Ile
65                  70                  75                  80

Pro Ala Val Pro Leu Val Leu Met Ala Leu Val Val Ile Trp Ala Leu
                85                  90                  95

Pro Glu Ala Arg Gln Ala Pro Thr Arg Leu Leu Ala Lys Leu Tyr Leu
```

```
            100                 105                 110
Ala Tyr Met Val Ala Ala Leu Val Trp Pro Asn Tyr Leu Ala Leu Ser
            115                 120                 125

Val Gly Gly Leu Pro Trp Ile Ser Ile Arg Met Ile Gly Ser Ile
130                 135                 140

Ala Leu Leu Thr Leu Met Ile Ser Leu Ser Val Ser Lys Lys Phe Arg
145                 150                 155                 160

Ser Glu Met Ala Ala Ile Met Arg Ala Ala Pro Ile Pro Ser Arg Leu
                165                 170                 175

Leu Leu Ala Phe Ile Met Val Gln Ile Val Ala Ser Ile Ala Thr Pro
                180                 185                 190

Ala Ala Ser Gln Thr Ile Pro Arg Leu Ile Gly Ile Val Leu Thr Val
                195                 200                 205

Thr Pro Met Ala Phe Ile Ser Leu Trp Leu Ile Gly Thr Asp Thr Arg
    210                 215                 220

Thr Pro Glu Trp Trp Val Thr Arg Leu Phe Trp Cys Val Gly Val Leu
225                 230                 235                 240

Met Ala Ile Gly Val Leu Glu Phe Arg Val Lys His Val Leu Trp Ala
                245                 250                 255

Tyr Ser Ile Pro Ser Phe Leu Arg Val Asp Glu Gln Phe Leu Thr Val
                260                 265                 270

Val Leu Thr Pro Gly Phe Arg Gly Thr Tyr Arg Val Leu Thr Thr Phe
                275                 280                 285

Ser Ser Pro Leu Val Trp Gly Glu Leu Thr Ala Leu Thr Ile Pro Phe
                290                 295                 300

Val Leu His Arg Ile Ala Asn Ser Arg Gly Val Gly Arg Leu Ala Phe
305                 310                 315                 320

Trp Ile Phe Phe Asp Phe Leu Val Val Ala Ser Gly Phe Leu Ser Gly
                325                 330                 335

Ser Arg Leu Ala Met Val Gly Gly Leu Val Ala His Thr Val Tyr Leu
                340                 345                 350

Leu Ile Trp Ala Ile Arg Arg Trp Arg Thr Thr Lys Gly Gly Leu Val
                355                 360                 365

Gly Ile Ser Leu Thr Leu Thr Tyr Pro Ala Leu Met Val Ala Leu Ser
                370                 375                 380

Leu Ala Val Met Phe Val Pro Ala Val His Asn Arg Val Leu Gly Gly
385                 390                 395                 400

Gly Ala Ser Gln Leu Ser Asn Gln Gly Arg Gln Glu Gln Phe Arg Leu
                405                 410                 415

Gly Val Pro Ala Ile Ala Arg Arg Pro Phe Phe Gly Tyr Gly Pro Gly
                420                 425                 430

Glu Gly Ala Gly Ala Val Gly Trp Arg Asn Gln Gln Gly Phe Leu Ser
                435                 440                 445

Ile Asp Ser Gly Phe Leu Ser Val Ala Ala Asp Tyr Gly Leu Leu Gly
                450                 455                 460

Phe Val Ser Leu Tyr Gly Thr Met Ile Thr Leu Met Ile Leu Leu Ala
465                 470                 475                 480

Phe Arg Gly Leu Lys Met Ser Gly Asp Gly Tyr Pro Leu Glu Leu Ala
                485                 490                 495

Val Ala Thr Phe Leu Ala Val Leu Leu Asn Thr Arg Ser Val Leu Ser
                500                 505                 510

Gln Gly Asp Asn Asp Pro Phe Ile Phe Met Thr Leu Gly Leu Gly Ile
                515                 520                 525
```

Ala Leu Leu Tyr Arg Ser Arg Pro Val Ser Leu Ser Val
    530                 535             540

<210> SEQ ID NO 6
<211> LENGTH: 1998
<212> TYPE: DNA
<213> ORGANISM: Sphingomonas sp. ATCC53159

<400> SEQUENCE: 6

```
atgccggata tcattgtcaa gaatcagacg gagttgaatg ctgcaatcgc ggcggcgaag      60
ggtggcgaaa ccatcaagct tgccgccggg gtctacacag atctcactgt aatgaccaag    120
acgtttacca gcatggtgac aattgagtcg ctcgactcgt cgaacccggt caatatccaa    180
aagctggtga tcgggaacag tagcaacgtt accgtcaaaa acatggtcgc tgcgaccgat    240
tacaagcccg ccgatgactg gaatcgactg aatacgatcc agggttcggc caacatcgtt    300
ttggacggcg tgcggttcag cggcggcact ggtgacccct tcgctctcga aggggcgggc    360
ttgttcgtgc gcaacagcac gtcggtgacg atgcagaatt cgtctatcga ccacttcggt    420
ctgggccttg aggcctacaa cgtcgatggc atggtggtcc agaacagcag cttccacgac    480
aaccggcgca tcatacgaa cttcactgag atgaacaatc ttgtcatcga cggaaattcg    540
ttcacgaacc tgtttcccgt gggcaccgaa catcccgacg ccattcagtt cttcacggcg    600
ggcaaggtca agggcaatac caacatcacc atctccaata cgtcatcat gcagggcgcg    660
ggctctggcg cgcaagggat tttcatgaat gacgaggccg gtaatcttcc ctatgtcaat    720
gtaaacatca aaaacaatct tatctatctg aatggttatt accacggtat caacgttgtt    780
aacggcgtta atgtcaatat cgaatccaat agcgtgatat cgcaagtgga tggcacatca    840
ttttggattc gcctcgacaa aaccaatggc gcgacgatca agaacaatgt tgcggacctg    900
atcaccgtca caagctcctc gagcaatatc gtgcagacag gcaatcgtac gctgacgagt    960
gactcggcaa cgatccgcaa gatctatggc ctcaacgatg gggctacggc gcggctcagc   1020
gatttgatcg ttcccggcgt cgggtaccag ccgcccgtgt cgagcgctgc tgccgctcag   1080
gtgactaccg aactgtcgac tgcgaaggcg gcaaatccgt cgctgctgct cgatctgtcg   1140
ttcagcaaca gcggcgtcgt ggacctttcg cactggaata ccggccagac gacaaaggcg   1200
gtggacgtgt cggcggtcgt gggcagcgcc ttccacgtct cgacgggcac gggggtggaa   1260
ctaaaccgga gctattcgcg gcagatttac gcattgtcgg cgttcacgct cagcttcgac   1320
ctcaagcggg actcggctac ggccacggcc gggcaaattc ttggcatctt ccagagctgg   1380
tcggtttcgc tgcaggccaa tggggaactg agcttcacca tgcgcaacgc cgcgggcgtc   1440
agccagacaa tggtgacgag cggcgccaag ctgcttgatg ctgccacaca caagatcgcc   1500
ctgacctacg acagcacgcg gaaaaccgcg attctgtacg tagacggcat gcaacgcggc   1560
acagcgacga tgaccggcac gacccggccc gccgaatcct gggggctgta tgtcggcagc   1620
ccgttctcga ccgcattcag cggaacggtc ggcgacatcg agatccgcga tggcgcgatc   1680
agcgccgccc aggtgcaggc gctggtgacc gcgtcgagcg ccagcgcggc ggcgacggtc   1740
aaggacagcc tcgtcaccgg cgcggccgcg caggccgctg cgctgctggc gggtgccggc   1800
gccgctagca cggcaacgcc gcttgcgacg gtggccacgg tgggcagtac gctgtctata   1860
ggtactgccg cgtcctcgca gatcgcgctc gtcagcaaga tcggtgtcga catgatgacc   1920
gcgggggcga tgggcgcaat ccgcagcgcg gcgacactga cgctacggc ggatcagtac   1980
aacctgtacc gcgcctga                                                 1998
```

```
<210> SEQ ID NO 7
<211> LENGTH: 665
<212> TYPE: PRT
<213> ORGANISM: Sphingomonas sp. ATCC53159

<400> SEQUENCE: 7

Met Pro Asp Ile Ile Val Lys Asn Gln Thr Glu Leu Asn Ala Ala Ile
1               5                   10                  15

Ala Ala Ala Lys Gly Gly Glu Thr Ile Lys Leu Ala Ala Gly Val Tyr
            20                  25                  30

Thr Asp Leu Thr Val Met Thr Lys Thr Phe Thr Ser Met Val Thr Ile
        35                  40                  45

Glu Ser Leu Asp Ser Ser Asn Pro Val Asn Ile Gln Lys Leu Val Ile
    50                  55                  60

Gly Asn Ser Ser Asn Val Thr Val Lys Asn Met Val Ala Ala Thr Asp
65                  70                  75                  80

Tyr Lys Pro Ala Asp Asp Trp Asn Arg Leu Asn Thr Ile Gln Gly Ser
                85                  90                  95

Ala Asn Ile Val Leu Asp Gly Val Arg Phe Ser Gly Gly Thr Gly Asp
            100                 105                 110

Pro Ser Leu Ser Lys Gly Ala Gly Leu Phe Val Arg Asn Ser Thr Ser
        115                 120                 125

Val Thr Met Gln Asn Ser Ser Ile Asp His Phe Gly Leu Gly Leu Glu
    130                 135                 140

Ala Tyr Asn Val Asp Gly Met Val Val Gln Asn Ser Ser Phe His Asp
145                 150                 155                 160

Asn Arg Arg Asp His Thr Asn Phe Thr Glu Met Asn Asn Leu Val Ile
                165                 170                 175

Asp Gly Asn Ser Phe Thr Asn Leu Phe Pro Val Gly Thr Glu His Pro
            180                 185                 190

Asp Ala Ile Gln Phe Phe Thr Ala Gly Lys Val Lys Gly Asn Thr Asn
        195                 200                 205

Ile Thr Ile Ser Asn Asn Val Ile Met Gln Gly Ala Gly Ser Gly Ala
    210                 215                 220

Gln Gly Ile Phe Met Asn Asp Glu Ala Gly Asn Leu Pro Tyr Val Asn
225                 230                 235                 240

Val Asn Ile Lys Asn Asn Leu Ile Tyr Leu Asn Gly Tyr Tyr His Gly
                245                 250                 255

Ile Asn Val Val Asn Gly Val Asn Val Asn Ile Glu Ser Asn Ser Val
            260                 265                 270

Ile Ser Gln Val Asp Gly Thr Ser Phe Trp Ile Arg Leu Asp Lys Thr
        275                 280                 285

Asn Gly Ala Thr Ile Lys Asn Asn Val Ala Asp Leu Ile Thr Val Thr
    290                 295                 300

Ser Ser Ser Ser Asn Ile Val Gln Thr Gly Asn Arg Thr Leu Thr Ser
305                 310                 315                 320

Asp Ser Ala Thr Ile Arg Lys Ile Tyr Gly Leu Asn Asp Gly Ala Thr
                325                 330                 335

Ala Arg Leu Ser Asp Leu Ile Val Pro Gly Val Gly Tyr Gln Pro Pro
            340                 345                 350

Val Ser Ser Ala Ala Ala Gln Val Thr Thr Glu Leu Ser Thr Ala
        355                 360                 365

Lys Ala Ala Asn Pro Ser Leu Leu Leu Asp Leu Ser Phe Ser Asn Ser
```

Gly Val Val Asp Leu Ser His Trp Asn Thr Gly Gln Thr Thr Lys Ala
385                 390                 395                 400

Val Asp Val Ser Ala Val Val Gly Ser Ala Phe His Val Ser Thr Gly
            405                 410                 415

Thr Gly Val Glu Leu Asn Arg Ser Tyr Ser Arg Gln Ile Tyr Ala Leu
        420                 425                 430

Ser Ala Phe Thr Leu Ser Phe Asp Leu Lys Arg Asp Ser Ala Thr Ala
    435                 440                 445

Thr Ala Gly Gln Ile Leu Gly Ile Phe Gln Ser Trp Ser Val Ser Leu
450                 455                 460

Gln Ala Asn Gly Glu Leu Ser Phe Thr Met Arg Asn Ala Ala Gly Val
465                 470                 475                 480

Ser Gln Thr Met Val Thr Ser Gly Ala Lys Leu Leu Asp Ala Ala Thr
            485                 490                 495

His Lys Ile Ala Leu Thr Tyr Asp Ser Thr Arg Lys Thr Ala Ile Leu
        500                 505                 510

Tyr Val Asp Gly Met Gln Arg Gly Thr Ala Thr Met Thr Gly Thr Thr
    515                 520                 525

Arg Pro Ala Glu Ser Trp Gly Leu Tyr Val Gly Ser Pro Phe Ser Thr
530                 535                 540

Ala Phe Ser Gly Thr Val Gly Asp Ile Glu Ile Arg Asp Gly Ala Ile
545                 550                 555                 560

Ser Ala Ala Gln Val Gln Ala Leu Val Thr Ala Ser Ser Ala Ser Ala
            565                 570                 575

Ala Ala Thr Val Lys Asp Ser Leu Val Thr Gly Ala Ala Ala Gln Ala
        580                 585                 590

Ala Ala Leu Leu Ala Gly Ala Gly Ala Ala Ser Thr Ala Thr Pro Leu
    595                 600                 605

Ala Thr Val Ala Thr Val Gly Ser Thr Leu Ser Ile Gly Thr Ala Ala
    610                 615                 620

Ser Ser Gln Ile Ala Leu Val Ser Lys Ile Gly Val Asp Met Met Thr
625                 630                 635                 640

Ala Gly Ala Met Gly Ala Ile Arg Ser Ala Ala Thr Leu Ser Ala Thr
            645                 650                 655

Ala Asp Gln Tyr Asn Leu Tyr Arg Ala
        660                 665

<210> SEQ ID NO 8
<211> LENGTH: 939
<212> TYPE: DNA
<213> ORGANISM: Sphingomonas sp. ATCC53159

<400> SEQUENCE: 8
atgcagatgc tcccaacgcc cgatgtcagc atactcgtgg tcgctttcaa ctcgaccgag    60
tatatcgaag actgcctgcg cggcatcgcc gaaggagcgg gcaagacccc ccacgaagtt   120
ctgctgatcg acaatggcga cgggcgaacc gaagcgctgg tccggcagcg gttccaccac   180
gtccgcatcg ttcccagtga gggcaatatt ggtttcgggg ccggcaataa tcgcctggca   240
gcgcaggctg ccggcccgct cctgctgctc gtcaaccccg atgccattcc ccagcccggc   300
gcaatcgatc agttggtcac ctttgccaaa cagcatcccg aggcggcggc atggggcggc   360
cgttcctact cgcccagcgg cgatctagaa cccgcaaatt tcatgtccct gccgacgccc   420
gccgactttc tgacggcgat tttcaacgcg cgtgcgctac gcagcggcgg gctgcaagaa   480

```
ggcgcgacca cccccggagc ggtcgaggtg ttgaatggcg gcttcatgat ggtacgcacc    540
gatgtctggc aggcgatcgg cggttttgac gagagctttt ttctttattc ggaagagatc    600
gatctcttcc agcgaatccg cacgttgggg cacaaggtgc tcgtcgaccc ctcggtcaaa    660
gtggtacaca atacggggag tggtcagtcg atgtcccaga accgcctgat gtatctcacg    720
accgggcgca tgcactatgc gcgaaagcat tttggcgcac tcggcaccct tgccaccggg    780
tgcgcgcttt ggctgatcgc cgccaaatac acgttggtcg gggcggcact ctggcgcctg    840
tcgccgcgga cgggcacgcg atacaaagag ctgagcaacg gtggcgtgc cgtatttagc     900
aatcctggcc gatggtggag cggctatccg cgtcgctaa                           939
```

<210> SEQ ID NO 9
<211> LENGTH: 312
<212> TYPE: PRT
<213> ORGANISM: Sphingomonas sp. ATCC53159

<400> SEQUENCE: 9

```
Met Gln Met Leu Pro Thr Pro Asp Val Ser Ile Leu Val Val Ala Phe
1               5                   10                  15

Asn Ser Thr Glu Tyr Ile Glu Asp Cys Leu Arg Gly Ile Ala Glu Gly
            20                  25                  30

Ala Gly Lys Thr Pro His Glu Val Leu Leu Ile Asp Asn Gly Asp Gly
        35                  40                  45

Arg Thr Glu Ala Leu Val Arg Gln Arg Phe His His Val Arg Ile Val
    50                  55                  60

Pro Ser Glu Gly Asn Ile Gly Phe Gly Ala Gly Asn Asn Arg Leu Ala
65                  70                  75                  80

Ala Gln Ala Ala Gly Pro Leu Leu Leu Val Asn Pro Asp Ala Ile
            85                  90                  95

Pro Gln Pro Gly Ala Ile Asp Gln Leu Val Thr Phe Ala Lys Gln His
            100                 105                 110

Pro Glu Ala Ala Ala Trp Gly Gly Arg Ser Tyr Ser Pro Ser Gly Asp
        115                 120                 125

Leu Glu Pro Ala Asn Phe Met Ser Leu Pro Thr Pro Ala Asp Phe Leu
    130                 135                 140

Thr Ala Ile Phe Asn Ala Arg Ala Leu Arg Ser Gly Gly Leu Gln Glu
145                 150                 155                 160

Gly Ala Thr Thr Pro Gly Ala Val Glu Val Leu Asn Gly Gly Phe Met
            165                 170                 175

Met Val Arg Thr Asp Val Trp Gln Ala Ile Gly Gly Phe Asp Glu Ser
        180                 185                 190

Phe Phe Leu Tyr Ser Glu Glu Ile Asp Leu Phe Gln Arg Ile Arg Thr
    195                 200                 205

Leu Gly His Lys Val Leu Val Asp Pro Ser Val Lys Val Val His Asn
    210                 215                 220

Thr Gly Ser Gly Gln Ser Met Ser Gln Asn Arg Leu Met Tyr Leu Thr
225                 230                 235                 240

Thr Gly Arg Met His Tyr Ala Arg Lys His Phe Gly Ala Leu Gly Thr
            245                 250                 255

Leu Ala Thr Gly Cys Ala Leu Trp Leu Ile Ala Ala Lys Tyr Thr Leu
        260                 265                 270

Val Gly Ala Ala Leu Trp Arg Leu Ser Pro Arg Thr Gly Thr Arg Tyr
    275                 280                 285
```

Lys Glu Leu Ser Asn Gly Trp Arg Ala Val Phe Ser Asn Pro Gly Arg
    290                 295                 300

Trp Trp Ser Gly Tyr Pro Arg Arg
305                 310

<210> SEQ ID NO 10
<211> LENGTH: 972
<212> TYPE: DNA
<213> ORGANISM: Sphingomonas sp. ATCC53159

<400> SEQUENCE: 10

```
atgctgcact gccaacgcta ttgcggatgc ccgcccgtcc gaataggttc aagtagaagt      60
ttgtgccgtg cgcaattccg tgccggcggg gaggtcttca tgaagaaatt gtacctggtt     120
acggcggtgg ctgcggccgc gctggccgtc tccggatgtg gcggcaaggg cggcaagctc     180
gacaaggggc aggtggtcgc cagcgtcgat ggcgaagaaa tcaccgtctt cgagctgaat     240
gccgaactgc aggcctccca ggtacccccg ggaccgatc gcaagctggc cgagcagctg      300
gcgctgcagc gcatcatcga gcgcaagatc ctcgccaagg tcgcccgcga gcagaagctg     360
gacaagacgc ctgccttcct gatccaggag cgccgggccg acgagctgat cctcaccgcc     420
atgctgcgcg acaagatcgc cggcggcatc gcccagccga ccgatgccga gatcgagaaa     480
tatcaggccg cgcatccgga gcggttcgcg cagcgcaaga tctacgcgat cgatcaggtc     540
gtcttcgctc cgccgagctc ggccgcaaag ctcaagcaat cgcgccgct gaagacgctg       600
gaccagctaa ccgccaagct ctcggcggac aatgtccagt ccgtcgcgc gccgtcgcag       660
atcgacaccg ctgcgctgcc gccggaaatc gctgccaaga tcgcgtcgct gccggcacag     720
gagatgttca tcctgccgac ccagcaggga ctgaccgcga atatcatcac gtcgaccacg     780
gtgctgccgg tgcggccga ccaggcgcgc gagatcgcgc tcagcgggct gcgtaccgag      840
cgcttcggca aggcggctga cgcacagctc aacgaccgcc tgaagaaggc gcgggaaacc     900
gtgaaatatc aggccggcta cagcgcaccg ccgcagcttc gcggcagcgg cgcaacgccg     960
gcggggaact ga                                                         972
```

<210> SEQ ID NO 11
<211> LENGTH: 323
<212> TYPE: PRT
<213> ORGANISM: Sphingomonas sp. ATCC53159

<400> SEQUENCE: 11

Met Leu His Cys Gln Arg Tyr Cys Gly Cys Pro Pro Val Arg Ile Gly
1               5                   10                  15

Ser Ser Arg Ser Leu Cys Arg Ala Gln Phe Arg Ala Gly Gly Glu Val
            20                  25                  30

Phe Met Lys Lys Leu Tyr Leu Val Thr Ala Val Ala Ala Ala Ala Leu
        35                  40                  45

Ala Val Ser Gly Cys Gly Gly Lys Gly Gly Lys Leu Asp Lys Gly Gln
    50                  55                  60

Val Val Ala Ser Val Asp Gly Glu Glu Ile Thr Val Phe Glu Leu Asn
65                  70                  75                  80

Ala Glu Leu Gln Ala Ser Gln Val Pro Pro Gly Thr Asp Arg Lys Leu
                85                  90                  95

Ala Glu Gln Leu Ala Leu Gln Arg Ile Ile Glu Arg Lys Ile Leu Ala
            100                 105                 110

Lys Val Ala Arg Glu Gln Lys Leu Asp Lys Thr Pro Ala Phe Leu Ile
        115                 120                 125

```
Gln Glu Arg Arg Ala Asp Glu Leu Ile Leu Thr Ala Met Leu Arg Asp
    130                 135                 140
Lys Ile Ala Gly Gly Ile Ala Gln Pro Thr Asp Ala Glu Ile Glu Lys
145                 150                 155                 160
Tyr Gln Ala Ala His Pro Glu Arg Phe Ala Gln Arg Lys Ile Tyr Ala
                165                 170                 175
Ile Asp Gln Val Val Phe Ala Pro Pro Ser Ser Ala Ala Lys Leu Lys
                180                 185                 190
Gln Phe Ala Pro Leu Lys Thr Leu Asp Gln Leu Thr Ala Lys Leu Ser
            195                 200                 205
Ala Asp Asn Val Gln Phe Arg Arg Ala Pro Ser Gln Ile Asp Thr Ala
    210                 215                 220
Ala Leu Pro Pro Glu Ile Ala Ala Lys Ile Ala Ser Leu Pro Ala Gln
225                 230                 235                 240
Glu Met Phe Ile Leu Pro Thr Gln Gln Gly Leu Thr Ala Asn Ile Ile
                245                 250                 255
Thr Ser Thr Thr Val Leu Pro Val Pro Ala Asp Gln Ala Arg Glu Ile
                260                 265                 270
Ala Leu Ser Gly Leu Arg Thr Glu Arg Phe Gly Lys Ala Ala Asp Ala
            275                 280                 285
Gln Leu Asn Asp Arg Leu Lys Lys Ala Arg Glu Thr Val Lys Tyr Gln
    290                 295                 300
Ala Gly Tyr Ser Ala Pro Pro Gln Leu Arg Gly Ser Gly Ala Thr Pro
305                 310                 315                 320
Ala Gly Asn

<210> SEQ ID NO 12
<211> LENGTH: 1047
<212> TYPE: DNA
<213> ORGANISM: Sphingomonas sp. ATCC53159

<400> SEQUENCE: 12
atggcagaag cgaacgcggt agatggaaag gcctccaagc cgctgaaaat gtgccttgca      60
gcgtcgggcg gcggccatct ccggcaaatc ctcgatctgg aatcggtgtg gcgcgaacac     120
gattatttct tcgttactga agataccgcg ctcggccgga gccttgccga aaaacatccc     180
gtcgaactgg tggagcacta tgcgctcggc caggccaagc tgggccatcc cttgcgcatg     240
ctgggcggcg catggcgcaa cctgcgccag agcctttcga tcctgcgccg gcacaagccg     300
gatgtggtga tttccaccgg cgcgggcgca gtctatttca ccgcgctgct cgccaaactg     360
tcgggcgcca gttcgtcca  tatcgaaagc ttcgcgcgct cgaccaccc  gtctgccttc     420
ggcaagatgt gaagggcat  cgcgacggtg acgatcgtcc agtcggcggc gctgaaagaa     480
acctggcctg atgccgagct gttcgatccg ttccgcctgc tcgatacacc cgcccgccc      540
aagcaggcgc taatcttcgc gacggtcggc gccaccctgc ccttcccgcg ctggtgcag      600
gcagtgctcg acctgaagcg cgccggcggg ctgccgggca agctgatcct gcaatatggc     660
gaccaggacc tgcccgatcc cggcatcccc gacgtcgaga ccgccgtac  catcccgttc     720
gacgatctgc agctgctgct gcgcgatgcg gatatggta  tatgccacgg cggcaccgga     780
tcgctggtca ggcgctgcg cgccggctgc cgggtcgtcg cctttccgcg ccgccacgat      840
ctgggcgagc attatgacga tcaccaggaa gagatcgccc agaccttcgc cgaccggggc     900
ctgctccagg cggtgcgcga cgagcgccag ctcggcgccg ctgtggaagc ggccaaggca     960
```

-continued

```
accgagccgc agctggcgac caccgaccac acggccctcg cggcgcggct gcgccagctg    1020
ctggcgcagt ggagtgccaa gcgatga                                        1047
```

<210> SEQ ID NO 13
<211> LENGTH: 348
<212> TYPE: PRT
<213> ORGANISM: Sphingomonas sp. ATCC53159

<400> SEQUENCE: 13

```
Met Ala Glu Ala Asn Ala Val Asp Gly Lys Ala Ser Lys Pro Leu Lys
1               5                   10                  15

Met Cys Leu Ala Ala Ser Gly Gly His Leu Arg Gln Ile Leu Asp
            20                  25                  30

Leu Glu Ser Val Trp Arg Glu His Asp Tyr Phe Phe Val Thr Glu Asp
        35                  40                  45

Thr Ala Leu Gly Arg Ser Leu Ala Glu Lys His Pro Val Glu Leu Val
    50                  55                  60

Glu His Tyr Ala Leu Gly Gln Ala Lys Leu Gly His Pro Leu Arg Met
65                  70                  75                  80

Leu Gly Gly Ala Trp Arg Asn Leu Arg Gln Ser Leu Ser Ile Leu Arg
                85                  90                  95

Arg His Lys Pro Asp Val Val Ile Ser Thr Gly Ala Gly Ala Val Tyr
            100                 105                 110

Phe Thr Ala Leu Leu Ala Lys Leu Ser Gly Ala Lys Phe Val His Ile
        115                 120                 125

Glu Ser Phe Ala Arg Phe Asp His Pro Ser Ala Phe Gly Lys Met Val
130                 135                 140

Lys Gly Ile Ala Thr Val Thr Ile Val Gln Ser Ala Ala Leu Lys Glu
145                 150                 155                 160

Thr Trp Pro Asp Ala Glu Leu Phe Asp Pro Phe Arg Leu Leu Asp Thr
                165                 170                 175

Pro Arg Pro Pro Lys Gln Ala Leu Ile Phe Ala Thr Val Gly Ala Thr
            180                 185                 190

Leu Pro Phe Pro Arg Leu Val Gln Ala Val Leu Asp Leu Lys Arg Ala
        195                 200                 205

Gly Gly Leu Pro Gly Lys Leu Ile Leu Gln Tyr Gly Asp Gln Asp Leu
    210                 215                 220

Pro Asp Pro Gly Ile Pro Asp Val Glu Ile Arg Arg Thr Ile Pro Phe
225                 230                 235                 240

Asp Asp Leu Gln Leu Leu Leu Arg Asp Ala Asp Met Val Ile Cys His
                245                 250                 255

Gly Gly Thr Gly Ser Leu Val Thr Ala Leu Arg Ala Gly Cys Arg Val
            260                 265                 270

Val Ala Phe Pro Arg Arg His Asp Leu Gly Glu His Tyr Asp Asp His
        275                 280                 285

Gln Glu Glu Ile Ala Gln Thr Phe Ala Asp Arg Gly Leu Leu Gln Ala
    290                 295                 300

Val Arg Asp Glu Arg Gln Leu Gly Ala Ala Val Glu Ala Ala Lys Ala
305                 310                 315                 320

Thr Glu Pro Gln Leu Ala Thr Thr Asp His Thr Ala Leu Ala Ala Arg
                325                 330                 335

Leu Arg Gln Leu Leu Ala Gln Trp Ser Ala Lys Arg
            340                 345
```

<210> SEQ ID NO 14
<211> LENGTH: 867
<212> TYPE: DNA
<213> ORGANISM: Sphingomonas sp. ATCC53159

<400> SEQUENCE: 14

```
atgagcacgc cccggatcag cgtcgtcatc ccgcactata acgatccgca atccttgcgg      60
ctctgcctgg atgcgctgga gcggcagacg atcggtcgcg acgcgttcga gatcatcgtc     120
ggcgacaaca attcgccctg tgggctcgcg gcggtggagg cggcggtcgc cggacgtgcg     180
cggatcgtga ccattctgga aaaggggcg ggccccgcgc gcaacggggc ggcagccgca      240
gcgcgtggcg agatcctcgc ctttaccgac agtgactgcg tggtggagcc cggctggctg     300
gcgggcggca cgaccagggt cgcgcctggc cgtttcatcg gcgggcacat gtatgtgcgc     360
aagcccgaag ggccgccgaa cggcgccgag gcgctggaga tggcgctggc gttcgacaat     420
gaaggctatg tgcggcgcac ccagttcacg gtcaccgcaa acctgttcgt gatgcgcgcc     480
gatttcgaac gggtcggcgg cttccgcgtt ggcgtgtccg aggatctgga atggtgccac     540
cgggcgatcg ccagcggcct caccatcaac tatgcaccgg atgcatcggt gggccacccg     600
ccccggcccg actggtcggc cctgctggtg aagacgcggc gcatccagcg cgaactctat     660
ctgttcaaca tcgagcggcc gaagggcagg ctgcgctggc tggtccgttc cgtggcgcaa     720
ccggcgatga tcccacagga cgtggccaag atcctgcgca caccgggtac caagggcgcg     780
cgcctcgctg cggtcaccac gctggtccgg ctgcggctgt ggcgcggcgg cgccggcttg     840
ttgcagttgc tcggccgcga catctga                                         867
```

<210> SEQ ID NO 15
<211> LENGTH: 288
<212> TYPE: PRT
<213> ORGANISM: Sphingomonas sp. ATCC53159

<400> SEQUENCE: 15

Met Ser Thr Pro Arg Ile Ser Val Val Ile Pro His Tyr Asn Asp Pro
1               5                   10                  15

Gln Ser Leu Arg Leu Cys Leu Asp Ala Leu Glu Arg Gln Thr Ile Gly
            20                  25                  30

Arg Asp Ala Phe Glu Ile Ile Val Gly Asp Asn Asn Ser Pro Cys Gly
        35                  40                  45

Leu Ala Ala Val Glu Ala Ala Val Ala Gly Arg Ala Arg Ile Val Thr
    50                  55                  60

Ile Leu Glu Lys Gly Ala Gly Pro Ala Arg Asn Gly Ala Ala Ala Ala
65                  70                  75                  80

Ala Arg Gly Glu Ile Leu Ala Phe Thr Asp Ser Asp Cys Val Val Glu
                85                  90                  95

Pro Gly Trp Leu Ala Gly Gly Thr Thr Arg Val Ala Pro Gly Arg Phe
            100                 105                 110

Ile Gly Gly His Met Tyr Val Arg Lys Pro Glu Gly Pro Pro Asn Gly
        115                 120                 125

Ala Glu Ala Leu Glu Met Ala Leu Ala Phe Asp Asn Glu Gly Tyr Val
    130                 135                 140

Arg Arg Thr Gln Phe Thr Val Thr Ala Asn Leu Phe Val Met Arg Ala
145                 150                 155                 160

Asp Phe Glu Arg Val Gly Gly Phe Arg Val Gly Val Ser Glu Asp Leu
                165                 170                 175

Glu Trp Cys His Arg Ala Ile Ala Ser Gly Leu Thr Ile Asn Tyr Ala

|     |     |     |     | 180 |     |     |     | 185 |     |     |     | 190 |     |     |
| --- | --- | --- | --- | --- | --- | --- | --- | --- | --- | --- | --- | --- | --- | --- |
| Pro | Asp | Ala | Ser | Val | Gly | His | Pro | Pro | Arg | Pro | Asp | Trp | Ser | Ala | Leu |
|     |     |     | 195 |     |     |     |     | 200 |     |     |     |     | 205 |     |     |

| Leu | Val | Lys | Thr | Arg | Arg | Ile | Gln | Arg | Glu | Leu | Tyr | Leu | Phe | Asn | Ile |
| --- | --- | --- | --- | --- | --- | --- | --- | --- | --- | --- | --- | --- | --- | --- | --- |
|     |     | 210 |     |     |     |     | 215 |     |     |     |     | 220 |     |     |     |

| Glu | Arg | Pro | Lys | Gly | Arg | Leu | Arg | Trp | Leu | Val | Arg | Ser | Val | Ala | Gln |
| --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |

| Pro | Ala | Met | Ile | Pro | Gln | Asp | Val | Ala | Lys | Ile | Leu | Arg | Thr | Pro | Gly |
| --- | --- | --- | --- | --- | --- | --- | --- | --- | --- | --- | --- | --- | --- | --- | --- |
|     |     |     |     | 245 |     |     |     |     | 250 |     |     |     |     | 255 |     |

| Thr | Lys | Gly | Ala | Arg | Leu | Ala | Ala | Val | Thr | Thr | Leu | Val | Arg | Leu | Arg |
| --- | --- | --- | --- | --- | --- | --- | --- | --- | --- | --- | --- | --- | --- | --- | --- |
|     |     |     | 260 |     |     |     |     | 265 |     |     |     |     | 270 |     |     |

| Leu | Trp | Arg | Gly | Gly | Ala | Gly | Leu | Leu | Gln | Leu | Leu | Gly | Arg | Asp | Ile |
| --- | --- | --- | --- | --- | --- | --- | --- | --- | --- | --- | --- | --- | --- | --- | --- |
|     | 275 |     |     |     |     | 280 |     |     |     |     | 285 |     |     |     |     |

<210> SEQ ID NO 16
<211> LENGTH: 1389
<212> TYPE: DNA
<213> ORGANISM: Sphingomonas sp. ATCC53159

<400> SEQUENCE: 16

| gtggctgtag | gttccgcgct | gagattcttg | tggccgttcg | gccgtcgaga | agaacctgaa | 60 |
| --- | --- | --- | --- | --- | --- | --- |
| gaagagggct | atttcccgct | gactgcgaca | gtggtgccgc | atcgcgatgc | ccatagcggc | 120 |
| cgtggtcgcc | cggatttccc | aaccttccgt | gcctccgcgc | tggaccgccc | gctggatcgc | 180 |
| cgccgcgacg | agcgccgcga | gatcacgcgc | gcccggttcg | cgctggcgac | cttcttcaca | 240 |
| cccacccagc | cggtggccga | tcggtcgagc | ttcgccgggc | gcctcggcgt | gctggcgcgc | 300 |
| ctaatctcct | cgatcgagag | ccagcgcagc | catgtcgtgc | tctatggcga | gcgcggcatc | 360 |
| ggcaagacct | cgctgctcca | cgtgctgacc | gatgtcgccc | gcgaatccag | ctatatcgtc | 420 |
| agctatgcga | cctgcggtgc | gaacgcgaat | tcagcgatg | tcttccgcgc | cgtgctggaa | 480 |
| gacgtgccgc | tgctgttcca | tcgcggcgtg | gcgcccaacg | ccggcgaggc | ggagagcggc | 540 |
| ggcaacttgg | ccgaccgcct | gccgacgggc | agcttcgggc | ccggcgaact | ggccgacctg | 600 |
| tgcgccgaca | tcacgggcac | acgcgtgctg | atcatcctcg | acgaatatga | tcgcgtcagc | 660 |
| gattccgcct | tccgtcagca | ggtcgccgag | ctgatcaaga | acctgtcgga | ccgttcggcg | 720 |
| cgcgtccagc | tggtgatcgc | gggcgtcgcc | tcgaacctgc | aggagctgat | cggttatgcg | 780 |
| ccgtcgatcc | gccgcaacgt | catcggcctg | ccgatgcccc | ggctggagga | atcggaggtg | 840 |
| caggagatga | tcgcgctcgg | cgaaaccgcc | tcgggcgttc | gcttcgatcc | ggacctgact | 900 |
| cacatgatcc | acctgctcgc | gctggggtcg | ccctatttcg | cgcggctgct | gtgccaccat | 960 |
| tccgcgctgg | aagccctgga | ccagggccgc | ctcacggtcg | acgccgggca | tctgcgtcgt | 1020 |
| gcgctcgacc | aggcgatcct | tgagatcgag | ggccgcatgc | cgccgcgcgc | ggtgatcgag | 1080 |
| atgcgcaagt | cgtcggcgg | ccgctacgat | ccactcgtcg | cggcgctggg | cgaggcctcg | 1140 |
| cgctcggcgg | atggctggtt | cagcggccaa | gccgtggtgg | atctgctgcc | gggcgcgcac | 1200 |
| atcacggcgg | cgcaggtcga | gcaggagctg | ggcgagctca | ccgtcaact | cggcctcgaa | 1260 |
| tccgaaacgc | aggacggcga | ttgccgcttc | cgcttcaccg | acgatacgct | gccggtctat | 1320 |
| ctgtggctga | tgatcggccg | cctgcggctc | gacagcggca | cgctggaaga | cgcgctggcc | 1380 |
| accgtctga |     |     |     |     |     | 1389 |

<210> SEQ ID NO 17
<211> LENGTH: 462

<212> TYPE: PRT
<213> ORGANISM: Sphingomonas sp. ATCC53159

<400> SEQUENCE: 17

```
Val Ala Val Gly Ser Ala Leu Arg Phe Leu Trp Pro Phe Gly Arg Arg
1               5                   10                  15

Glu Glu Pro Glu Glu Gly Tyr Phe Pro Leu Thr Ala Thr Val Val
            20                  25                  30

Pro His Arg Asp Ala His Ser Gly Arg Gly Arg Pro Asp Phe Pro Thr
            35                  40                  45

Phe Arg Ala Ser Ala Leu Asp Arg Pro Leu Asp Arg Arg Asp Glu
50                  55                  60

Arg Arg Glu Ile Thr Arg Ala Arg Phe Ala Leu Ala Thr Phe Phe Thr
65                  70                  75                  80

Pro Thr Gln Pro Val Ala Asp Arg Ser Ser Phe Ala Gly Arg Leu Gly
                85                  90                  95

Val Leu Ala Arg Leu Ile Ser Ser Ile Glu Ser Gln Arg Ser His Val
            100                 105                 110

Val Leu Tyr Gly Glu Arg Gly Ile Gly Lys Thr Ser Leu Leu His Val
            115                 120                 125

Leu Thr Asp Val Ala Arg Glu Ser Ser Tyr Ile Val Ser Tyr Ala Thr
130                 135                 140

Cys Gly Ala Asn Ala Asn Phe Ser Asp Val Phe Arg Ala Val Leu Glu
145                 150                 155                 160

Asp Val Pro Leu Leu Phe His Arg Gly Val Ala Pro Asn Ala Gly Glu
                165                 170                 175

Ala Glu Ser Gly Gly Asn Leu Ala Asp Arg Leu Pro Thr Gly Ser Phe
            180                 185                 190

Gly Pro Gly Glu Leu Ala Asp Leu Cys Ala Asp Ile Thr Gly Thr Arg
            195                 200                 205

Val Leu Ile Ile Leu Asp Glu Tyr Asp Arg Val Ser Asp Ser Ala Phe
210                 215                 220

Arg Gln Gln Val Ala Glu Leu Ile Lys Asn Leu Ser Asp Arg Ser Ala
225                 230                 235                 240

Arg Val Gln Leu Val Ile Ala Gly Val Ala Ser Asn Leu Gln Glu Leu
                245                 250                 255

Ile Gly Tyr Ala Pro Ser Ile Arg Arg Asn Val Ile Gly Leu Pro Met
            260                 265                 270

Pro Arg Leu Glu Glu Ser Glu Val Gln Glu Met Ile Ala Leu Gly Glu
            275                 280                 285

Thr Ala Ser Gly Val Arg Phe Asp Pro Asp Leu Thr His Met Ile His
290                 295                 300

Leu Leu Ala Leu Gly Ser Pro Tyr Phe Ala Arg Leu Leu Cys His His
305                 310                 315                 320

Ser Ala Leu Glu Ala Leu Asp Gln Gly Arg Leu Thr Val Asp Ala Gly
                325                 330                 335

His Leu Arg Arg Ala Leu Asp Gln Ala Ile Leu Glu Ile Glu Gly Arg
            340                 345                 350

Met Pro Pro Arg Ala Val Ile Glu Met Arg Lys Phe Val Gly Gly Arg
            355                 360                 365

Tyr Asp Pro Leu Val Ala Ala Leu Gly Glu Ala Ser Arg Ser Ala Asp
370                 375                 380

Gly Trp Phe Ser Gly Gln Ala Val Val Asp Leu Leu Pro Gly Ala His
385                 390                 395                 400
```

Ile Thr Ala Ala Gln Val Glu Gln Glu Leu Gly Glu Leu Thr Gly Gln
                405                 410                 415

Leu Gly Leu Glu Ser Glu Thr Gln Asp Gly Asp Cys Arg Phe Arg Phe
            420                 425                 430

Thr Asp Asp Thr Leu Pro Val Tyr Leu Trp Leu Met Ile Gly Arg Leu
        435                 440                 445

Arg Leu Asp Ser Gly Thr Leu Glu Asp Ala Leu Ala Thr Val
    450                 455                 460

<210> SEQ ID NO 18
<211> LENGTH: 1299
<212> TYPE: DNA
<213> ORGANISM: Sphingomonas sp. ATCC53159

<400> SEQUENCE: 18
atgaagccga gacccggggg aacctttatg caagtaaatt tcaatcgaca ggctcgcaag      60
ctcggtgccg gcaatgcgct cgcgcggggg gggcccgtgc ttgcgctgct tgcgaccgcg     120
gcatggacac aacctgcgct ggcgcagcga caggcatttg agtcccgccc ctccggtagc     180
gagcgacagg tcgatattcg cgcgacgggg tcgctggaat atgacgacaa cgtcgtgctg     240
aacgaccagc ggatcacgga cggcgcgcgt ggcgatgtga tcgcatcgcc cgggctggac     300
gtgaccctag ttctgccccg cgccaccggg cagctctacc tcaccggcaa tgtcggatat     360
cgcttttaca gcgatatac caactttaac cgcgagcaga tctcgctcac cggcggcgca     420
gatcagcggt tcgcctcctg cgtcgtgcac ggggaagtcg gctatcagcg ccacctcacc     480
gacctgtcca gcatcttgat ccaggacacc acgcctgcgc tcaacaacac cgaagaggcc     540
cggcagtaca ccgcggatat cggctgcggc gcgacctacg gcctgcggcc tgccgttttcc    600 tacacccgca acgaagtgcg caacagcctt gccgagcgcc gatacgcgga ctcgaatacc     660 aacacctttta ccgcacagct tggcctgact tcgcctgccc tggggaccgt ggcggtatt    720 gggcgtatgt ccgacagcag ctatgtccat cgcgtccttc ccggcattac cggccaggac     780
gggatgaaga gctacgcggc cggcgtccag ctcgagcgct cggtggccaa ccgactccat     840
ttcaacggct cggtgaatta caccgaggtt gacccaaagc tcgcatccac caaaggattc     900
aagggcgtag gatttaacgt tccggcgat tatgctggtg atcagtacag cctccaattg     960
ctggcttcac gatcgcccca gccttcactt cttctgttcg tgggttacga gattgtgaca    1020
gcggtttcgg cgaatgcgac gcgccggctg agcgatcgca ttcagatatc gctgcaaggc    1080
agccgaacct ggcgcgagct cgcgtcttcg cggctgctca ccaacgtgcc gatttccggc    1140
aacgacaaca cctcgacgtt gttcgcctcc gctaccttcc ggccgaatcg ccggctgagc    1200
tttgtgctgg gtgccggcct tcagcggcgc accagcaaca cgcagctata cagttacagc    1260
tccaaacgca tcaatctctc gacgtcgctt tcgctctga                           1299

<210> SEQ ID NO 19
<211> LENGTH: 432
<212> TYPE: PRT
<213> ORGANISM: Sphingomonas sp. ATCC53159

<400> SEQUENCE: 19

Met Lys Pro Arg Pro Gly Gly Thr Phe Met Gln Val Asn Phe Asn Arg
1               5                   10                  15

Gln Ala Arg Lys Leu Gly Ala Gly Asn Ala Leu Ala Arg Gly Gly Pro
            20                  25                  30

Val Leu Ala Leu Leu Ala Thr Ala Ala Trp Thr Gln Pro Ala Leu Ala
            35                  40                  45

Gln Arg Gln Ala Phe Glu Ser Arg Pro Ser Gly Ser Glu Arg Gln Val
 50                  55                  60

Asp Ile Arg Ala Thr Gly Ser Leu Glu Tyr Asp Asp Asn Val Val Leu
65                  70                  75                  80

Asn Asp Gln Arg Ile Thr Asp Gly Ala Arg Gly Asp Val Ile Ala Ser
                85                  90                  95

Pro Gly Leu Asp Val Thr Leu Val Leu Pro Arg Ala Thr Gly Gln Leu
            100                 105                 110

Tyr Leu Thr Gly Asn Val Gly Tyr Arg Phe Tyr Lys Arg Tyr Thr Asn
            115                 120                 125

Phe Asn Arg Glu Gln Ile Ser Leu Thr Gly Gly Ala Asp Gln Arg Phe
        130                 135                 140

Ala Ser Cys Val Val His Gly Glu Val Gly Tyr Gln Arg His Leu Thr
145                 150                 155                 160

Asp Leu Ser Ser Ile Leu Ile Gln Asp Thr Thr Pro Ala Leu Asn Asn
                165                 170                 175

Thr Glu Glu Ala Arg Gln Tyr Thr Ala Asp Ile Gly Cys Gly Ala Thr
            180                 185                 190

Tyr Gly Leu Arg Pro Ala Val Ser Tyr Thr Arg Asn Glu Val Arg Asn
            195                 200                 205

Ser Leu Ala Glu Arg Arg Tyr Ala Asp Ser Asn Thr Asn Thr Phe Thr
        210                 215                 220

Ala Gln Leu Gly Leu Thr Ser Pro Ala Leu Gly Thr Val Ala Val Phe
225                 230                 235                 240

Gly Arg Met Ser Asp Ser Ser Tyr Val His Arg Val Leu Pro Gly Ile
                245                 250                 255

Thr Gly Gln Asp Gly Met Lys Ser Tyr Ala Ala Gly Val Gln Leu Glu
            260                 265                 270

Arg Ser Val Ala Asn Arg Leu His Phe Asn Gly Ser Val Asn Tyr Thr
            275                 280                 285

Glu Val Asp Pro Lys Leu Ala Ser Thr Lys Gly Phe Lys Gly Val Gly
        290                 295                 300

Phe Asn Val Ser Gly Asp Tyr Ala Gly Asp Gln Tyr Ser Leu Gln Leu
305                 310                 315                 320

Leu Ala Ser Arg Ser Pro Gln Pro Ser Leu Leu Phe Val Gly Tyr
                325                 330                 335

Glu Ile Val Thr Ala Val Ser Ala Asn Ala Thr Arg Arg Leu Ser Asp
            340                 345                 350

Arg Ile Gln Ile Ser Leu Gln Gly Ser Arg Thr Trp Arg Glu Leu Ala
            355                 360                 365

Ser Ser Arg Leu Leu Thr Asn Val Pro Ile Ser Gly Asn Asp Asn Thr
        370                 375                 380

Ser Thr Leu Phe Ala Ser Ala Thr Phe Arg Pro Asn Arg Leu Ser
385                 390                 395                 400

Phe Val Leu Gly Ala Gly Leu Gln Arg Arg Thr Ser Asn Thr Gln Leu
                405                 410                 415

Tyr Ser Tyr Ser Ser Lys Arg Ile Asn Leu Ser Thr Ser Leu Ser Leu
            420                 425                 430

<210> SEQ ID NO 20
<211> LENGTH: 918
<212> TYPE: DNA

<213> ORGANISM: Sphingomonas sp. ATCC53159

<400> SEQUENCE: 20

```
atgcatatca agaatcgctt cgtgaatatc tcgacgttgg ccatcgccgc cgcgctggcc      60
acgccggcgg cggcgcagat ccccacgcgg tccgtgcccg cgccggcccg cccgcggcct     120
gcaacgccgc cggcgcaaca gcagaaccag gcgccgtcga cgcccgcagc ggcaaccccg     180
gcgcagaccg ccgcaaccgt tgcccctgca gcaaccgcac ccgcaggtta caaaatcggc     240
gtggacgacg tgatcgaggc cgacgtgctc ggccagaccg acttcaagac gcgcgcccgt     300
gtgcaggcgg acggcacggt gaccctgccc tatctgggcg ccgtgcaggt caagggcgag     360
accgcgacct cgctcgccga aaagctggcc gggctgctgc gcgccggcgg ctattatgcc     420
aagccgatcg tcagcgtcga aatcgtcggt ttcgtcagca actatgtgac ggtgctgggc     480
caggtgaaca gttccggcct gcagccggtc gaccgcggct atcacgtttc cgagatcatc     540
gcccgtgccg gcggcctgcg ccccgaagcg gccgatttcg tcgttctcac ccgcgccgat     600
ggctccagcg ccaagctgga ctacaagaag ctcgcccaag gtggcccaa tgacgatccg     660
atggtgacgc cggggacaa ggtctttgtc ccggaagtcg agcatttcta catttatggt     720
caaattaacg cgcctggcgt atacgcgatt cgatcggaca tgacgctccg tcgcgcgctg     780
gcccagggcg gtgggcttgc ccccgcaggc tccgtcaagc gtgtgaaggt cacgcgggat     840
ggcaatgaac tcaagttgaa gctggacgat ccgattctcc aggcgacac gatcgtcatc     900
ggcgaacgat tgttctga                                                  918
```

<210> SEQ ID NO 21
<211> LENGTH: 305
<212> TYPE: PRT
<213> ORGANISM: Sphingomonas sp. ATCC53159

<400> SEQUENCE: 21

```
Met His Ile Lys Asn Arg Phe Val Asn Ile Ser Thr Leu Ala Ile Ala
1               5                   10                  15

Ala Ala Leu Ala Thr Pro Ala Ala Gln Ile Pro Thr Arg Ser Val
            20                  25                  30

Pro Ala Pro Ala Arg Pro Arg Pro Ala Thr Pro Pro Ala Gln Gln Gln
        35                  40                  45

Asn Gln Ala Pro Ser Thr Pro Ala Ala Ala Thr Pro Ala Gln Thr Ala
    50                  55                  60

Ala Thr Val Ala Pro Ala Ala Thr Ala Pro Ala Gly Tyr Lys Ile Gly
65                  70                  75                  80

Val Asp Asp Val Ile Glu Ala Asp Val Leu Gly Gln Thr Asp Phe Lys
                85                  90                  95

Thr Arg Ala Arg Val Gln Ala Asp Gly Thr Val Thr Leu Pro Tyr Leu
            100                 105                 110

Gly Ala Val Gln Val Lys Gly Glu Thr Ala Thr Ser Leu Ala Glu Lys
        115                 120                 125

Leu Ala Gly Leu Leu Arg Ala Gly Gly Tyr Tyr Ala Lys Pro Ile Val
    130                 135                 140

Ser Val Glu Ile Val Gly Phe Val Ser Asn Tyr Val Thr Val Leu Gly
145                 150                 155                 160

Gln Val Asn Ser Ser Gly Leu Gln Pro Val Asp Arg Gly Tyr His Val
                165                 170                 175

Ser Glu Ile Ile Ala Arg Ala Gly Gly Leu Arg Pro Glu Ala Ala Asp
            180                 185                 190
```

```
Phe Val Val Leu Thr Arg Ala Asp Gly Ser Ser Ala Lys Leu Asp Tyr
        195                 200                 205
Lys Lys Leu Ala Gln Gly Gly Pro Asn Asp Asp Pro Met Val Thr Pro
    210                 215                 220
Gly Asp Lys Val Phe Val Pro Glu Val Glu His Phe Tyr Ile Tyr Gly
225                 230                 235                 240
Gln Ile Asn Ala Pro Gly Val Tyr Ala Ile Arg Ser Asp Met Thr Leu
                245                 250                 255
Arg Arg Ala Leu Ala Gln Gly Gly Leu Ala Pro Ala Gly Ser Val
            260                 265                 270
Lys Arg Val Lys Val Thr Arg Asp Gly Asn Glu Leu Lys Leu Lys Leu
        275                 280                 285
Asp Asp Pro Ile Leu Pro Gly Asp Thr Ile Val Ile Gly Glu Arg Leu
    290                 295                 300
Phe
305

<210> SEQ ID NO 22
<211> LENGTH: 1347
<212> TYPE: DNA
<213> ORGANISM: Sphingomonas sp. ATCC53159

<400> SEQUENCE: 22
gtgaatatca ttcagttctt ccgcattctg tgggtgcgcc gatggatcat cctcccggcg      60
tttctcgttt gcgttaccac tgccaccatt gtggtccagt ttctgcccga acgctacaag     120
gccactacgc gggtggtgct cgacacgttt aagcccgatc ccgtcaccgg acaggtgatg     180
agctcgcagt tcatgcgcgc ctatgtcgag actcagaccc agctgatcga ggactatgcg     240
accgccggtc gcgtggtcga cgaactgggc tgggtgaatg atccggcgaa catctccgcg     300
ttcaacaact cgtccgcggc tgccaccggc gacatccgcc gctggctcgc caagcagatc     360
atcgacaata ccaaggccga tgtgatggag gggagcaaca tcctcgaaat cacctattcg     420
gacagctcgc ccgagcgcgc cgaacgcatc gccaacctga tccgcacctc gttcctcgcc     480
cagtcgctcg ccgccaagcg ccaggccgcg accaagtcgg ccgactggta cgcccagcag     540
gccgaagctg cccgcgattc gctcgctgcg gcggtccagg cccgcaccga tttcgtgaag     600
aagaccggca tcgtgctgac cgaaaccggc gccgacctgg aaacccagaa gctccagcag     660 atcgagggc agacgacgac cgccaccgcc ccggttgcca tggccccag cggcatgggc     720 ccggcgcaga tgcagctcgc ccagatcgac cagcagatcc agcaggcagc gaccagccta     780
ggtccgaacc acccaacttt ccaggccttg cagcggcagc gcgaagtgtt cgccaaggca     840 gcggcggcg aacgcgcgca ggcgaacggc gtatccggtc cggcacgcgg ggccatcgaa     900
agcgcagcca cgcccagcg cgcgcgggtt ctcggcaatc gtcaggatgt cgacaagctt     960
acgcagctgc agcgtgacgt ctcgctgaag caggatcagt acatgaaggc ggcacagcgc    1020
gtcgccgatc tgcggctgga agcaagcagc aacgatgtcg gcatgtcgac gctcagcgaa    1080
gcatcggcgc cggaaacgcc ctattacccc aaggtgccgc tcatcatcgg tggtgcagcc    1140
ggcttcggcc tcgggctcgg tctgctggtc gcgctgctcg tcgagctgct cggccgccgc    1200
gtccgcagcc ccgaggatct ggaagttgcg atcgatgcac cggtgctggg cgtgatccag    1260
agccgcgcct cgcttgccgc ccgccttcgc gcgcccaag aaaccctcgg cgaaggtgcc    1320
gacacgcacg gagcttcagt aaactga                                        1347
```

<210> SEQ ID NO 23
<211> LENGTH: 448
<212> TYPE: PRT
<213> ORGANISM: Sphingomonas sp. ATCC53159

<400> SEQUENCE: 23

```
Val Asn Ile Ile Gln Phe Phe Arg Ile Leu Trp Val Arg Arg Trp Ile
1               5                   10                  15

Ile Leu Pro Ala Phe Leu Val Cys Val Thr Thr Ala Thr Ile Val Val
            20                  25                  30

Gln Phe Leu Pro Glu Arg Tyr Lys Ala Thr Thr Arg Val Val Leu Asp
        35                  40                  45

Thr Phe Lys Pro Asp Pro Val Thr Gly Gln Val Met Ser Ser Gln Phe
    50                  55                  60

Met Arg Ala Tyr Val Glu Thr Gln Thr Gln Leu Ile Glu Asp Tyr Ala
65                  70                  75                  80

Thr Ala Gly Arg Val Val Asp Glu Leu Gly Trp Val Asn Asp Pro Ala
                85                  90                  95

Asn Ile Ser Ala Phe Asn Asn Ser Ala Ala Ala Thr Gly Asp Ile
            100                 105                 110

Arg Arg Trp Leu Ala Lys Gln Ile Ile Asp Asn Thr Lys Ala Asp Val
        115                 120                 125

Met Glu Gly Ser Asn Ile Leu Glu Ile Thr Tyr Ser Asp Ser Ser Pro
    130                 135                 140

Glu Arg Ala Glu Arg Ile Ala Asn Leu Ile Arg Thr Ser Phe Leu Ala
145                 150                 155                 160

Gln Ser Leu Ala Ala Lys Arg Gln Ala Ala Thr Lys Ser Ala Asp Trp
                165                 170                 175

Tyr Ala Gln Gln Ala Glu Ala Ala Arg Asp Ser Leu Ala Ala Ala Val
            180                 185                 190

Gln Ala Arg Thr Asp Phe Val Lys Lys Thr Gly Ile Val Leu Thr Glu
        195                 200                 205

Thr Gly Ala Asp Leu Glu Thr Gln Lys Leu Gln Gln Ile Glu Gly Gln
    210                 215                 220

Thr Thr Thr Ala Thr Ala Pro Val Ala Met Ala Pro Ser Gly Met Gly
225                 230                 235                 240

Pro Ala Gln Met Gln Leu Ala Gln Ile Asp Gln Ile Gln Gln Ala
                245                 250                 255

Ala Thr Ser Leu Gly Pro Asn His Pro Thr Phe Gln Ala Leu Gln Arg
            260                 265                 270

Gln Arg Glu Val Phe Ala Lys Ala Ala Ala Glu Arg Ala Gln Ala
        275                 280                 285

Asn Gly Val Ser Gly Pro Ala Arg Gly Ala Ile Glu Ser Ala Ala Asn
    290                 295                 300

Ala Gln Arg Ala Arg Val Leu Gly Asn Arg Gln Asp Val Asp Lys Leu
305                 310                 315                 320

Thr Gln Leu Gln Arg Asp Val Ser Leu Lys Gln Asp Gln Tyr Met Lys
                325                 330                 335

Ala Ala Gln Arg Val Ala Asp Leu Arg Leu Glu Ala Ser Ser Asn Asp
            340                 345                 350

Val Gly Met Ser Thr Leu Ser Glu Ala Ser Pro Glu Thr Pro Tyr
        355                 360                 365

Tyr Pro Lys Val Pro Leu Ile Ile Gly Gly Ala Ala Gly Phe Gly Leu
    370                 375                 380
```

Gly Leu Gly Leu Leu Val Ala Leu Leu Val Glu Leu Gly Arg Arg
385                 390                 395                 400

Val Arg Ser Pro Glu Asp Leu Glu Val Ala Ile Asp Ala Pro Val Leu
            405                 410                 415

Gly Val Ile Gln Ser Arg Ala Ser Leu Ala Ala Arg Leu Arg Arg Ala
        420                 425                 430

Gln Glu Thr Leu Gly Glu Gly Ala Asp Thr His Gly Ala Ser Val Asn
    435                 440                 445

<210> SEQ ID NO 24
<211> LENGTH: 708
<212> TYPE: DNA
<213> ORGANISM: Sphingomonas sp. ATCC53159

<400> SEQUENCE: 24
atggacgcga tgaccagcga accgctgccc gaaggcgatc gtccgagcgc cgtgccgacc      60
acgccggata cgatcggcat gctcgaatac cagctcgtcc tctccgatcc gaccgggatc     120
gaggcggaag cgatccgcgc gctacgcacg cgcatcatga cccagcacct ccgcgagggc     180
cggcgcgcgc tcgcgatctg cgccgcctcg gcgggatccg gctgcagctt caccgccgtc     240
aatctggcga cggcgctggc gcagatcggc gttaagactg cgctggtcga tgccaatctg     300
cgcgatccca gcatcggcgc agccttcggc ctcgccgccg acaagcccgg cctggccgat     360
tatctcgcct cgggcgatgt cgacctcgcc tcgatcatcc atgcgacccg cctcgaccag     420
ctctcgatca tcccggccgg gcatgtcgag cacagcccgc aggaactgct cgcgtccgaa     480
cagttccatg atctggcgac gcagctgctg cgcgagttcg acatcacgat cttcgacacc     540
acggcgtcca cacctgcgc cgacgcgcag cgtgtcgcgc atatcgccgg ctatgcgatc     600
atcgtggcgc gcaaggatgc gagctacatc cgcgacgtga acacgctcag ccgcacgctg     660
cgtgcagacc gcaccaacgt catcggctgc gtactgaacg gctattga                 708

<210> SEQ ID NO 25
<211> LENGTH: 235
<212> TYPE: PRT
<213> ORGANISM: Sphingomonas sp. ATCC53159

<400> SEQUENCE: 25

Met Asp Ala Met Thr Ser Glu Pro Leu Pro Glu Gly Asp Arg Pro Ser
1               5                   10                  15

Ala Val Pro Thr Thr Pro Asp Thr Ile Gly Met Leu Glu Tyr Gln Leu
            20                  25                  30

Val Leu Ser Asp Pro Thr Gly Ile Glu Ala Glu Ala Ile Arg Ala Leu
        35                  40                  45

Arg Thr Arg Ile Met Thr Gln His Leu Arg Glu Gly Arg Ala Leu
    50                  55                  60

Ala Ile Cys Ala Ala Ser Ala Gly Ser Gly Cys Ser Phe Thr Ala Val
65                  70                  75                  80

Asn Leu Ala Thr Ala Leu Ala Gln Ile Gly Val Lys Thr Ala Leu Val
            85                  90                  95

Asp Ala Asn Leu Arg Asp Pro Ser Ile Gly Ala Ala Phe Gly Leu Ala
            100                 105                 110

Ala Asp Lys Pro Gly Leu Ala Asp Tyr Leu Ala Ser Gly Asp Val Asp
        115                 120                 125

Leu Ala Ser Ile Ile His Ala Thr Arg Leu Asp Gln Leu Ser Ile Ile
    130                 135                 140

Pro Ala Gly His Val Glu His Ser Pro Gln Glu Leu Leu Ala Ser Glu
145                 150                 155                 160

Gln Phe His Asp Leu Ala Thr Gln Leu Leu Arg Glu Phe Asp Ile Thr
            165                 170                 175

Ile Phe Asp Thr Thr Ala Ser Asn Thr Cys Ala Asp Ala Gln Arg Val
        180                 185                 190

Ala His Ile Ala Gly Tyr Ala Ile Val Ala Arg Lys Asp Ala Ser
    195                 200                 205

Tyr Ile Arg Asp Val Asn Thr Leu Ser Arg Thr Leu Arg Ala Asp Arg
210                 215                 220

Thr Asn Val Ile Gly Cys Val Leu Asn Gly Tyr
225                 230                 235

<210> SEQ ID NO 26
<211> LENGTH: 882
<212> TYPE: DNA
<213> ORGANISM: Sphingomonas sp. ATCC53159

<400> SEQUENCE: 26
atggcagcga ccgcgatgac gcggcagcag gagaggaagg gcggtggcta ttggctggcc      60
gttgccggtc ttgccgcgct aaccatcccg accttcatca ccctgggtcg cgaggtttgg     120
agtgcggaag gcggcgtgca gggtccgatc gtgctcgcca cgggcgcctg gatgctggcc     180
cgccagtgct cgacgatcga ggcgctacgc cgccccggca gcgtgctgct cggcgcgctg     240
ttcctgctgg cgacgcttgc cttctacacc gttggacggg tgttcgactt catcagtgtc     300
gaaaccttcg gactggtcgc gacctatctg gtcgtcgcct atctctattt cggtgccagg     360
gtgctccgtg ccgcctggtt cccggtgctg tggctgttct tcctggtgcc gccgccggc      420 tgggccgtcg accgcatcac cgcaccgctc aaggagttcg tctcctatgc ggcaacgggc     480
ctgctttcct gggtggatta ccgatcctg cgccagggcg tgacactgtt cgtcggcccc      540
tatcagctgc tcgtcgaaga tgcctgttcg ggtctgcgct cgctgtccag cctggtcgtc     600
gtgacgctgc tctacatcta catcaagaac aagccgtcct ggcgctacgc ggcgttcatc     660
gcagcgctgg tgatcccggt ggcagtggtg accaacgtcc tgcggatcat catcctggta     720
ctgatcacct atcatctggg cgacgaggcg gcgcagagct tcctccacgt ctccaccggc     780
atggtgatgt tcgtggtcgc cctgctttgc atcttcgcga tcgactgggt ggtcgagcaa     840
cttcttctcc tgcgtcggag gcatcatgtt caaccggcgt ga                        882

<210> SEQ ID NO 27
<211> LENGTH: 293
<212> TYPE: PRT
<213> ORGANISM: Sphingomonas sp. ATCC53159

<400> SEQUENCE: 27

Met Ala Ala Thr Ala Met Thr Arg Gln Gln Glu Arg Lys Gly Gly Gly
1               5                   10                  15

Tyr Trp Leu Ala Val Ala Gly Leu Ala Ala Leu Thr Ile Pro Thr Phe
            20                  25                  30

Ile Thr Leu Gly Arg Glu Val Trp Ser Ala Glu Gly Gly Val Gln Gly
        35                  40                  45

Pro Ile Val Leu Ala Thr Gly Ala Trp Met Leu Ala Arg Gln Cys Ser
    50                  55                  60

Thr Ile Glu Ala Leu Arg Arg Pro Gly Ser Val Leu Leu Gly Ala Leu
65                  70                  75                  80

```
Phe Leu Leu Ala Thr Leu Ala Phe Tyr Thr Val Gly Arg Val Phe Asp
                85                  90                  95

Phe Ile Ser Val Glu Thr Phe Gly Leu Val Ala Thr Tyr Leu Val Val
            100                 105                 110

Ala Tyr Leu Tyr Phe Gly Ala Arg Val Leu Arg Ala Ala Trp Phe Pro
        115                 120                 125

Val Leu Trp Leu Phe Phe Leu Val Pro Pro Gly Trp Ala Val Asp
130                 135                 140

Arg Ile Thr Ala Pro Leu Lys Glu Phe Val Ser Tyr Ala Ala Thr Gly
145                 150                 155                 160

Leu Leu Ser Trp Val Asp Tyr Pro Ile Leu Arg Gln Gly Val Thr Leu
                165                 170                 175

Phe Val Gly Pro Tyr Gln Leu Leu Val Glu Asp Ala Cys Ser Gly Leu
            180                 185                 190

Arg Ser Leu Ser Ser Leu Val Val Thr Leu Leu Tyr Ile Tyr Ile
        195                 200                 205

Lys Asn Lys Pro Ser Trp Arg Tyr Ala Ala Phe Ile Ala Ala Leu Val
    210                 215                 220

Ile Pro Val Ala Val Thr Asn Val Leu Arg Ile Ile Ile Leu Val
225                 230                 235                 240

Leu Ile Thr Tyr His Leu Gly Asp Glu Ala Ala Gln Ser Phe Leu His
                245                 250                 255

Val Ser Thr Gly Met Val Met Phe Val Val Ala Leu Leu Cys Ile Phe
            260                 265                 270

Ala Ile Asp Trp Val Val Glu Gln Leu Leu Leu Leu Arg Arg Arg His
        275                 280                 285

His Val Gln Pro Ala
    290
```

<210> SEQ ID NO 28
<211> LENGTH: 699
<212> TYPE: DNA
<213> ORGANISM: Sphingomonas sp. ATCC53159

<400> SEQUENCE: 28

```
atgttcaacc ggcgtgacct gctgatcggc gcaggctgct cgccgccgc tggcgcctcg      60
ctcggcctga agccgcaccg gcggatggac ctgctgggcg gcaccaagct cgacacgctg    120
atgcccaagg cattcggcgc atggaaggca gaggataccg gttcgctgat cgcgccggcg    180
cgcgaaggca gcctggagga caagctctac aaccaggtgg tcacccgcgc cttctcccgc    240
gcggacggtg cccaagtgat gctgctgatc gcctatggca acgcccagac cgatctactg    300
cagctgcacc ggccgaaaat atgctacccg ttcttcggct tcaccgtggt ggaaagccat    360
gagcagacca tcccggtgac gccgcaggtg acgatccccg tcgcgcgct gaccgccacc    420
aacttcaacc gcaccgagca gatcctctac tggacccgcg tcggcgaata tctgccgcag    480
aacggcaatc agcagatgct cgcgcggctg aagagccagg tccagggctg gatcgtcgac    540
ggtgtgctgg tgcgcatctc gacggtgacg cccgaggcgg aagatggcct gagcgccaat    600
ctcgatttcg cgcgcgagct ggtgaagacg ctcgacccgc gcgtgctgcg cccgctgctc    660
gggaacgggc tcacacggca gctcggtcac caggtctga                            699
```

<210> SEQ ID NO 29
<211> LENGTH: 232
<212> TYPE: PRT

<213> ORGANISM: Sphingomonas sp. ATCC53159

<400> SEQUENCE: 29

```
Met Phe Asn Arg Arg Asp Leu Leu Ile Gly Ala Gly Cys Phe Ala Ala
1               5                   10                  15
Ala Gly Ala Ser Leu Gly Leu Lys Pro His Arg Arg Met Asp Leu Leu
            20                  25                  30
Gly Gly Thr Lys Leu Asp Thr Leu Met Pro Lys Ala Phe Gly Ala Trp
        35                  40                  45
Lys Ala Glu Asp Thr Gly Ser Leu Ile Ala Pro Ala Arg Glu Gly Ser
    50                  55                  60
Leu Glu Asp Lys Leu Tyr Asn Gln Val Val Thr Arg Ala Phe Ser Arg
65                  70                  75                  80
Ala Asp Gly Ala Gln Val Met Leu Leu Ile Ala Tyr Gly Asn Ala Gln
                85                  90                  95
Thr Asp Leu Leu Gln Leu His Arg Pro Glu Ile Cys Tyr Pro Phe Phe
            100                 105                 110
Gly Phe Thr Val Val Glu Ser His Glu Gln Thr Ile Pro Val Thr Pro
        115                 120                 125
Gln Val Thr Ile Pro Gly Arg Ala Leu Thr Ala Thr Asn Phe Asn Arg
    130                 135                 140
Thr Glu Gln Ile Leu Tyr Trp Thr Arg Val Gly Glu Tyr Leu Pro Gln
145                 150                 155                 160
Asn Gly Asn Gln Gln Met Leu Ala Arg Leu Lys Ser Gln Val Gln Gly
                165                 170                 175
Trp Ile Val Asp Gly Val Leu Val Arg Ile Ser Thr Val Thr Pro Glu
            180                 185                 190
Ala Glu Asp Gly Leu Ser Ala Asn Leu Asp Phe Ala Arg Glu Leu Val
        195                 200                 205
Lys Thr Leu Asp Pro Arg Val Leu Arg Pro Leu Leu Gly Asn Gly Leu
    210                 215                 220
Thr Arg Gln Leu Gly His Gln Val
225                 230
```

<210> SEQ ID NO 30
<211> LENGTH: 1395
<212> TYPE: DNA
<213> ORGANISM: Sphingomonas sp. ATCC53159

<400> SEQUENCE: 30

```
atgaacgccg ttgttccgat gcgccgcggc ggcccgctcg cccgcatgcg cgataccgtg      60
ctgcctgccc gcgtcgacgc ttatgacacc gccttcctgc ctgccgcgct ggagatcatc     120
gagcggccgg tttcgcccac cgcgcggctt accgccaagg tgatgctggc cgggctggcg     180
atcaccgccg cctggctggc gatcggcaag gtcgaagtcg tcgcgccgac gcaggggcgg     240
atcgcgccga tcggcgagac caagatcgtc cagtcgcccg aatcggggat cgtccgccgc     300
atcctggtgg gcgaggggca gaaggtcgcc aagggccagg tgctgatcac gctcgacccg     360
accgtgtcgt cggcggaggc ggcacaggcg aaggtggcgc tgctcagcgc ccagctcgac     420
gccgcacgca accaggcgat catcgacgcg ctggacggca gggcttccg cttcgtcgcg     480
cctgccgccg ccagcccggg cgaagtggcg acgcatcgcg gcctcgcccg cgccggctg      540
ggccagatcg aggcggcgct ggccggcggc cgctccgatc gcgtgccgc cgtctcggcc      600
gcggccgagg cgcaggcaca ggtgcggaag ctcgaacagt cgctgccgct gctcgaacag     660
```

```
cagatcgccg cgaacgagac gatggccgcc aagggctatg tctcgaagct gcgcgtcgtg    720
gagatgcgtc gccagctgat cgccgagcgg caggacctga cggcggcgcg cgctacgctc    780
gccaaactcg gccagcagtc gctgagcgtc tccagcctgt cggccaagac gcgcgaggag    840
gcgcgggcgc aggtgctgca ggatctggtc aaggcgcagg acgaggtgcg tgcccgcggc    900
gaggacgtcg ccaaggcgaa tctgcgcagc tcgttccgcg aactgcgcgc gccggtgagc    960
ggtaccgtct cgcagctgca ggtccacacc gaaggcggcg tggtggaagg ggccaagccg   1020
ctcctcagcc tggttcccga caatgcccgg ctcgaggccg aggtgatggt cgacaacagc   1080
gacatcggct tcgtccacat cggcatgccg gtaaaggtga agctgcaggc ctttccctat   1140
acccgctacg gcatgattcc cggcacggtg gcgggcatca gccccgaggc ggtgcagatg   1200
aaggagaacc agccgccggt ctacaaggcg cggatcgcgc tggcgcgcgg gtatgtgctg   1260
gcccatggcg cacaggtgcc gctgcggccg gggatgctcg cgagcgcgga catcgtcacc   1320
ggcaagcgaa ccctgttcag ctatctggtg gggcccgtgc tcgagacggg gagtgacgcg   1380
ctgcacgagc ggtga                                                    1395
```

<210> SEQ ID NO 31
<211> LENGTH: 464
<212> TYPE: PRT
<213> ORGANISM: Sphingomonas sp. ATCC53159

<400> SEQUENCE: 31

```
Met Asn Ala Val Val Pro Met Arg Arg Gly Gly Pro Leu Ala Arg Met
1               5                   10                  15

Arg Asp Thr Val Leu Pro Ala Arg Val Asp Ala Tyr Asp Thr Ala Phe
            20                  25                  30

Leu Pro Ala Ala Leu Glu Ile Ile Glu Arg Pro Val Ser Pro Thr Ala
        35                  40                  45

Arg Leu Thr Ala Lys Val Met Leu Ala Gly Leu Ala Ile Thr Ala Ala
    50                  55                  60

Trp Leu Ala Ile Gly Lys Val Glu Val Val Ala Pro Thr Gln Gly Arg
65                  70                  75                  80

Ile Ala Pro Ile Gly Glu Thr Lys Ile Val Gln Ser Pro Glu Ser Gly
                85                  90                  95

Ile Val Arg Arg Ile Leu Val Gly Glu Gly Gln Lys Val Ala Lys Gly
            100                 105                 110

Gln Val Leu Ile Thr Leu Asp Pro Thr Val Ser Ser Ala Glu Ala Ala
        115                 120                 125

Gln Ala Lys Val Ala Leu Leu Ser Ala Gln Leu Asp Ala Ala Arg Asn
    130                 135                 140

Gln Ala Ile Ile Asp Ala Leu Asp Gly Arg Gly Phe Arg Phe Val Ala
145                 150                 155                 160

Pro Ala Ala Ala Ser Pro Gly Glu Val Ala Thr His Arg Gly Leu Ala
                165                 170                 175

Arg Ala Arg Leu Gly Gln Ile Glu Ala Ala Leu Ala Gly Gly Arg Ser
            180                 185                 190

Asp Arg Gly Ala Ala Val Ser Ala Ala Ala Glu Ala Gln Ala Gln Val
        195                 200                 205

Arg Lys Leu Glu Gln Ser Leu Pro Leu Leu Glu Gln Gln Ile Ala Ala
    210                 215                 220

Asn Glu Thr Met Ala Ala Lys Gly Tyr Val Ser Lys Leu Arg Val Val
225                 230                 235                 240
```

```
Glu Met Arg Arg Gln Leu Ile Ala Glu Arg Gln Asp Leu Thr Ala Ala
            245                 250                 255

Arg Ala Thr Leu Ala Lys Leu Gly Gln Gln Ser Leu Ser Val Ser Ser
        260                 265                 270

Leu Ser Ala Lys Thr Arg Glu Glu Ala Arg Ala Gln Val Leu Gln Asp
    275                 280                 285

Leu Val Lys Ala Gln Asp Glu Val Arg Ala Arg Gly Glu Asp Val Ala
290                 295                 300

Lys Ala Asn Leu Arg Ser Ser Phe Arg Glu Leu Arg Ala Pro Val Ser
305                 310                 315                 320

Gly Thr Val Ser Gln Leu Gln Val His Thr Glu Gly Gly Val Val Glu
            325                 330                 335

Gly Ala Lys Pro Leu Leu Ser Leu Val Pro Asp Asn Ala Arg Leu Glu
        340                 345                 350

Ala Glu Val Met Val Asp Asn Ser Asp Ile Gly Phe Val His Ile Gly
    355                 360                 365

Met Pro Val Lys Val Lys Leu Gln Ala Phe Pro Tyr Thr Arg Tyr Gly
    370                 375                 380

Met Ile Pro Gly Thr Val Ala Gly Ile Ser Pro Glu Ala Val Gln Met
385                 390                 395                 400

Lys Glu Asn Gln Pro Pro Val Tyr Lys Ala Arg Ile Ala Leu Ala Arg
            405                 410                 415

Gly Tyr Val Leu Ala His Gly Ala Gln Val Pro Leu Arg Pro Gly Met
        420                 425                 430

Leu Ala Ser Ala Asp Ile Val Thr Gly Lys Arg Thr Leu Phe Ser Tyr
    435                 440                 445

Leu Val Gly Pro Val Leu Glu Thr Gly Ser Asp Ala Leu His Glu Arg
450                 455                 460

<210> SEQ ID NO 32
<211> LENGTH: 2187
<212> TYPE: DNA
<213> ORGANISM: Sphingomonas sp. ATCC53159

<400> SEQUENCE: 32
atgacacgcg acgaaatgca ggccaccctg cagagcgcgc tcgcggccca tggggcggcg      60
gagcgcgagg cggagctgcg cgaatccgga ctggtggcgt tgtcgctgct gctcggcgcg     120
cacaacatcg ccatcacgcc cgaacagctg cgccacgcgc tgggccatgc cgaggcggca     180
agcgccgacg acctgatcct cctggccaag cgccagcagg cgtgcgcgc caaggccgtc     240 gaggtgccgc gcggcggact cgcccgccag ccgctgcccg cgatcgccga cgggcccgaa     300
ggctggttcg tgatcggcgg cctgaccgaa catggcgtga tcatccagcg cccgggccat     360
gccccggaac aggtcgaccg ggacgcgctg acgcgatct ggtccggcgc gctggtgctg     420
ctcaccaccc gcgcggtggc gggacggccg ctgcggttcg gcctctcctg gttcaccgcg     480
cagttccggc gctatcgcac gctgttcctc gaggtgctcg catcaccct cgcgctcaac     540 ctgctcggcc tcgccgcgcc gctgttgttc cagagcgtga tcgacaaggt gctgatccac     600
aacagcatga gcacgctgag cgtgctcgcc ttcgccttcc tggcggtttc ggtgtgggaa     660
gtggcgctcg gctggatccg caccgcctg ttcaccgaga cgacgcagaa gatcgacgtc     720
gagctgggtg cccggctgtt ccaccacctg ctggcgctgc cgctcgccta tttcgagaag     780
cgccgcgtgg cgacaccgt cacccgcgtc gccagctcg agacgatccg cgaattcctt     840
accagcgcct cgctgacggt gatggtggac ccgctgttca ccttcgtgtt cctcgccgcg     900
```

```
atgctgttct actcgccgat gctctcgggc atcgtgctcg tgtcgctgat cgcctatgcg    960
atcgtatcgt tcagcgtcgc cgggccgctc cgcgcgcggg tggaggacaa gttcgagaag   1020
agctccgcca gcaacgcgct gctcgtcgag agcgtctcgg gcatccacac gatcaaggcg   1080
accgcggtcg agccgcactg gcagaatcgc tgggagcgcc agctcgccgc ccataccgcc   1140
gcgtcgcagc ggctgatcaa taccgccaac accggcagcc aggcgatcga gctgatctcg   1200
aagctgagct tcgcggcgat cctgttcttc ggcgccaagg cggtgatcgg cggcgcgatg   1260
agcgtaggcg cgctggtggc gttcaacatg ttcgcccagc gcgtgtccgg gccggtgatc   1320
cgcatggcgc agctgtggca ggatttccag caggtgcgca tctcggtcga gcggctgggc   1380
gacgtgctca accatccggt ggaaccgcgc ccggcctcgg cggcgacgct gccggtgctg   1440
cgcggtgcga ttcgcttcga gaatgtcagc ttccgctatg ccgaggacca gccgccggtg   1500
ctgagcgaca tcacgctcga cattccggcg ggcacctcgc tcggcatcgt cggttcgtcg   1560
ggctcgggca gtcgacgct ggccaagctg ctccagcggc tcaacctgcc gaatctcggc   1620
cgcgtgctgg tcgacgaggt cgacgtggcg cagctcgatc ccgcctggct cgtcgccag   1680
atcggcgtcg tgctgcagga gaatctgctg ttcagccgct cgatccgcga gaacatcgcg   1740
ctctccaacc ccgccatgcc gttcgagaat gtcgtcgcgg cggcgacgct ggccggcgcg   1800
catgatttca tcctgcgcca gccgcgcggc tatgacaccg agatcgtcga gcgcggcgtc   1860
aatctctccg gcggccagcg ccagcggctc gccatcgccc gcgcgctcgt cggcaatccg   1920
cgcatcctgg tgttcgacga agcgaccctc gcgctcgatg ccgagagcga ggagctgatc   1980
cagaacaacc tgcgcgccat ctcggccggc cgcacgctcg tggtgatcgc gcatcgcctg   2040
agcgcggtgc gcagctgcga ccggatcatc acgctcgaac agggccgcat cgtcgagagc   2100
ggccgacacg acgaattgtt gcgcctgggc ggccgctatg ccgacctgca ccgccgccag   2160
ggcggctatg gggagattgc cgcatga                                       2187
```

<210> SEQ ID NO 33
<211> LENGTH: 728
<212> TYPE: PRT
<213> ORGANISM: Sphingomonas sp. ATCC53159

<400> SEQUENCE: 33

```
Met Thr Arg Asp Glu Met Gln Ala Thr Leu Gln Ser Ala Leu Ala Ala
1               5                   10                  15

His Gly Ala Ala Glu Arg Glu Ala Glu Leu Arg Glu Ser Gly Leu Val
            20                  25                  30

Ala Leu Ser Leu Leu Gly Ala His Asn Ile Ala Ile Thr Pro Glu
        35                  40                  45

Gln Leu Arg His Ala Leu Gly His Ala Glu Ala Ala Ser Ala Asp Asp
    50                  55                  60

Leu Ile Leu Leu Ala Lys Arg Gln Gln Gly Val Arg Ala Lys Ala Val
65                  70                  75                  80

Glu Val Pro Arg Gly Leu Ala Arg Gln Pro Leu Pro Ala Ile Ala
            85                  90                  95

Asp Gly Pro Glu Gly Trp Phe Val Ile Gly Gly Leu Thr Glu His Gly
            100                 105                 110

Val Ile Ile Gln Arg Pro Gly His Ala Pro Glu Gln Val Asp Arg Asp
        115                 120                 125

Ala Leu Asp Ala Ile Trp Ser Gly Ala Leu Val Leu Leu Thr Thr Arg
    130                 135                 140
```

```
Ala Val Ala Gly Arg Pro Leu Arg Phe Gly Leu Ser Trp Phe Thr Ala
145                 150                 155                 160

Gln Phe Arg Arg Tyr Arg Thr Leu Phe Leu Glu Val Leu Gly Ile Thr
            165                 170                 175

Leu Ala Leu Asn Leu Leu Gly Leu Ala Ala Pro Leu Leu Phe Gln Ser
        180                 185                 190

Val Ile Asp Lys Val Leu Ile His Asn Ser Met Ser Thr Leu Ser Val
    195                 200                 205

Leu Ala Phe Ala Phe Leu Ala Val Ser Val Trp Glu Val Ala Leu Gly
210                 215                 220

Trp Ile Arg Thr Arg Leu Phe Thr Glu Thr Thr Gln Lys Ile Asp Val
225                 230                 235                 240

Glu Leu Gly Ala Arg Leu Phe His His Leu Leu Ala Leu Pro Leu Ala
                245                 250                 255

Tyr Phe Glu Lys Arg Arg Val Gly Asp Thr Val Thr Arg Val Arg Gln
            260                 265                 270

Leu Glu Thr Ile Arg Glu Phe Leu Thr Ser Ala Ser Leu Thr Val Met
        275                 280                 285

Val Asp Pro Leu Phe Thr Phe Val Phe Leu Ala Ala Met Leu Phe Tyr
    290                 295                 300

Ser Pro Met Leu Ser Gly Ile Val Leu Val Ser Leu Ile Ala Tyr Ala
305                 310                 315                 320

Ile Val Ser Phe Ser Val Ala Gly Pro Leu Arg Ala Arg Val Glu Asp
                325                 330                 335

Lys Phe Glu Lys Ser Ser Ala Ser Asn Ala Leu Leu Val Glu Ser Val
            340                 345                 350

Ser Gly Ile His Thr Ile Lys Ala Thr Ala Val Glu Pro His Trp Gln
        355                 360                 365

Asn Arg Trp Glu Arg Gln Leu Ala Ala His Thr Ala Ala Ser Gln Arg
    370                 375                 380

Leu Ile Asn Thr Ala Asn Thr Gly Ser Gln Ala Ile Glu Leu Ile Ser
385                 390                 395                 400

Lys Leu Ser Phe Ala Ala Ile Leu Phe Phe Gly Ala Lys Ala Val Ile
                405                 410                 415

Gly Gly Ala Met Ser Val Gly Ala Leu Val Ala Phe Asn Met Phe Ala
            420                 425                 430

Gln Arg Val Ser Gly Pro Val Ile Arg Met Ala Gln Leu Trp Gln Asp
        435                 440                 445

Phe Gln Gln Val Arg Ile Ser Val Glu Arg Leu Gly Asp Val Leu Asn
    450                 455                 460

His Pro Val Glu Pro Arg Pro Ala Ser Ala Ala Thr Leu Pro Val Leu
465                 470                 475                 480

Arg Gly Ala Ile Arg Phe Glu Asn Val Ser Phe Arg Tyr Ala Glu Asp
                485                 490                 495

Gln Pro Pro Val Leu Ser Asp Ile Thr Leu Asp Ile Pro Ala Gly Thr
            500                 505                 510

Ser Leu Gly Ile Val Gly Ser Ser Gly Ser Gly Lys Ser Thr Leu Ala
        515                 520                 525

Lys Leu Leu Gln Arg Leu Asn Leu Pro Asn Leu Gly Arg Val Leu Val
    530                 535                 540

Asp Glu Val Asp Val Ala Gln Leu Asp Pro Ala Trp Leu Arg Arg Gln
545                 550                 555                 560
```

```
Ile Gly Val Val Leu Gln Glu Asn Leu Leu Phe Ser Arg Ser Ile Arg
            565                 570                 575
Glu Asn Ile Ala Leu Ser Asn Pro Ala Met Pro Phe Glu Asn Val Val
        580                 585                 590
Ala Ala Ala Thr Leu Ala Gly Ala His Asp Phe Ile Leu Arg Gln Pro
        595                 600                 605
Arg Gly Tyr Asp Thr Glu Ile Val Glu Arg Gly Val Asn Leu Ser Gly
        610                 615                 620
Gly Gln Arg Gln Arg Leu Ala Ile Ala Arg Ala Leu Val Gly Asn Pro
625                 630                 635                 640
Arg Ile Leu Val Phe Asp Glu Ala Thr Ser Ala Leu Asp Ala Glu Ser
            645                 650                 655
Glu Glu Leu Ile Gln Asn Asn Leu Arg Ala Ile Ser Ala Gly Arg Thr
        660                 665                 670
Leu Val Val Ile Ala His Arg Leu Ser Ala Val Arg Ser Cys Asp Arg
        675                 680                 685
Ile Ile Thr Leu Glu Gln Gly Arg Ile Val Glu Ser Gly Arg His Asp
        690                 695                 700
Glu Leu Leu Arg Leu Gly Gly Arg Tyr Ala Asp Leu His Arg Arg Gln
705                 710                 715                 720
Gly Gly Tyr Gly Glu Ile Ala Ala
            725
```

<210> SEQ ID NO 34
<211> LENGTH: 1413
<212> TYPE: DNA
<213> ORGANISM: Sphingomonas sp. ATCC53159

<400> SEQUENCE: 34

```
atgaacgctt tcgaagcaca gcgcgccttt gaggagcaac ttcgggcgca ttcccgggtt    60
acgccatctg ccgctcccgt gtggcgtcgc tcgacgctgc ggatggtcct ctataccgag   120
ttgctgctgc tggacagtct ctcgatcctg gccggattcc acgtcgcggc gggcacgcgc   180
gacggcaact ggctgtcgct ggcgggcatc aacgtcggcg tcttcctgct gccgatcgct   240
ctcggcaccg cgctcgcaag cggcacctac tcgctgaact gcctgcgcta cccggtcagc   300
ggcgtgaaga gcatcttctc ggcattcttc ttctcgatct tcgtcgtcct gctcggcagc   360
tacctgctga cggccgagct gccgctgtcc cgcgtgcagc tggcggaggg cgcgatcctc   420
tcgctggtcc tcctgatggt gggccgcctg atgttccgcc gccacgtccg cgcggttacc   480
ggcggcaggc tgctcgacga actggtcatc atcgacggcg tctcgctcga cgtcgcgggc   540
aatgcggtcg cgctcgacgc gcggatcatc aatctctcgc cgaacccgcg cgatccgcaa   600
atgctgcatc gcctgggcac caccgtgatc gggttcgacc gggtgatcgt cgcctgcacc   660
aaggagcatc gcgcggtctg ggcgctgctg ctcaagggca tgaacatcaa gggcgagatc   720
ctcgtccccc agttcaatgc gctgggcgcg atcggcgtgg acgcctttga cgggaaggat   780
acgctggtcg tctcgcaggg cccgctcaac atgcccaacc gcgcgaagaa gcgcgcgctc   840
gatctcgcga tcaccgtacc ggccgtgctc gcgctggcgc cgctgatgat cctggtggcg   900
atcctgatca agctggagag cccgggcccg gtgttgttcg cgcaggatcg cgtcggccgc   960
ggcaaccggc tgttcaagat catgaagttc cgctcgatgc gcgtaacgct gtcgacgcg  1020
aacggcaacg tctcggccag ccgcgacgac gatcgcatca ccaaggtcgg ccgcttcatc  1080
cgcaagacca gcatcgacga actgccgcag ctgctgaacg tgctgcgcgg cgacatgagc  1140
```

```
gtcgtcggcc cgcggccgca tgcgctgggc tcgcgcgccg ccgatcacct gttctgggaa    1200
atcgacgagc gctactggca ccgccacacg ctcaagccgg gcatgaccgg tctggcccag    1260
gtgcgcggtt ccgcggggc gaccgatcgc cgcgtcgatc tgaccaaccg gctccaggca    1320
gacatggaat atatcgacgg atgggatatc tggcgcgata tcacgatcct gttcaagacg    1380
ctgcgggtga tcgtgcattc gaacgcattc tga                                 1413
```

<210> SEQ ID NO 35
<211> LENGTH: 470
<212> TYPE: PRT
<213> ORGANISM: Sphingomonas sp. ATCC53159

<400> SEQUENCE: 35

```
Met Asn Ala Phe Glu Ala Gln Arg Ala Phe Glu Glu Gln Leu Arg Ala
1               5                   10                  15

His Ser Arg Val Thr Pro Ser Ala Ala Pro Val Trp Arg Arg Ser Thr
            20                  25                  30

Leu Arg Met Val Leu Tyr Thr Glu Leu Leu Leu Asp Ser Leu Ser
        35                  40                  45

Ile Leu Ala Gly Phe His Val Ala Ala Gly Thr Arg Asp Gly Asn Trp
50                  55                  60

Leu Ser Leu Ala Gly Ile Asn Val Gly Val Phe Leu Leu Pro Ile Ala
65                  70                  75                  80

Leu Gly Thr Ala Leu Ala Ser Gly Thr Tyr Ser Leu Asn Cys Leu Arg
                85                  90                  95

Tyr Pro Val Ser Gly Val Lys Ser Ile Phe Ser Ala Phe Phe Phe Ser
            100                 105                 110

Ile Phe Val Val Leu Leu Gly Ser Tyr Leu Leu Thr Ala Glu Leu Pro
        115                 120                 125

Leu Ser Arg Val Gln Leu Ala Glu Gly Ala Ile Leu Ser Leu Val Leu
130                 135                 140

Leu Met Val Gly Arg Leu Met Phe Arg Arg His Val Arg Ala Val Thr
145                 150                 155                 160

Gly Gly Arg Leu Leu Asp Glu Leu Val Ile Ile Asp Gly Val Ser Leu
                165                 170                 175

Asp Val Ala Gly Asn Ala Val Ala Leu Asp Ala Arg Ile Ile Asn Leu
            180                 185                 190

Ser Pro Asn Pro Arg Asp Pro Gln Met Leu His Arg Leu Gly Thr Thr
        195                 200                 205

Val Ile Gly Phe Asp Arg Val Ile Val Ala Cys Thr Lys Glu His Arg
210                 215                 220

Ala Val Trp Ala Leu Leu Leu Lys Gly Met Asn Ile Lys Gly Glu Ile
225                 230                 235                 240

Leu Val Pro Gln Phe Asn Ala Leu Gly Ala Ile Gly Val Asp Ala Phe
                245                 250                 255

Asp Gly Lys Asp Thr Leu Val Val Ser Gln Gly Pro Leu Asn Met Pro
            260                 265                 270

Asn Arg Ala Lys Lys Arg Ala Leu Asp Leu Ala Ile Thr Val Pro Ala
        275                 280                 285

Val Leu Ala Leu Ala Pro Leu Met Ile Leu Val Ala Ile Leu Ile Lys
290                 295                 300

Leu Glu Ser Pro Gly Pro Val Leu Phe Ala Gln Asp Arg Val Gly Arg
305                 310                 315                 320

Gly Asn Arg Leu Phe Lys Ile Met Lys Phe Arg Ser Met Arg Val Thr
```

```
                325                 330                 335
Leu Cys Asp Ala Asn Gly Asn Val Ser Ala Ser Arg Asp Asp Arg
            340                 345                 350

Ile Thr Lys Val Gly Arg Phe Ile Arg Lys Thr Ser Ile Asp Glu Leu
            355                 360                 365

Pro Gln Leu Leu Asn Val Leu Arg Gly Asp Met Ser Val Val Gly Pro
            370                 375                 380

Arg Pro His Ala Leu Gly Ser Arg Ala Ala Asp His Leu Phe Trp Glu
385                 390                 395                 400

Ile Asp Glu Arg Tyr Trp His Arg His Thr Leu Lys Pro Gly Met Thr
            405                 410                 415

Gly Leu Ala Gln Val Arg Gly Phe Arg Gly Ala Thr Asp Arg Arg Val
            420                 425                 430

Asp Leu Thr Asn Arg Leu Gln Ala Asp Met Glu Tyr Ile Asp Gly Trp
            435                 440                 445

Asp Ile Trp Arg Asp Ile Thr Ile Leu Phe Lys Thr Leu Arg Val Ile
            450                 455                 460

Val His Ser Asn Ala Phe
465                 470

<210> SEQ ID NO 36
<211> LENGTH: 879
<212> TYPE: DNA
<213> ORGANISM: Sphingomonas sp. ATCC53159

<400> SEQUENCE: 36
atgaagggca tcatccttgc gggggggcagc gggacgcgcc tgtaccccgc aacgctatcg      60
atctcgaagc agctgcttcc cgtctatgac aagccgatga tcttctatcc gctgtcggtg     120
ctgatgctca ccggcatccg ggacatcctg attatctcca ccccgcgcga cctgccgatg     180
ttccaggcgc tgctgggcga cggctcggcc ttcggcatca acctcagcta tgccgagcag     240
ccctccccca acgggctggc cgaagcgttc atcatcggcg cggatttcgt cggcaacgat     300
cccagcgcgc tgatcctggg cgacaacatc tatcacggcg aaaagatggg cgagcgctgc     360
caggcagccg cagcgcaggc agcgcagggc ggtgcaaacg tcttcgccta tcatgtcgac     420
gaccccgagc gctacggcgt ggtcgcgttc gaccccggaga cgggcgtcgc caccagcgtc     480
gaggaaaagc cggccgagcc caagtccaac tgggcgatca ccggcctgta tttctacgac     540
aaggacgtgg tcgacatcgc caagtcgatc cagccctcgg cgcgcggcga actcgagatc     600
accgacgtca accgcgttta catggagcgc ggcgacctgc acatcacgcg cctcggccgc     660
ggctatgcct ggctcgacac cggcacgcat gacagcctgc acgaagccgg ctcgttcgtt     720
cgcacgctcg agcatcggac gggcgtgaag atcgcctgcc cggaggaaat cgccttcgaa     780
agcggctggc tcggcgccga agacctgctc aagcgcgccg ccggcctcgg caagaccggc     840
tatgccgcct atctccgcaa ggttgcgacc gcagcatga                           879

<210> SEQ ID NO 37
<211> LENGTH: 292
<212> TYPE: PRT
<213> ORGANISM: Sphingomonas sp. ATCC53159

<400> SEQUENCE: 37

Met Lys Gly Ile Ile Leu Ala Gly Gly Ser Gly Thr Arg Leu Tyr Pro
1               5                   10                  15

Ala Thr Leu Ser Ile Ser Lys Gln Leu Leu Pro Val Tyr Asp Lys Pro
```

```
              20                  25                  30
Met Ile Phe Tyr Pro Leu Ser Val Leu Met Leu Thr Gly Ile Arg Asp
         35                  40                  45

Ile Leu Ile Ile Ser Thr Pro Arg Asp Leu Pro Met Phe Gln Ala Leu
     50                  55                  60

Leu Gly Asp Gly Ser Ala Phe Gly Ile Asn Leu Ser Tyr Ala Glu Gln
 65                  70                  75                  80

Pro Ser Pro Asn Gly Leu Ala Glu Ala Phe Ile Ile Gly Ala Asp Phe
                 85                  90                  95

Val Gly Asn Asp Pro Ser Ala Leu Ile Leu Gly Asp Asn Ile Tyr His
            100                 105                 110

Gly Glu Lys Met Gly Glu Arg Cys Gln Ala Ala Ala Gln Ala Ala
        115                 120                 125

Gln Gly Gly Ala Asn Val Phe Ala Tyr His Val Asp Asp Pro Glu Arg
    130                 135                 140

Tyr Gly Val Val Ala Phe Asp Pro Glu Thr Gly Val Ala Thr Ser Val
145                 150                 155                 160

Glu Glu Lys Pro Ala Glu Pro Lys Ser Asn Trp Ala Ile Thr Gly Leu
                165                 170                 175

Tyr Phe Tyr Asp Lys Asp Val Val Asp Ile Ala Lys Ser Ile Gln Pro
            180                 185                 190

Ser Ala Arg Gly Glu Leu Glu Ile Thr Asp Val Asn Arg Val Tyr Met
        195                 200                 205

Glu Arg Gly Asp Leu His Ile Thr Arg Leu Gly Arg Gly Tyr Ala Trp
    210                 215                 220

Leu Asp Thr Gly Thr His Asp Ser Leu His Glu Ala Gly Ser Phe Val
225                 230                 235                 240

Arg Thr Leu Glu His Arg Thr Gly Val Lys Ile Ala Cys Pro Glu Glu
                245                 250                 255

Ile Ala Phe Glu Ser Gly Trp Leu Gly Ala Glu Asp Leu Leu Lys Arg
            260                 265                 270

Ala Ala Gly Leu Gly Lys Thr Gly Tyr Ala Ala Tyr Leu Arg Lys Val
        275                 280                 285

Ala Thr Ala Ala
    290

<210> SEQ ID NO 38
<211> LENGTH: 567
<212> TYPE: DNA
<213> ORGANISM: Sphingomonas sp. ATCC53159

<400> SEQUENCE: 38
atgacccagg tccatcatca cgaactgtcc ggcgtcatcg agttcacgcc gcccaaatat      60
ggcgaccacc gcggcttctt ctccgaagtg ttcaagcagt cggtgctcga tgccgaaggc     120
gtcgaggcac gctgggtgca ggacaatcag agcttctcgg cggccccggg cacgatccgc     180
ggcctgcatc tccaggcgcc gcccttcgcc caggccaagc tggtccgcgt gttgcgcggc     240
gcgatcttcg acgtcgcggt cgacatccgt cgcggctcgc ccacctatgg caaatgggtc     300
ggcgtcgagc tctcggccga aagtggaac cagctgctgg tccccgccgg ctatgcgcac     360
ggcttcatga cgctcgttcc ggattgcgag atcctctaca aggtcagcgc caaatattcg     420
aaggattcgg agatggcgat ccgttgggac gatcccgatc tcgccatcgc ctggccggac     480
atcggcgtcg agccggtcct ctccgaaaag gacgcggtcg ccacgccctt cgccgaattc     540
```

```
aacacccct tcttctatca gggctga                                          567
```

<210> SEQ ID NO 39
<211> LENGTH: 188
<212> TYPE: PRT
<213> ORGANISM: Sphingomonas sp. ATCC53159

<400> SEQUENCE: 39

```
Met Thr Gln Val His His His Glu Leu Ser Gly Val Ile Glu Phe Thr
1               5                   10                  15

Pro Pro Lys Tyr Gly Asp His Arg Gly Phe Phe Ser Glu Val Phe Lys
            20                  25                  30

Gln Ser Val Leu Asp Ala Glu Gly Val Glu Ala Arg Trp Val Gln Asp
        35                  40                  45

Asn Gln Ser Phe Ser Ala Ala Pro Gly Thr Ile Arg Gly Leu His Leu
    50                  55                  60

Gln Ala Pro Pro Phe Ala Gln Ala Lys Leu Val Arg Val Leu Arg Gly
65                  70                  75                  80

Ala Ile Phe Asp Val Ala Val Asp Ile Arg Arg Gly Ser Pro Thr Tyr
                85                  90                  95

Gly Lys Trp Val Gly Val Glu Leu Ser Ala Glu Lys Trp Asn Gln Leu
            100                 105                 110

Leu Val Pro Ala Gly Tyr Ala His Gly Phe Met Thr Leu Val Pro Asp
        115                 120                 125

Cys Glu Ile Leu Tyr Lys Val Ser Ala Lys Tyr Ser Lys Asp Ser Glu
130                 135                 140

Met Ala Ile Arg Trp Asp Asp Pro Asp Leu Ala Ile Ala Trp Pro Asp
145                 150                 155                 160

Ile Gly Val Glu Pro Val Leu Ser Glu Lys Asp Ala Val Ala Thr Pro
                165                 170                 175

Phe Ala Glu Phe Asn Thr Pro Phe Phe Tyr Gln Gly
            180                 185
```

<210> SEQ ID NO 40
<211> LENGTH: 1062
<212> TYPE: DNA
<213> ORGANISM: Sphingomonas sp. ATCC53159

<400> SEQUENCE: 40

```
atgcagcaga ccttcctcgt caccggcggc gccggcttca tcggctcggc ggtggtgcgc    60
cacctcgtcc gccagggcgc gcgcgtcatc aatctcgaca agctcaccta tgccggcaac   120
ccggcctcgc tgactgcgat cgagaacgcg cccaactatc gcttcgtcca tgccgacatc   180
gccgacaccg cgacgatcct accgctgctg cgcgaggagc aggtcgatgt ggtgatgcac   240
ctcgccgccg agagccatgt cgatcgctcg atcgacggcc ctggcgagtt catcgagacc   300
aatgtcgtcg gcaccttcaa gctgctccag tcggcgctgc aatattggcg cgagctggag   360
ggcgagaaac gcgacgcgtt ccgcttccac cacatctcca ccgacgaagt gttcggcgac   420
ctgccgttcg acagcggcat cttcaccgaa gagacgccct atgatccctc ctcgccctat   480
tcggcgtcga aggcggcgag cgaccatctg gtgcgcgccc ggggccacac ctatggcctg   540
ccggtggtgc tgtcgaactg ctcgaacaat tacgggccgt ccacttccc cgagaagctg    600 atcccgttga ccatcctcaa cgcgctcgag gcaagccgc tgccggtcta cggcaagggc   660
gagaatatcc gcgactggct gtatgtcgac gatcacgcca aggcgctggc gaccatcgcc   720
accaccggca aggtcggcca gagctacaat gtcggcggcc gcaacgagcg gaccaacctg   780
```

```
caggtggtcg agacgatctg cgacctgctc gaccagcgca ttccgctggc cgacggtcgc    840
aagcgccgcg aactgatcac cttcgtcacc gatcgcccg gccatgaccg ccgctacgcg    900
atcgacgcga ccaagctcga gaccgagctg gctggaagg ctgaggagaa tttcgacacc    960
ggcatcgccg cgacgatcga ctggtatctg gcgaacgagt ggtggtgggg cccgatccgc    1020
tccggcaaat atgccggcga gcggctgggg cagaccgcct ga                       1062
```

<210> SEQ ID NO 41  
<211> LENGTH: 353  
<212> TYPE: PRT  
<213> ORGANISM: Sphingomonas sp. ATCC53159

<400> SEQUENCE: 41

```
Met Gln Gln Thr Phe Leu Val Thr Gly Gly Ala Gly Phe Ile Gly Ser
1               5                   10                  15

Ala Val Val Arg His Leu Val Arg Gln Gly Ala Arg Val Ile Asn Leu
            20                  25                  30

Asp Lys Leu Thr Tyr Ala Gly Asn Pro Ala Ser Leu Thr Ala Ile Glu
        35                  40                  45

Asn Ala Pro Asn Tyr Arg Phe Val His Ala Asp Ile Ala Asp Thr Ala
    50                  55                  60

Thr Ile Leu Pro Leu Leu Arg Glu Glu Gln Val Asp Val Val Met His
65                  70                  75                  80

Leu Ala Ala Glu Ser His Val Asp Arg Ser Ile Asp Gly Pro Gly Glu
                85                  90                  95

Phe Ile Glu Thr Asn Val Val Gly Thr Phe Lys Leu Leu Gln Ser Ala
            100                 105                 110

Leu Gln Tyr Trp Arg Glu Leu Glu Gly Glu Lys Arg Asp Ala Phe Arg
        115                 120                 125

Phe His His Ile Ser Thr Asp Glu Val Phe Gly Asp Leu Pro Phe Asp
    130                 135                 140

Ser Gly Ile Phe Thr Glu Glu Thr Pro Tyr Asp Pro Ser Ser Pro Tyr
145                 150                 155                 160

Ser Ala Ser Lys Ala Ala Ser Asp His Leu Val Arg Ala Trp Gly His
                165                 170                 175

Thr Tyr Gly Leu Pro Val Val Leu Ser Asn Cys Ser Asn Asn Tyr Gly
            180                 185                 190

Pro Phe His Phe Pro Glu Lys Leu Ile Pro Leu Thr Ile Leu Asn Ala
        195                 200                 205

Leu Glu Gly Lys Pro Leu Pro Val Tyr Gly Lys Gly Glu Asn Ile Arg
    210                 215                 220

Asp Trp Leu Tyr Val Asp Asp His Ala Lys Ala Leu Ala Thr Ile Ala
225                 230                 235                 240

Thr Thr Gly Lys Val Gly Gln Ser Tyr Asn Val Gly Gly Arg Asn Glu
                245                 250                 255

Arg Thr Asn Leu Gln Val Val Glu Thr Ile Cys Asp Leu Leu Asp Gln
            260                 265                 270

Arg Ile Pro Leu Ala Asp Gly Arg Lys Arg Glu Leu Ile Thr Phe
        275                 280                 285

Val Thr Asp Arg Pro Gly His Asp Arg Arg Tyr Ala Ile Asp Ala Thr
    290                 295                 300

Lys Leu Glu Thr Glu Leu Gly Trp Lys Ala Glu Glu Asn Phe Asp Thr
305                 310                 315                 320
```

Gly Ile Ala Ala Thr Ile Asp Trp Tyr Leu Ala Asn Glu Trp Trp
                325                 330                 335

Gly Pro Ile Arg Ser Gly Lys Tyr Ala Gly Glu Arg Leu Gly Gln Thr
            340                 345                 350

Ala

<210> SEQ ID NO 42
<211> LENGTH: 867
<212> TYPE: DNA
<213> ORGANISM: Sphingomonas sp. ATCC53159

<400> SEQUENCE: 42

```
atgcgtatcc tcgtcaccgg gcatgacggc caggtcgccc agtcgctggc cgagcaggcg      60
gtgggccacg agctggtctt caccacctac cccgaattcg atctctccaa gccggagacg     120
atcgaggccg gtgtggcgcg ggtgcacccg gacctgatcg tctccgccgc cgcctacacg     180
gcggtcgaca aggcggaaag cgaacccgag ctggcgatgg cgatcaacgg cgacggtccc     240
ggcgtgctgg cgcgcgcggg cgcgaagatc ggcgcgccga tcatccacct gtcgaccgat     300
tatgtgttcg acggcagtct cgaccgccct tggcgcgagg acgatcccac cggcccgctc     360
ggcgtctatg gcgcgaccaa gctggccggc gagcaggcgg tgcaggcctc gggtgccacc     420
aacgccgtga tccggctggc ctgggtctac agcccgttcg caacaatttt cgtcaagacg     480
atgctccgcc tcgccgagac gcgcgacgcg ctgaacgtcg tggaggacca gtggggctgc     540
cccagttcgg cgctggacat cgcgaccgcg atcctgacgg tggtcgggca ctggcagcag     600
gacggcgcga cgagcggcct ctaccatttc gccggcaccg gcgagaccaa ctgggccgac     660
ttcgcatcga cgatcttcgc cgagagcgcc aagcgcggtg gcccctcggc caccgtcacc     720
ggcattccca gctcgggcta tccgactccg gccacgcgcc cggccaattc gcggctggac     780
tgcacccgct cgcggagac cttcggctac cgggcgcctg cctggcagga ttcgctgaac     840
gtcgtactgg atcgcctgct cggctga                                         867
```

<210> SEQ ID NO 43
<211> LENGTH: 288
<212> TYPE: PRT
<213> ORGANISM: Sphingomonas sp. ATCC53159

<400> SEQUENCE: 43

Met Arg Ile Leu Val Thr Gly His Asp Gly Gln Val Ala Gln Ser Leu
1               5                   10                  15

Ala Glu Gln Ala Val Gly His Glu Leu Val Phe Thr Thr Tyr Pro Glu
            20                  25                  30

Phe Asp Leu Ser Lys Pro Glu Thr Ile Glu Ala Gly Val Ala Arg Val
        35                  40                  45

His Pro Asp Leu Ile Val Ser Ala Ala Tyr Thr Ala Val Asp Lys
    50                  55                  60

Ala Glu Ser Glu Pro Glu Leu Ala Met Ala Ile Asn Gly Asp Gly Pro
65                  70                  75                  80

Gly Val Leu Ala Arg Ala Gly Ala Lys Ile Gly Ala Pro Ile Ile His
                85                  90                  95

Leu Ser Thr Asp Tyr Val Phe Asp Gly Ser Leu Asp Arg Pro Trp Arg
            100                 105                 110

Glu Asp Asp Pro Thr Gly Pro Leu Gly Val Tyr Gly Ala Thr Lys Leu
        115                 120                 125

Ala Gly Glu Gln Ala Val Gln Ala Ser Gly Ala Thr Asn Ala Val Ile

```
                130               135                140
Arg Leu Ala Trp Val Tyr Ser Pro Phe Gly Asn Asn Phe Val Lys Thr
145                 150                 155                 160

Met Leu Arg Leu Ala Glu Thr Arg Asp Ala Leu Asn Val Val Glu Asp
                165                 170                 175

Gln Trp Gly Cys Pro Ser Ser Ala Leu Asp Ile Ala Thr Ala Ile Leu
            180                 185                 190

Thr Val Val Gly His Trp Gln Gln Asp Gly Ala Thr Ser Gly Leu Tyr
        195                 200                 205

His Phe Ala Gly Thr Gly Glu Thr Asn Trp Ala Asp Phe Ala Ser Thr
    210                 215                 220

Ile Phe Ala Glu Ser Ala Lys Arg Gly Gly Pro Ser Ala Thr Val Thr
225                 230                 235                 240

Gly Ile Pro Ser Ser Gly Tyr Pro Thr Pro Ala Thr Arg Pro Ala Asn
                245                 250                 255

Ser Arg Leu Asp Cys Thr Arg Phe Ala Glu Thr Phe Gly Tyr Arg Ala
            260                 265                 270

Pro Ala Trp Gln Asp Ser Leu Asn Val Val Leu Asp Arg Leu Leu Gly
        275                 280                 285

<210> SEQ ID NO 44
<211> LENGTH: 132
<212> TYPE: DNA
<213> ORGANISM: Sphingomonas sp. ATCC53159

<400> SEQUENCE: 44
atccggctgt gcctggggtg ctggcggtcg cccaaggaaa tcgccggctg gagcgagctg      60
agtcctaagg gaaagcgcgc ggtgctagag gcattgccgg cgcgcgaacg ggagcatggc     120 gggggggcgct ga                                                        132

<210> SEQ ID NO 45
<211> LENGTH: 43
<212> TYPE: PRT
<213> ORGANISM: Sphingomonas sp. ATCC53159

<400> SEQUENCE: 45

Ile Arg Leu Cys Leu Gly Cys Trp Arg Ser Pro Lys Glu Ile Ala Gly
1               5                   10                  15

Trp Ser Glu Leu Ser Pro Lys Gly Lys Arg Ala Val Leu Glu Ala Leu
            20                  25                  30

Pro Ala Arg Glu Arg Glu His Gly Gly Gly Arg
        35                  40

<210> SEQ ID NO 46
<211> LENGTH: 336
<212> TYPE: DNA
<213> ORGANISM: Sphingomonas sp. ATCC53159

<400> SEQUENCE: 46
gctgcaggtc gacggatcgc cagcggcctc accatcaact atgcaccgga tgcatcggtg      60
ggccacccgc cccggcccga ctggtcggcc ctgctggtga agacgcggcg catccagcgc     120
gaactctatc tgttcaacat cgagcggccg aagggcaggc tgcgctggct ggtccgttcc     180
gtggcgcaac cggcgatgat cccacaggac gtggccaaga tcctgcgcac accgggtacc     240
aagggcgcgc gcctcgctgc ggtcaccacg ctggtccggc tgcggctgtg gcgcggcggc     300
gccggcttgt tgcagttgct cggccgcgac atctga                                336
```

<210> SEQ ID NO 47
<211> LENGTH: 111
<212> TYPE: PRT
<213> ORGANISM: Sphingomonas sp. ATCC53159

<400> SEQUENCE: 47

```
Ala Ala Gly Arg Arg Ile Ala Ser Gly Leu Thr Ile Asn Tyr Ala Pro
1               5                   10                  15

Asp Ala Ser Val Gly His Pro Pro Arg Pro Asp Trp Ser Ala Leu Leu
            20                  25                  30

Val Lys Thr Arg Arg Ile Gln Arg Glu Leu Tyr Leu Phe Asn Ile Glu
        35                  40                  45

Arg Pro Lys Gly Arg Leu Arg Trp Leu Val Arg Ser Val Ala Gln Pro
    50                  55                  60

Ala Met Ile Pro Gln Asp Val Ala Lys Ile Leu Arg Thr Pro Gly Thr
65                  70                  75                  80

Lys Gly Ala Arg Leu Ala Ala Val Thr Thr Leu Val Arg Leu Arg Leu
                85                  90                  95

Trp Arg Gly Gly Ala Gly Leu Leu Gln Leu Leu Gly Arg Asp Ile
                100                 105                 110
```

<210> SEQ ID NO 48
<211> LENGTH: 837
<212> TYPE: DNA
<213> ORGANISM: Sphingomonas sp. ATCC53159

<400> SEQUENCE: 48

```
gtgacgacct cggacgagga gcagtttccg ccgctcgtcc gcctgatgat gatgcagttt    60
cagtcgggca tcttctgcaa cttcctcgac cggctgagcg ccacaagca cctgctgccg    120
gatcccaacc attatggctg cggcctgcac tcgaccggct cgggcgggcg gctgatgctc    180
cacatcgatg cctcgcgcca ccccaacaag aagctcagcc agcagatcaa ctgcatctat    240
tactgcacgc cagactggca ggaggaatgg ggcggcgacc tggagctgtg ggacgaggat    300
gcgaccaggt gcgtttccag catcacgccc aagttcaatc gcctcgcgat cttccgcgtc    360
tcgggcaagt cgtggcacgg ccagcccttc ccgctgcaga cgccgccgaa catccgccgc    420
aactcgctcg cactctacta ctacagcgca gaggaggata ccgagggtcg cggctattcg    480
aacttcgtgc gttggaaggg ccgtctcggc gcacgacaag cgcaccgcgc tgcaccgggt    540
gaagggcctg atccgcgact atgcgccgac cccggtgatc aacggcctcg ccaagttcgc    600
ccgcaagacg gggctgaact tcaagcgctg atggggctgt tctcgcgctt tgccgccgca    660
ccgccggaat cgccctgtcg caaggtctgc cgcctcgaca tggagatccg gctgtgcctg    720
gggtgctggc ggtcgcccaa ggaaatcgcc ggctggagcg agctgagtcc taagggaaag    780
cgcgcggtgc tagaggcatt gccggcgcgc gaacgggagc atggcggggg cgctga       837
```

<210> SEQ ID NO 49
<211> LENGTH: 278
<212> TYPE: PRT
<213> ORGANISM: Sphingomonas sp. ATCC53159

<400> SEQUENCE: 49

```
Val Thr Thr Ser Asp Glu Glu Gln Phe Pro Pro Leu Val Arg Leu Met
1               5                   10                  15

Met Met Gln Phe Gln Ser Gly Ile Phe Cys Asn Phe Leu Asp Arg Leu
            20                  25                  30
```

Ser Gly His Lys His Leu Leu Pro Asp Pro Asn His Tyr Gly Cys Gly
         35                  40                  45

Leu His Ser Thr Gly Ser Gly Gly Arg Leu Met Leu His Ile Asp Ala
    50                  55                  60

Ser Arg His Pro Asn Lys Lys Leu Ser Gln Gln Ile Asn Cys Ile Tyr
65                  70                  75                  80

Tyr Cys Thr Pro Asp Trp Gln Glu Glu Trp Gly Gly Asp Leu Glu Leu
                85                  90                  95

Trp Asp Glu Asp Ala Thr Arg Cys Val Ser Ser Ile Thr Pro Lys Phe
            100                 105                 110

Asn Arg Leu Ala Ile Phe Arg Val Ser Gly Lys Ser Trp His Gly Gln
        115                 120                 125

Pro Phe Pro Leu Gln Thr Pro Pro Asn Ile Arg Arg Asn Ser Leu Ala
    130                 135                 140

Leu Tyr Tyr Tyr Ser Ala Glu Glu Asp Thr Glu Gly Arg Gly Tyr Ser
145                 150                 155                 160

Asn Phe Val Arg Trp Lys Gly Arg Leu Gly Ala Arg Gln Ala His Arg
                165                 170                 175

Ala Ala Pro Gly Glu Gly Pro Asp Pro Arg Leu Cys Ala Asp Pro Gly
            180                 185                 190

Asp Gln Arg Pro Arg Gln Val Arg Pro Gln Asp Gly Ala Glu Leu Gln
        195                 200                 205

Ala Leu Met Gly Leu Phe Ser Arg Phe Ala Ala Ala Pro Pro Glu Ser
    210                 215                 220

Pro Cys Arg Lys Val Cys Arg Leu Asp Met Glu Ile Arg Leu Cys Leu
225                 230                 235                 240

Gly Cys Trp Arg Ser Pro Lys Glu Ile Ala Gly Trp Ser Glu Leu Ser
                245                 250                 255

Pro Lys Gly Lys Arg Ala Val Leu Glu Ala Leu Pro Ala Arg Glu Arg
            260                 265                 270

Glu His Gly Gly Gly Arg
        275

<210> SEQ ID NO 50
<211> LENGTH: 816
<212> TYPE: DNA
<213> ORGANISM: Sphingomonas sp. ATCC53159

<400> SEQUENCE: 50
atgctccacg tgatcctgac tcgcttcaac atcgccagcc cgggacgcga ggtggcgatt      60
cgcaactcgc cgggctggct ggaacgccgt ttcggcctgt cgagcagtt ctgcctgccg      120 agcatcgcgg ccagaccga gcgcaacttc cactggctga tctatttcga caaggatacg      180
ccggttgaat ccgcgagcg atcgagcgc gatcgccaga tcttcaattt taccccacgc      240
tatgtggcga tgttcgacaa ggcgatgatc gccgaggacg tgcgggcact cgcgacggcg      300
ggcgagacgc tgatcgtcac cacgcggctg acaatgatg atgcggtgtc gagcgatttc      360
gtcgcgcggg tgcaggacgc cgccaaggaa gcgccggcgc agaccgtgct gaacttcccc      420
cacggcatcg cgatgcgggg cggcaactc tacaccgcca gcgatcacag cagcccgttc      480
acctcgctgg tcgagaaaga cgtggccggg atcgagacga tctgggccaa gccgcaccac      540
gagctgggcg agaagtggac gatccgccag gtgccgagca gccgctatg gctgcaggtg      600 gtgcacggcg agaatgtaac caaccggatc aagggcaagc tggtttcgga catcgacatc      660

```
atcaatatgt tcaagatccg cagcgatgtc gccgcacggc cggtggcggc cggcgcgatt    720
ctgtgggacc atgcgtgcg cacgccgatc cggcgcttcc gcgaattcgg tatccgcctg    780
gtcaagccga tcgtggttcg ataagggat cgctaa                               816
```

<210> SEQ ID NO 51
<211> LENGTH: 271
<212> TYPE: PRT
<213> ORGANISM: Sphingomonas sp. ATCC53159

<400> SEQUENCE: 51

```
Met Leu His Val Ile Leu Thr Arg Phe Asn Ile Ala Ser Pro Gly Arg
1               5                   10                  15

Glu Val Ala Ile Arg Asn Ser Pro Gly Trp Leu Glu Arg Arg Phe Gly
            20                  25                  30

Leu Phe Glu Gln Phe Cys Leu Pro Ser Ile Ala Gly Gln Thr Glu Arg
        35                  40                  45

Asn Phe His Trp Leu Ile Tyr Phe Asp Lys Asp Thr Pro Val Glu Phe
    50                  55                  60

Arg Glu Arg Ile Glu Arg Asp Arg Gln Ile Phe Asn Phe Thr Pro Arg
65                  70                  75                  80

Tyr Val Ala Met Phe Asp Lys Ala Met Ile Ala Glu Asp Val Arg Ala
                85                  90                  95

Leu Ala Thr Ala Gly Glu Thr Leu Ile Val Thr Thr Arg Leu Asp Asn
            100                 105                 110

Asp Asp Ala Val Ser Ser Asp Phe Val Ala Arg Val Gln Asp Ala Ala
        115                 120                 125

Lys Glu Ala Pro Ala Gln Thr Val Leu Asn Phe Pro His Gly Ile Ala
    130                 135                 140

Met Arg Gly Gly Gln Leu Tyr Thr Ala Ser Asp His Ser Ser Pro Phe
145                 150                 155                 160

Thr Ser Leu Val Glu Lys Asp Val Ala Gly Ile Glu Thr Ile Trp Ala
                165                 170                 175

Lys Pro His His Glu Leu Gly Glu Lys Trp Thr Ile Arg Gln Val Pro
            180                 185                 190

Ser Lys Pro Leu Trp Leu Gln Val Val His Gly Glu Asn Val Thr Asn
        195                 200                 205

Arg Ile Lys Gly Lys Leu Val Ser Asp Ile Asp Ile Ile Asn Met Phe
    210                 215                 220

Lys Ile Arg Ser Asp Val Ala Ala Arg Pro Val Ala Ala Gly Ala Ile
225                 230                 235                 240

Leu Trp Asp His Ala Val Arg Thr Pro Ile Arg Arg Phe Arg Glu Phe
                245                 250                 255

Gly Ile Arg Leu Val Lys Pro Ile Val Val Arg Ile Arg Asp Arg
            260                 265                 270
```

<210> SEQ ID NO 52
<211> LENGTH: 933
<212> TYPE: DNA
<213> ORGANISM: Sphingomonas sp. ATCC53159

<400> SEQUENCE: 52

```
atggcttgcc cctacccgag cccggtgtcg ccccctcgtc ccgacagcat cgccaccggc    60
ctggcgcttc gcctgttcgc gatcgcctgc atgtcgacca tgtcggcgct catcaagatg   120
tccgaactgc gcggcgcctc gctgatcgag acgatgtttc accgccagct ctgggcggtg   180
```

```
cccttggtca ccctgtgggt cacgctgggg ccgggcctca agtcgctcag gaccgcgcgg    240
ttcggcgcgc atgtctggcg caccgcggtg ggacttaccg gcatgatctt caccttcggc    300
gcggtgatcc tgctgccgct cgccgaagcg cagaccttcc agttcaccgt ccccatcttc    360
gcgacgctgc tcggcgcgct gatcctaggc gaaccgaccg gctggcaccg ctggagcgcg    420
gtgatcctcg ggttcgtcgg cgtgcttatc gtcgtccagc cggggcacga ggcgatcccg    480
gtgttcggtg cgttcgtggg cctgatggcg gcgctgttcg tcgccatcgt cgcgatcacg    540
ctccgccaga tcgggaagac cgaaagcgcc ggcaccacgg tgttctggtt ctcgctgttg    600
tcggtgccgg tgctgggcgc aatctatgcc ttccactaca gccccatga tgccgagacc    660 tgggccatcc tgatcgccac gggcctggtc ggcggcgtcg gccagctcgc gctgaccggg    720
gcgatgcgct tcgctcccgt gtcggcagtg gtgccgatgg actattcggg gctgctctgg    780
gcgacgctct atggctggct gctgttcggc gtgctgccga ccttttccac ctggctcggc    840
gcgccggtga tcatcgccag cggcctgtac atcgtctatc gcgagcagaa gctggcgcgc    900
ggccaggcta gctacgccga aacgccacta tga    933
```

<210> SEQ ID NO 53
<211> LENGTH: 310
<212> TYPE: PRT
<213> ORGANISM: Sphingomonas sp. ATCC53159

<400> SEQUENCE: 53

```
Met Ala Cys Pro Tyr Pro Ser Pro Val Ser Pro Pro Arg Pro Asp Ser
1               5                   10                  15

Ile Ala Thr Gly Leu Ala Leu Arg Leu Phe Ala Ile Ala Cys Met Ser
            20                  25                  30

Thr Met Ser Ala Leu Ile Lys Met Ser Glu Leu Arg Gly Ala Ser Leu
        35                  40                  45

Ile Glu Thr Met Phe His Arg Gln Leu Trp Ala Val Pro Leu Val Thr
    50                  55                  60

Leu Trp Val Thr Leu Gly Pro Gly Leu Lys Ser Leu Arg Thr Ala Arg
65                  70                  75                  80

Phe Gly Ala His Val Trp Arg Thr Ala Val Gly Leu Thr Gly Met Ile
                85                  90                  95

Phe Thr Phe Gly Ala Val Ile Leu Leu Pro Leu Ala Glu Ala Gln Thr
            100                 105                 110

Phe Gln Phe Thr Val Pro Ile Phe Ala Thr Leu Leu Gly Ala Leu Ile
        115                 120                 125

Leu Gly Glu Pro Thr Gly Trp His Arg Trp Ser Ala Val Ile Leu Gly
    130                 135                 140

Phe Val Gly Val Leu Ile Val Val Gln Pro Gly His Glu Ala Ile Pro
145                 150                 155                 160

Val Phe Gly Ala Phe Val Gly Leu Met Ala Ala Leu Phe Val Ala Ile
                165                 170                 175

Val Ala Ile Thr Leu Arg Gln Ile Gly Lys Thr Glu Ser Ala Gly Thr
            180                 185                 190

Thr Val Phe Trp Phe Ser Leu Leu Ser Val Pro Val Leu Gly Ala Ile
        195                 200                 205

Tyr Ala Phe His Tyr Lys Pro His Asp Ala Glu Thr Trp Ala Ile Leu
    210                 215                 220

Ile Ala Thr Gly Leu Val Gly Gly Val Gly Gln Leu Ala Leu Thr Gly
225                 230                 235                 240
```

```
Ala Met Arg Phe Ala Pro Val Ser Ala Val Val Pro Met Asp Tyr Ser
            245                 250                 255

Gly Leu Leu Trp Ala Thr Leu Tyr Gly Trp Leu Leu Phe Gly Val Leu
            260                 265                 270

Pro Thr Phe Ser Thr Trp Leu Gly Ala Pro Val Ile Ile Ala Ser Gly
            275                 280                 285

Leu Tyr Ile Val Tyr Arg Glu Gln Lys Leu Ala Arg Gly Gln Ala Ser
            290                 295                 300

Tyr Ala Glu Thr Pro Leu
305                 310

<210> SEQ ID NO 54
<211> LENGTH: 20779
<212> TYPE: DNA
<213> ORGANISM: Sphingomonas sp. ATCC53159

<400> SEQUENCE: 54
```

| | | | | | |
|---|---|---|---|---|---|
| gctgcaggtc | gacggatcgc | cagcggcctc | accatcaact | atgcaccgga | tgcatcggtg | 60 |
| ggccacccgc | ccggcccga | ctggtcggcc | ctgctggtga | agacgcggcg | catccagcgc | 120 |
| gaactctatc | tgttcaacat | cgagcggccg | aagggcaggc | tgcgctggct | ggtccgttcc | 180 |
| gtggcgcaac | cggcgatgat | cccacaggac | gtggccaaga | tcctgcgcac | accgggtacc | 240 |
| aagggcgcgc | gcctcgctgc | ggtcaccacg | ctggtccggc | tgcggctgtg | gcgcggcggc | 300 |
| gccggcttgt | tgcagttgct | cggccgcgac | atctgatcga | ccggcgatcg | gccgacgagc | 360 |
| gcgtcgccgg | ccgatcgcat | tgcatcagac | ggtggccagc | gcgtcttcca | gcgtgccgct | 420 |
| gtcgagccgc | aggcggccga | tcatcagcca | cagatagacc | ggcagcgtat | cgtcggtgaa | 480 |
| gcggaagcgg | caatcgccgt | cctgcgtttc | ggattcgagg | ccgagttgac | cggtgagctc | 540 |
| gcccagctcc | tgctcgacct | cgccgccgt | gatgtgcgcg | cccggcagca | gatccaccac | 600 |
| ggcttggccg | ctgaaccagc | catccgccga | gcgcgaggcc | tcgcccagcg | ccgcgacgag | 660 |
| tggatcgtag | cggccgccga | cgaacttgcg | catctcgatc | accgcgcgcg | gcggcatgcg | 720 |
| gccctcgatc | tcaaggatcg | cctggtcgag | cgcacgacgc | agatgcccgg | cgtcgaccgt | 780 |
| gaggcggccc | tggtccaggg | cttccagcgc | ggaatggtgg | cacagcagcc | gcgcgaaata | 840 |
| gggcgacccc | agcgcgagca | ggtggatcat | gtgagtcagg | tccggatcga | agcgaacgcc | 900 |
| cgaggcggtt | tcgccgagcg | cgatcatctc | ctgcacctcc | gattcctcca | gccggggcat | 960 |
| cggcaggccg | atgacgttgc | ggcggatcga | cggcgcataa | ccgatcagct | cctgcaggtt | 1020 |
| cgaggcgacg | cccgcgatca | ccagctggac | gcgcgccgaa | cggtccgaca | ggttcttgat | 1080 |
| cagctcggcg | acctgctgac | ggaaggcgga | atcgctgacg | cgatcatatt | cgtcgaggat | 1140 |
| gatcagcacg | cgtgtgcccg | tgatgtcggc | gcacaggtcg | gccagttcgc | cgggcccgaa | 1200 |
| gctgcccgtc | ggcaggcggt | cggccaagtt | gccgccgctc | tccgcctcgc | ggcgttgggg | 1260 |
| cgccacgccg | cgatgaaca | gcagcggcac | gtcttccagc | acggcgcgga | agacatcgct | 1320 |
| gaaattcgcg | ttcgcaccgc | aggtcgcata | gctgacgata | tagctggatt | cgcgggcgac | 1380 |
| atcggtcagc | acgtggagca | gcgaggtctt | gccgatgccg | cgctcgccat | agagcacgac | 1440 |
| atggctgcgc | tggctctcga | tcgaggagat | taggcgcgcc | agcacgccga | ggcgcccggc | 1500 |
| gaagctcgac | cgatcggcca | ccggctgggt | gggtgtgaag | aaggtcgcca | gcgcgaaccg | 1560 |
| ggcgcgcgtg | atctcgcggc | gctcgtcgcg | cggcgatcc | agcgggcggt | ccagcgcgga | 1620 |
| ggcacggaag | gttgggaaat | ccgggcgacc | acggccgcta | tgggcatcgc | gatgcggcac | 1680 |

-continued

```
cactgtcgca gtcagcggga aatagccctc ttcttcaggt tcttctcgac ggccgaacgg    1740
ccacaagaat ctcagcgcgg aacctacagc cactcgaaca cctcttaaat tcgtgcgcca    1800
tcggcaccga cggcgcaccc tggttcgcgc ccctggcgc cccctcctaa cgaacccacg     1860
ccttgcctgg cctatcggcg cttgaagaac tcgtacggtt tgatcaccaa ggcgatgtac    1920
gccaggacca gagcgatcgt caaaattgca aagacgtgat aattctcatt gcccagataa    1980
ttggcgacgg cgcaaccgac tgcgggcggc aaatagctga tcatcgtgtc ccggactgcc    2040
gaatcggctt gggaccgttg caggaatata acgatcaggc cggcaaatat cgcgatggtg    2100
acccaatcat agggcgtctg catgcatgtc ctttctattc gacaccggaa tcgaaccatt    2160
tccggcgacg ctattgcacg cactagcagt gcgcgcggcc gctcgctagg tagcgccgca    2220
ccggataaac cgacgttaag atggcgcggc tcgatcgaaa tggagtcaaa cgggcttgcc    2280
cggccgaccg aagcatggcg ccatggcgca tgcaccgtat tgtgaccacg caaaccgcga    2340
gggtcattcg atgcggttgc ttgtacagga ggccattgat aatgaagccg agacccgggg    2400
gaacctttat gcaagtaaat ttcaatcgac aggctcgcaa gctcggtgcc ggcaatgcgc    2460
tcgcgcgggg ggggcccgtg cttgcgctgc ttgcgaccgc ggcatggaca caacctgcgc    2520
tggcgcagcg acaggcattt gagtcccgcc cctccggtag cgagcgacag gtcgatattc    2580
gcgcgacggg gtcgctggaa tatgacgaca acgtcgtgct gaacgaccag cggatcacgg    2640
acggcgcgcg tggcgatgtg atcgcatcgc ccgggctgga cgtgaccta gttctgcccc     2700
gcgccaccgg gcagctctac ctcaccggca atgtcggata tcgcttttac aagcgatata    2760
ccaactttaa ccgcgagcag atctcgctca ccggcggcgc agatcagcgg ttcgcctcct    2820
gcgtcgtgca cggggaagtc ggctatcagc gccacctcac cgacctgtcc agcatcttga    2880
tccaggacac cacgcctgcg ctcaacaaca ccgaagaggc ccggcagtac accgcggata    2940
tcggctgcgg cgcgacctac ggcctgcggc ctgccgtttc ctacacccgc aacgaagtgc    3000
gcaacagcct tgccgagcgc cgatacgcgg actcgaatac caacacccttt accgcacagc    3060
ttggcctgac ttcgcctgcc ctggggaccg tggcggtatt tgggcgtatg tccgacagca    3120
gctatgtcca tcgcgtcctt cccggcatta ccggccagga cgggatgaag agctacgcgg    3180
ccggcgtcca gctcgagcgc tcggtggcca accgactcca tttcaacggc tcggtgaatt    3240
acaccgaggt tgacccaaag ctcgcatcca ccaaaggatt caaggcgta ggatttaacg     3300
tttccggcga ttatgctggt gatcagtaca gcctccaatt gctggcttca cgatcgcccc    3360
agccttcact tcttctgttc gtgggttacg agattgtgac agcggtttcg gcgaatgcga    3420
cgcgccggct gagcgatcgc attcagatat cgctgcaagg cagccgaacc tggcgcgagc    3480
tcgcgtcttc gcggctgctc accaacgtgc cgatttccgg caacgacaac acctcgacgt    3540
tgttcgcctc cgctaccttc cggccgaatc gccggctgag ctttgtgctg ggtgccggcc    3600
ttcagcggcg caccagcaac acgcagctat acagttacag ctccaaacgc atcaatctct    3660
cgacgtcgct ttcgctctga caagggccgt aatcatgcat atcaagaatc gcttcgtgaa    3720
tatctcgacg ttggccatcg ccgccgcgct ggccacgccg gcggcggcgc agatccccac    3780
gcggtccgtg cccgcgccgg cccgcccgcg gcctgcaacg ccgccggcgc aacagcagaa    3840
ccaggcgccg tcgacgcccg cagcggcaac cccgcgcag accgccgcaa ccgttgcccc     3900
tgcagcaacc gcaccgcag gttacaaaat cggcgtggac gacgtgatcg aggccgacgt    3960
gctcggccag accgacttca agacgcgcgc ccgtgtgcag gcggacggca cggtgaccct    4020
gccctatctg ggcgccgtgc aggtcaaggg cgagaccgcg acctcgctcg ccgaaaagct    4080
```

-continued

```
ggccgggctg ctgcgcgccg gcggctatta tgccaagccg atcgtcagcg tcgaaatcgt    4140
cggtttcgtc agcaactatg tgacggtgct gggccaggtg aacagttccg gcctgcagcc    4200
ggtcgaccgc ggctatcacg tttccgagat catcgcccgt gccggcggcc tgcgccccga    4260
agcggccgat ttcgtcgttc tcacccgcgc cgatggctcc agcgccaagc tggactacaa    4320
gaagctcgcc caaggtggcc ccaatgacga tccgatggtg acgcccgggg acaaggtctt    4380
tgtcccggaa gtcgagcatt tctacattta tggtcaaatt aacgcgcctg cgtatacgc     4440 gattcgatcg gacatgacgc tccgtcgcgc gctggcccag ggcggtgggc ttgccccgc     4500 aggctccgtc aagcgtgtga aggtcacgcg ggatggcaat gaactcaagt tgaagctgga    4560
cgatccgatt ctcccaggcg acacgatcgt catcggcgaa cgattgttct gatcttggca    4620
acgatggcag cggacgaggc ccaccagtga atatcattca gttcttccgc attctgtggg    4680
tgcgccgatg gatcatcctc ccggcgtttc tcgtttgcgt taccactgcc accattgtgg    4740
tccagtttct gcccgaacgc tacaaggcca ctacgcgggt ggtgctcgac acgtttaagc    4800
ccgatcccgt caccggacag gtgatgagct cgcagttcat gcgcgcctat gtcgagactc    4860
agacccagct gatcgaggac tatgcgaccg ccggtcgcgt ggtcgacgaa ctgggctggg    4920
tgaatgatcc ggcgaacatc tccgcgttca caactcgtc cgcggctgcc accggcgaca     4980
tccgccgctg gctcgccaag cagatcatcg acaataccaa ggccgatgtg atggagggga    5040
gcaacatcct cgaaatcacc tattcggaca gctcgcccga gcgcgccgaa cgcatcgcca    5100
acctgatccg cacctcgttc ctcgcccagt cgctcgccgc caagcgccag gccgcgacca    5160
agtcggccga ctggtacgcc cagcaggccg aagctgcccg cgattcgctc gctgcggcgg    5220
tccaggcccg caccgatttc gtgaagaaga ccggcatcgt gctgaccgaa accggcgccg    5280
acctggaaac ccagaagctc cagcagatcg agggcagac gacgaccgcc accgccccgg     5340
ttgccatggc cccagcggc atgggcccgg cgcagatgca gctcgcccag atcgaccagc     5400
agatccagca ggcagcgacc agcctaggtc cgaaccaccc aactttccag gccttgcagc    5460
ggcagcgcga agtgttcgcc aaggcagcgg cggcggaacg cgcgcaggcg aacggcgtat    5520
ccggtccggc acgcggggcc atcgaaagcg cagccaacgc ccagcgcgcg cgggttctcg    5580
gcaatcgtca ggatgtcgac aagcttacgc agctgcagcg tgacgtctcg ctgaagcagg    5640
atcagtacat gaaggcggca cagcgcgtcg ccgatctgcg gctggaagca agcagcaacg    5700
atgtcggcat gtcgacgctc agcgaagcat cggcgccgga aacgccctat taccccaagg    5760
tgccgctcat catcggtggt gcagccggct tcggcctcgg gctcggtctg ctggtcgcgc    5820
tgctcgtcga gctgctcggc cgccgcgtcc gcagccccga ggatctggaa gttgcgatcg    5880
atgcaccggt gctgggcgtg atccagagcc gcgcctcgct tgccgcccgc cttcgccgcg    5940
cccaagaaac cctcggcgaa ggtgccgaca cgcacggagc ttcagtaaac tgatggacgc    6000
gatgaccagc gaaccgctgc cgaaggcga tcgtccgagc gccgtgccga ccacgccgga    6060
tacgatcggc atgctcgaat accagctcgt cctctccgat ccgaccggga tcgaggcgga    6120
agcgatccgc gcgctacgca cgcgcatcat gacccagcac ctccgcgagg gccggcgcgc    6180
gctcgcgatc tgcgccgcct cggcgggatc cggctgcagc ttcaccgccg tcaatctggc    6240
gacggcgctg gcgcagatcg gcgttaagac tgcgctggtc gatgccaatc tgcgcgatcc    6300
cagcatcggc gcagccttcg gcctcgccgc cgacaagccc ggcctggccg attatctcgc    6360
ctcgggcgat gtcgacctcg cctcgatcat ccatgcgacc cgcctcgacc agctctcgat    6420
```

-continued

```
catcccggcc gggcatgtcg agcacagccc gcaggaactg ctcgcgtccg aacagttcca    6480
tgatctggcg acgcagctgc tgcgcgagtt cgacatcacg atcttcgaca ccacggcgtc    6540
caacacctgc gccgacgcgc agcgtgtcgc gcatatcgcc ggctatgcga tcatcgtggc    6600
gcgcaaggat gcgagctaca tccgcgacgt gaacacgctc agccgcacgc tgcgtgcaga    6660
ccgcaccaac gtcatcggct gcgtactgaa cggctattga tttggaccat atggcagcga    6720
ccgcgatgac gcggcagcag gagaggaagg gcggtggcta ttggctggcc gttgccggtc    6780
ttgccgcgct aaccatcccg accttcatca ccctgggtcg cgaggtttgg agtgcggaag    6840
gcggcgtgca gggtccgatc gtgctcgcca cgggcgcctg gatgctggcc cgccagtgct    6900
cgacgatcga ggcgctacgc cgccccggca gcgtgctgct cggcgcgctg ttcctgctgg    6960
cgacgcttgc cttctacacc gttggacggg tgttcgactt catcagtgtc gaaaccttcg    7020
gactggtcgc gacctatctg gtcgtcgcct atctctattt cggtgccagg gtgctccgtg    7080
ccgcctggtt cccggtgctg tggctgttct tcctggtgcc gccgcccggc tgggccgtcg    7140
accgcatcac cgcaccgctc aaggagttcg tctcctatgc ggcaacgggc ctgctttcct    7200
gggtggatta tccgatcctg cgccagggcg tgacactgtt cgtcggcccc tatcagctgc    7260
tcgtcgaaga tgcctgttcg ggtctgcgct cgctgtccag cctggtcgtc gtgacgctgc    7320
tctacatcta catcaagaac aagccgtcct ggcgctacgc ggcgttcatc gcagcgctgg    7380
tgatcccggt ggcagtggtg accaacgtcc tgcggatcat catcctggta ctgatcacct    7440
atcatctggg cgacgaggcg cgcagagct tcctccacgt ctccaccggc atggtgatgt    7500
tcgtggtcgc cctgctttgc atcttcgcga tcgactgggg ggtcgagcaa cttcttctcc    7560
tgcgtcggag gcatcatgtt caaccggcgt gacctgctga tcggcgcagg ctgcttcgcc    7620
gccgctggcg cctcgctcgg cctgaagccg caccggcgga tggacctgct gggcggcacc    7680
aagctcgaca cgctgatgcc caaggcattc ggcgcatgga aggcagagga taccggttcg    7740
ctgatcgcgc cggcgcgcga aggcagcctg gaggacaagc tctacaacca ggtggtcacc    7800
cgcgccttct cccgcgcgga cggtgcccaa gtgatgctgc tgatcgccta tggcaacgcc    7860
cagaccgatc tactgcagct gcaccggccg gaaatatgct acccgttctt cggcttcacc    7920
gtggtggaaa gccatgagca gaccatcccg gtgacgccgc aggtgacgat ccccggtcgc    7980
gcgctgaccg ccaccaactt caaccgcacc gagcagatcc tctactggac ccgcgtcggc    8040
gaatatctgc cgcagaacgg caatcagcag atgctcgcgc ggctgaagag ccaggtccag    8100
ggctggatcg tcgacggtgt gctggtgcgc atctcgacgg tgacgcccga gcggaagat    8160
ggcctgagcg ccaatctcga tttcgcgcgc gagctggtga agacgctcga cccgcgcgtg    8220
ctgcgccccgc tgctcgggaa cgggctcaca cggcagctcg gtcaccaggt ctgaaccggt    8280
gcgccgcacg cggcgccccc ggcaacaaaa aaggagcggc gcggccgcc gccgctccct    8340
ctccttctca tgcggcgccc tgccctcacc gctcgtgcag cgcgtcactc cccgtctcga    8400
gcacgggccc caccagatag ctgaacaggg ttcgcttgcc ggtgacgatg tccgcgctcg    8460
cgagcatccc cggccgcagc ggcacctgtg cgccatgggc cagcacatac ccgcgcgcca    8520
gcgcgatccg cgccttgtag accgcgcgct ggttctcctt catctgcacc gctcggggc    8580
tgatgcccgc caccgtgccg ggaatcatgc cgtagcgggt atagggaaag gcctgcagct    8640
tcacctttac cggcatgccg atgtggacga agccgatgtc gctgttgtcg accatcacct    8700
cggcctcgag ccgggcattg tcgggaacca ggctgaggag cggcttggcc ccttccacca    8760
cgccgccttc ggtgtggacc tgcagctgcg agacggtacc gctcaccggc gcgcgcagtt    8820
```

```
cgcggaacga gctgcgcaga ttcgccttgg cgacgtcctc gccgcgggca cgcacctcgt    8880
cctgcgcctt gaccagatcc tgcagcacct gcgcccgcgc ctcctcgcgc gtcttggccg    8940
acaggctgga gacgctcagc gactgctggc cgagtttggc gagcgtagcg cgcgccgccg    9000
tcaggtcctg ccgctcggcg atcagctggc gacgcatctc cacgacgcgc agcttcgaga    9060
catagccctt ggcggccatc gtctcgttcg cggcgatctg ctgttcgagc agcggcagcg    9120
actgttcgag cttccgcacc tgtgcctgcg cctcggccgc ggccgagacg gcggcaccgc    9180
gatcggagcg gccgccggcc agcgccgcct cgatctggcc cagccgggcg cgggcgaggc    9240
cgcgatgcgt cgccacttcg cccgggctgg cggcggcagg cgcgacgaag cggaagcccc    9300
tgccgtccag cgcgtcgatg atcgcctggt tgcgtgcggc gtcgagctgg gcgctgagca    9360
gcgccacctt cgcctgtgcc gcctccgccg acgacgggt cgggtcgagc gtgatcagca    9420
cctggcccctt ggcgaccttc tgccctcgc ccaccaggat gcggcggacg atccccgatt    9480
cgggcgactg gacgatcttg gtctcgccga tcggcgcgat ccgcccctgc gtcggcgcga    9540
cgacttcgac cttgccgatc gccagccagg cggcggtgat cgccagcccg ccagcatca    9600
ccttggcggt aagccgcgcg gtgggcgaaa ccggccgctc gatgatctcc agcgcggcag    9660
gcaggaaggc ggtgtcataa gcgtcgacgc gggcaggcag cacggtatcg cgcatgcggg    9720
cgagcggggcc gccgcggcgc atcggaacaa cggcgttcat gcggcaatct ccccatagcc    9780
gccctggcgg cggtgcaggt cggcatagcg gccgcccagg cgcaacaatt cgtcgtgtcg    9840
gccgctctcg acgatgcggc cctgttcgag cgtgatgatc cggtcgcagc tgcgcaccgc    9900
gctcaggcga tgcgcgatca ccacgagcgt gcggccggcc gagatggcgc gcaggttgtt    9960
ctggatcagc tcctcgctct cggcatcgag cgccgaggtc gcttcgtcga acaccaggat   10020
gcgcggattg ccgacgagcg cgcgggcgat ggcgagccgc tggcgctggc cgccggagag   10080
attgacgccg cgctcgacga tctcggtgtc atagccgcgc ggctggcgca ggatgaaatc   10140
atgcgcgccg gccagcgtcg ccgccgcgac gacattctcg aacggcatgg cggggttgga   10200
gagcgcgatg ttctcgcgga tcgagcggct gaacagcaga ttctcctgca gcacgacgcc   10260
gatctggcga cgcagccagg cgggatcgag ctgcgccacg tcgacctcgt cgaccagcac   10320
gcggccgaga ttcggcaggt tgagccgctg gagcagcttg gccagcgtcg acttgcccga   10380
gcccgacgaa ccgacgatgc cgagcgaggt gcccgccgga atgtcgagcg tgatgtcgct   10440
cagcaccggc ggctggtcct cggcatagcg gaagctgaca ttctcgaagc gaatcgcacc   10500
gcgcagcacc ggcagcgtcg ccgccgaggc cgggcgcggt tccaccggat ggttgagcac   10560
gtcgcccagc cgctcgaccg agatgcgcac ctgctggaaa tcctgccaca gctgcgccat   10620
gcggatcacc ggcccggaca cgcgctgggc gaacatgttg aacgccacca gcgcgcctac   10680
gctcatcgcg ccgccgatca ccgccttggc gccgaagaac aggatcgccg cgaagctcag   10740
cttcgagatc agctcgatcg cctggctgcc ggtgttggcg gtattgatca gccgctgcga   10800
cgcggcggta tgggcggcga gctggcgctc ccagcgattc tgccagtgcg gctcgaccgc   10860
ggtcgccttg atcgtgtgga tgcccgagac gctctcgacg agcagcgcgt tgctggcgga   10920
gctcttctcg aacttgtcct ccacccgcgc gcggagcggc ccggcgacgc tgaacgatac   10980
gatcgcatag gcgatcagcg acacgagcac gatgcccgag agcatcggcg agtagaacag   11040
catcgcggcg aggaacacga aggtgaacag cgggtccacc atcaccgtca gcgaggcgct   11100
ggtaaggaat tcgcggatcg tctcgagctg gcggacgcgg gtgacggtgt cgcccacgcg   11160
```

```
gcgcttctcg aaataggcga gcggcagcgc cagcaggtgg tggaacagcc gggcacccag    11220
ctcgacgtcg atcttctgcg tcgtctcggt gaacaggcgg gtgcggatcc agccgagcgc    11280
cacttcccac accgaaaccg ccaggaaggc gaaggcgagc acgctcagcg tgctcatgct    11340
gttgtggatc agcaccttgt cgatcacgct ctggaacaac agcggcgcgg cgaggccgag    11400
caggttgagc gcgagggtga tgccgagcac ctcgaggaac agcgtgcgat agcgccggaa    11460
ctgcgcggtg aaccaggaga ggccgaaccg cagcggccgt cccgccaccg cgcgggtggt    11520
gagcagcacc agcgcgccgg accagatcgc gtccagcgcg tcccggtcga cctgttccgg    11580
ggcatggccc gggcgctgga tgatcacgcc atgttcggtc aggccgccga tcacgaacca    11640
gccttcgggc ccgtcggcga tcgcgggcag cggctggcgg gcgagtccgc cgcgcggcac    11700
ctcgacggcc ttggcgcgca cgccctgctg gcgcttggcc aggaggatca ggtcgtcggc    11760
gcttgccgcc tcggcatggc ccagcgcgtg gcgcagctgt tcgggcgtga tggcgatgtt    11820
gtgcgcgccg agcagcagcg acaacgccac cagtccggat tcgcgcagct ccgcctcgcg    11880
ctccgccgcc ccatgggccg cgagcgcgct ctgcagggtg gcctgcattt cgtcgcgtgt    11940
catttccgga actctgcctc catggcgata ctgagagcgc catgatgaag aaggctggta    12000
aagactcact taatcctagc ttttctggta tttacccgta gctgccgacc cgatttggga    12060
caggcctggc ttagcaggtc cttaaactcg accgactata ccgcgacgcc gaggaggggg    12120
aggattggcg ccgcatcgcg cggcgaaacg cgggtgcgtc gcaacatttc gccggagtcg    12180
atccgtcgcg aatgctgcac ccgcgaacgc aatgacggcc gccacgcaat ccggcttgat    12240
cccgggcggc ggatcgcgat aagccgcgcc acggtcgcca aaactcgtcg aaataaccga    12300
caaaaccacg gcatatggct ggatattgca gcgtttgccc tgcgtttccg tcgttcaacc    12360
gcccttcgaa tcaggcaggc ccagcgtgac catgattgat cttcctcttg gaacggcaca    12420
ctttggtcga cacggagact tccggtcggg caattgtccc gttatagtgc aatgcaacag    12480
gccgaatcgg ccgctgtcgg cgtgcacatt ccgttgaggg agcccgatga ggcaatgaac    12540
gctttcgaag cacagcgcgc ctttgaggag caacttcggg cgcattcccg ggttacgcca    12600
tctgccgctc ccgtgtggcg tcgctcgacg ctgcggatgg tcctctatac cgagttgctg    12660
ctgctggaca gtctctcgat cctggccgga ttccacgtcg cggcgggcac gcgcgacggc    12720
aactggctgt cgctggcggg catcaacgtc ggcgtcttcc tgctgccgat cgctctcggc    12780
accgcgctcg caagcggcac ctactcgctg aactgcctgc gctacccggt cagcggcgtg    12840
aagagcatct tctcggcatt cttcttctcg atcttcgtcg tcctgctcgg cagctacctg    12900
ctgacggccg agctgccgct gtcccgcgtg cagctggcgg agggcgcgat cctctcgctg    12960
gtcctcctga tggtgggccg cctgatgttc cgccgccacg tccgcgcggt taccggcggc    13020
aggctgctcg acgaactggt catcatcgac ggcgtctcgc tcgacgtcgc gggcaatgcg    13080
gtcgcgctcg acgcgcggat catcaatctc tcgccgaacc cgcgcgatcc gcaaatgctg    13140
catcgcctgg gcaccaccgt gatcgggttc gaccgggtga tcgtcgcctg caccaaggag    13200
catcgcgcgg tctgggcgct gctgctcaag ggcatgaaca tcaagggcga gatcctcgtc    13260
ccccagttca atgcgctggg cgcgatcggc gtggacgcct tgacgggaa ggatacgctg    13320 gtcgtctcgc agggcccgct caacatgccc aaccgcgcga agaagcgcgc gctcgatctc    13380
gcgatcaccg taccggccgt gctcgcgctg gcgccgctga tgatcctggt ggcgatcctg    13440
atcaagctga agagcccggg cccggtgttg ttcgcgcagg atcgcgtcgg ccgcggcaac    13500
cggctgttca agatcatgaa gttccgctcg atgcgcgtaa cgctgtgcga cgcgaacggc    13560
```

```
aacgtctcgg ccagccgcga cgacgatcgc atcaccaagg tcggccgctt catccgcaag   13620
accagcatcg acgaactgcc gcagctgctg aacgtgctgc gcggcgacat gagcgtcgtc   13680
ggcccgcggc cgcatgcgct gggctcgcgc gccgccgatc acctgttctg ggaaatcgac   13740
gagcgctact ggcaccgcca cacgctcaag ccgggcatga ccggtctggc ccaggtgcgc   13800
ggtttccgcg gggcgaccga tcgccgcgtc gatctgacca accggctcca ggcagacatg   13860
gaatatatcg acgatggga tatctggcgc gatatcacga tcctgttcaa gacgctgcgg   13920
gtgatcgtgc attcgaacgc attctgatcc gcgcacgacg ctgggccgca gcctcgatcc   13980
gcaaatggat tgacagcggc ccggcttccg ttttctcgtt tgattttcgt tgcggccggt   14040
ccgcgccatg ggggattact gaatgaaggg catcatcctt gcggggggca gcgggacgcg   14100 cctgtaccc gcaacgctat cgatctcgaa gcagctgctt cccgtctatg acaagccgat   14160
gatcttctat ccgctgtcgg tgctgatgct caccggcatc cgggacatcc tgattatctc   14220
caccccgcgc gacctgccga tgttccaggc gctgctgggc gacggctcgg ccttcggcat   14280
caacctcagc tatgccgagc agccctcccc caacgggctg gccgaagcgt tcatcatcgg   14340
cgcggatttc gtcggcaacg atcccagcgc gctgatcctg ggcgacaaca tctatcacgg   14400
cgaaaagatg ggcgagcgct gccaggcagc cgcagcgcag gcagcgcagg cggtgcaaa   14460 cgtcttcgcc tatcatgtcg acgacccga gcgctacggc gtggtcgcgt tcgaccgga   14520 gacgggcgtc gccaccagcg tcgaggaaaa gccggccgag cccaagtcca actgggcgat   14580
caccggcctg tatttctacg acaaggacgt ggtcgacatc gccaagtcga tccagccctc   14640
ggcgcgcggc gaactcgaga tcaccgacgt caaccgcgtt tacatggagc gcggcgacct   14700
gcacatcacg cgcctcggcc gcggctatgc ctggctcgac accggcacgc atgacagcct   14760
gcacgaagcc ggctcgttcg ttcgcacgct cgagcatcgg acgggcgtga agatcgcctg   14820
cccggaggaa atcgccttcg aaagcggctg gctcggcgcc gaagacctgc tcaagcgcgc   14880
cgccggcctc ggcaagaccg gctatgccgc ctatctccgc aaggttgcga ccgcagcatg   14940
acccaggtcc atcatcacga actgtccggg gtcatcgagt tcacgccgcc caaatatggc   15000
gaccaccgcg gcttcttctc cgaagtgttc aagcagtcgg tgctcgatgc cgaaggcgtc   15060
gaggcacgct gggtgcagga caatcagagc ttctcggcgg ccccgggcac gatccgcggc   15120
ctgcatctcc aggcgccgcc cttcgcccag gccaagctgg tccgcgtgtt gcgcggcgcg   15180
atcttcgacg tcgcggtcga catccgtcgc ggctcgccca cctatggcaa atgggtcggc   15240
gtcgagctct cggccgagaa gtggaaccag ctgctggtcc ccgccggcta tgcgcacggc   15300
ttcatgacgc tcgttccgga ttgcgagatc ctctacaagg tcagcgccaa atattcgaag   15360
gattcggaga tggcgatccg ttgggacgat cccgatctcg ccatcgcctg gccggacatc   15420
ggcgtcgagc cggtcctctc cgaaaaggac gcggtcgcca cgcccttcgc cgaattcaac   15480 accccttct tctatcaggg ctgagccatg cagcagacct tcctcgtcac cggcggcgcc   15540
ggcttcatcg gctcggcggt ggtgcgccac ctcgtccgcc agggcgcgcg cgtcatcaat   15600
ctcgacaagc tcacctatgc cggcaacccg gcctcgctga ctgcgatcga aacgcgccc   15660 aactatcgct tcgtccatgc cgacatcgcc gacaccgcga cgatcctacc gctgctgcgc   15720
gaggagcagg tcgatgtggt gatgcacctc gccgccgaga gccatgtcga tcgctcgatc   15780 gacgccctg gcgagttcat cgagaccaat gtcgtcggca ccttcaagct gctccagtcg   15840
gcgctgcaat attggcgcga gctggagggc gagaaacgcg acgcgttccg cttccaccac   15900
```

```
atctccaccg acgaagtgtt cggcgacctg ccgttcgaca gcggcatctt caccgaagag   15960
acgccctatg atccctcctc gccctattcg gcgtcgaagg cggcgagcga ccatctggtg   16020
cgcgcctggg gccacaccta tggcctgccg gtggtgctgt cgaactgctc gaacaattac   16080
gggccgttcc acttccccga gaagctgatc ccgttgacca tcctcaacgc gctcgagggc   16140
aagccgctgc cggtctacgg caagggcgag aatatccgcg actggctgta tgtcgacgat   16200
cacgccaagg cgctggcgac catcgccacc accggcaagg tcggccagag ctacaatgtc   16260
ggcggccgca acgagcggac caacctgcag gtggtcgaga cgatctgcga cctgctcgac   16320
cagcgcattc cgctggccga cggtcgcaag cgccgcgaac tgatcacctt cgtcaccgat   16380
cgccccggcc atgaccgccg ctacgcgatc gacgcgacca gctcgagac cgagctgggc    16440 tggaaggctg aggagaattt cgacaccggc atccgcgcga cgatcgactg gtatctggcg   16500
aacgagtggt ggtggggccc gatccgctcc ggcaaatatg ccggcgagcg gctggggcag   16560
accgcctgat gcgtatcctc gtcaccgggc atgacggcca ggtcgcccag tcgctggccg   16620
agcaggcggt gggccacgag ctggtcttca ccacctaccc cgaattcgat ctctccaagc   16680
cggagacgat cgaggccggt gtggcgcggg tgcacccgga cctgatcgtc tccgccgccg   16740
cctacacggc ggtcgacaag gcggaaagcg aacccgagct ggcgatggcg atcaacggcg   16800
acggtcccgg cgtgctggcg cgcgcggggcg cgaagatcgg cgcgccgatc atccacctgt   16860
cgaccgatta tgtgttcgac ggcagtctcg accgcccttg gcgcgaggac gatcccaccg   16920
gcccgctcgg cgtctatggc gcgaccaagc tggccggcga gcaggcggtg caggcctcgg   16980
gtgccaccaa cgccgtgatc cggctggcct gggtctacag cccgttcggc aacaatttcg   17040
tcaagacgat gctccgcctc gccgagacgc gcgacgcgct gaacgtcgtg gaggaccagt   17100
ggggctgccc cagttcggcg ctggacatcg cgaccgcgat cctgacggtg gtcgggcact   17160
ggcagcagga cggcgcgacg agcggcctct accatttcgc cggcaccggc gagaccaact   17220
gggccgactt cgcatcgacg atcttcgccg agagcgccaa gcgcggtggc ccctcggcca   17280
ccgtcaccgg cattcccagc tcgggctatc cgactccggc cacgcgcccg gccaattcgc   17340
ggctggactg caccccgcttc gcggagacct tcggctaccg ggcgcctgcc tgcaggatt    17400 cgctgaacgt cgtactggat cgcctgctcg gctgatccga aacgggggc ctcagcgccc    17460 cccgccatgc tcccgttcgc gcgccggcaa tgcctctagc accgcgcgct ttcccttagg   17520
actcagctcg ctccagccgg cgatttcctt gggcgaccgc cagcacccca ggcacagccg   17580
gatctccatg tcgaggcggc agaccttgcg acagggcgat tccggcggtg cggcggcaaa   17640
gcgcgagaac agccccatca gcgcttgaag ttcagccccg tcttgcgggc gaacttggcg   17700
aggccgttga tcaccggggt cggcgcatag tcgcggatca ggccctttcac ccggtgcagc   17760 gcggtgcgct tgtcgtgcgc cgagacggcc cttccaacgc acgaagttcg aatagccgcg   17820
accctcggta tcctcctctg cgctgtagta gtagagtgcg agcgagttgc ggcggatgtt   17880
cggcggcgtc tgcagcggga agggctgcc gtgccacgac ttgcccgaga cgcggaagat    17940
cgcgaggcga ttgaacttgg gcgtgatgct ggaaacgcac ctggtcgcat cctcgtccca   18000
cagctccagg tcgccgcccc attcctcctg ccagtctggc gtgcagtaat agatgcagtt   18060
gatctgctgg ctgagcttct tgttggggtg gcgcgaggca tcgatgtgga gcatcagccg   18120
cccgcccgag ccggtcgagt gcaggccgca gccataatgg ttgggatccg gcagcaggtg   18180
cttgtggccc ctcagccggt cgaggaagtt gcagaagatg cccgactgaa actgcatcat   18240
catcaggcgg acgagcggcg gaaactgctc ctcgtccgag gtcgtcacct ttcgatcttg   18300
```

```
cgatcaccgc tgtgcgcgct atcgcccggc ccttccaggc gccagttgac gtcgtccagc   18360
ttcgggaagg catccccgag ccgccgcgcc acgtcgtcgg gcaggaaatt gtcgatcgcg   18420
acatgctcat agggctcggc gttcaggaag cgatcatgat attcgtccgc gagcgcatat   18480
agcttctcgc gcgtgaagaa gaagaagtcc gaagtatctg caccgaccga catgcaatcc   18540
cccccgaaga aacggacgca gcgatcataa acgattcacc gcaatcgcgt aacccgtctt   18600
gcacagcacc gtaacactta gcgatccctt atccgaacca cgatcggctt gaccaggcgg   18660
ataccgaatt cgcggaagcg ccggatcggc gtgcgcaccg catggtccca cagaatcgcg   18720
ccggccgcca ccgccgtgc ggcgacatcg ctgcggatct tgaacatatt gatgatgtcg   18780
atgtccgaaa ccagcttgcc cttgatccgg ttggttacat tctcgccgtg caccacctgc   18840
agccatagcg gcttgctcgg cacctggcgg atcgtccact tctcgcccag ctcgtggtgc   18900
ggcttggccc agatcgtctc gatcccggcc acgtctttct cgaccagcga ggtgaacggg   18960
ctgctgtgat cgctggcggt gtagagttgc ccgccccgca tcgcgatgcc gtgggggaag   19020
ttcagcacgg tctgcgccgg cgcttccttg gcggcgtcct gcacccgcgc gacgaaatcg   19080
ctcgacaccg catcatcatt gtccagccgc gtggtgacga tcagcgtctc gcccgccgtc   19140
gcgagtgccc gcacgtcctc ggcgatcatc gccttgtcga acatcgccac atagcgtggg   19200
gtaaaattga agatctggcg atcgcgctcg atccgctcgc ggaattcaac cggcgtatcc   19260
ttgtcgaaat agatcagcca gtggaagttg cgctcggtct ggcccgcgat gctcggcagg   19320
cagaactgct cgaacaggcc gaaacggcgt tccagccagc ccggcgagtt gcgaatcgcc   19380
acctcgcgtc ccgggctggc gatgttgaag cgagtcagga tcacgtggag catggggttg   19440 atcagcccctt gtttgcggaa ggaatggcgc ggggcacggc gaccgggcat gccaggaacc   19500
gggagcggcg cttcgcgaca tggcggagct tcgccctgaa tggcacgcgc tgcacggctg   19560
ctagccccct ttattgccgt tcacctgctt cggttaaggg atattccgga gcccggcaac   19620
cggcgattgc tgcgctgcgc aatgaacggc gccgccgcgt ggtggccaag ggcgcgccaa   19680
tccacacctg ccgggccggc gatcgcgcgc ccaaagcgcc gccaacgcat tcgcaaggct   19740
tgcgaaataa atggcttgcc cctacccgag cccggtgtcg cccctcgtc ccgacagcat   19800 cgccaccggc ctggcgcttc gcctgttcgc gatcgcctgc atgtcgacca tgtcggcgct   19860
catcaagatg tccgaactgc gcggcgcctc gctgatcgag acgatgtttc accgccagct   19920
ctgggcggtg cccttggtca ccctgtgggt cacgctgggg ccgggcctca gtcgctcag   19980 gaccgcgcgg ttcggcgcgc atgtctggcg caccgcggtg ggacttaccg gcatgatctt   20040
caccttcggc gcggtgatcc tgctgccgct cgccgaagcg cagaccttcc agttcaccgt   20100
ccccatcttc gcgacgctgc tcggcgcgct gatcctaggc gaaccgaccg gctggcaccg   20160
ctggagcgcg gtgatcctcg ggttcgtcgg cgtgcttatc gtcgtccagc cggggcacga   20220
ggcgatcccg gtgttcggtg cgttcgtggg cctgatggcg gcgctgttcg tcgccatcgt   20280
cgcgatcacg ctccgccaga tcgggaagac cgaaagcgcc ggcaccacgg tgttctggtt   20340
ctcgctgttg tcggtgccgg tgctgggcgc aatctatgcc ttccactaca agccccatga   20400
tgccgagacc tgggccatcc tgatcgccac gggcctggtc ggcggcgtcg gccagctcgc   20460
gctgaccggg gcgatgcgct tcgctcccgt gtcggcagtg gtgccgatgg actattcggg   20520
gctgctctgg gcgacgctct atggctggct gctgttcggc gtgctgccga ccttttccac   20580
ctggctcggc gcgccggtga tcatcgccag cggcctgtac atcgtctatc gcgagcagaa   20640
```

```
gctggcgcgc ggccaggcta gctacgccga aacgccacta tgaggttgtt ggcgggcatc  20700 gccaccogcc gctcgaacac cagccctgc gcttccgccg ccgccacgac atcgcccagc  20760
aaccgcaggc cccaggcgg                                              20779
```